United States Patent
Guan et al.

(10) Patent No.: US 9,868,737 B2
(45) Date of Patent: Jan. 16, 2018

(54) PYRIDINO[1,2-A]PYRIMIDONE ANALOGUE USED AS MTOR/P13K INHIBITOR

(71) Applicant: CISEN PHARMACEUTICAL CO., LTD., Jining (CN)

(72) Inventors: Huiping Guan, Shanghai (CN); Chengde Wu, Shanghai (CN); Tao Yu, Shanghai (CN); Lei Huang, Shanghai (CN); Dongling Hao, Shanghai (CN); Bo Gao, Shanghai (CN); Jikui Sun, Shanghai (CN); Nengyang Shi, Shanghai (CN); Shuhui Chen, Shanghai (CN)

(73) Assignee: CISEN PHARMACEUTICAL CO., LTD., Jining (CN)

( * ) Notice: Subject to any disclaimer, the term of this patent is extended or adjusted under 35 U.S.C. 154(b) by 0 days.

(21) Appl. No.: 15/319,728

(22) PCT Filed: Jun. 16, 2015

(86) PCT No.: PCT/CN2015/081519
§ 371 (c)(1),
(2) Date: Dec. 19, 2016

(87) PCT Pub. No.: WO2015/192761
PCT Pub. Date: Dec. 23, 2015

(65) Prior Publication Data
US 2017/0129888 A1 May 11, 2017

(30) Foreign Application Priority Data

Jun. 17, 2014 (CN) .......................... 2014 1 0271554
Jun. 12, 2015 (CN) .......................... 2015 1 0326169

(51) Int. Cl.
C07D 471/04 (2006.01)
C07D 487/04 (2006.01)
C07D 491/147 (2006.01)

(52) U.S. Cl.
CPC ......... C07D 471/04 (2013.01); C07D 487/04 (2013.01); C07D 491/147 (2013.01)

(58) Field of Classification Search
CPC . C07D 471/04; C07D 487/04; C07D 491/147
See application file for complete search history.

(56) References Cited

U.S. PATENT DOCUMENTS 9,284,315 B2 3/2016 Wu et al.

FOREIGN PATENT DOCUMENTS

| CN | 103539777 A | 1/2014 |
|----|---|---|
| WO | 2008/103636 A1 | 8/2008 |
| WO | WO-2008144463 A1 | 11/2008 |
| WO | 2013/071698 A1 | 5/2013 |
| WO | 2014/022128 A1 | 2/2014 |

OTHER PUBLICATIONS

English translation of the International Search Report dated Sep. 15, 2015 corresponding to International Patent Application No. PCT/CN2015/081519, filed on Jun. 16, 2015, 2 pages.

*Primary Examiner* — Kahsay Habte
(74) *Attorney, Agent, or Firm* — Mintz Levin Cohn Ferris Glovsky and Popeo PC

(57) ABSTRACT

The present invention relates to novel pyridino[1,2-α]pyrimidone compounds represented by formula (I) or pharmaceutically acceptable salts thereof; and a method of use thereof for treating tumors.

8 Claims, 3 Drawing Sheets

PYRIDINO[1,2-A]PYRIMIDONE ANALOGUE USED AS MTOR/PI3K INHIBITOR

TECHNICAL FIELD

The present invention relates to a class of pyridino[1,2-a]pyrimidinone analogs as mTOR/PI3K inhibitor, and particularly, the present invention relates to a compound of formula (I) or a pharmaceutically acceptable salt thereof.

BACKGROUND ART

PI3K pathway is a site in human cancer cells where mutations most commonly occur and can lead to cell proliferation, activation, and signal amplification. PI3K and mTOR are the two most important kinases in the PI3K signaling pathway.

PI3 kinase (phosphatidylinositol 3-kinase, PI3Ks) belongs to the family of lipid kinases and can phosphorylate the 3'-OH terminus of the inositol ring of phosphatidylinositol. Phosphatidylinositol-3-kinase (PI3K) is a lipid kinase composed of a regulatory subunit p85 or p101 and a catalysis subunit p110 and plays a key role in cell proliferation, survival and metabolism etc. by catalyzing the phosphorylation of phosphatidylinositol 4,5-bisphosphate (PIP2) to form phosphatidylinositol 3,4,5-triphosphate (PIP3) and thereby activating the downstream Akt and the like. Therefore, the inhibition of phosphatidylinositol 3-kinase may affect the PI3K pathway and thus inhibit the proliferation and activation of cancer cells.

Tumor suppressor gene PTEN (phosphatase and tension homolog deleted on chromosome ten) dephosphorylates PIP3 to generate PIP2, thus achieving negative regulation of the PI3K/Akt signaling pathway, inhibiting cell proliferation and promoting apoptosis. The frequent occurrence of PI3K gene mutation and amplification as well as the loss of PTEN in cancer and the like indicate that PI3K is closely related to tumorigenesis.

mTOR (mammalian rapamycin target protein) is a serine/threonine protein kinase present in the cytoplasm, which belongs to the phosphatidylinositol 3-kinase related kinase family and plays an important role in the regulation of signal transduction of many pathways. mTOR has been identified as a downstream target of PI3K/Akt. It has currently been found that two different mTOR complexes, i.e. mTORC1 and mTORC2, are present in the cells. They separately exercise different functions, wherein the main function of mTORC1 is to stimulate cell growth and proliferation, while mTORC2 regulates cell survival and cytoskeleton by activating AKT, PKC and other kinases. Studies have shown that the mTOR signaling pathway is related to the occurrence of cancer and the simultaneous inhibition of the activities of the two mTOR complexes in cancer cells have a more extensive and effective anti-cancer effect.

A PI3K-mTOR dual inhibitor can simultaneously block multiple segments in the signal transduction and will more effectively prevent the kinase signal transduction, thereby overcoming or delaying the emergence of drug resistance.

The patent applications WO2008163636 of Novartis and WO2008144463 of GSK have reported a series of compounds having an inhibition effect on both PI3K and mTOR which have good tumor therapeutic activity. However, for present there is no drug having an inhibition effect on both PI3K and mTOR in the market. Therefore, it is necessary to develop multi-targeting drugs having an inhibition effect on both PI3K and mTOR to facilitate the treatment of cancer.

SUMMARY OF THE INVENTION

The object of the present invention is to provide a compound of formula (I), or a pharmaceutically acceptable salt thereof,

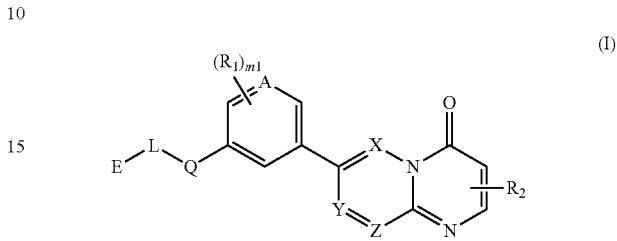

wherein,
the structure unit

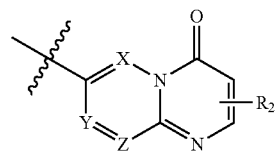

can be replaced with

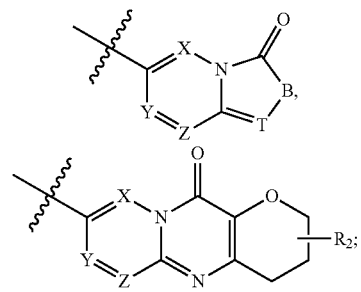

E is selected from the group consisting of $C_{1-6}$ alkyl, 3- to 10-membered cyclohydrocarbyl and heterocyclohydrocarbyl, optionally substituted with 1, 2 or 3 $R_3$;

one of L and Q is selected from the group consisting of $-C(R_3)(R_3)-$, $-C(=O)N(R_a)-$, $-N(R_a)-$, $-C(=NR_a)-$, $-S(=O)_2N(R_a)-$, $-S(=O)N(R_a)-$, $-O-$, $-S-$, $-C(=O)O-$, $-C(=O)-$, $-C(=S)-$, $-S(=O)-$, $-S(=O)_2-$, and $-N(R_a)C(=O)N(R_a)-$, and the other is selected from the group consisting of a single bond and $-C(R_3)(R_3)-$;

A and T are independently selected from the group consisting of N and $C(R_3)$;

zero or one of X, Y, and Z is selected from the group consisting of N, and the others are $C(R_3)$;

B is selected from the group consisting of $-C(R_3)R_3-$, $-C(=O)N(R_a)-$, $-N(R_a)-$, $-C(=NR_a)-$, $-S(=O)_2N(R_a)-$, $-S(=O)N(R_a)-$, $-O-$, $-S-$, $-C(=O)O-$, $-C(=O)-$, $-C(=S)-$, $-S(=O)-$, $-S(=O)_2-$, and $-N(R_a)C(=O)N(R_a)-$;

The heteroatom or heteroatom group is independently selected from the group consisting of $-C(=O)N(R_a)-$, —N($R_a$)—, —C(=N$R_a$)—, —S(=O)$_2$N($R_a$)—, —S(=O)N($R_a$)—, —O—, —S—, —C(=O)O—, —C(=O)—, —C(=S)—, —S(=O)—, —S(=O)$_2$—, and —N($R_a$)C(=O)N($R_a$)—;

each $m_1$ is independently selected from the group consisting of 0, 1, 2 or 3;

$R_{1-3}$ are independently selected from the group consisting of H, F, Cl, Br, I, CN, O$R_a$, N($R_b$)($R_c$), $C_{1-3}$ alkyl optionally substituted by $R_d$,

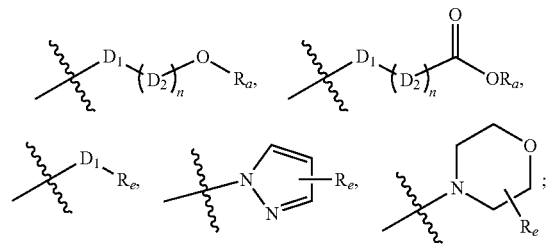

$D_1$ is selected from the group consisting of a single bond, —C(Re)(Re)—, —C(=O)N($R_a$)—, —N($R_a$)—, —C(=N$R_a$)—, —S(=O)$_2$N($R_a$)—, —S(=O)N($R_a$)—, —O—, —S—, —C(=O)O—, —C(=O)—, —C(=S)—, —S(=O)—, —S(=O)$_2$—, and —N($R_a$)C(=O)N($R_a$)—;

$D_2$ is selected from —C($R_a$)($R_a$)—;

n is selected from the group consisting of 1, 2, 3, 4, 5, or 6:

$R_a$, $R_b$, and $R_c$ are independently selected from the group consisting of H, and $C_{3-6}$ cycloalkyl or $C_{1-6}$ alkyl optionally substituted by $R_d$;

$R_e$ is selected from the group consisting of H, $C_{1-6}$ alkyl or alkoxy optionally substituted by $R_d$, $C_{3-6}$ cycloalkyl or cycloalkyloxy optionally substituted by $R_4$;

$R_d$ is selected from the group consisting of F, Cl, Br, I, CN, OH, CHO, COOH, $CH_3$, $CF_3$, $CH_3O$, and $CH_3CH_2O$, and the number of $R_d$ is selected from the group consisting of 0, 1, 2, or 3;

optionally, any two $R_1$, $R_a$ and $R_a$ in the same $D_2$, two $D_2$, or $R_a$ and one $D_2$, together with the same carbon atom or oxygen atom to which they both attach, form one or two 3-, 4-, 5- or 6-membered carbocyclic rings or oxygen-containing heterocyclic rings, wherein the number of oxygen atom is 1 or 2.

In one embodiment of the present invention, said E is selected from $C_{3-6}$ cycloalkyl or $C_{1-6}$ alkyl substituted by $R_3$, the number of $R_3$ is 0, 1, 2 or 3, or E is selected from the group consisting of

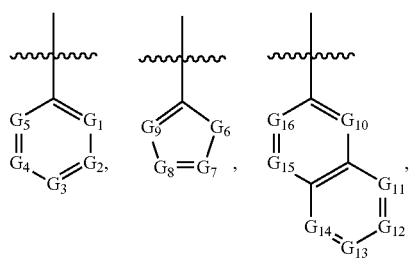

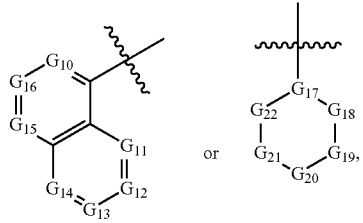

wherein, zero, one, two or three of $G_{1-5}$ are selected from N, and the others are selected from C($R_3$);

$G_6$ is selected from the group consisting of —C($R_3$)($R_3$)—, —C(=O)N($R_3$)—, —N($R_3$)—, —C(=N$R_3$)—, —S(=O)$_2$N($R_3$)—, —S(=O)N($R_3$)—, —O—, —S—, —C(=O)O—, —C(=O)—, —C(=S)—, —S(=O)—, —S(=O)$_2$—, and —N($R_3$)C(=O)N($R_3$)—;

zero, one, or two of $G_{7-9}$ are selected from N, and the others are selected from C($R_3$);

zero, one, two, three or four of $G_{10\sim16}$ are selected from N, and the others are selected from C($R_3$);

$G_{17}$ is selected from N or C($R_3$);

zero, one, two or three of $G_{18\sim22}$ are selected from —C(=O)N($R_3$)—, —N($R_3$)—, —C(=N$R_3$)—, —S(=O)$_2$N($R_3$)—, —S(=O)N($R_3$)—, —O—, —S—, —C(=O)O—, —C(=O)—, —C(=S)—, —S(=O)—, —S(=O)$_2$—, and —N($R_3$)C(=O)N($R_3$)—, and the others are selected from —C($R_3$)($R_3$)—; and the other variables are defined as above.

In one embodiment of the present invention, said E is selected from the group consisting of methyl, ethyl, propyl,

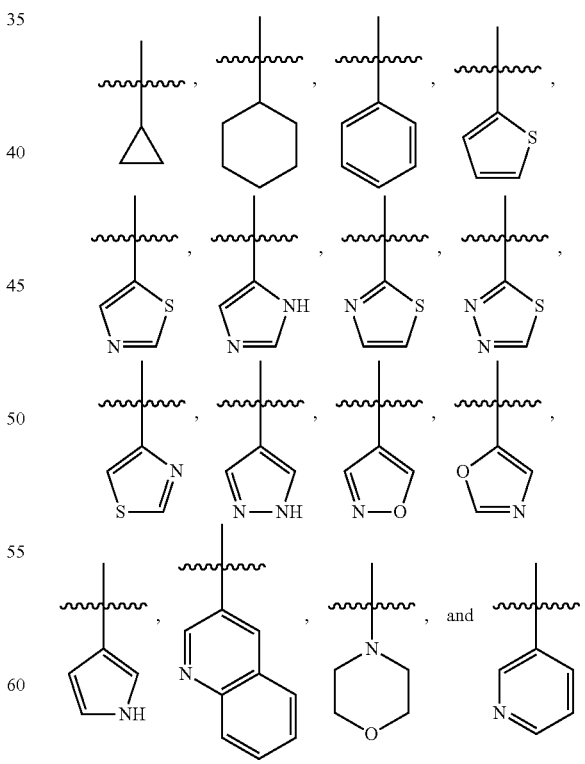

which is optionally substituted by 1, 2, or 3 $R_3$.

In one embodiment of the present invention, said E is selected from the group consisting of

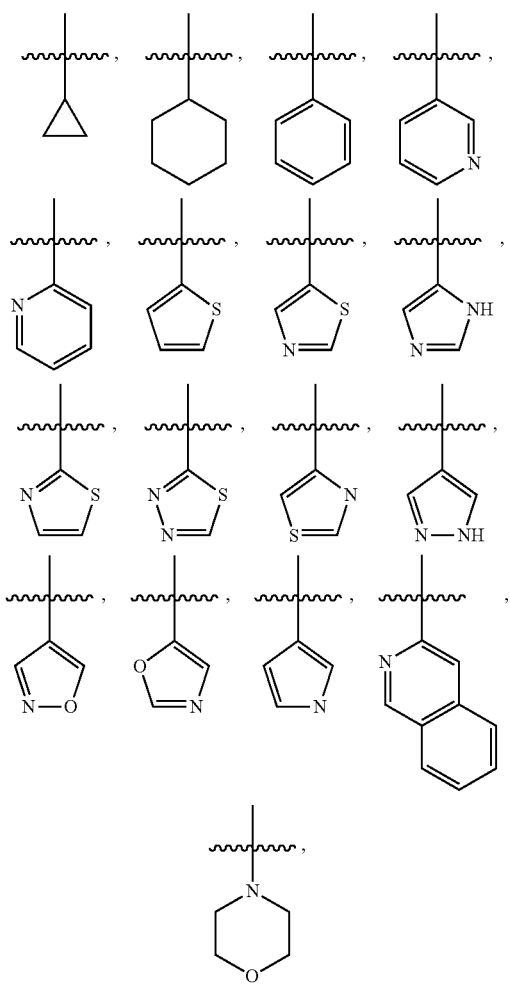
and $C_{1-3}$ alkyl, which is optionally substituted by 1, 2, or 3 halogen, OH, $OC_{1-3}$ alkyl, CN, $NH_2$, $NH(C_{1-3}$ alkyl), $N(C_{1-3}$ alkyl$)_2$, $C_{1-3}$ alkyl, trifluoromethyl, trifluoroethyl, $C(=O)NH_2$, $C_{1-3}$ alkylC$(=O)$, $C_{1-3}$ alkylC$(=O)$NH, $C_{1-3}$ alkylS$(=O)$, $C_{1-3}$ alkylS$(=O)$NH, $C_{1-3}$ alkylS$(=O)_2$ or $C_{1-3}$ alkylS$(=O)_2$NH.
In one embodiment of the present invention, said E is selected from the group consisting of
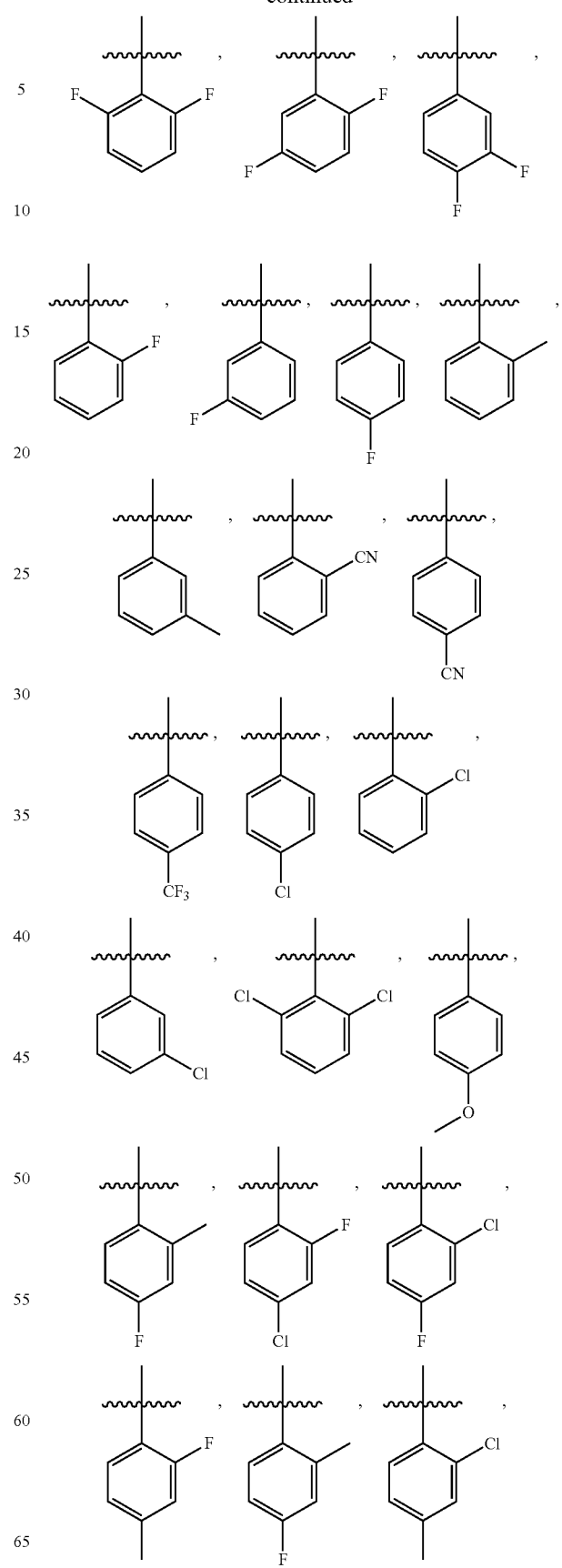

-continued
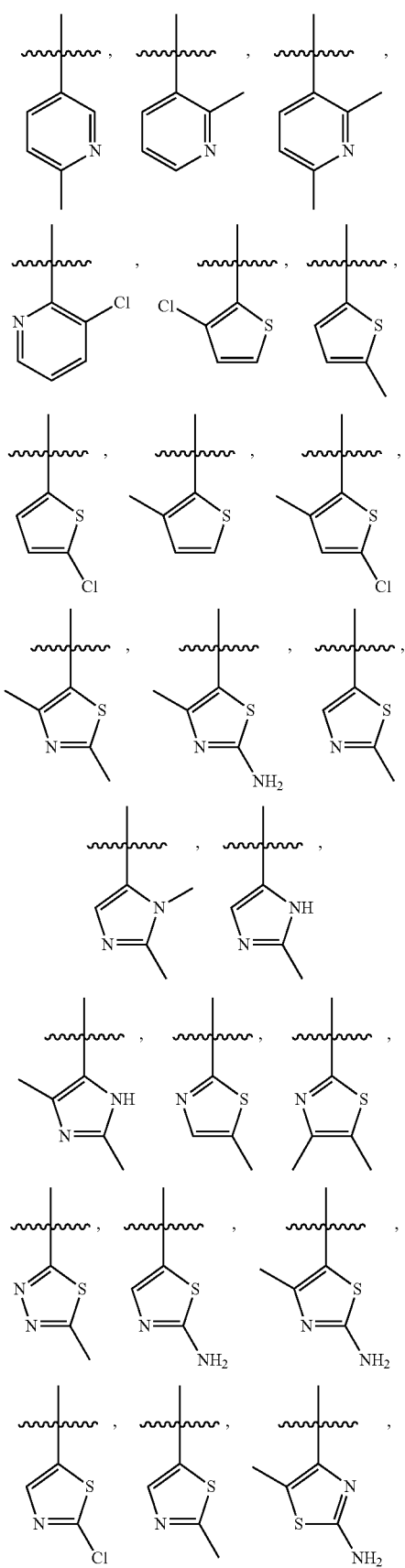
-continued
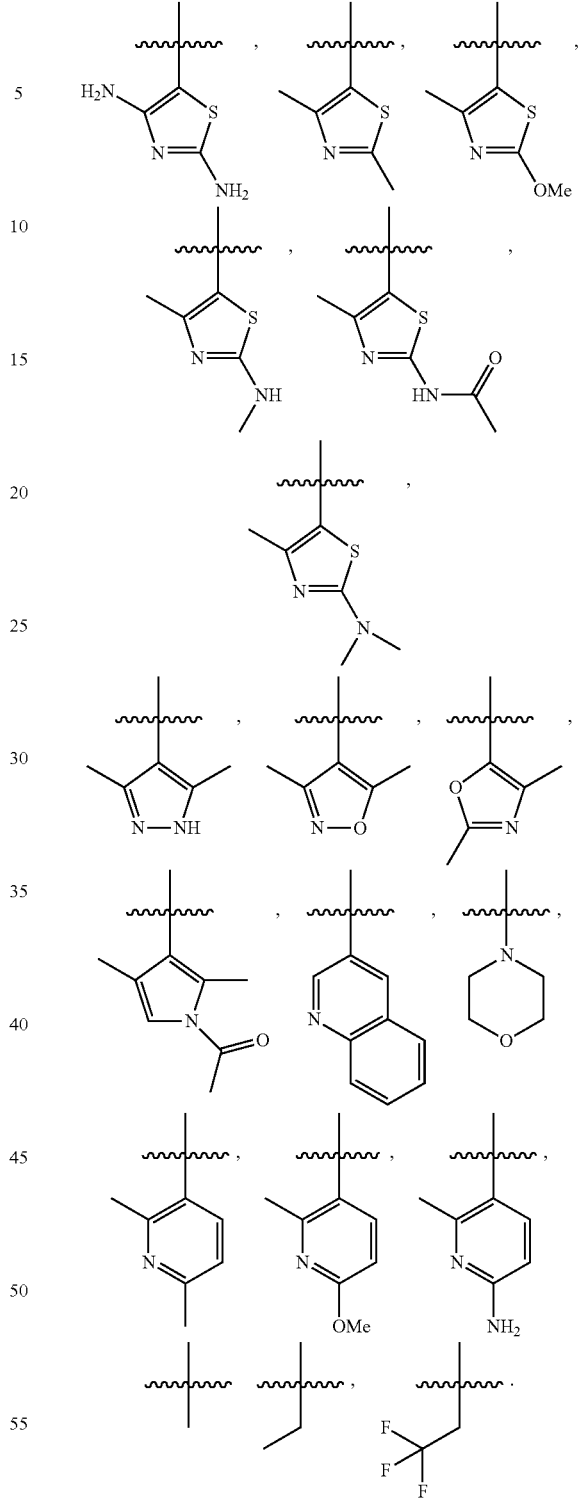
In one embodiment of the present invention, one of L and Q is selected from the group consisting of —S(=O)$_2$NH—, —S(=O)$_2$—, —NH—, and —NHC(=O)NH—, and the other is selected from a single bond, or —CH$_2$—.
In one embodiment of the present invention, zero or one of X, Y, and Z is selected from N, and the others are selected from the group consisting of CH, C(CH$_3$), C(CF$_3$), CCl, and CF.

In one embodiment of the present invention, A and T are independently selected from the group consisting of N, CH, C(CH$_3$), C(CF$_3$), CCl, and CF; or B is selected from the group consisting of NH, N(CH$_3$) and N(CF$_3$).

In one embodiment of the present invention, the ring formed between any two R$_1$, R$_a$ and R$_a$ in the same D$_2$, two D$_2$, or R$_a$ and one D$_2$ is selected from the group consisting of cyclopropyl, cyclobutyl, cyclopentyl, cyclohexyl, oxetanyl, 1,3-dioxolanyl.

In one embodiment of the present invention, said R$_{1-3}$ is selected from the group consisting of H, F, Cl, Br, I, CN, OH, NH$_2$, methyl, ethyl, propyl, methoxy, ethoxy, methylamino, dimethylamino, halomethyl, haloethyl, halopropyl, aminomethyl, aminoethyl, aminopropyl, cyclopropyl,

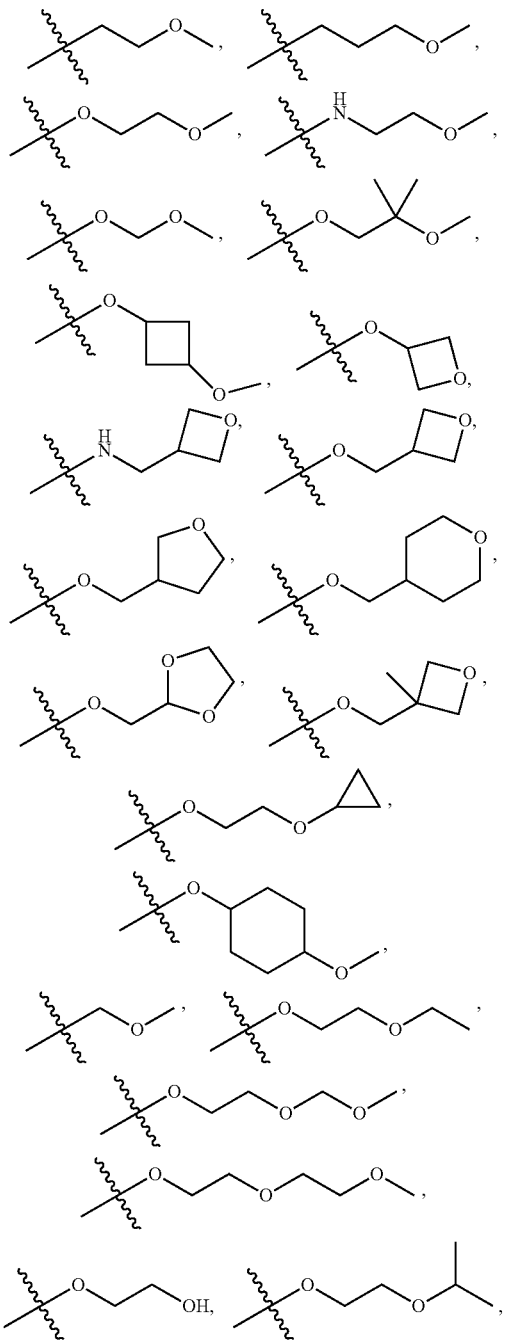

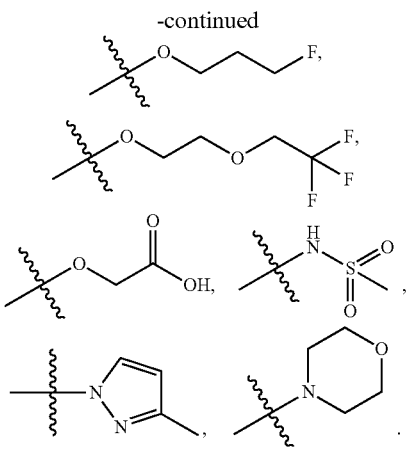

In one embodiment of the present invention, the above-mentioned compounds or pharmaceutically acceptable salts thereof are selected from the group consisting of: Compound 1 to Compound 284.

Related Definitions:

Unless otherwise stated, the terms and phrases used herein are intended to have the following meanings. A specific term or phrase should not be considered unclear or uncertain in the absence of a specific definition and should be understood in accordance with the common meaning. When a trade name appears herein, it is intended to refer to the corresponding product or the active ingredient thereof.

C$_{1-10}$ is selected from the group consisting of C$_1$, C$_2$, C$_3$, C$_4$, C$_5$, C$_6$, C$_7$, C$_8$, C$_9$ and C$_{10}$; C$_{3-10}$ is selected from the group consisting of C$_3$, C$_4$, C$_5$, C$_6$, C$_7$, C$_8$, C$_9$, and C$_{10}$.

C$_{1-10}$ alkyl or heteroalkyl, C$_{3-10}$ cyclohydrocarbyl or heterocyclohydrocarbyl, C$_{1-10}$ alkyl or heteroalkyl substituted by C$_{3-10}$ cyclohydrocarbyl or heterocyclohydrocarbyl include, but are not limited to:

C$_{1-10}$ alkyl, C$_{1-10}$ alkylamino, N,N-di(C$_{1-10}$ alkyl)amino, C$_{1-10}$ alkoxy, C$_{1-10}$ alkanoyl, C$_{1-10}$ alkoxycarbonyl, C$_{1-10}$ alkylsulfonyl. C$_{1-10}$ alkylsulfinyl, C$_{3-10}$ cycloalkyl, C$_{3-10}$ cycloalkylamino, C$_{3-10}$ heterocycloalkylamino, C$_{3-10}$ cycloalkyloxy, C$_{3-10}$ cycloalkylacyl, C$_{3-10}$ cycloalkyloxycarbonyl, C$_{3-10}$ cycloalkylsulfonyl, C$_{3-10}$ cycloalkylsulfinyl;

methyl, ethyl, n-propyl, isopropyl, —CH$_2$C(CH$_3$)(CH$_3$)(OH), cyclopropyl, cyclobutyl, propylmethylene, cyclopropionyl, benzyloxy, trifluoromethyl, aminomethyl, hydroxymethyl, methoxy, formyl, methoxycarbonyl, methylsulfonyl, methylsulfinyl, ethoxy, acetyl, ethanesulfonyl, ethoxycarbonyl, dimethylamino, diethylamino, dimethylaminocarbonyl, diethylaminocarbonyl;

N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN,

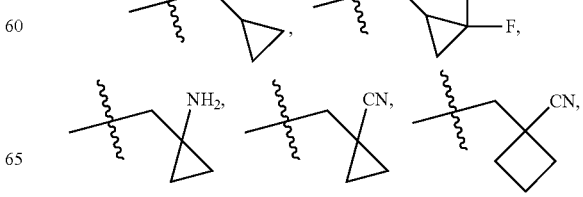

-continued
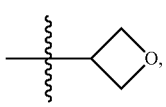
—CH₂CH(OH)(CH₃)₂, —CH₂CH(F)(CH₃)₂, —CH₂CH₂F, —CH₂CF₃, —CH₂CH₂CF₃, —CH₂CH₂NH₂, —CH₂CH₂OH, —CH₂CH₂OCH₃, —CH₂CH₂CH₂OCH₃, —CH₂CH₂N(CH₃)₂, —S(=O)₂CH₃, —CH₂CH₂S(=O)₂CH₃,
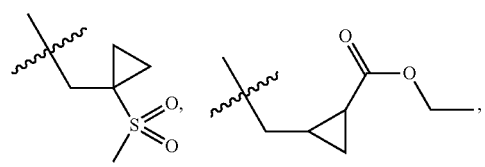
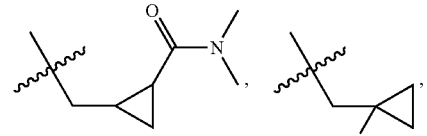
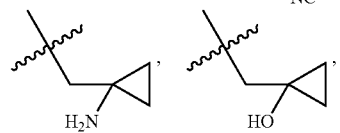
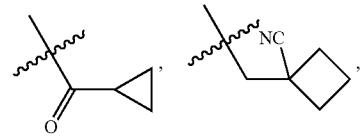
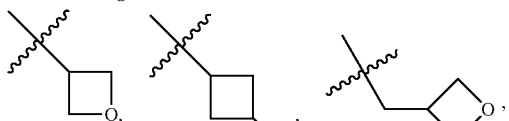
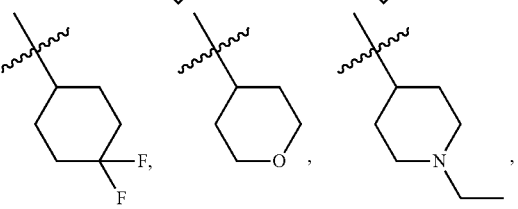
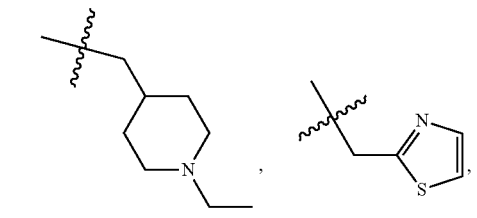
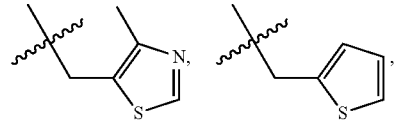
-continued
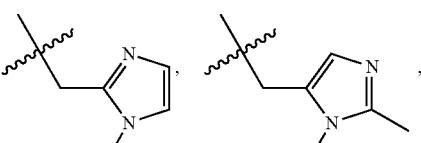
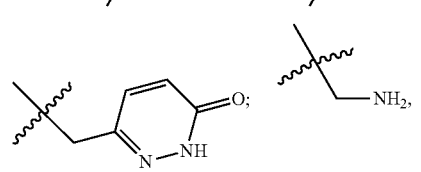
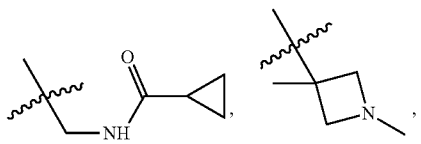
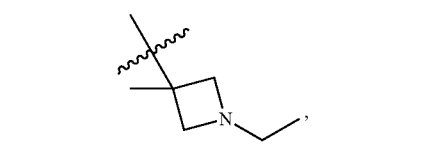
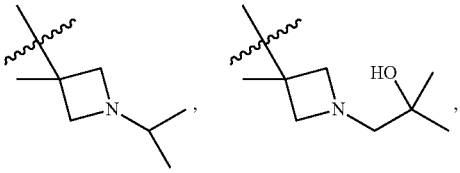
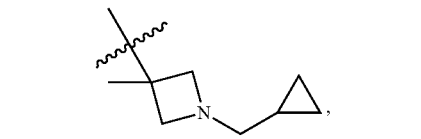
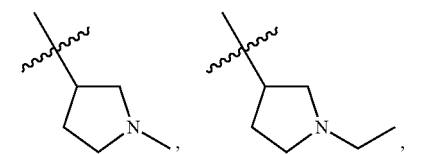
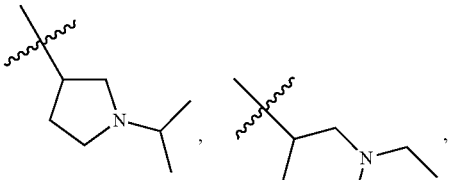
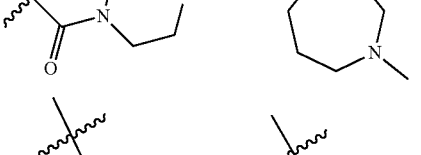
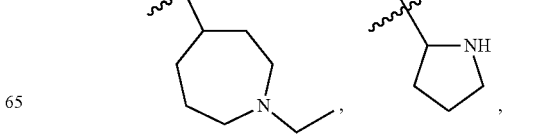

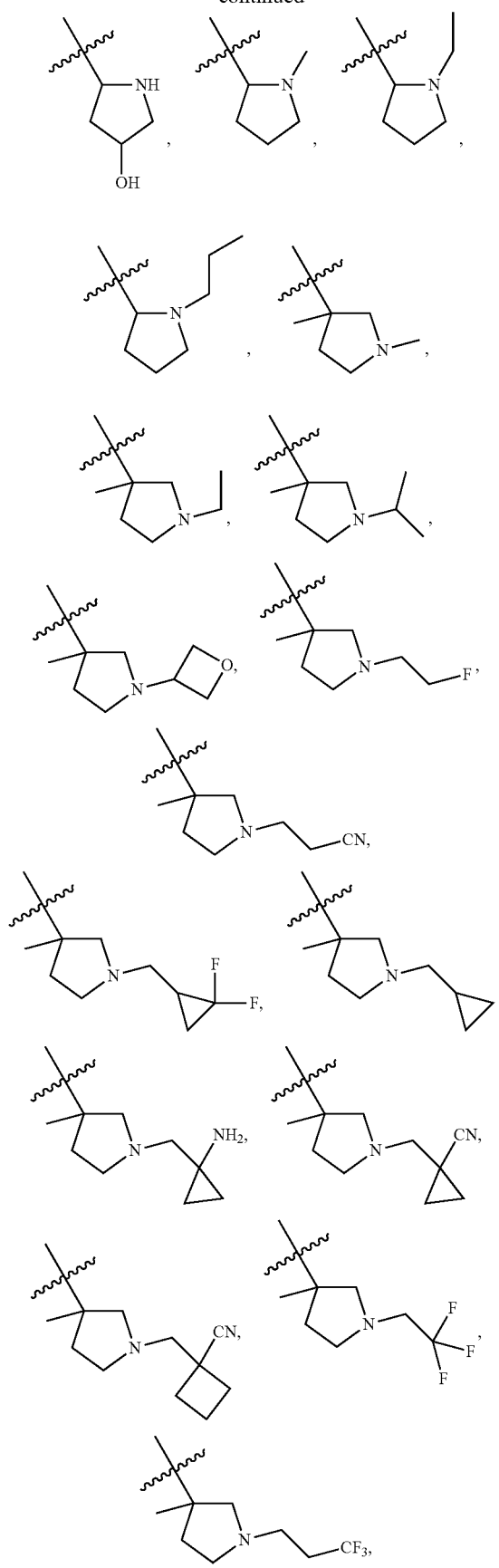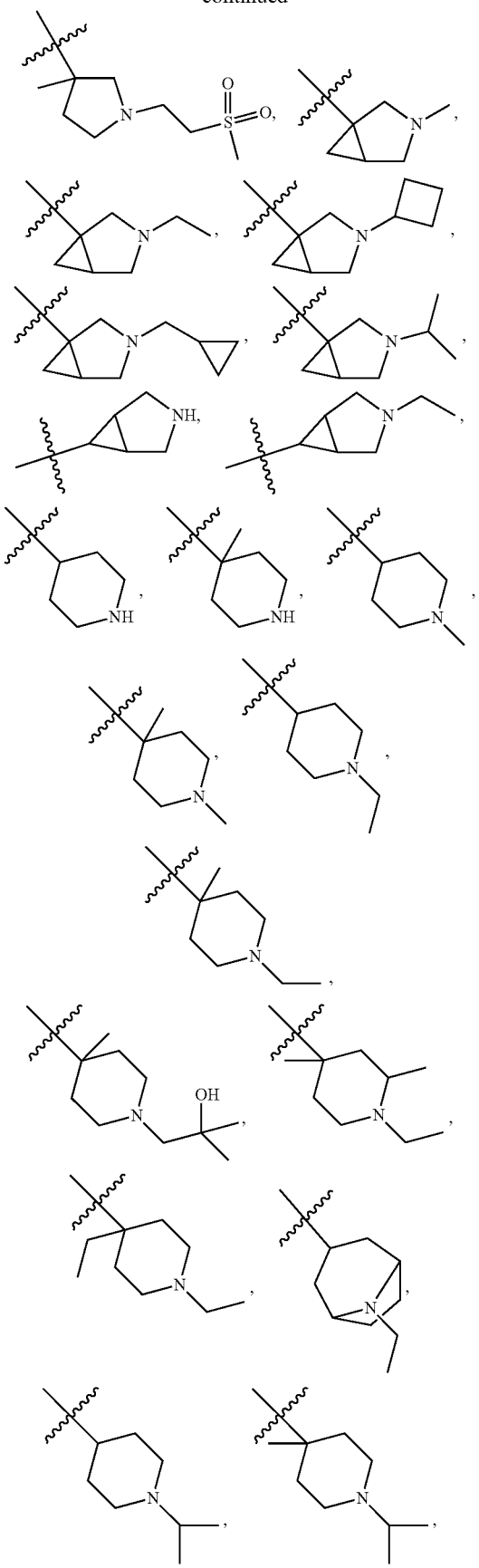

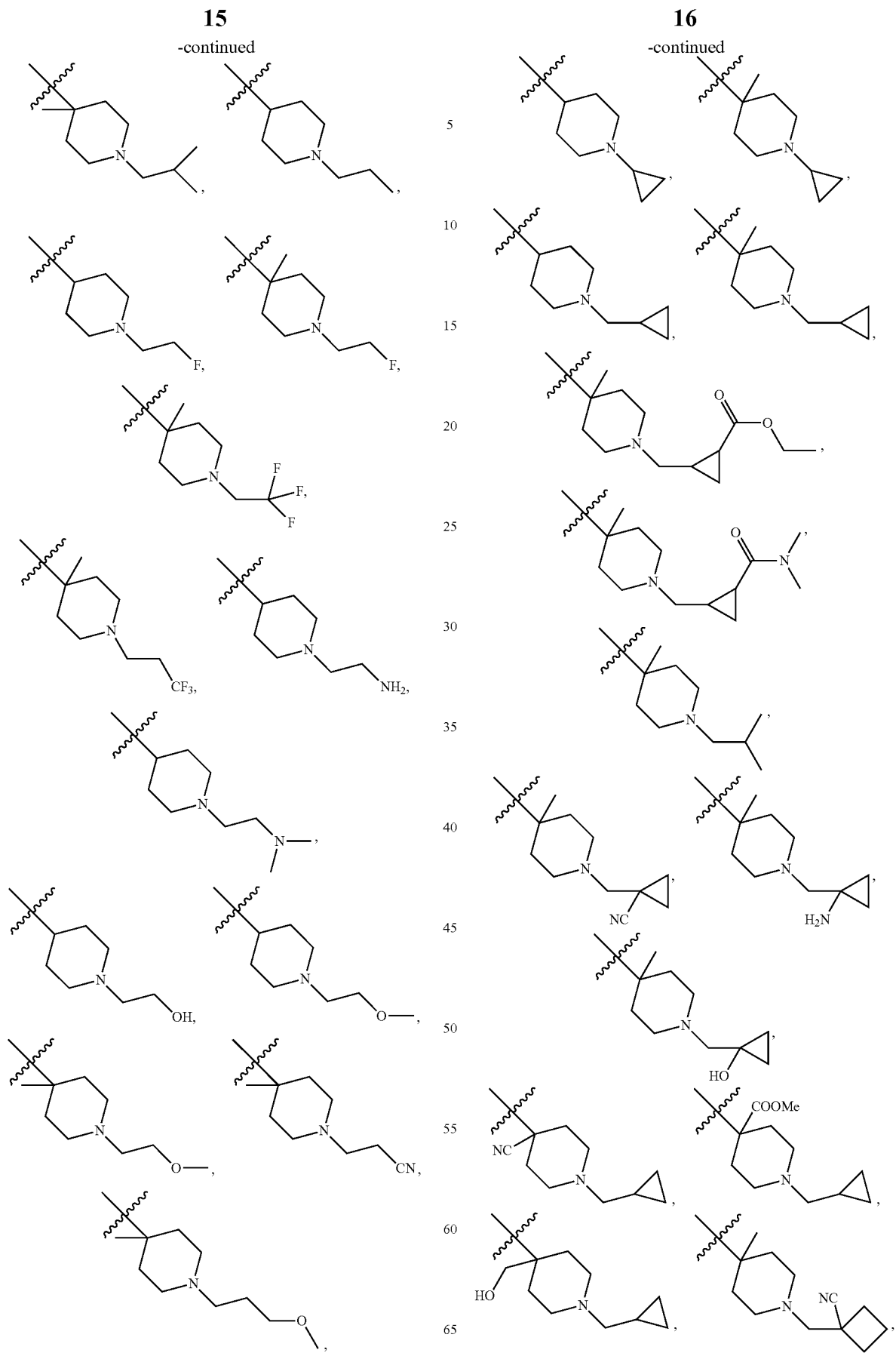

-continued
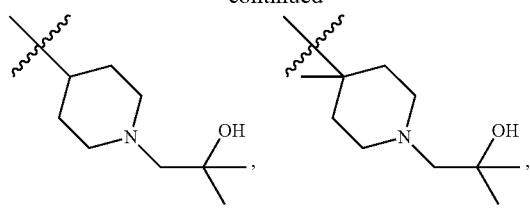
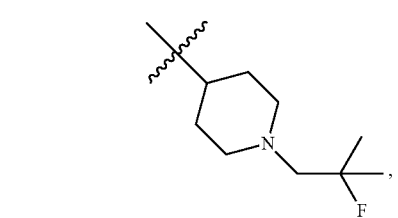
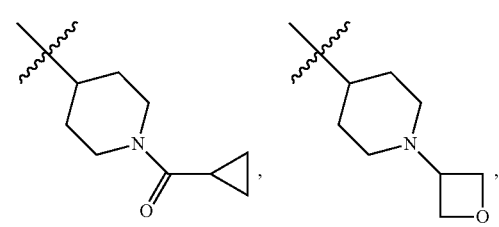
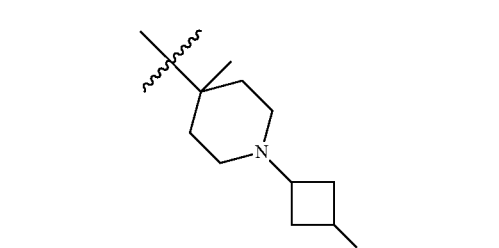
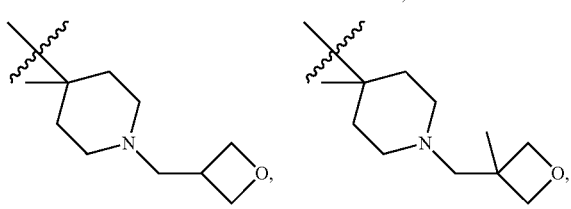
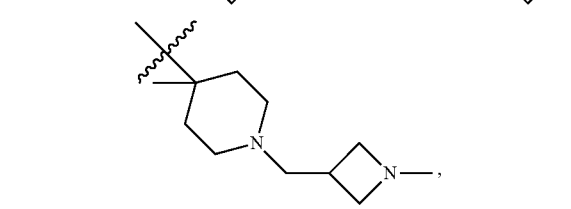
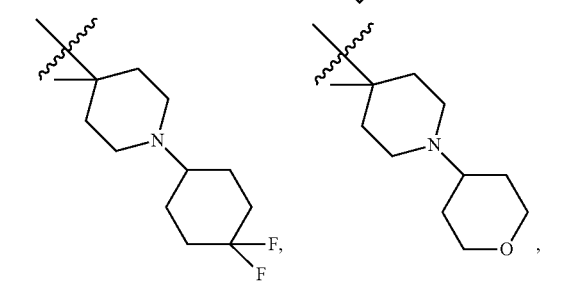
-continued
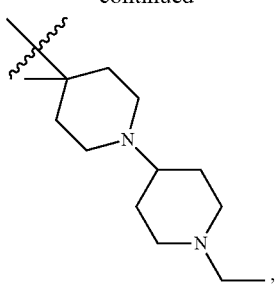
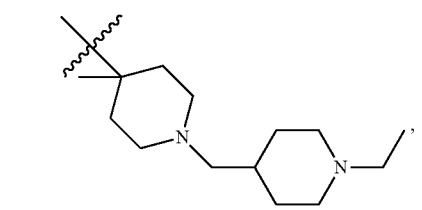
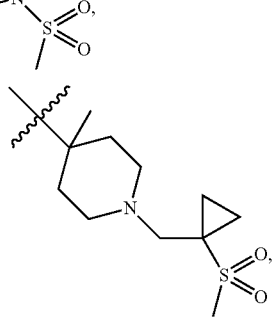
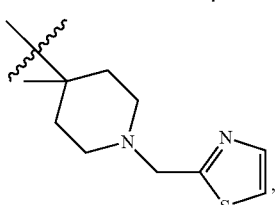
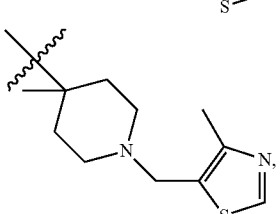
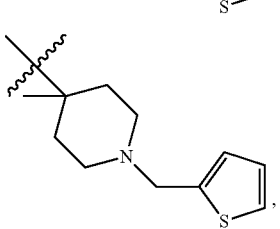

-continued

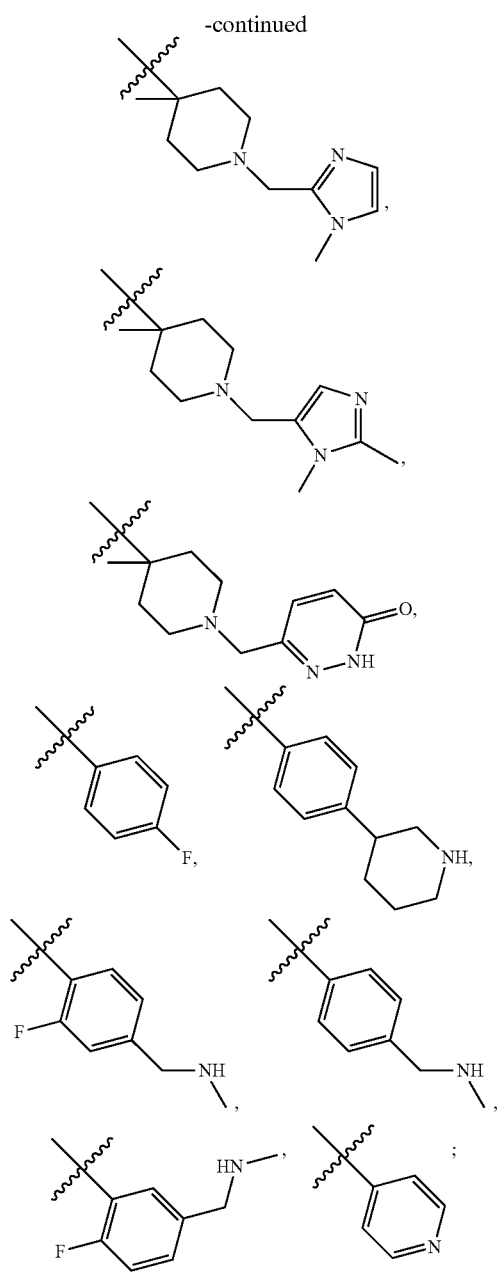

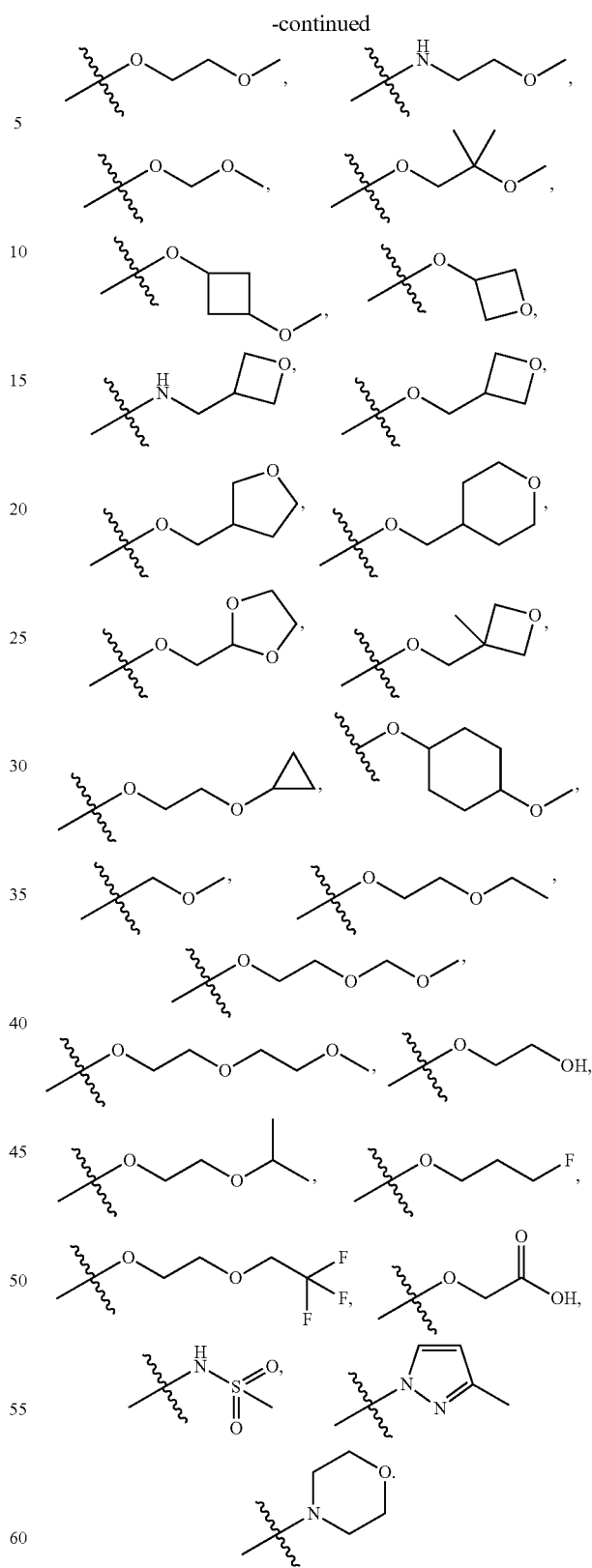

phenyl, thiazolyl, biphenyl, naphthyl, cyclopentyl, furyl, 3-pyrrolinyl, pyrrolidinyl, 1,3-dioxolanly, pyrazolyl, 2-pyrazolinyl, pyrazolidinyl, imidazolyl, oxazolyl, thiazolyl, 1,2,3-azolyl, 1,2,3-triazolyl, 1,2,4-triazolyl, 1,3,4-thiadiazolyl, 4H-pyranyl, pyridinyl, piperndinyl, 1,4-dioxanyl, morpholinyl, pyridazinyl, pyrimidinyl, pyrazinyl, piperazinyl, 1,3,5-trithianyl, 1,3,5-triazinyl, benzofuranyl, benzothienyl, indolyl, benzimidazolyl, benzothiazolyl, purinyl, quinolyl, isoquinolyl, cinnolinyl or quinoxalinyl, and methyl, ethyl, propyl, methoxy, ethoxy, methylamino, dimethylamino, halomethyl, haloethyl, halopropyl, aminomethyl, aminoethyl, aminopropyl, cyclopropyl,

The term "pharmaceutically acceptable" used herein refers to those compounds, materials, compositions, and/or dosage forms which are, within the scope of reliable medical judgment, suitable for access of human and animal tissues without excessive toxicity, irritation, allergic reaction or other problem or complication, and can match a reasonable benefit/risk ratio.

The term "pharmaceutically acceptable salt" refers to salts of the compounds of the present invention which are prepared from the compounds having particular substituent moieties found in the present invention and relatively non-toxic acids or bases. When compounds of the present invention contain relatively acidic functionalities, base addition salts can be obtained by contacting a sufficient amount of base with the neutral form of such compounds in a neat solution or in a suitable inert solvent. The pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting a sufficient amount of acid with the neutral form of such compounds in a neat solution or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, phosphorous acids and the like; as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic acid and the like (see, Berge et al. "Pharmaceutical salts". Journal of Pharmaceutical Science 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms thereof in certain physical properties, such as different solubility in polar solvents.

"Pharmaceutically acceptable salts" used herein belong to derivatives of the disclosed compounds wherein the parent compound is modified by forming salts with an acid or base. Examples of pharmaceutically acceptable salts include, but are not limited to, inorganic or organic acid salts of basic residues such as amines; alkali or organic salts of acid radicals such as carboxylic acids; and the like. The pharmaceutically acceptable salts include the conventional non-toxic salts or the quaternary ammonium salts of the parent compound formed, for example, from non-toxic inorganic or organic acids. The conventional non-toxic salts include, but are not limited to, those derived from inorganic acids and organic acids, wherein the inorganic acids or organic acids are selected from the group consisting of 2-acetoxybenzoic, 2-hydroethanesulfonic, acetic, ascorbic, benzenesulfonic, benzoic, monohydrogencarbonic, carbonic, citric, edetic, ethane disulfonic, ethane sulfonic, fumaric, glucoheptonic, gluconic, glutamic, glycolic, hydrobromic, hydrochloric, hydriodic, hydroxyl, hydroxylnaphthoic, isethionic, lactic, lactose, dodecyl sulphonic, maleic, malic, mandelic, methane sulfonic, nitric, oxalic, pamoic, pantothenic, phenylacetic, phosphoric, poly-galacturonic, propionic, salicylic, stearic, ethylene acetic, succinic, aminosulfuric, sulfanilic, sulfuric, tannin, tartaric, and p-toluenesulfonic acids.

The pharmaceutically acceptable salts of the present invention can be prepared with the parent compounds containing acid radical or base by the conventional chemical methods. In general, the preparation of such salts is carried out by the reaction of free acid or base forms of these compounds with a stoichiometric amount of an appropriate acid or base in water or in an organic solvent or a mixture of the two solvents. In general, non-aqueous medium such as ether, ethyl acetate, ethanol, isopropanol, or acetonitrile and the like is preferable.

In addition to salt forms, the compounds provided by the present invention have prodrug forms. Prodrugs of the compounds described herein readily undergo chemical changes under physiological conditions to provide the compounds of the present invention. Additionally, prodrugs can be converted to the compounds of the present invention by chemical or biochemical methods in an in vivo environment.

Certain compounds of the present invention may be presented in non-solvated forms or solvated forms including hydrate form. In general, the non-solvated form is equivalent to the solvated form, and both forms are within the scope of the present invention. Certain compounds of the present invention may exist in multiple crystalline or amorphous form.

Certain compounds of the present invention may have an asymmetric carbon atom (optical center) or a double bond. Racemate, diastereomer, geometric isomer and individual isomer are included within the scope of the present invention.

The graphic representations of racemic, ambiscalemic and scalemic or enantiomerically pure compounds used herein are from Maehr J. Chem. Ed. 62, 114-120 (1985). Unless otherwise stated, wedged bond and dashed bond are used to denote the absolute configuration of a stereogenic center. Unless otherwise stated, when the compounds in the present invention contain an olefinic double bond or any other geometric asymmetry center, they include E and Z geometric isomers. Likewise, all tautomeric forms are included within the scope of the present invention.

The compounds of the present invention may have specific geometric or stereoisomeric forms. The present invention contemplates all such compounds, including cis and trans isomers, (−)- and (+)-enantiomers, (R)- and (S)-enantiomers, diastereoisomers, (D)-isomers, (L)-isomers, and racemic mixtures and other mixtures, for example, enantiomers- or diastereoisomers-enriched mixtures, all of which belong to the scope of the present invention. The substituents such as alkyl, etc. may have additional asymmetric carbon atoms. All these isomers and mixtures thereof are included within the scope of the present invention.

Optically active (R)- and (S)-isomers, or (D)- and (L)-isomers may be prepared using chiral synthesis, chiral reagents or other conventional techniques. If one kind of enantiomer of certain compound of the present invention is to be obtained, the pure desired enantiomer can be obtained by asymmetric synthesis or derivatization with a chiral auxiliary, followed by separation of the resulting diastereomeric mixture and cleavage of the auxiliary group. Alternatively, when the molecule contains a basic functional group (such as amino) or acidic functional group (such as a carboxyl), the compound reacts with an appropriate optically active acid or base to form a salt of diastereomeric isomer, then the diastereomeric isomer is subjected to resolution through fractional crystallization or chromatography well known in the art and recovered to give pure enantiomer. In addition, the enantiomers and diastereomers are separated generally using chromatography which uses a chiral stationary phase, and optionally also a chemical derivative method (for example, carbamate generated from amine).

The compounds of the present invention may also contain unnatural proportions of atomic isotopes at one or more of the atoms that constitute such compounds. For example, the compounds may be labeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable carrier" refers to any agent or carrier medium which can deliver an effective amount of the active substances of the present invention, does not interfere with the biological activity of the active substances and have no toxic side effects on the host or patient. The representative carrier includes water, oil, vegetable and mineral, cream base, lotion base, ointment base and the like. These bases include suspensions, thickeners, penetration enhancers and the like. Their formulations are well known to the skilled in the cosmetic field or topical pharmaceutical field. Additional information about carriers can be referred to Remington: The Science and Practice of Pharmacy, 21st Ed, Lippincott, Williams & Wilkins (2005), the disclosure of which is incorporated herein by reference.

The term "excipient" generally refers to a carrier, diluent and/or vehicle required for formulating the effective pharmaceutical compositions.

For a drug or pharmacologically active agent, the term "effective amount" or "therapeutically effective amount" refers to a nontoxic but sufficient amount to achieve the desired effect of the drug or agent. For oral dosage forms of the present invention, an "effective amount" of an active substance in the composition refers to an amount required for achieving the desired effect when combining with another active substance in the composition. An effective amount varies from person to person and is determined depending on the age and general condition of recipients as well as the specific active substance. An appropriate effective amount in individual cases can be determined by the skilled in the art based on routine experiment.

The term "active ingredient", "therapeutic agent", "active substance" or "active agent" refers to a chemical entity which can effectively treat the target disorder, disease or condition.

The term "substituted" means that any one or more hydrogen atoms on a specific atom are substituted by substituent(s), including deuterium and hydrogen variants, as long as the valence state of the specific atom is normal and the substituted compound is stable. When a substituent is keto- (i.e., =O), this means that two hydrogen atoms are substituted. The ketone substitution will not occur on the aromatic group. The term "optionally substituted" means that one may be substituted, or may not be substituted, and unless otherwise specified, the kind and number of substituents may be arbitrary as long as it can be achieved chemically.

When any variable (e.g., R) occurs more than once in the composition or structure of the compound, its definition in each case is independent. Thus, for example, if a group is substituted with 0-2 R, then the group may optionally be substituted with up to two R and the R in each case has an independent option. Moreover, the combination of substituents and/or variants thereof is allowed only if such combination can result in a stable compound.

When one of the variables is selected from a single bond, it represents that two groups are connected directly. For example, when L in A-L-Z represents a single bond, the structure of A-L-Z is actually A-Z.

When a bond of a substituent can cross link to two atoms on a ring, such substituent may be bonded to any atom of the ring. When it is not specified through which atom an enlisted substituent is linked to a compound that is encompassed by the general chemical structure but is not specifically mentioned, such substituent may be bonded through any of its atoms. The combination of substituents and/or variants thereof is allowed only if such combination can result in a stable compound. For example, the structural unit

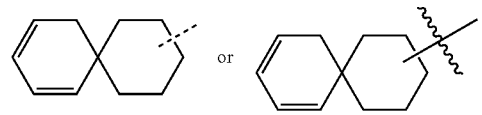

represents that any position on cyclohexyl or cyclohexadiene can be substituted.

The substituents of alkyl and heteroalkyl radicals (including those groups commonly referred to as alkylene, alkenyl, heteroalkylene, heteroalkenyl, alkynyl, cycloalkyl, heterocycloalkyl, cycloalkenyl and heterocycloalkenyl) are generally known as "alkyl substituents", which may be selected from, but not limited to one or more of the following groups: —R', —OR', =O, =NR', =N—OR', —NR'R'', —SR', halogen, —SiR'R''R''', OC(O)R', —C(O)R', —CO$_2$R', —CONR'R'', —OC(O)NR'R'', —NR''C(O)R', NR'C(O)NR''R''', —NR''C(O)$_2$R', —NR''''-C(NR'R''R''')=NR'''', NR''∝1C(NR'R'')=NR''', —S(O)R', —S(O)$_2$R', —S(O)$_2$NR'R'', NR''SO$_2$R', —CN, —NO$_2$, —N$_3$, —CH(Ph)$_2$ and fluoro(C$_1$-C$_4$) alkyl: the number of substituents is 0~(2m'+1), wherein m' is the total number of carbon atoms in such radical. R', R'', R''', R'''' and R'''''' are each independently and preferably hydrogen, substituted or unsubstituted heteroalkyl, substituted or unsubstituted aryl (e.g., 1 to 3 halogens-substituted aryl), substituted or unsubstituted alkyl, alkoxy, thioalkoxy or aralkyl. When the compound of the present invention includes more than one R, for example, each R is to be selected independently as for each of R', R'', R''', R'''', and R'''''' when more than one R', R'', R''', R'''', and R'''''' exist. When R', and R'' are attached to the same nitrogen atom, they can form a 5-, 6- or 7-membered ring together with the nitrogen atom. For example, —NR'R'' is meant to include, but not limited to 1-pyrrolidinyl and 4-morpholinyl. According to the above discussion of substituents, one skilled in the art will appreciate that the term "alkyl" is meant to include a group formed by the linkage of carbon atom with a non-hydrogen group, such as haloalkyl (e.g., —CF$_3$, —CH$_2$CF$_3$) and acyl (e.g., —C(O)CH$_3$, —C(O)CF$_3$, —C(O)CH$_2$OCH$_3$, etc.).

Similar to the alkyl substituent, aryl and heteroaryl substituents are generally both referred to as "aryl substituents", and selected from the group consisting of, for example —R', —OR', —NR'R'', —SR', -halogen, —SiR'R''R''', OC(O)R', —C(O)R', —CO$_2$R', —CONR'R'', —OC(O)NR'R'', —NR''C(O)R', NR'C(O)NR''R''', —NR''C(O)2R', —NR''''-C(NR'R''R''')=NR'''', NR'''' C(NR'R'')=NR''', —S(O)R', —S(O)$_2$R', —S(O)$_2$NR'R'', NR''SO$_2$R', —CN, —NO$_2$, —N$_3$, —CH(Ph)$_2$, fluoro(C$_1$-C$_4$)alkoxy and fluoro(C$_1$-C$_4$) alkyl and the like, and the number of substituents is between 0 and the total number of open valences on the aromatic ring: wherein R', R'', R''', R'''' and R'''''' are each independently and preferably selected from the group consisting of hydrogen, substituted or unsubstituted alkyl, substituted or unsubstituted heteroalkyl, substituted or unsubstituted aryl and substituted or unsubstituted heteroaryl. When the compound of the present invention includes more than one R, for example, each R is to be independently selected, as each of R', R'', R''', R'''', and R''''' when more than one of these groups exist.

Two substituents of the adjacent atoms on an aryl or heteroaryl ring may optionally be substituted by a substituent of the formula -T-C(O)—(CRR')q-U-, wherein T and U are independently selected from the group consisting of —NR—, —O—, CRR'— and a single bond, and q is an integer of 0-3. Alternatively, two substituents of the adjacent atoms on an aryl or heteroaryl ring may optionally be substituted by a substituent of the formula -A(CH$_2$)$_r$B—, wherein A and B are independently selected from the group consisting of —CRR'—, —O—, —NR—, —S—, —S(O)—, S(O)$_2$—, —S(O)$_2$NR'— and a single bond, and r is an integer of 1-4. Optionally, one single bond of the new ring thus formed can be replaced with a double bond. Alternatively, two substituents of the adjacent atoms on an aryl or heteroaryl ring may optionally be substituted by a substituent of the formula -A(CH$_2$)$_s$B—, wherein s and d are independently selected from an integer of 0-3. X is selected from the group consisting of —O—, —NR', —S—, —S(O)—, —S(O)$_2$—, and —S(O)$_2$NR'—. The substituents R', R', R'' and R''' are each independently and preferably selected from the group consisting of hydrogen, and substituted or unsubstituted (C$_1$-C$_6$) alkyl.

Unless otherwise specified, the term "halogen" or "halo", by itself or as part of another substituent, refers to fluorine, chlorine, bromine or iodine atom. Furthermore, the term "haloalkyl" is meant to include monohaloalkyl and polyhaloalkyl. For example, the term "halo(C$_1$-C$_4$)alkyl" is intended to include, but not limited to, trifluoromethyl, 2,2,2-trifluoroethyl, 4-chlorobutyl, 3-bromopropyl and the like.

Examples of haloalkyl include, but not limited to: trifluoromethyl, trichloromethyl, pentafluoroethyl and pentachloroethyl. "Alkoxy" represents the above-mentioned alkyl having a specified number of carbon atoms attached by an oxygen. C$_{1-6}$ alkoxy includes C$_1$, C$_2$, C$_3$, C$_4$, C$_5$ and C$_6$ alkoxy. Examples of alkoxy include, but not limited to: methoxy, ethoxy, n-propoxy, isopropoxy, n-butoxy, sec-butoxy, tert-butoxy, n-pentyloxy and S-pentoxy. "Cycloalkyl" includes saturated ring groups, such as cyclopropyl, cyclobutyl or cyclopentyl, 3-7 cycloalkyl include C$_3$, C$_4$, C$_5$, C$_6$ and C$_7$ cycloalkyl. "Alkenyl" includes straight or branched chain hydrocarbon, wherein one or more carbon-carbon double bonds are present in any stable site on the chain, such as vinyl and propenyl.

The term "halo" or "halogen" refers to fluoro, chloro, bromo and iodo.

Unless otherwise specified, the term "hetero" represents a hetero atom or hetero atom group (i.e., an atom group containing a hetero atom), including atoms other than carbon (C) and hydrogen (H) and atom groups containing these hetero atoms, for example, including oxygen (O), nitrogen (N), sulfur (S), silicon (Si), germanium (Ge), aluminum (Al), boron (B), —O—, —S—, =O, =S. —C(=O)O—, —C(=O)—, —C(S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, "ring" represents a substituted or unsubstituted cycloalkyl, heterocycloalkyl, cycloalkenyl, heterocycloalkenyl, cycloalkynyl, heterocycloalkynyl, aryl or heteroaryl. The so-called ring includes mono-ring, linked ring, spiro-ring, fused ring or bridged ring. The number of ring atoms is usually defined as member number of the ring, for example, "5- to 7-membered ring" means that 5 to 7 atoms are arranged along the ring. Unless otherwise specified, the ring optionally contains 1 to 3 hetero atoms. Therefore, "5- to 7-membered ring" includes for example, phenyl pyridine and piperidinyl; on the other hand, the term "5- to 7-membered heterocycloalkyl ring" includes pyridyl and piperidyl, but excluding phenyl. The term "ring" also includes a ring system containing at least one ring, each ring independently meeting the above definition.

Unless otherwise specified, the term "heterocycle", "heterocyclic ring" or "heterocyclo" means a stable mono-cycle, bi-cycle or tri-cycle containing a hetero atom or hetero atom group, which may be saturated, partially unsaturated or unsaturated (aromatic) and contains carbon atoms and 1, 2, 3 or 4 ring heteroatoms independently selected from N, O and S, wherein said heterocycle may be optionally fused to a benzene ring to form a bi-cycle. Nitrogen and sulfur heteroatoms may optionally be oxidized (i.e., NO and S(O) p). Nitrogen atom may be substituted or unsubstituted (i.e., N or NR, wherein R is H or other substituents already defined herein). The heterocyclic ring may be attached to the pendant group of any heteroatom or carbon atom to form a stable structure. If the resulting compound is stable, heterocycle described herein may be substituted on a carbon or nitrogen position. Nitrogen atom in the heterocycle is optionally quaternized. In a preferred embodiment, when the total number of S and O atoms in a heterocycle is more than 1, these heteroatoms are not adjacent to each other. In another preferred embodiment, the total number of S and O atoms in the heterocycle is no more than 1. As used herein, the term "aromatic heterocycle" or "heteroaryl" refers to a stable aryl ring of 5-, 6-, 7-membered monocycle or bi-cycle or 7-, 8-, 9- or 10-membered bicyclic heterocycle which contains carbon atoms and 1, 2, 3 or 4 ring heteroatoms independently selected from N, O and S. Nitrogen atom may be substituted or unsubstituted (i.e., N or NR, wherein R is H or other substituents already defined herein). Nitrogen and sulfur heteroatoms may optionally be oxidized (i.e., NO and S(O)p). It is worth noting that the total number of S and O atoms in the aromatic heterocycle is not more than one. Bridged ring is also included in the definition of heterocycle. Bridged ring is formed when one or more atoms (i.e., C, O, N or S) are linked to two non-adjacent carbon or nitrogen atoms. Preferred bridged ring includes, but not limited to: one carbon atom, two carbon atoms, one nitrogen atom, two nitrogen atoms and one carbon-nitrogen group. It is worth noting that a bridge always converts a monocycle into a tricycle. The substituent may also be present on the bridge of a bridged ring.

Examples of the heterocyclic compounds include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydro-furo[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatino group, isobenzofuranyl, isoindolyl, isoindolinyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazole, pyrido-imidazole, pyrido-thiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl 1,2,3-triazolyl, 1,2,4-triazolyl, 1,2,5-triazolyl, 1,3,4-triazolyl and xanthenyl. Also included are fused ring and spiro-ring compounds.

Unless otherwise specified, the term "hydrocarbyl" or any specific concepts thereof (such as alkyl, alkenyl, alkynyl, phenyl, etc.), by itself or as part of another substituent, means a straight, branched chain or cyclic hydrocarbon radicals or combinations thereof, may be fully saturated, mono- or poly-unsaturated, can be mono-, di- or poly-substituted, may include a divalent or multivalent radical, and have a specified number of carbon atoms (for example, $C_1$-$C_{10}$ indicates 1 to 10 carbons). The "hydrocarbyl" includes, but is not limited to, aliphatic hydrocarbyl and aromatic hydrocarbyl, wherein the aliphatic hydrocarbyl includes linear and cyclic hydrocarbyl, specifically including but not limited to, an alkyl, alkenyl, and alkynyl, and the aromatic hydrocarbyl includes but is not limited to 6- to 12-membered aromatic hydrocarbyl such as phenyl, naphthyl and the like. In some embodiments, the term "alkyl" means a straight or branched radical or a combination thereof which may be fully saturated, mono- or poly-unsaturated, and may include a divalent or multivalent radical. Examples of saturated hydrocarbon radical include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and homologs or isomers of radicals such as n-pentyl, n-hexyl, n-heptyl, n-octyl and the like. The unsaturated alkyl has one or more double or triple bonds, and examples of which include but are not limited to, ethenyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the term "heterohydrocarbyl" or any specific concepts thereof (such as heteroalkyl, heteroalkenyl, heteroalkynyl, heteroaryl, etc.), by itself or as part of another substituent, means a straight, branched chain or cyclic hydrocarbon radicals or combinations thereof which have a certain number of carbon atoms and at least one hetero atom. In some embodiments, the term "heteroalkyl" by itself or in combination with another term represents a stable straight chain, branched chain hydrocarbon radical or combinations thereof which have a certain number of carbon atoms and at least one hetero atom. In one exemplary embodiment, a hetero atom is selected from B, O, N and S, wherein nitrogen and sulfur atoms are optionally oxidized and the nitrogen atom is optionally quaternized. Heteroatom B, O, N and S may be located at any interior position in the heterohydrocarbyl (including the position where the hydrocarbyl attaches to the rest part of the molecule). Examples include, but are not limited to, —CH₂—CH₂—O—CH₃, —CH₂—CH₂—NH—CH, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH═CH—O—CH₃, —CH₂—CH═N—OCH₃, and —CH═CH—N(CH₃)—CH₃. Up to two heteroatoms may be consecutive, such as —CH₂—NH—OCH₃.

The term "alkoxy", "alkylamino" and "alkylthio" (or thioalkoxy) belong to idiomatic expressions and refer to those alkyl groups connected to the remainder of the molecule via an oxygen atom, an amino or a sulfur atom, respectively.

Unless otherwise specified, the term "cyclohydrocarbyl", "heterocyclohydrocarbyl" or any specific concepts thereof (such as aryl, heteroaryl, cycloalkyl, heterocycloalkyl, cycloalkenyl, heterocycloalkenyl, cycloalkynyl, heterocycloalkynyl, etc.), by itself or in combination with another term, represents cyclized "hydrocarbyl", and "heterohydrocarbyl". Furthermore, for heterohydrocarbyl or heterocyclohydrocarbyl (e.g. heteroalkyl, heterocycloalkyl), the heteroatom can occupy the position where the heterocycle attaches to the remainder part of the molecule. Examples of cycloalkyl include, but are not limited to, cyclopentyl, cyclohexyl, 1-cyclohexenyl, 3-cyclohexenyl, cycloheptyl and the like. Non-limiting examples of heterocyclic group include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuranindol-3-yl, tetrahydro-thiophen-2-yl, tetrahydro-thiophen-3-yl, 1-piperazinyl and 2-piperazinyl.

Unless otherwise specified, the term "aryl" means polyunsaturated aromatic hydrocarbon substituents, which may be mono-, di- or poly-substituted, and it may be a single ring or multiple rings (preferably 1-3 rings) wherein they are fused together or linked covalently. The term "heteroaryl" refers to an aryl (or ring) containing one to four hetero atoms. In one exemplary embodiment, the hetero atom is selected from B, O, N and S, wherein nitrogen and sulfur atoms are optionally oxidized and the nitrogen atom is optionally quaternized. The heteroaryl may attach to the rest part of the molecule via the heteroatom. Non-limiting examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of anyone of the above-mentioned aryl and heteroaryl ring systems is selected from an acceptable substituent described below.

For the sake of convenience, when used in combination with other term (e.g. aryloxy, arylthio, arylalkyl), the term "taryl" includes the aryl and heteroaryl ring defined above. Thus, the term "aralkyl" is meant to include those radicals formed from an aryl attached to an alkyl (e.g. benzyl, phenethyl, pyridylmethyl, etc.), including those alkyls wherein the carbon atom (e.g., methylene) is replaced by, e.g., an oxygen atom, e.g., phenoxymethyl, 2-pyridyloxymethyl, 3-(1-naphthyloxy)propyl, and the like.

The term "leaving group" refers to a functional group or atom that can be substituted by another functional group or atom through substitution reaction (such as nucleophilic substitution reaction). For example, representative leaving groups include triflate; chlorine, bromine and iodine; sulfonate groups, such as mesylate, tosylate, brosylate, tosylate and the like; acyloxy, such as acetoxy, trifluoroacetoxy and the like.

The term "protecting group" includes, but is not limited to, "amino protecting group", "hydroxy protecting group" or "mercapto-protecting group." The term "amino protecting group" means a protecting group suitable for blocking side reaction on nitrogen of the amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenyl methoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group suitable for blocking side reaction on hydroxyl. Representative hydroxy protecting groups include, but are not limited to: alkyl such as methyl, ethyl and t-butyl; acyl, e.g. alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compounds of the present invention may be prepared by a variety of synthetic methods well known to the skilled in the art, including the specific embodiments illustrated below, the embodiments formed in conjunction with other chemical synthesis methods, and the equivalents well known to the skilled in the art. The preferred embodiments include, but are not limited to the examples of the present invention.

All solvents used in the present invention are commercially available and used without further purification. The reaction is generally conducted under inert nitrogen in the anhydrous solvent. Proton nuclear magnetic resonance data are recorded on a Bruker Avance III 400 (400 MHz) spectrometer, wherein chemical shifts are indicated as (ppm) of tetramethylsilane at low field. Mass spectra are measured on Agilent 1200 Series plus 6110 (& 1956A). LC/MS or Shimadzu MS contains a DAD: SPD-M20A (LC) and Shimadzu Micromass 2020 detector. Mass spectrometer is equipped with an electrospray ionization source (ESI) operated under a positive or negative mode.

The present invention employs the following abbreviations: aq represents water; HATU represents O-7-aza-benzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent, an equivalent amount; CDI represents a carbonyl diimidazole; DCM represents dichloromethane: PE represents petroleum ether: DIAD represents diisopropyl azodicarboxylate: DMF represents N,N-dimethylformamide; DMSO represents dimethylsulfoxide: EtOAc represents ethyl acetate; EtOH represents ethanol; MeOH represents methanol: CBz represents benzyloxycarbonyl which is an amine protecting group; BOC represents t-butyl carbonyl which is an amine protecting group; HOAc represents acetic acid; NaCNBH3 represents sodium cyano borohydride: r.t. represents room temperature; O/N represents overnight; THF represents tetrahydrofuran; Boc$_2$O represents di-tert-butyl dicarbonate: TFA represents trifluoroacetic acid; DIPEA represents diisopropylethylamine; SOC$_2$ represents thionyl chloride; CS$_2$ represents carbon disulfide; TsOH represents p-toluenesulfonic acid; NFSI represents N-fluoro-N-(phenylsulfonyl)benzenesulfonamide; NCS represents 1-chloro pyrrolidine-2,5-dione; n-Bu$_4$NF represents tetrabutylammonium fluoride: iPrOH represents 2-propanol; and mp represents melting point.

Compounds are named by hand or by ChemDraw® software. The commercially available compounds use the vendor directory name.

2) the administration volume: 10 μg body weight of mouse. If the weight loss exceeds 15%, the dosing regimen should be adjusted accordingly;

3) the vehicle used for the test compounds and the Vehicle group was: 1% MC, PO, QD×19 days.

Figure 1:
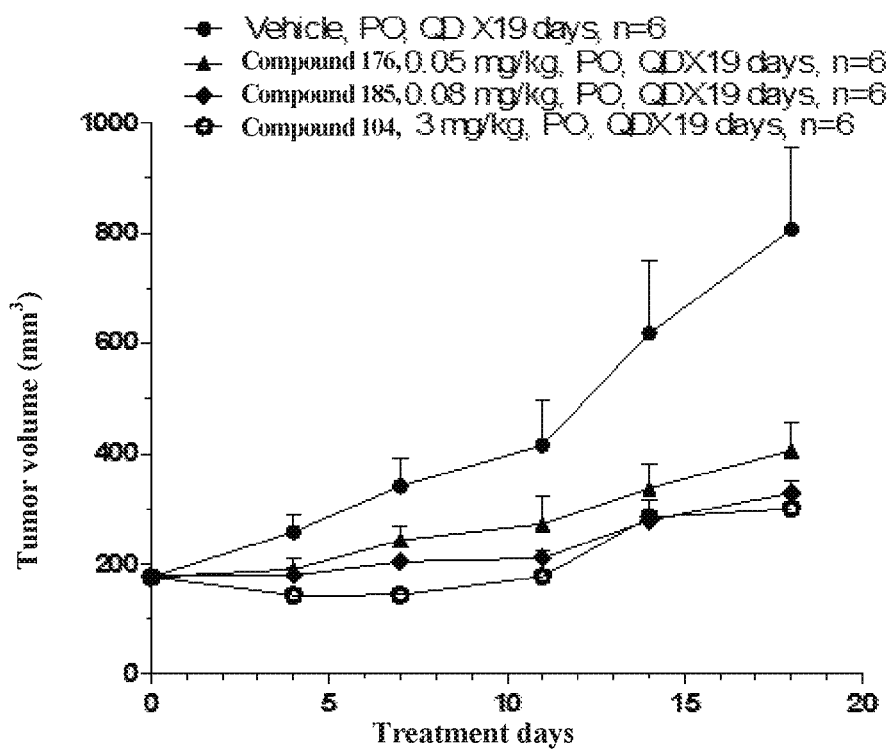
FIG. 1 shows the in vivo pharmacodynamics experiment results of the test drugs on subcutaneous xenograft tumor models of human ovarian cancer SK-OV-3 cells, wherein, 1) the number of mice per group was 6.
Figures 1, 2:
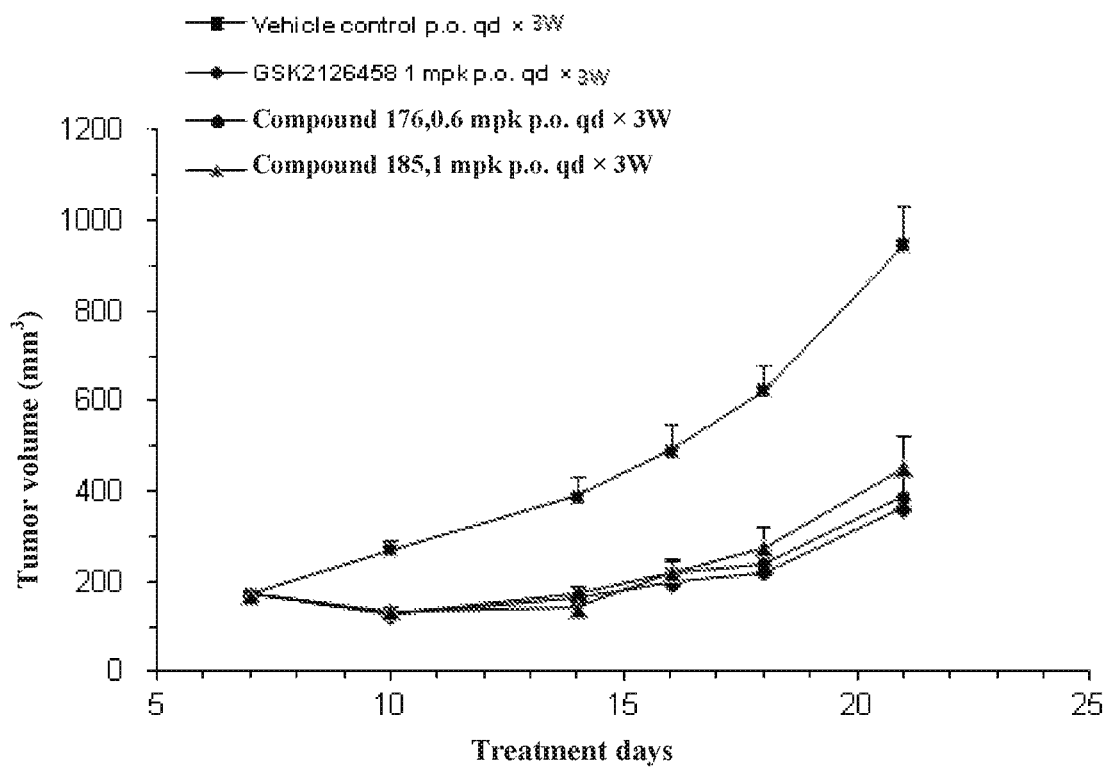
Figure 2:
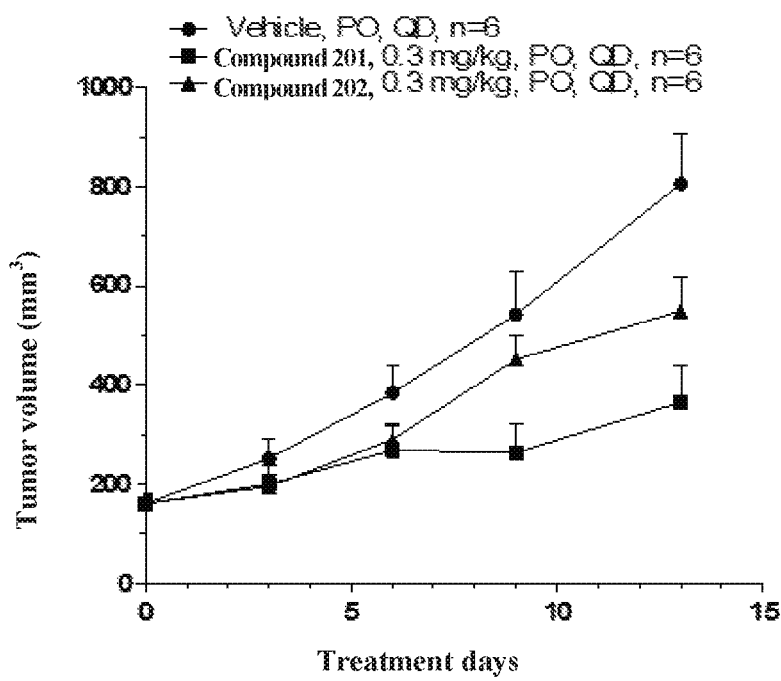

FIG. 2-1 shows the results of the in vivo pharmacodynamics experiment (I) of the test drugs on subcutaneous xenograft tumor models of human prostate cancer PC-3M cells, wherein, 1) the number of mice per group was 7:

2) the administration volume: 10 μl/g body weight of mouse. If the weight loss exceeds 15%, the dosing regimen should be adjusted accordingly.

FIG. 2-2 shows the results of the in vivo pharmacodynamics experiment (II) of the test drugs on subcutaneous xenograft tumor models of human prostate cancer PC-3M cells, wherein, 1) the number of mice per group was 6;

2) the administration: 10 μl/g body weight of mouse. If the weight loss exceeds 15%, the dosing regimen should be adjusted accordingly;

3) the vehicle used for the test compounds and the Vehicle group was: 1% DMSO+99% (1% MC), PO, QD×2W.

Figures 2, 3, 3A:
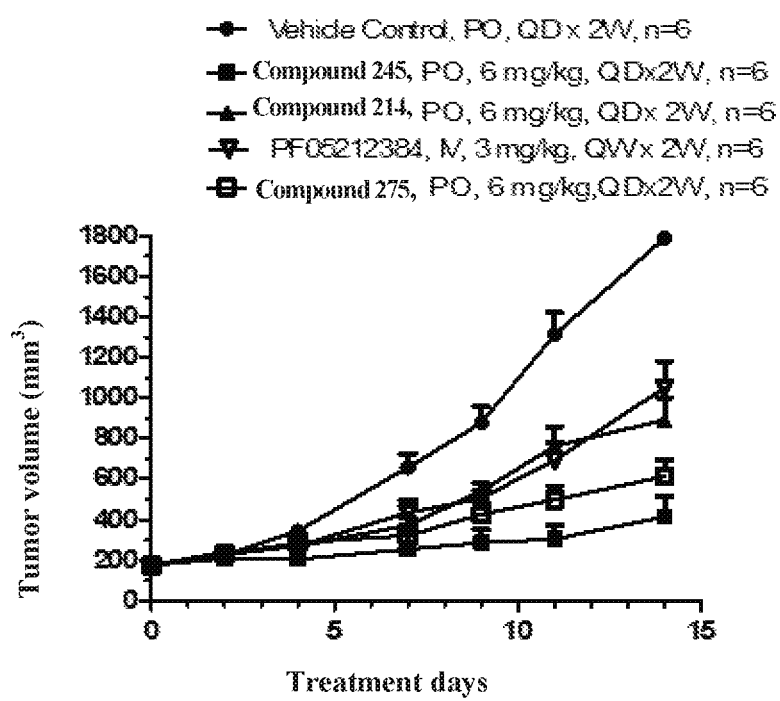

FIG. 2-3a shows the results of the in vivo pharmacodynamics experiment (III) of the test drugs on subcutaneous xenograft tumor models of human prostate cancer PC-3M cells, wherein, 1) the number of mice per group was 6:

2) the administration volume: 10 μl/g body weight of mouse. If the weight loss exceeds 15%, the dosing regimen should be adjusted accordingly;

3) the vehicle used for PF0512384: 30 propylene glycol+5% Tween 80+65% D5W, IV, QW×2W:

4) the vehicle used for the test compounds and the Vehicle group was: 5% DMSO+60% PEG400+35% water, PO, QD×2W.

Figures 2, 3, 3B:
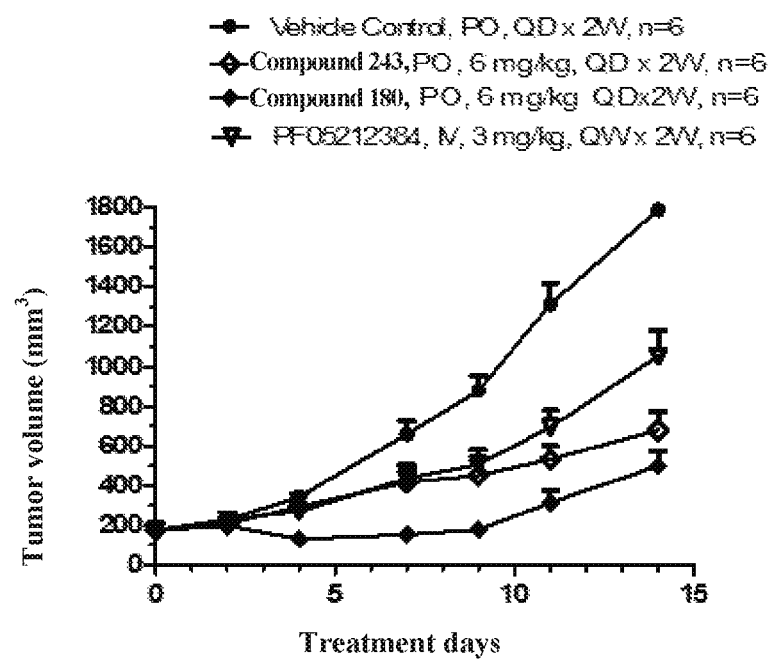

FIG. 2-3b shows the results of the in vivo pharmacodynamics experiment (III) of the test drugs on subcutaneous xenograft tumor models of human prostate cancer PC-3M cells, wherein, 1) the number of mice per group was 6:

2) the administration volume: 10 μl/g body weight of mouse. If the weight loss exceeds 15%, the dosing regimen should be adjusted accordingly;

3) the vehicle used for PF0512384: 30% propylene glycol+5% Tween 80+65% D5W, IV, QW×2W;

4) the vehicle used for the test compounds and the Vehicle group was: 5% DMSO+60% PEG400+35% water, PO, QD×2W.

DETAILED DESCRIPTION OF THE INVENTION

In order to illustrate the present invention in more detail, the following examples are given, but the scope of the present invention is not limited thereto.

Scheme 1:

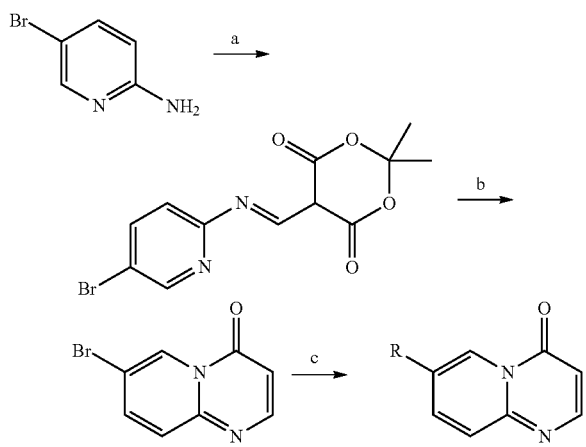

Reaction conditions: a) triethyl orthoformate, 2,2-dimethyl-1,3-dioxane-4,6-dione, heating; EtOH, heating; b) diphenyl ether, reflux; c) R boric acid (borate), palladium reagent (tetrakistriphenylphosphine palladium, [1,1′-bis(diphenylphosphino)ferrocene]palladium chloride, etc.), potassium carbonate, dioxane, water, heating.

Example 1

2,4-difluoro-N-(2-methoxy-5-(4-oxo-4H-pyrido[1,2-a]pyrimidin-7-yl)pyridin-3-yl)benzsulfamide

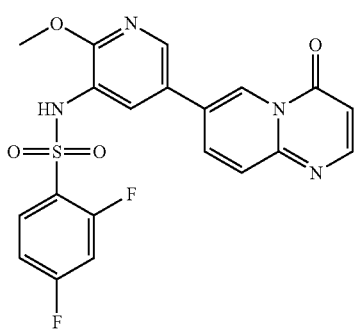

compound 1 a) (E)-5-(((5-bromopyridin-2-yl)imino)methyl)-2,2-dimethyl-1,3-dioxane-4,6-dione Triethyl orthoformate (25.8 g, 0.174 mol) and 2,2-dimethyl-1,3-dioxane-4,6-dione (25.1 g, 0.174 mol) were placed in a three-necked round-bottomed flask and the reaction was carried out with stirring for 2 hours at 60° C. To this mixture, 2-amino-5-bromopyridine (30 g, 0.174 mol) in ethanol (150 mL) was added drop % wise. The reaction solution was stirred at 60° C. for 2 hours and then cooled to 25° C. and filtered. The filter cake was rinsed with ethanol (200 mL×3) to give the title compound as a white solid (40 g, 70%).

1H NMR (400 MHz; CDCl$_3$) ppm δ 1.77 (s, 6H), 6.93-7.04 (m, 1H), 8.44-8.53 (m, 1H), 7.85-7.91 (m, 1H), 9.31-9.42 (m, 1H), 11.28-11.40 (m, 1H).

b) 7-bromo-4H-pyrido[1,2-a]pyrimidin-4-one (E)-5-(((5-bromopyridin-2-yl)imino)methyl)-2,2-dimethyl-1,3-dioxane-4,6-dione (18 g, 0.056 mmol) and diphenyl ether (180 mL) were placed in a 250 mL round-bottomed flask and stirred at 220° C. for 1 hour. TLC showed the reaction was complete. The reaction solution was cooled to room temperature and purified by column chromatography on silica gel to give the title compound (10 g, 80%).

1H NMR (400 MHz, CDCl$_3$) ppm δ 6.46 (d, 1H), 7.53 (d, 1H), 7.75 (dd, 1H), 8.27 (d, 1H), 9.19 (d, 1H).

c) 2,4-difluoro-N-(2-methoxy-5-(4-oxo-4H-pyrido[1,2-a]pyrimidin-7-yl)pyridin-3-yl)benzsulfamide 7-bromo-4H-pyrido[1,2-a]pyrimidin-4-one (0.28 mmol) was dissolved in dioxane (2 mL) and water (0.4 mL), and 2,4-difluoro-N-(2-methoxy-5-(4,4,5,5-tetramethyl-1,3,2-dioxaborolan-2-yl)pyridin-3-yl)benzsulfamide(0.28 mmol), potassium carbonate(0.56 mmol) and 1,1′-bis(diphenylphosphino)ferrocene palladium chloride (20 mg) were added under nitrogen. The reaction mixture was placed under microwave conditions at 100° C. for 2 hours. The liquid mass spectrometry showed that the reaction was complete. The reaction solution was filtered and concentrated to give crude product which was purified by preparative high performance liquid chromatography (HPLC) to give the title product.

1H NMR (400 MHz, CDCl$_3$) ppm δ 3.87 (s, 3H), 6.53 (d, 1H), 7.12 (t, 1H), 7.24 (t, 1H), 7.83 (d, 1H), 7.87-7.97 (m, 1H), 8.10 (s, 1H), 8.26 (d, 1H), 8.31-8.40 (m, 2H), 9.21 (s, 1H).

The following 37 compounds were also synthesized by reference to the preparation of compound 1.

| compound | structure | MS(ES) [M + H]$^+$ |
|---|---|---|
| 2 | 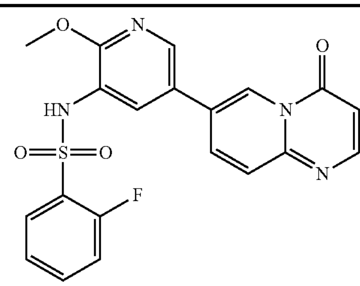 | 427 |
| 3 | 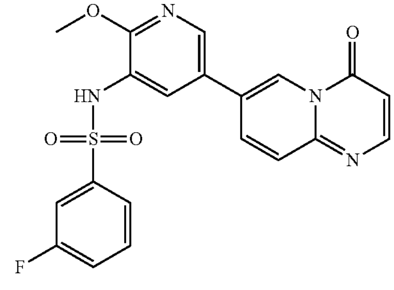 [SMILES: COc1ncc(-c2ccc3nccc(=O)n3c2)cc1NS(=O)(=O)c1cccc(F)c1] | 427 |
| 4 | 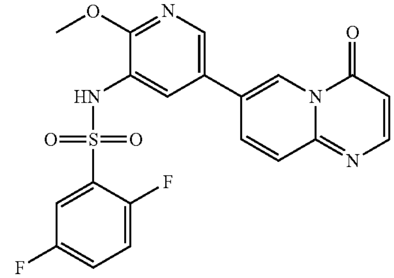 [SMILES: COc1ncc(-c2ccc3nccc(=O)n3c2)cc1NS(=O)(=O)c1cc(F)ccc1F] | 445 |

| compound | structure | MS(ES) [M + H]+ |
|---|---|---|
| 5 | 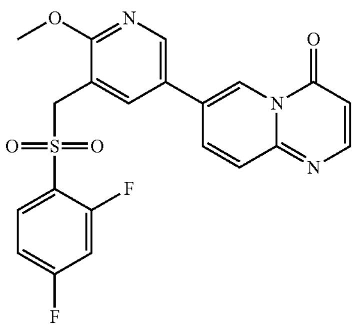 [SMILES: COc1ncc(-c2ccc3nccc(=O)n3c2)cc1CS(=O)(=O)c1ccc(F)cc1F] | 444 |
| 6 | 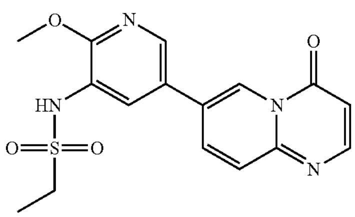 [SMILES: CCS(=O)(=O)Nc1cc(-c2ccc3nccc(=O)n3c2)cnc1OC] | 341 |
| 7 | 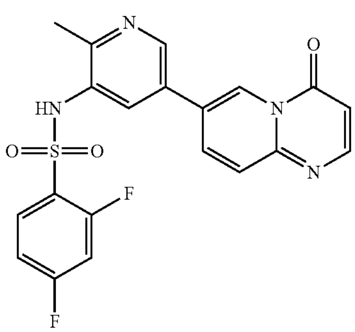 [SMILES: Cc1ncc(-c2ccc3nccc(=O)n3c2)cc1NS(=O)(=O)c1ccc(F)cc1F] | 429 |
| 8 | 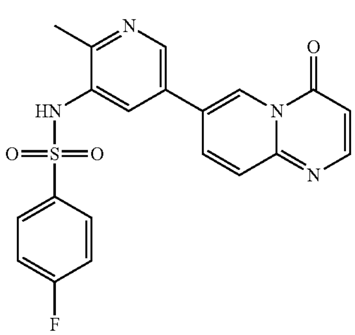 [SMILES: Cc1ncc(-c2ccc3nccc(=O)n3c2)cc1NS(=O)(=O)c1ccc(F)cc1] | 411 |
| 9 | 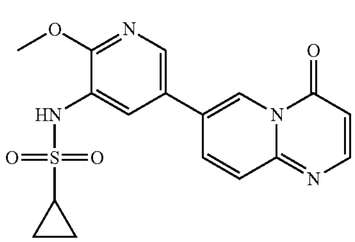 [SMILES: COc1ncc(-c2ccc3nccc(=O)n3c2)cc1NS(=O)(=O)C1CC1] | 373 |
| 10 | | 411 |
| 11 | | 427 |
| 12 | | 409 |
| 13 | | 415 |
| 14 | | 429 |

-continued
| compound | structure | MS(ES) [M + H]+ |
|---|---|---|
| 15 | 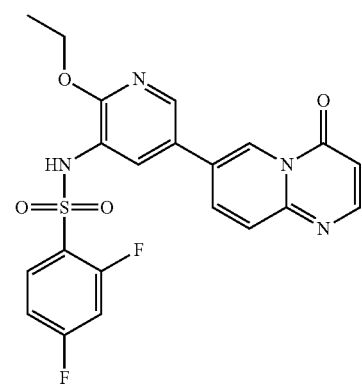 [SMILES: CCOc1ncc(-c2ccc3nccc(=O)n3c2)cc1NS(=O)(=O)c1ccc(F)cc1F] | 459 |
| 16 | 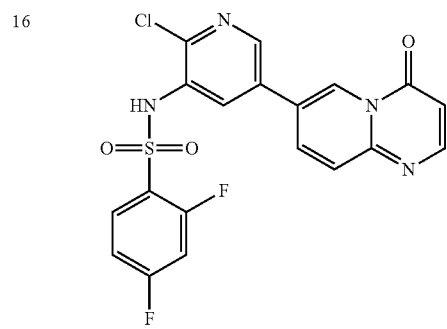 | 449 |
| 17 | 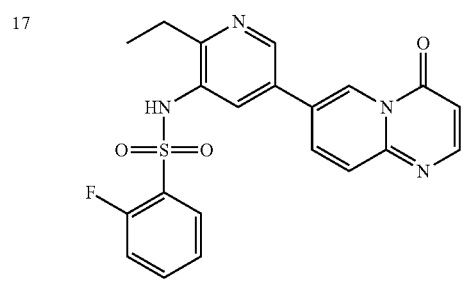 | 425 |
| 18 | 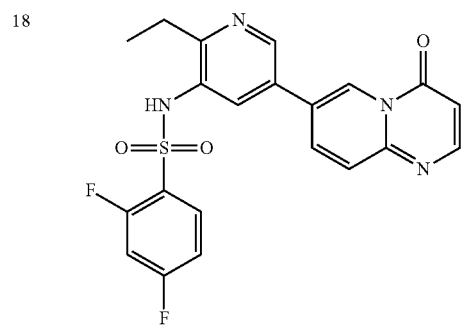 | 443 |
-continued
| compound | structure | MS(ES) [M + H]+ |
|---|---|---|
| 19 | 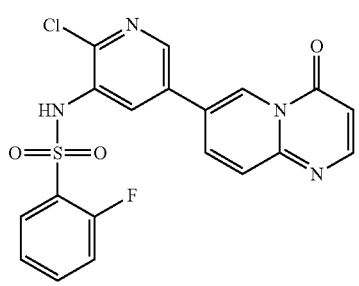 [SMILES: O=c1ccnc2ccc(-c3cnc(Cl)c(NS(=O)(=O)c4ccccc4F)c3)cn12] | 431 |
| 20 | 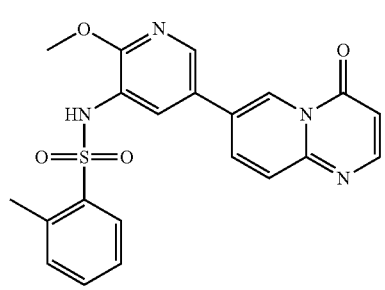 [SMILES: COc1ncc(-c2ccc3nccc(=O)n3c2)cc1NS(=O)(=O)c1ccccc1C] | 423 |
| 21 | 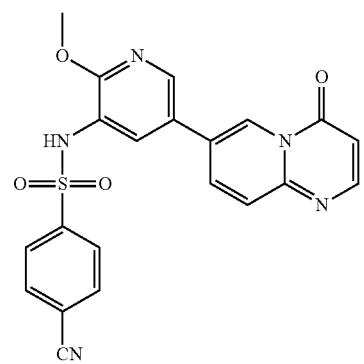 [SMILES: COc1ncc(-c2ccc3nccc(=O)n3c2)cc1NS(=O)(=O)c1ccc(C#N)cc1] | 434 |
| 22 | 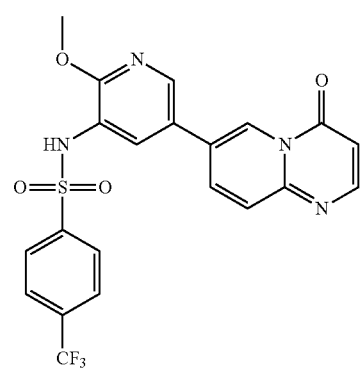 [SMILES: COc1ncc(-c2ccc3nccc(=O)n3c2)cc1NS(=O)(=O)c1ccc(C(F)(F)F)cc1] | 477 |

-continued

| compound | structure | MS(ES) [M + H]+ |
|---|---|---|
| 23 | | 443 |
| 24 | | 439 |
| 25 | | 461 |
| 26 | | 441 |
| 27 | 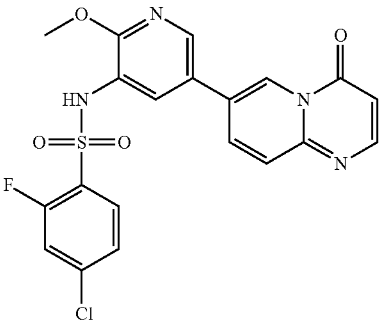 [SMILES: COc1ncc(-c2ccc3nccc(=O)n3c2)cc1NS(=O)(=O)c1ccc(Cl)cc1F] | 461 |
| 28 | 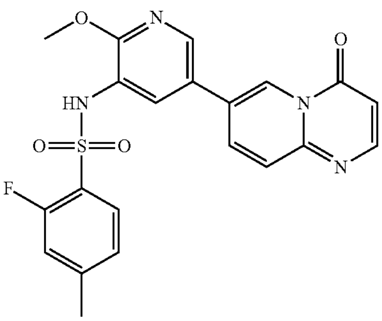 [SMILES: COc1ncc(-c2ccc3nccc(=O)n3c2)cc1NS(=O)(=O)c1ccc(C)cc1F] | 441 |
| 29 | 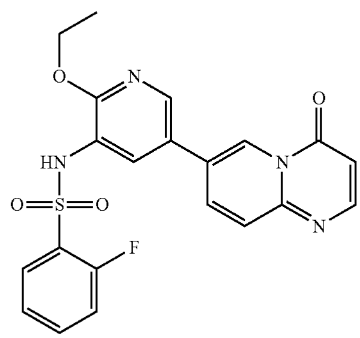 [SMILES: CCOc1ncc(-c2ccc3nccc(=O)n3c2)cc1NS(=O)(=O)c1ccccc1F] | 441 |
| 30 | 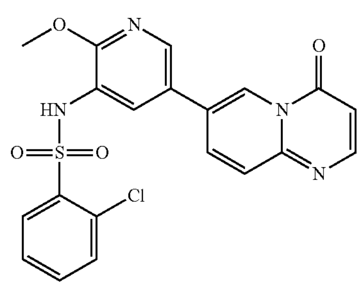 | 443 |
| 31 | 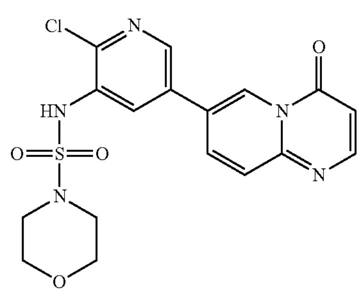 [SMILES: O=c1ccnc2ccc(-c3cnc(Cl)c(NS(=O)(=O)N4CCOCC4)c3)cn12] | 422 |

-continued

| compound | structure | MS(ES) [M + H]⁺ |
|---|---|---|
| 32 | 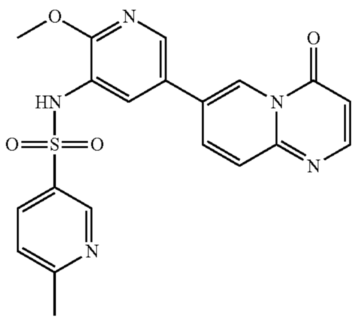 [SMILES: COc1ncc(-c2ccc3nccc(=O)n3c2)cc1NS(=O)(=O)c1ccc(C)nc1] | 424 |
| 33 | 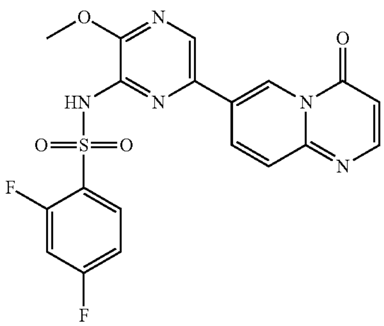 [SMILES: COc1ncc(-c2ccc3nccc(=O)n3c2)nc1NS(=O)(=O)c1ccc(F)cc1F] | 446 |
| 34 | 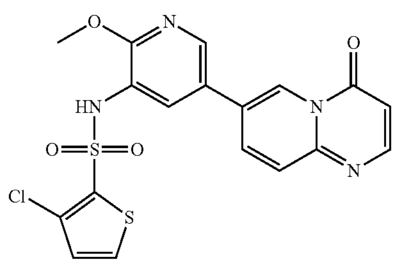 [SMILES: COc1ncc(-c2ccc3nccc(=O)n3c2)cc1NS(=O)(=O)c1sccc1Cl] | 449 |
| 35 | 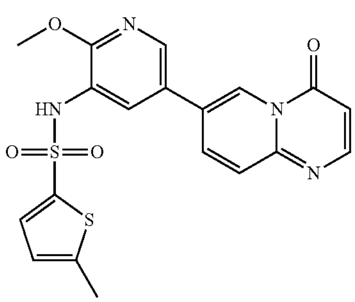 [SMILES: COc1ncc(-c2ccc3nccc(=O)n3c2)cc1NS(=O)(=O)c1ccc(C)s1] | 429 |
| 36 | 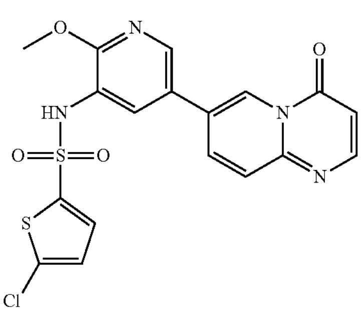 [SMILES: COc1ncc(-c2ccc3nccc(=O)n3c2)cc1NS(=O)(=O)c1ccc(Cl)s1] | 449 |
| 37 | 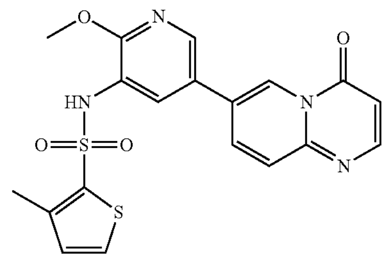 [SMILES: COc1ncc(-c2ccc3nccc(=O)n3c2)cc1NS(=O)(=O)c1sccc1C] | 429 |
| 38 | 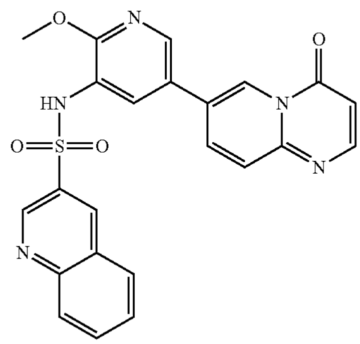 [SMILES: COc1ncc(-c2ccc3nccc(=O)n3c2)cc1NS(=O)(=O)c1cnc2ccccc2c1] | 460 |

Scheme 2:

Reaction conditions: a) triethyl orthoformate, 2,2-dimethyl-1,3-dioxane-4,6-dione, heating; EtOH, heating; b) diphenyl ether, reflux; c) R boric acid (borate), palladium reagent (tetrakistriphenylphosphine palladium, [1.1′-bis(diphenylphosphino)ferrocene]palladium chloride, etc.), potassium carbonate, dioxane, water, heating.

Example 39

2,4-difluoro-N-(2-methoxy-5-(4-oxo-4H-pyrazino[1,2-a]pyrimidin-7-yl)pyridin-3-yl)benzsulfamide

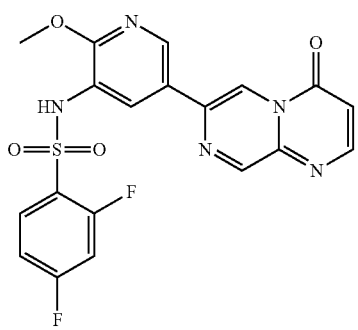

compound 39 a) (E)-5-(((5-bromopyrimidin-2-yl)imino)methyl)-2,2-dimethyl-1,3-dioxane-4,6-dione Triethyl orthoformate (9.9 g, 0.0689 mol) and 2,2-dimethyl-1,3-dioxane-4,6-dione (10.8 g, 0.073 mol) were placed in a three-necked round-bottomed flask, and the reaction was carried out with stirring for 2 hours at 60° C. To this mixture, 5-bromo-2-aminopyrazine (12 g, 0.0689 mol) in ethanol (50 mL) was added dropwise. The reaction solution was stirred for at 60° C. for 2 hours. The mixture was cooled to 25° C. and filtered, and then the filter cake was rinsed with ethanol (200 mL×3) to give the title compound as a white solid (12.5 g, 55.3%).

1H NMR (400 MHz, DMSO-$D_6$) ppm δ11.601 (s, 1H), 9.039 (s, 1H), 8.825 (s, 1H), 8.712 (s, 1H), 1.690 (s, 6H).

b) 7-bromo-4H-pyrazino[1,2-a]pyrimidin-4-one (E)-5-(((5-bromopyrimidin-2-yl)imino)methyl)-2,2-dimethyl-1,3-dioxane-4,6-dione (12 g, 0.0368 mol) and diphenyl ether (50 mL) were placed in a 500 mL round-bottomed flask and the reaction was carried out with stirring at 220° C. for 1 hour. The reaction solution was cooled to room temperature. The rude product was purified by column chromatography on silica gel to give the title compound as an orange solid (2 g, 24.4%).

1H NMR (400 MHz, DMSO-$D_6$) ppm δ 8.944-8.919 (d, 2H), 8.485-8.399 (s, 1H), 6.687-6.672 (d, 1H).

c) 2,4-difluoro-N-(2-methoxy-5-(4-oxo-4H-pyrazino[1,2-a]pyrimidin-7-yl)pyridin-3-yl)benzsulfamide 7-bromo-4H-pyrazino[1,2-a]pyrimidin-4-one (0.22 mmol) was dissolved in dioxane (0.22 mL) and water (0.44 mL), and 2,4-difluoro-N-(2-methoxy-5-(4,4,5,5-tetramethyl-1,3,2-dioxaborolan-2-yl)pyridin-3-yl)benzsulfamide (0.22 mmol), potassium carbonate (0.56 mmol) and 1,1'-bis(diphenylphosphino)ferrocene palladium chloride (20 mg) were added under nitrogen. The reaction mixture was placed under microwave conditions at 100° C. for 2 hours. The liquid mass spectrometry showed that the reaction was complete. The reaction solution was filtered and the orange organic phase was concentrated to give crude product which was purified by preparative HPLC to give the title product.

1H NMR (400 MHz, $CD_3OD$) ppm δ 9.169 (s, 1H), 8.999 (s, 1H), 8.473 (s, 1H), 8.439-8.423 (d, 1H), 8.197 (s, 1H), 7.941-7.922 (d, 1H), 7.145-7.098 (m, 1H), 6.684-6.669 (d, 1H), 3.884 (s, 3H).

The following 12 compounds were also synthesized by reference to the preparation of compound 39.

| compound | structure | MS(ES) [M + H]+ |
|---|---|---|
| 40 | 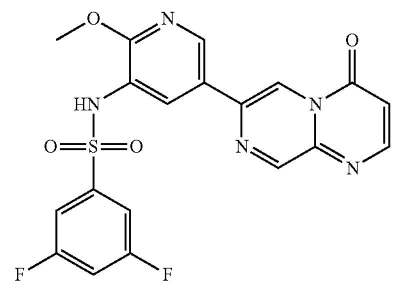 [SMILES: COc1ncc(-c2cn3c(=O)ccnc3cn2)cc1NS(=O)(=O)c1cc(F)cc(F)c1] | 446 |
| 41 | 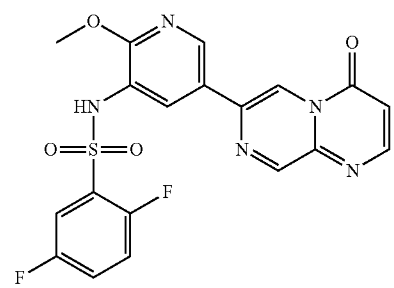 [SMILES: COc1ncc(-c2cn3c(=O)ccnc3cn2)cc1NS(=O)(=O)c1cc(F)ccc1F] | 446 |
| 42 | 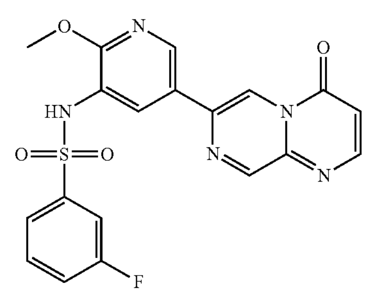 [SMILES: COc1ncc(-c2cn3c(=O)ccnc3cn2)cc1NS(=O)(=O)c1cccc(F)c1] | 428 |
| 43 | 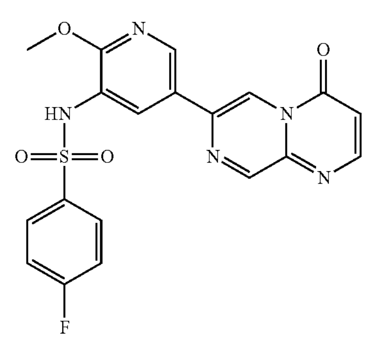 [SMILES: COc1ncc(-c2cn3c(=O)ccnc3cn2)cc1NS(=O)(=O)c1ccc(F)cc1] | 428 |

-continued
| compound | structure | MS(ES) [M + H]+ |
|---|---|---|
| 44 | 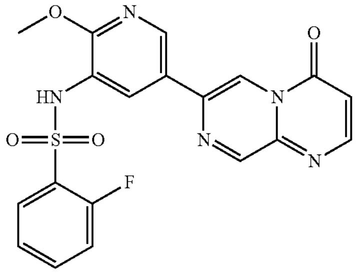 [SMILES: COc1ncc(-c2cn3c(=O)ccnc3cn2)cc1NS(=O)(=O)c1ccccc1F] | 428 |
| 45 | 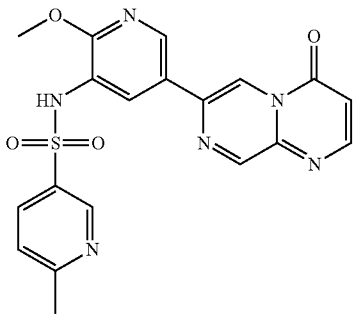 [SMILES: COc1ncc(-c2cn3c(=O)ccnc3cn2)cc1NS(=O)(=O)c1ccc(C)nc1] | 425 |
| 46 | 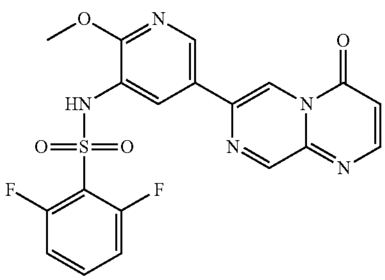 [SMILES: COc1ncc(-c2cn3c(=O)ccnc3cn2)cc1NS(=O)(=O)c1c(F)cccc1F] | 446 |
| 47 | 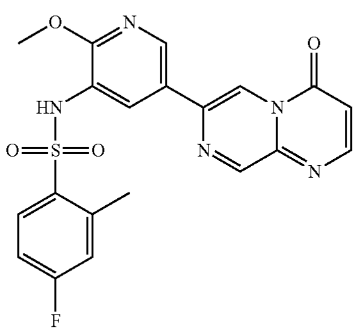 [SMILES: COc1ncc(-c2cn3c(=O)ccnc3cn2)cc1NS(=O)(=O)c1ccc(F)cc1C] | 442 |
| 48 | 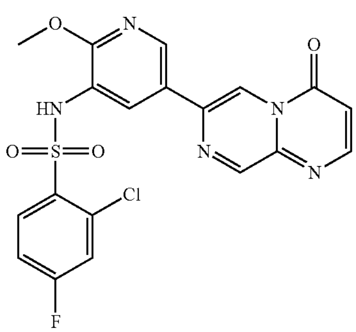 [SMILES: COc1ncc(-c2cn3c(=O)ccnc3cn2)cc1NS(=O)(=O)c1ccc(F)cc1Cl] | 462 |
-continued
| compound | structure | MS(ES) [M + H]+ |
|---|---|---|
| 49 | 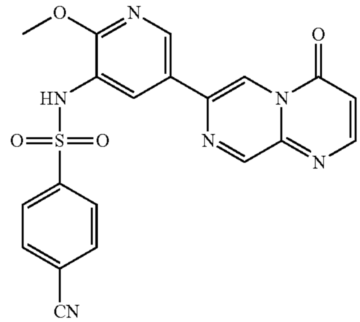 [SMILES: COc1ncc(-c2cn3c(=O)ccnc3cn2)cc1NS(=O)(=O)c1ccc(C#N)cc1] | 435 |
| 50 | 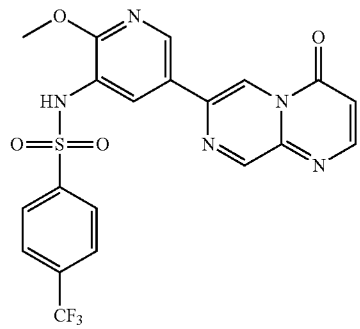 [SMILES: COc1ncc(-c2cn3c(=O)ccnc3cn2)cc1NS(=O)(=O)c1ccc(C(F)(F)F)cc1] | 478 |
| 51 | 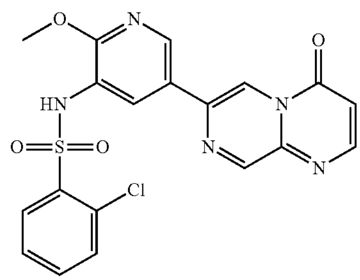 [SMILES: COc1ncc(-c2cn3c(=O)ccnc3cn2)cc1NS(=O)(=O)c1ccccc1Cl] | 444 |
Scheme 3:
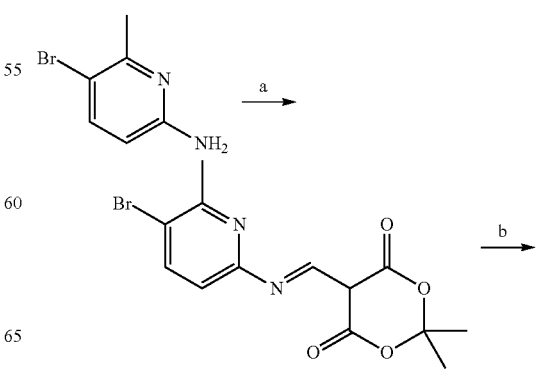

45

-continued

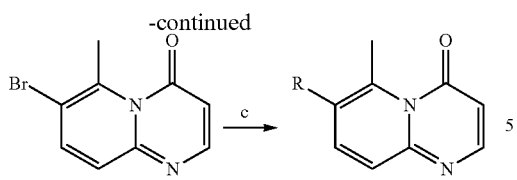

Reaction conditions: a) triethyl orthoformate, 2,2-dimethyl-1,3-dioxane-4,6-dione, heating; ethanol, heating; b) diphenyl ether, reflux; c) R boric acid (borate), palladium reagent (tetrakistriphenylphosphine palladium, [1,1'-bis(diphenylphosphino)ferrocene]palladium chloride, etc.), potassium carbonate, dioxane, water, heating.

Example 52

2,4-difluoro-N-(2-methoxy-5-(6-methyl-4-oxo-4H-pyrido[1,2-a]pyrimidin-7-yl)pyridin-3-yl)benzsulfamide

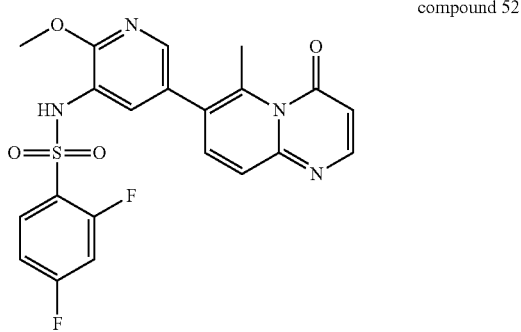 [SMILES: COc1ncc(-c2ccc3nccc(=O)n3c2C)cc1NS(=O)(=O)c1ccc(F)cc1F]

compound 52 a) (E)-5-(((5-bromo-6-methylpyridin-2-yl)imino)methyl)-2,2-dimethyl-1,3-dioxane-4,6-dione Trimethyl orthoformate (4.39 g, 0.03 mmol) and 2,2-dimethyl-1,3-dioxane-4,6-dione (4.03 g, 0.028 mmol) were placed in a three-neck round bottom flask equipped with a mechanical stirrer. The resulting suspension was stirred at 60° C. for 2 hours. To this mixture, 2-amino-5-bromopyrazine (5 g, 0.027 mmol) in ethanol (50 mL) was added dropwise. The reaction solution was stirred at 60° C. for 2 hours and then cooled to 25° C. and filtered. The filter cake was rinsed with ethanol (200 mL×3) to give the title compound as a white solid (6 g, 65.6%).

1H NMR (400 MHz, DMSO-D6) ppm δ 11.344-11.378 (d, 1H), 9.143-9.177 (d, 1H), 8.066-8.087 (d, 1H), 7.457-7.479 (d, 1H), 2.578 (s, 3H), 1.678 (s, 6H).

b) 7-bromo-6-methyl-4H-pyrido[1,2-a]pyrimidin-4-one ((E)-5-(((5-bromo-6-methylpyridin-2-yl)imino)methyl)-2,2-dimethyl-1,3-dioxane-4,6-dione(200 mg, 0.59 mmol) and diphenyl ether(4 mL) in a 50 mL round bottom flask were stirred at 220° C. in a microwave instrument for 0.5 hours. The reaction solution was cooled to room temperature. The crude product was purified by column chromatography on silica gel to give the title compound as an orange solid (60.7 mg, 43.2%).

1H NMR (400 MHz, CDCl₃) ppm δ 8.075-8.090 (d, 1H), 7.625-7.649 (d, 1H), 7.246 (d, 1H), 6.337-6.352 (d, 1H), 3.026 (s, 3H).

46 c) 2,4-difluoro-N-(2-methoxy-5-(6-methyl-4-oxo-4H-pyrido[1,2-a]pyrimidin-7-yl)pyridin-3-yl)benzsulfamide 2,4-difluoro-N-(2-methoxy-5-(4,4,5,5-tetramethyl-1,3,2-dioxoboran-2-yl)pyridin-3-yl)benzsulfamide (0.28 mmol), potassium carbonate (0.5 mmol) and 1,1'-bis(diphenylphosphino) ferrocene palladium chloride (20 mg) were added to the solution of 7-bromo-6-methyl-4H-pyrido[1,2-a]pyrimidin-4-one(0.25 mmol) in dioxane (0.2 mL) and water (0.4 mL) under nitrogen. The reaction mixture was heated at 100° C. under microwave and stirred for 2 hours. The liquid mass spectrometry showed that the reaction was complete. The reaction solution was filtered and the organic phase was concentrated to give crude product which was purified by preparative HPLC to give the title compound.

1H NMR (400 MHz, CDCl₃) ppm δ 8.120-8.135 (d, 1H), 7.878-7.914 (m, 1H), 7.865-7.870 (d, 1H), 7.742-7.748 (d, 1H), 7.441-7.464 (d, 1H), 7.368-7.391 (d, 1H), 6.947-6.986 (m, 2H), 6.362-6.377 (d, 1H), 3.995 (s, 3H), 2.701 (s, 3H).

The following 8 compounds were also synthesized by reference to the preparation of compound 52.

| compound | structure | MS(ES) [M + H]⁺ |
|---|---|---|
| 53 | 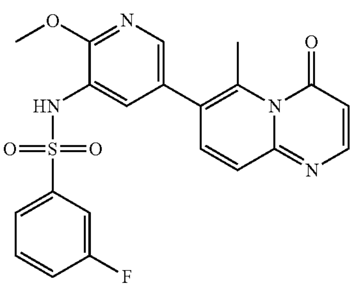 [SMILES: COc1ncc(-c2ccc3nccc(=O)n3c2C)cc1NS(=O)(=O)c1cccc(F)c1] | 441 |
| 54 | 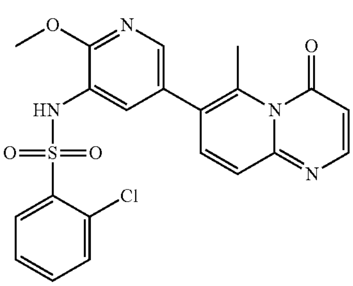 [SMILES: COc1ncc(-c2ccc3nccc(=O)n3c2C)cc1NS(=O)(=O)c1ccccc1Cl] | 457 |
| 55 | 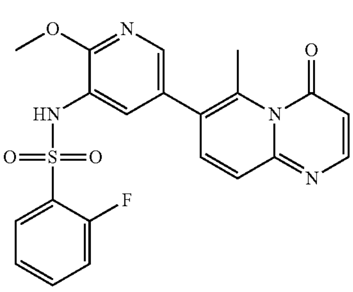 [SMILES: COc1ncc(-c2ccc3nccc(=O)n3c2C)cc1NS(=O)(=O)c1ccccc1F] | 441 |

-continued

| compound | structure | MS(ES) [M + H]+ |
|---|---|---|
| 56 | 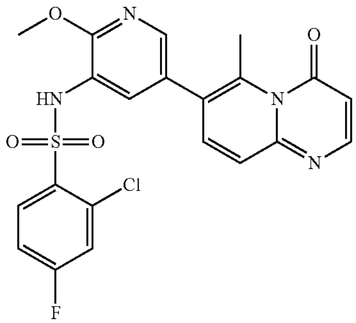 [SMILES: COc1ncc(-c2ccc3nccc(=O)n3c2C)cc1NS(=O)(=O)c1ccc(F)cc1Cl] | 475 |
| 57 | 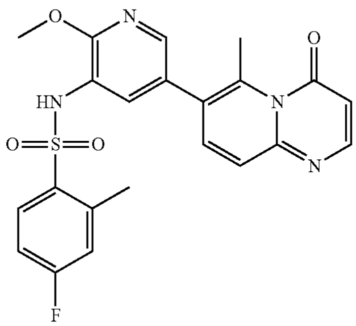 [SMILES: COc1ncc(-c2ccc3nccc(=O)n3c2C)cc1NS(=O)(=O)c1ccc(F)cc1C] | 455 |
| 58 | 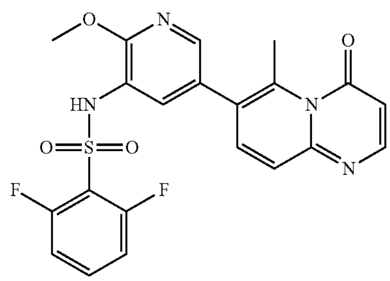 [SMILES: COc1ncc(-c2ccc3nccc(=O)n3c2C)cc1NS(=O)(=O)c1c(F)cccc1F] | 459 |
| 59 | 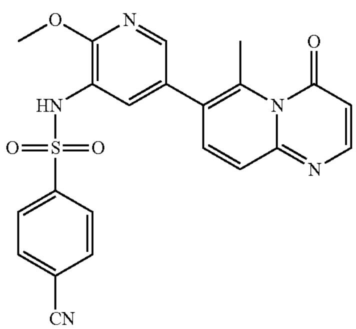 [SMILES: COc1ncc(-c2ccc3nccc(=O)n3c2C)cc1NS(=O)(=O)c1ccc(C#N)cc1] | 448 |
| 60 | 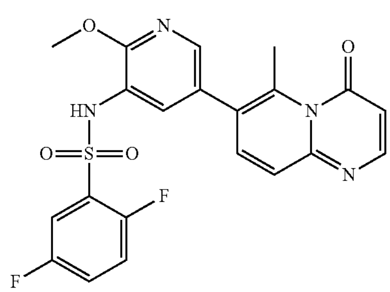 [SMILES: COc1ncc(-c2ccc3nccc(=O)n3c2C)cc1NS(=O)(=O)c1cc(F)ccc1F] | 459 |

Scheme 4:

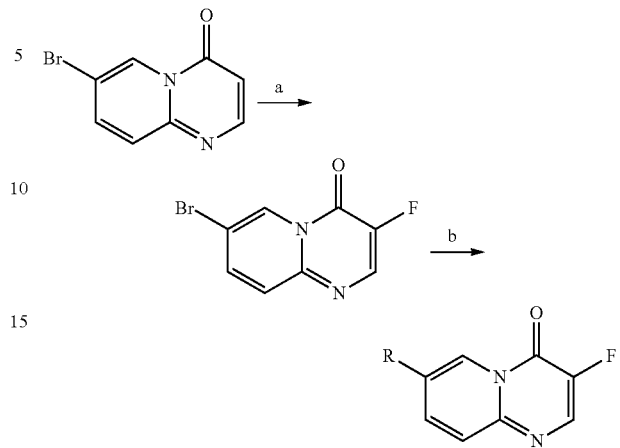

Reaction conditions: a) select F reagent, acetonitrile, heating; b) R boric acid (borate), palladium reagent (tetrakistriphenylphosphine palladium, [1,1'-bis(diphenylphosphino)ferrocene]palladium chloride, etc.), potassium carbonate, dioxane, water, heating.

Example 61

2,4-difluoro-N-(5-(3-fluoro-4-oxo-4H-pyrido[1,2-a]pyrimidin-7-yl)-2-methoxypyridin-3-yl)benzsulfamide compound 61

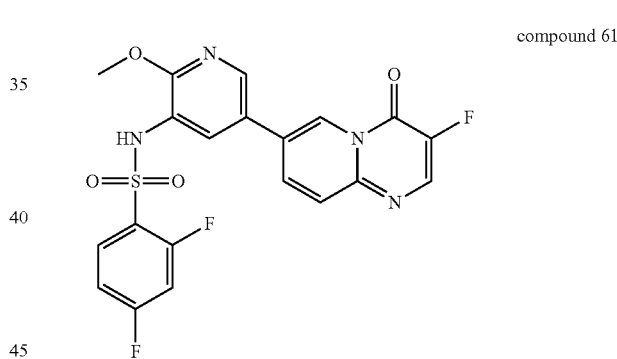

a) 7-bromo-3-fluoro-4H-pyrido[1,2-a]pyrimidin-4-one 7-bromo-4H-pyrido[1,2-a]pyrimidin-4-one (1 g, 4.46 mmol), select F (1.6 g, 4.46 mmol) and acetonitrile (15 mL) were placed in a 100 mL round-bottomed flask and stirred at 80° C. for 2 days. The reaction solution was concentrated and water (15 mL) was added. The mixture was extracted with dichloromethane (20 mL) three times. The organic phase was concentrated to give the crude product which was purified by column chromatography to give the title compound as a yellow solid (200 mg, 18.5%).

1H NMR (400 MHz, DMSO-$d_6$) ppm. δ 9.195 (s, 1H), 8.404 (s, 1H), 7.763-7.739 (d, 1H), 7.606-7.582 (d, 1H).

b) 2,4-difluoro-N-(5-(3-fluoro-4-oxo-4H-pyrido[1,2-a]pyrimidin-7-yl)-2-methoxypyridin-3-yl)benzsulfamide 2,4-difluoro-N-(2-methoxy-5-(4,4,5,5-tetramethyl-1,32-dioxoboran-2-yl)pyridin-3-yl)benzsulfamide(0.28 mmol), potassium carbonate (0.6 mmol) and 1,1'-bis(diphenylphosphino) ferrocene palladium chloride (20 mg) were added to the solution of 7-bromo-3-fluoro-4H-pyrido[1,2-a]pyrimidin-4-one(0.28 mmol) in dioxane(0.2 mL) and water (0.4 mL) under nitrogen. The reaction mixture was heated at 100° C. under microwave and stirred for 2 hours. The liquid mass spectrometry showed that the reaction was complete. The reaction solution was filtered and the organic phase was concentrated to give crude product which was purified by preparative HPLC to give the title compound.

1H NMR (400 MHz, DMSO-d$_6$) ppm δ 10.438 (s, 1H), 9.049 (s, 1H), 8.636-8.628 (d, 1H), 8.489 (s, 1H), 8.282-8.259 (d, 1H), 8.030 (s, 1H), 7.872-7.848 (d, 1H), 7.796-7.780 (d, 1H), 7.611-7.562 (m, 1H), 7.250-7.231 (m, 1H), 3.691 (s, 3H).

The following 9 compounds were also synthesized by reference to the preparation of compound 61.

| compound | structure | MS(ES) [M + H]+ |
|---|---|---|
| 62 | 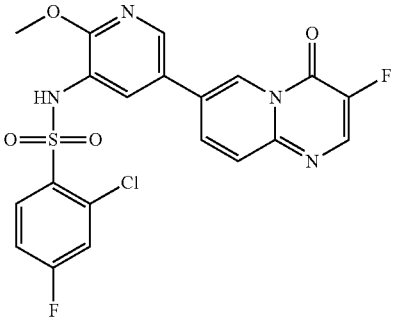 [SMILES: COc1ncc(-c2ccc3ncc(F)c(=O)n3c2)cc1NS(=O)(=O)c1ccc(F)cc1Cl] | 479 |
| 63 | 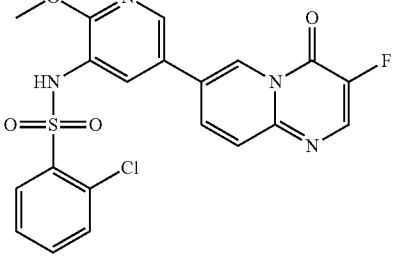 | 461 |
| 64 | 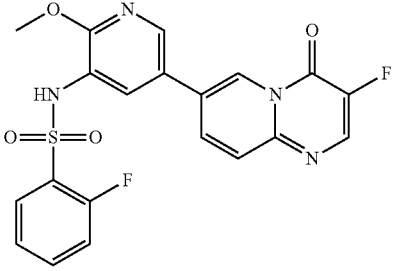 [SMILES: COc1ncc(-c2ccc3ncc(F)c(=O)n3c2)cc1NS(=O)(=O)c1ccccc1F] | 445 |
| 65 | 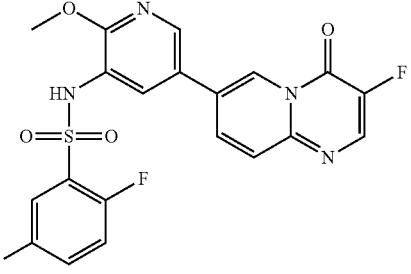 | 463 |
| 66 | 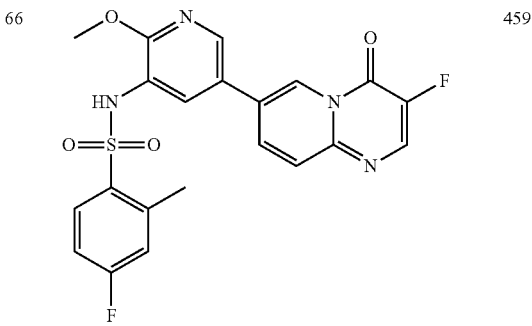 | 459 |
| 67 | 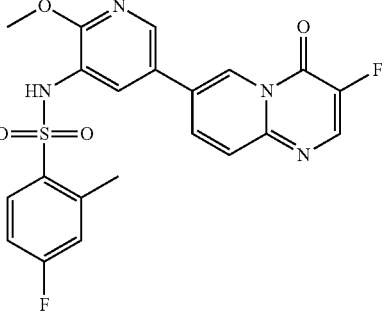 | 445 |
| 68 | 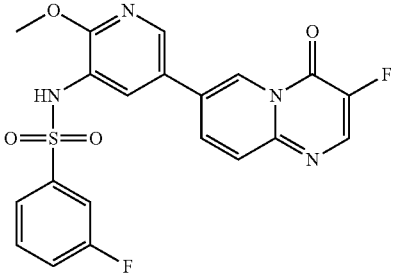 [SMILES: COc1ncc(-c2ccc3ncc(F)c(=O)n3c2)cc1NS(=O)(=O)c1cccc(F)c1] | 463 |
| 69 | 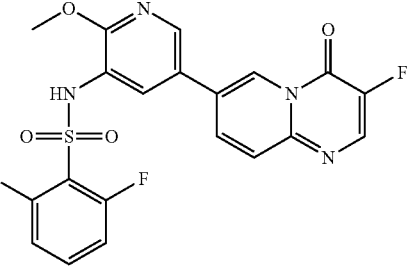 | 495 |

-continued

| compound | structure | MS(ES) [M + H]+ |
|---|---|---|
| 70 | 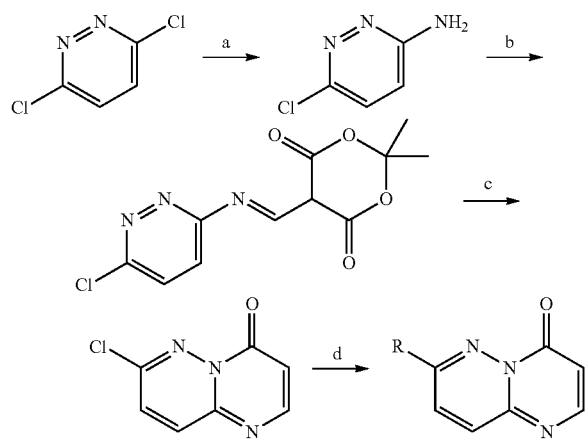 | 452 |

Scheme 5:

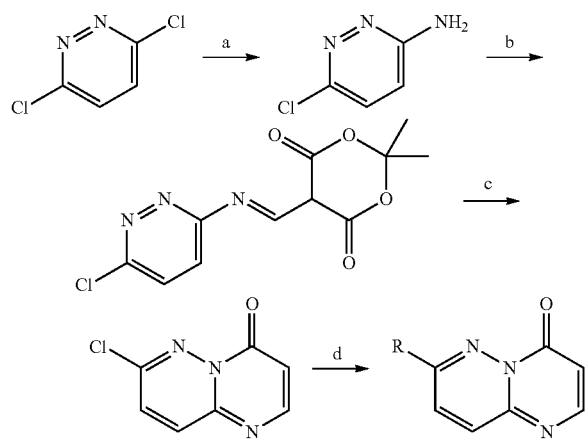

Reaction conditions: a) ammonium hydroxide, ammonium chloride, heating; b) triethoxy methane, 2,2-dimethyl-1,3-dioxane-4,6-dione, heating; ethanol, heating; c) diphenyl ether, reflux; d) R boric acid (borate), palladium reagent (tetrakistriphenylphosphine palladium, [1,1'-bis(diphenylphosphino)ferrocene]palladium chloride etc.), potassium carbonate, dioxane, water, heating.

Example 71

2,4-difluoro-N-(2-methoxy-5-(4-oxo-4H-pyrimido[1,2-b]pyridazin-7-yl)pyridin-3-yl)benzsulfamide compound 71
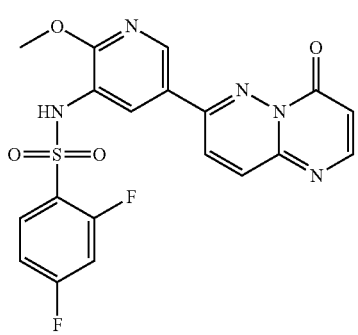

a) 6-chloro-pyridazin-3-amine 3,6-dichloro-pyridazine (20 g, 0.134 mol) and ammonium hydroxide solution (140 mL), ammonium chloride (11.47 g, 0.214 mol) and water (80 mL) were added to a 100 mL round bottom flask and then stirred at 90° C. for 20 hours. The reaction solution was cooled to room temperature and filtered. Then the filter cake was rinsed with water (100 mL) to give the product as a white solid (14.3 g, 82.7%).

1H NMR (400 MHz, DMSO-$d_6$) ppm δ 7.365-7.361 (d, 1H), 6.853-6.830 (d, 1H), 6.614 (s, 1H).

b) (E)-5-(((6-chloro-pyridazin-3-yl)imino)methyl)-2,2-dimethyl-1,3-dioxane-4,6-dione Triethoxy methane (16.3 g, 0.110 mol) and 2,2-dimethyl-1,3-dioxane-4,6-dione (14.5 g, 0.1 mmol) were added to 3 L round-bottom flask and stirred at 60° C. for 2 hours. The solution of 3-amino-6-chloro-pyridazine (13 g, 100.3 mmol) in ethanol (100 mL) was added dropwise to the reaction solution. The reaction solution is then stirred at 60° C. for another 2 hours. The reaction mixture was cooled to 25° C. and filtered. Then the filter cake was rinsed with ethanol (50 mL×3) to give the product as a white solid (16 g, 56%).

1H NMR (400 MHz, DMSO-$d_6$) δ ppm 11.521-11.484 (d, 1H), 9.219-9.185 (d, 1H), 8.100-7.984 (m, 2H).

c) 7-chloro-4H-pyrimido[1,2-b]pyridazin-4-one (E)-5-(((6-chloro-pyridazin-3-yl)imino)methyl)-2,2-dimethyl-1,3-dioxane-4,6-dione (15 g, 52.9 mmol) and diphenyl ether (70 mL) were added to a 250 mL round-bottomed flask and stirred at 220° C. for 1 hour. The reaction solution was cooled to room temperature. The rude product was purified by column chromatography on silica gel to give the product as an orange solid (2.4 g, 25.3%).

1H NMR (400 MHz, CD$_3$OD) ppm δ 8.329-8.313 (d, 1H), 8.003-8.979 (d, 1H), 7.788-7.764 (d, 1H), 6.713-6.696 (d, 1H).

d) 2,4-difluoro-N-(2-methoxy-5-(4-oxo-4H-pyrimido[1,2-b]pyridazin-7-yl)pyridin-3-yl)benzsulfamide 2,4-difluoro-N-(2-methoxy-5-(4,4,5,5-tetramethyl-1,3,2-dioxoboran-2-yl)pyridin-3-yl)benzsulfamide (0.22 mmol), potassium carbonate (0.44 mmol) and 1,1'-bis(diphenylphosphino) ferrocene palladium chloride (22 mg) were sequentially added to a mixed solution of 7-chloro-4H-pyrimido[1,2-b]pyridazin-4-one (0.22 mmol) in 1,4-dioxane (0.2 mL) and water (0.4 mL) under nitrogen. The reaction solution was heated at 100° C. under microwave and stirred for 2 hours. The liquid mass spectrometry showed that the reaction was complete. The reaction solution was filtered and the filtrate was concentrated to give crude product which was separated by preparative HPLC to give the product.

1H NMR (400 MHz, CDCl$_3$) ppm δ 8.37-7.89 (m, 6H), 7.30-7.02 (m, 2H), 6.67-6.54 (m, 1H), 3.85 (m, 3H).

The following 9 compounds were also synthesized by reference to the preparation of compound 71.

| compound | structure | MS(ES) [M + H]+ |
|---|---|---|
| 72 | 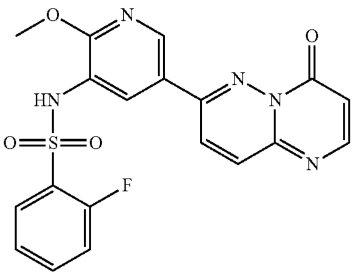 [SMILES: COc1ncc(-c2ccc3nccc(=O)n3n2)cc1NS(=O)(=O)c1ccccc1F] | 428 |
| 73 | 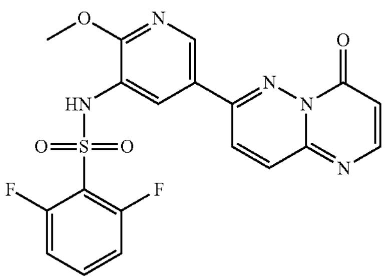 [SMILES: COc1ncc(-c2ccc3nccc(=O)n3n2)cc1NS(=O)(=O)c1c(F)cccc1F] | 446 |
| 74 | 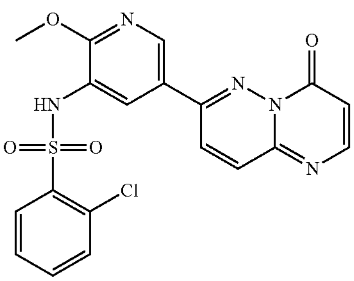 [SMILES: COc1ncc(-c2ccc3nccc(=O)n3n2)cc1NS(=O)(=O)c1ccccc1Cl] | 444 |
| 75 | 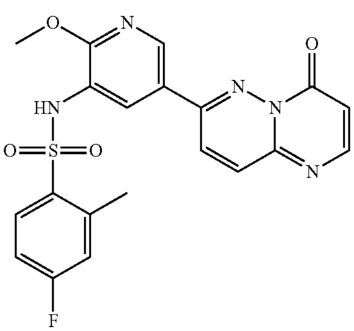 [SMILES: COc1ncc(-c2ccc3nccc(=O)n3n2)cc1NS(=O)(=O)c1ccc(F)cc1C] | 442 |
| 76 | 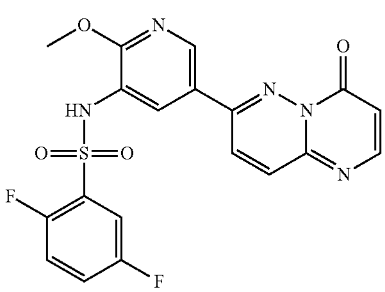 [SMILES: COc1ncc(-c2ccc3nccc(=O)n3n2)cc1NS(=O)(=O)c1cc(F)ccc1F] | 446 |
| 77 | 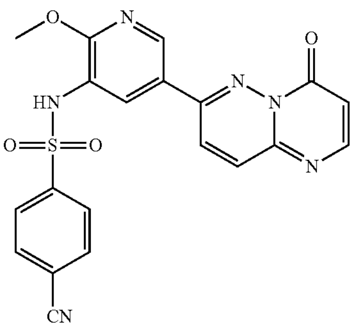 [SMILES: COc1ncc(-c2ccc3nccc(=O)n3n2)cc1NS(=O)(=O)c1ccc(C#N)cc1] | 435 |
| 78 | 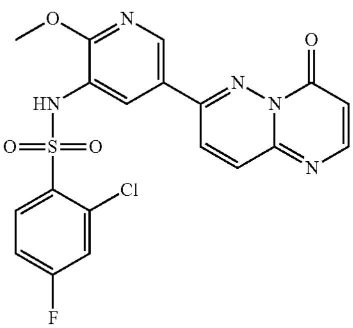 [SMILES: COc1ncc(-c2ccc3nccc(=O)n3n2)cc1NS(=O)(=O)c1ccc(F)cc1Cl] | 462 |
| 79 | 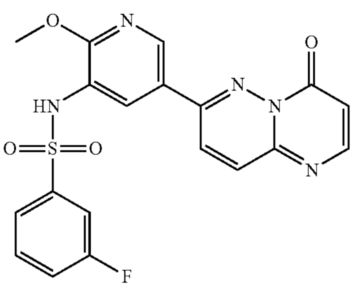 [SMILES: COc1ncc(-c2ccc3nccc(=O)n3n2)cc1NS(=O)(=O)c1cccc(F)c1] | 428 |
| 80 | 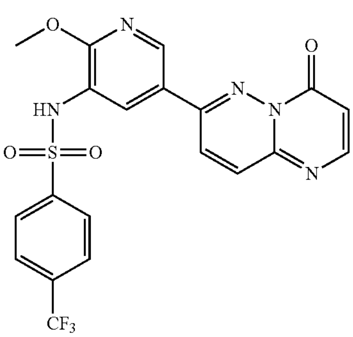 [SMILES: COc1ncc(-c2ccc3nccc(=O)n3n2)cc1NS(=O)(=O)c1ccc(C(F)(F)F)cc1] | 478 |
Scheme 6:
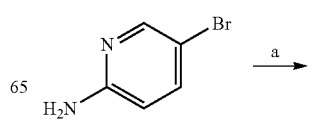

-continued

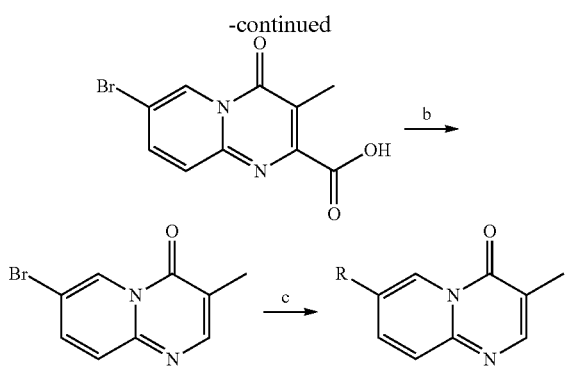

Reaction conditions: a) ethyl 2-methyl-3-oxosuccinate, ethanol, heating; b) diphenyl ether, heating; c) R boric acid (borate), palladium reagent (tetrakistriphenylphosphine palladium, [1,1'-bis(diphenylphosphino)ferrocene]palladium chloride, etc.), potassium carbonate, 1,4-dioxane, water, heating.

Example 81

2,4-difluoro-N-(2-methoxy-5-(3-methyl-4-oxo-4H-pyrido[1,2-a]pyrimidin-7-yl)pyridin-3-yl)benzsulfamide

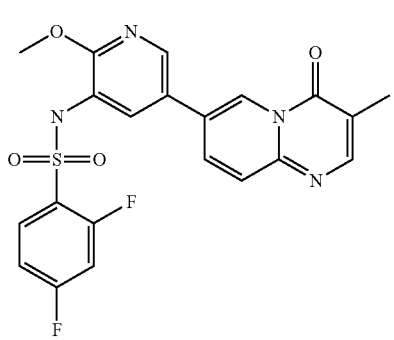

compound 81 a) 7-bromo-3-methyl-4-oxo-4H-pyrido[1,2-a]pyrimidin-2-carboxylic acid 2-amino-5-bromopyridine (6 g, 0.035 mol), diethyl-2-methyl-3-dioxoborane (7 g, 0.035 mol) and ethanol (165 mL) were added to a 250 mL round-bottom flask. The reaction solution was stirred at 100° C. for 30 hours. The reaction solution was cooled to room temperature, and the solid was rinsed with cold ethanol to give the product as a white solid (3 g, 30.6%).

1H NMR (400 MHz, DMSO-$d_6$) ppm δ 8.936 (s, 1H), 7.963-7.940 (d, 1H), 7.577-7.553 (d, 1H), 2.111 (s, 3H).

b) 7-bromo-3-methyl-4H-pyrido[1,2-a]pyrimidin-4-one

The mixed solution of 7-bromo-3-methyl-4-one-4H-pyrido[1,2-a]pyrimidin-2-carboxylic acid (1.5 g, 5.2 mmol) and diphenyl ether (20 mL) was stirred at 220° C. for 1.5 hours. The reaction solution was cooled to room temperature. The crude product was separated using column chromatography to give the product as an orange solid (550 mg, 44%).

1H NMR (400 MHz, CDCl$_3$) ppm δ 9.174 (s, 1H), 8.233 (s, 1H), 7.688-7.665 (d, 1H), 7.505-7.482 2.279 (s, 1H).

c) 2,4-difluoro-N-(2-methoxy-5-(3-methyl-4-oxo-4H-pyrido[1,2-a]pyrimidin-7-yl)pyridin-3-yl)benzsulfamide 2,4-difluoro-N-(2-methoxy-5-(4,4,5,5-tetramethyl-1,3,2-dioxoboran-2-yl)pyridin-3-yl)benzsulfamide (0.22 mmol), potassium carbonate (0.44 mmol) and 1,1'-bis(diphenylphosphino) ferrocene palladium chloride (22 mg) were added sequentially to a mixed solution of 7-bromo-3-methyl-4H-pyrido[1,2-a]pyrimidin-4-one (0.22 mmol) in 1,4-dioxane (2 mL) and water (0.4 mL) under nitrogen. The reaction solution was stirred at 90° C. for 1 hour under microwave reaction condition. The liquid mass spectrometry showed the reaction was completed. The reaction solution was filtered and the filtrate was dried through rotary evaporation to give the crude product which was separated using preparative high performance liquid chromatography to give the product as a white solid.

1H NMR (400 MHz, DMSO-$d_6$) ppm δ 8.935 (s, 1H), 8.274 (s, 1H), 8.150 (s, 1H) 8.096-8.074 (d, 1H), 7.797-7.761 (d, 2H), 7.683-7.660 (d, 1H), 7.392 (s, 1H), 7.157-7.115 (d, 2H), 3.676, 2.127 (s, 3H).

The following 5 compounds were also synthesized by reference to the preparation of compound 81.

| compound | structure | MS(ES) [M + H]$^+$ |
|---|---|---|
| 82 | 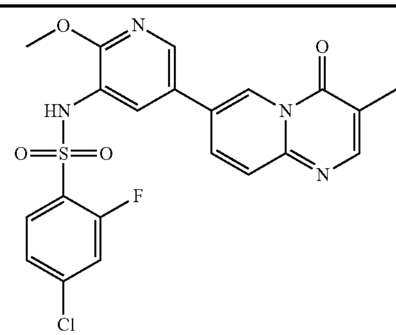 | 475 |
| 83 | 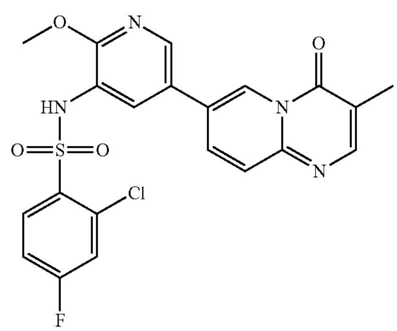 [SMILES: COc1ncc(-c2ccc3ncc(C)c(=O)n3c2)cc1NS(=O)(=O)c1ccc(F)cc1Cl] | 475 |
| 84 | 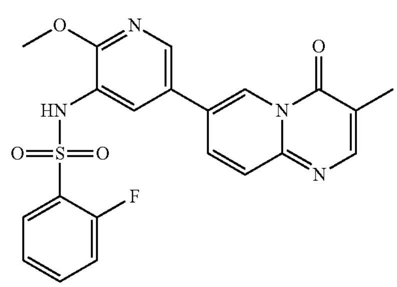 [SMILES: COc1ncc(-c2ccc3ncc(C)c(=O)n3c2)cc1NS(=O)(=O)c1ccccc1F] | 441 |

-continued

| compound | structure | MS(ES) [M + H]⁺ |
|---|---|---|
| 85 | 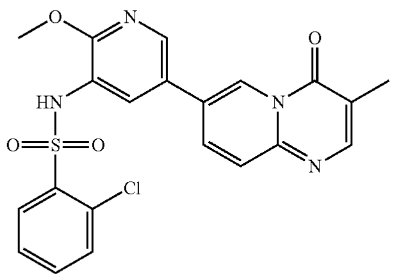 [SMILES: COc1ncc(-c2ccc3ncc(C)c(=O)n3c2)cc1NS(=O)(=O)c1ccccc1Cl] | 457 |
| 86 | 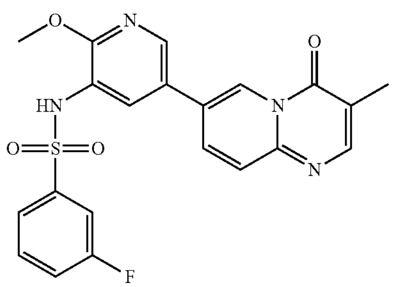 [SMILES: COc1ncc(-c2ccc3ncc(C)c(=O)n3c2)cc1NS(=O)(=O)c1cccc(F)c1] | 441 |

Scheme 7:

Reaction conditions: a) concentrated sulfuric acid, nitric acid; b) iron powder, ammonium chloride, heating; c) R boric acid (borate), palladium reagent (tetrakistriphenylphosphine palladium, [1,1'-bis(diphenylphosphino)ferrocene]palladium chloride, etc.), potassium carbonate, 1,4-dioxane, water, heating.

Example 87

N-(5-(3-amino-4-oxo-4H-pyrido[1,2-a]pyrimidin-7-yl)-2-methoxpyridin-3-yl)-2,4-difluorobenzsulfamide

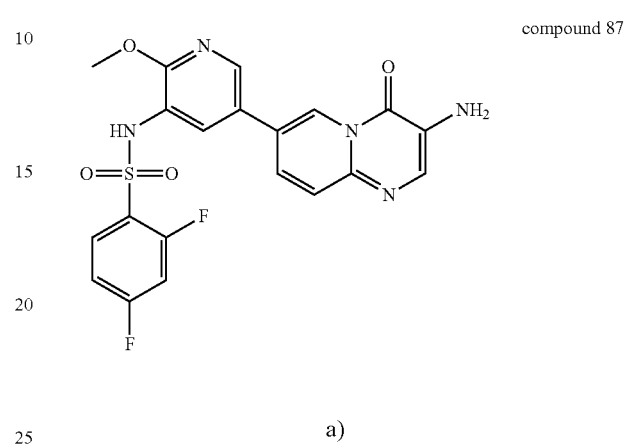

compound 87 a)
7-bromo-3-nitro-4H-pyrido[1,2-a]pyrimidin-4-one 7-bromo-4H-pyrido[1,2-a]pyrimidin-4-one (10 g, 0.045 mol) and concentrated sulfuric acid (50 mL) were added to a three-necked flask and nitric acid (8.65 g, 98%) was slowly added dropwise at 0° C. The mixture was stirred at 0° C. for one hour. The reaction solution was then poured into water (200 mL) and sodium hydroxide was added to adjust the pH to 9. The aqueous phase was extracted with ethyl acetate (200 mL×3) and the organic phases were combined, dried and concentrated to give the crude product. The crude product was separated by silica gel column chromatography to give the product as a white solid (1.3 g, 10.8%).
1H NMR (400 MHz, CDCl₃) ppm δ 9.489-9.485 (d, 1H), 9.368 (s, 1H), 8.178-8.150 (m, 1H), 7.843-7.820 (d, 1H).

b)
3-amino-7-bromo-4H-pyrido[1,2-a]pyrimidin-4-one

Ammonium chloride (1.2 g, 0.019 mol) and iron powder (1.0 g) were added to the mixed solution of 7-bromo-3-nitro-4H-pyrido[1,2-a]pyrimidin-4-one (1 g, 0.0037 mol) in ethanol (10 mL) and water (2 mL) and the reaction mixture was stirred at 70° C. for 4 hours. The reaction mixture was filtered, the filter cake was rinsed with ethyl acetate (30 mL×3) and the filtrate was concentrated to give the crude product. The crude product was dissolved in ethyl acetate (50 mL) and rinsed with water (20 mL), and then the organic phase was concentrated to give the product as a brown solid (0.8 g, 89.9%).
1H NMR (400 MHz, CDCl₃) ppm δ 9.013 (s, 1H), 7.974 (s, 1H), 7.395 (s, 2H), 4.235 (s, 2H).

c) N-(5-(3-amino-4-oxo-4H-pyrido[1,2-a]pyrimidin-7-yl)-2-methoxypyridin-3-yl)-2,4-difluorobenzsulfamide 2,4-difluoro-N-(2-methoxy-5-(4,4,55-tetramethyl-1,3,2-dioxoboran-2-yl)pyridin-3-yl)benzsulfamide (0.22 mmol),

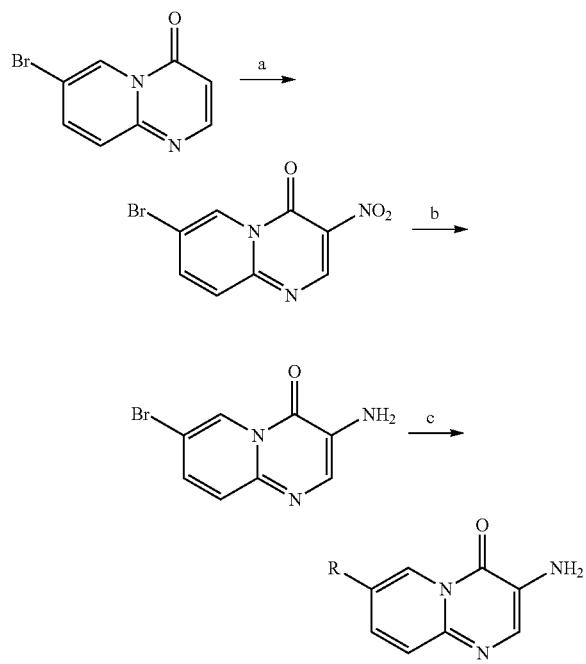

potassium carbonate (0.44 mmol) and 1,1'-bis(diphenyl-phosphino)ferrocene palladium chloride (22 mg) were added to the mixed solution of 3-amino-7-bromo-4H-pyrido[1,2-a]pyrimidin-4-one (0.22 mmol) in 1,4-dioxane (2 mL) and water (0.4 mL) under nitrogen. The reaction solution was stirred at 90° C. for 1 hour under microwave reaction condition. The liquid mass spectrometry showed that the reaction was complete. The reaction solution was filtered and the filtrate was concentrated to give crude product which was separated by preparative HPLC to give the product as a white solid.

1H NMR (400 MHz, DMSO-$d_6$) ppm δ 8.763 (s, 1H), 8.013-7.687 (m, 6H), 7.549-7.526 (d, 1H), 7.372-7.175 (m, 1H), 5.284 (s, 2H), 3.758 (s, 3H).

The following 7 compounds were also synthesized by reference to the preparation of compound 87.

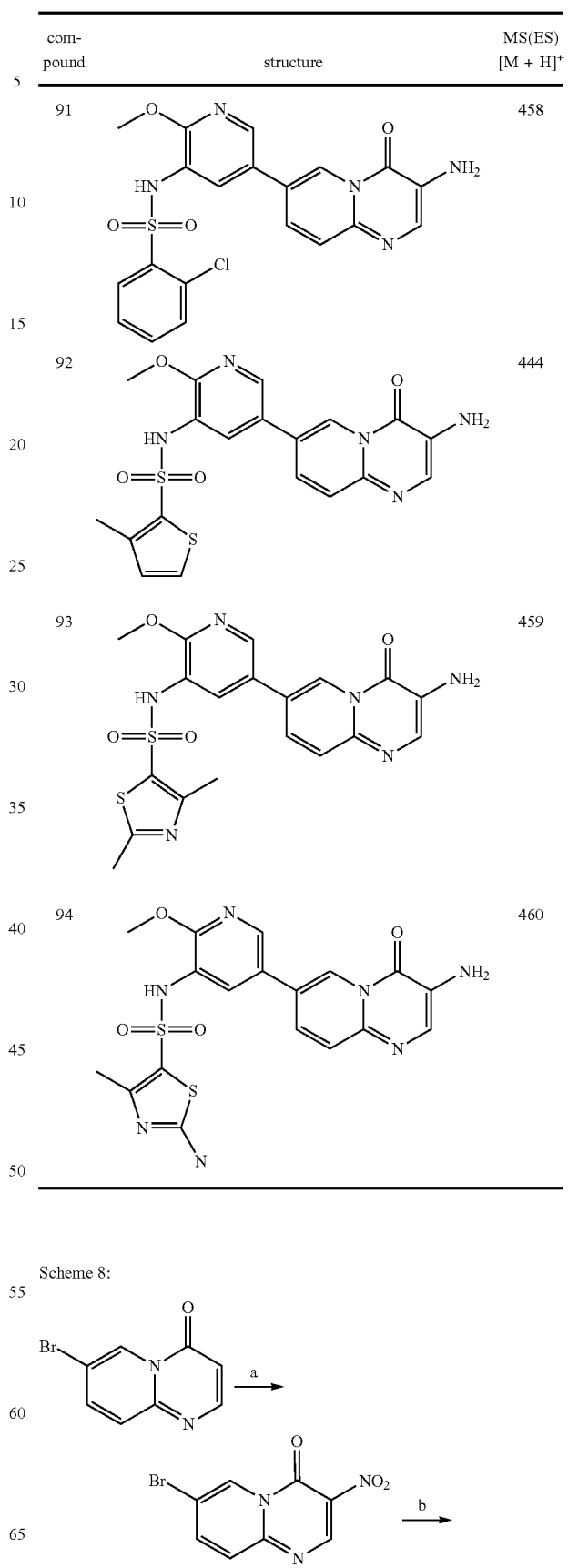

-continued

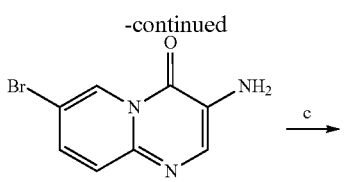

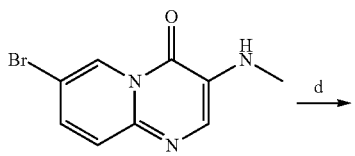

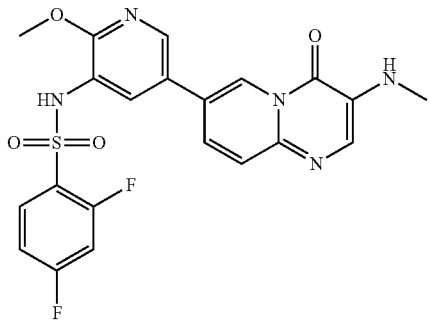

Conditions: a) nitric acid, concentrated sulfuric acid; b) ammonium chloride, iron powder, heating; c) potassium carbonate, methyl iodide, heating; d) microwave, palladium reagent (tetrakistriphenylphosphine palladium, [1,1'-bis(diphenylphosphino)ferrocene]palladium chloride, etc.), potassium carbonate, dioxane, water, heating.

Example 95

2,4-difluoro-N-(2-methoxy-5-(3-(methylamino)-4-oxo-4H-pyrido[1,2-a]pyrimidin-7-yl)pyridin-3-yl)benzulfamide compound 95

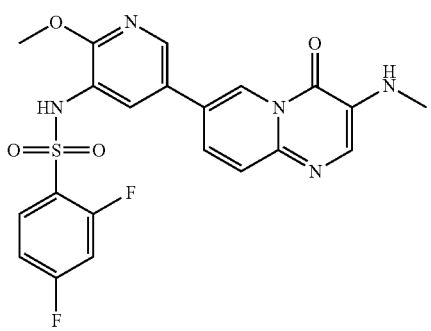

a)
7-bromo-3-nitro-4H-pyrido[1,2-a]pyrimidin-4-one 7-bromo-4H-pyrido[1,2-a]pyrimidin-4-one (5 g, 22.2 mmol) was dissolved in concentrated sulfuric acid (11.2 mL) and placed in a three-necked round bottom flask. Nitric acid (5.2 mL) was added dropwise at 5 to 10° C. The reaction mixture was stirred at 20° C. for 3 hours and then slowly poured into ice water. 1 eq. aqueous sodium hydroxide solution was added to adjust the pH to 8. The reaction mixture was filtered, and the filter cake was rinsed with water and drained to give the title compound as a yellow solid (4.0 g, 66.7%).

1H NMR (400 MHz, CDCl$_3$) ppm δ 9.47 (d, 1H), 9.35 (s, 1H), 8.14 (dd, 1H), 7.81 (d, 1H).

b)
3-amino-7-bromo-4H-pyrido[1,2-a]pyrimidin-4-one 7-bromo-3-nitro-4H-pyrido[1,2-a]pyrimidin-4-one (1.6 g, 5.93 mmol) was dissolved in ethanol (20 mL) and water (4 mL), and chloride ammonium (3.17 g, 59.25 mmol) and iron powder (3.17 g, 59.25 mmol) were added. The mixture was stirred at 70° C. for 16 hours. The reaction mixture was filtered, the filter cake rinsed with dichloromethane, the organic phase of the resulting filtrate was rinsed with saturated saline water (50 mL), dried over sodium sulphate, and concentrated to give crude title compound (3.56 g).

1H NMR (400 MHz, CDCl$_3$) ppm δ 8.99 (s, 1H), 7.96 (s, 1H), 7.38 (s, 2H), 4.13 (br. s., 2H).

c) 7-bromo-3-(methylamino)-4H-pyrido[1,2-a]pyrimidin-4-one 3-amino-7-bromo-4H-pyrido[1,2-a]pyrimidin-4-one (0.8 g, 3.33 mmol) was dissolved in acetone (30 mL) and potassium carbonate (1.38 g, 10.0 mmol) and methyl iodide (7.1 g, 49.99 mmol) were added. The mixture was stirred at 80° C. for 3 hours under nitrogen. The reaction solution was filtered and the filter cake was rinsed with dichloromethane. The filtrate was concentrated, and the resulting residue was purified by column chromatography on a silica gel to give the title compound (250 mg, 29.5%).

1H NMR (400 MHz, CDCl$_3$) ppm δ 8.91 (d, 1H), 7.66 (s, 1H), 7.36-7.32 (m, 1H), 7.28 (d, 1H), 4.72 (br. s., 1H), 2.97 (d, 3H).

d) 2,4-difluoro-N-(2-methoxy-5-(3-(methylamino)-4-oxo-4H-pyrido[1,2-a]pyrimidin-7-yl)pyridin-3-yl)benzsulfamide 7-bromo-3-(methylamino)-4H-pyrido[1,2-a]pyrimidin-4-one (100 mg, 0.39 mmol) was dissolved in dioxane (2 mL) and water (0.4 mL) and 2,4-dichloro-N-(2-methoxy-5-(4,4,5,5-tetra-methyl-1,3,2-dioxaborolan-2-yl)pyridin-3-yl)benzsulfamide (168 mg, 0.39 mmol), potassium carbonate (109 mg, 0.78 mmol) and [1,1'-bis(diphenyl-phosphino)ferrocene]palladium chloride (16 mg, 0.02 mmol) were added under nitrogen. The mixture was reacted at 100° C. under microwave for 1 hour. LCMS showed the reaction was complete. The reaction solution was filtered, and the organic phase was concentrated to give the crude product. The crude product was purified by preparative HPLC to give a yellow title product.

1H NMR (400 MHz, DMSO-d$_6$) ppm δ 8.84 (br. s., 1H), 8.12 (br. s., 1H), 7.97-7.87 (m, 2H), 7.70 (s, 1H), 7.55 (d, 1H), 7.39 (d, 1H), 7.04-6.89 (m, 2H), 4.70 (br. s., 1H), 3.97 (s, 3H), 2.99 (d, 3H).

The following 5 compounds were also synthesized by reference to the preparation of compound 95.

| compound | structure | MS(ES) [M + H]+ |
|---|---|---|
| 96 | 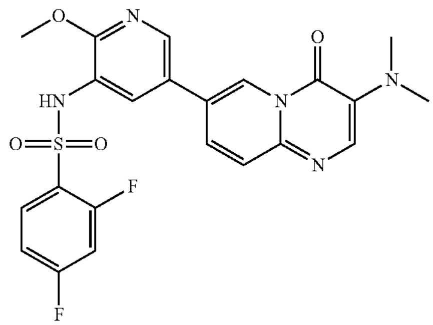 [SMILES: COc1ncc(-c2ccc3ncc(N(C)C)c(=O)n3c2)cc1NS(=O)(=O)c1ccc(F)cc1F] | 488 |
| 97 | 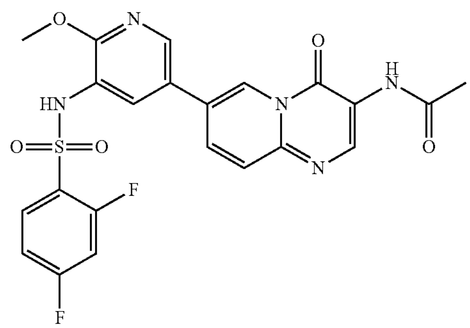 [SMILES: COc1ncc(-c2ccc3ncc(NC(C)=O)c(=O)n3c2)cc1NS(=O)(=O)c1ccc(F)cc1F] | 502 |
| 98 | 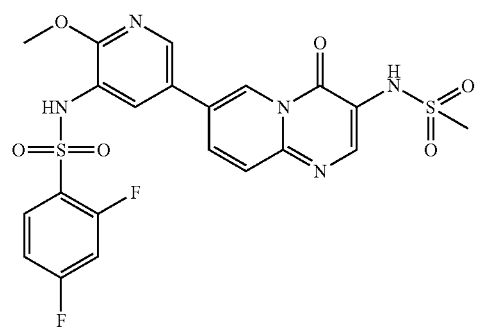 [SMILES: COc1ncc(-c2ccc3ncc(NS(C)(=O)=O)c(=O)n3c2)cc1NS(=O)(=O)c1ccc(F)cc1F] | 538 |
| 99 | 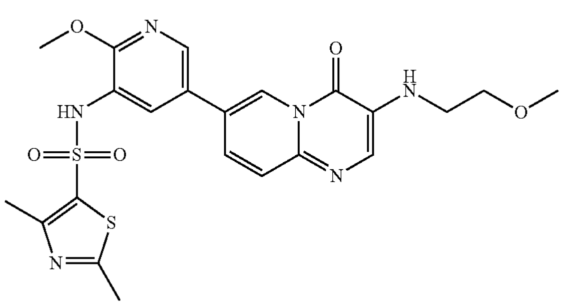 | 517 |
| 100 | 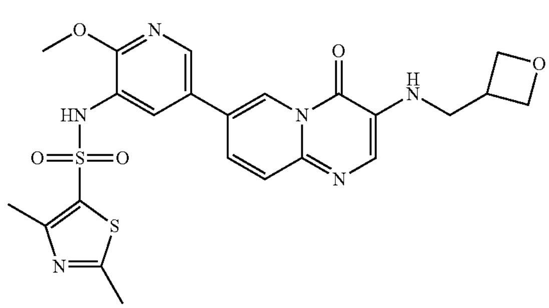 [SMILES: COc1ncc(-c2ccc3ncc(NCC4COC4)c(=O)n3c2)cc1NS(=O)(=O)c1sc(C)nc1C] | 529 |

Scheme 9:

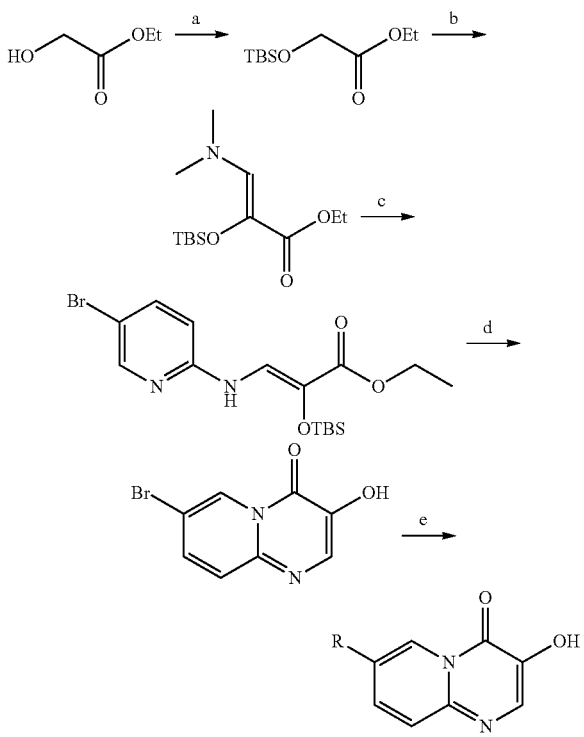

Reaction conditions: a) tert-butyldimethylsilyl chloride, 1H-imidazole; b) 1-t-butoxy-N,N,N',N'-tetramethyldiaminomethane, heating; c) 2-amino-5-bromopyridine, acetic acid, heating; d) acetic acid, microwave; e) R boric acid (borate), palladium reagent (tetrakistriphenylphosphine palladium, [1,1'-bis(diphenylphosphino)ferrocene]palladium chloride, etc.), potassium carbonate, dioxane, water, heating.

Example 101

2,4-difluoro-N-(5-(3-hydroxy-4-oxo-4H-pyrido[1,2-a]pyrimidin-7-yl)-2-methoxypyridin-3-yl) benzsulfamide compound 101

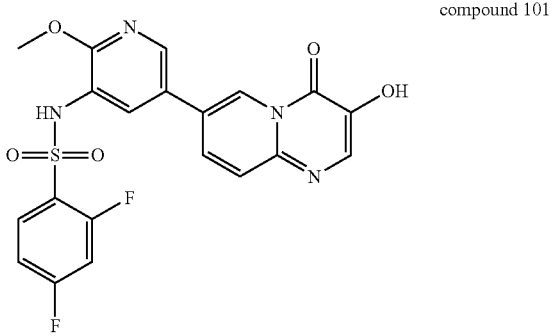 [SMILES: COc1ncc(-c2ccc3ncc(O)c(=O)n3c2)cc1NS(=O)(=O)c1ccc(F)cc1F]

a) ethyl 2-((tert-butyldimethylsilyl)oxy)acetate

Ethyl glycolate (10 g, 96.1 mmol) and 1H-imidazole(13 g, 0.19 mol) were dissolved in dichloromethane (100 mL) and placed in a three-necked round bottom flask. At 0° C., tert-butyldimethylsilyl chloride (15.8 g, 0.1 mol) was added and the mixture was stirred at room temperature for 8 hours, then rinsed with water (100 mL×3), dried over sodium sulfate and concentrated to give the title compound as a yellow oil (18 g, 85.8%).

1H NMR (400 MHz, CDCl$_3$) ppm δ 4.14-4.09 (m, 4H), 1.20-1.16 (t, 3H), 0.83 (s, 9H), 0.01 (s, 6H).

b) (Z)-ethyl 2-((tert-butyldimethylsilyl)oxy)-3-(dimethylamino)acrylate

Ethyl 2-((tert-butyldimethylsilyl)oxy)acetate (52 g, 0.24 mol) and 1-t-butoxy-N,N,N',N'-tetramethyldiaminomethane (50 g, 0.58 mol) were stirred at reflux for 24 hours. The mixture was concentrated, and the residue was purified by column chromatography on silica gel to give the title compound as a yellow oil (45 g, 47.1%).

1H NMR (400 MHz, CDCl$_3$) ppm δ 6.68 (s, 1H), 4.13-4.11 (q, 2H), 2.96 (s, 6H), 1.28-1.24 (t, 3H), 0.95 (s, 9H), 0.14 (s, 6H).

c) (Z)-ethyl 3-((5-bromopyridin-2-yl)amino)-2-((tert-butyldimethylsilyl)oxy) acrylate (Z)-ethyl 3-((5-bromopyridin-2-yl)amino)-2-((tert-butyldimethylsilyl)oxy)acrylate (15 g, 54.9 mmol) and 2-amino-5-bromopyridine (9.4 g, 54.9 mmol) were dissolved in acetic acid (150 mL) and stirred at 80° C. for 2 hours. The mixture was concentrated. Then the residue was dissolved in ethyl acetate (100 mL), rinsed with sodium carbonate solution (100 mL) and saturated brine (100 mL), dried over sodium sulphate and concentrated. The resulting residue was purified by column chromatography on silica gel to give the title compound as a yellow oil (14 g, 63.7%).

1H NMR (400 MHz, CDCl$_3$) ppm δ 8.24 (s, 1H), 7.75-7.72 (d, 1H), 7.63-7.60 (d, 1H), 6.75-6.72 (d, 1H), 6.57-6.54 (d, 1H), 4.25-4.20 (q, 2H), 1.34-1.30 (t, 3H), 1.02 (s, 9H), 0.22 (s, 6H).

d) 7-bromo-3-hydroxy-4H-pyrido[1,2-a]pyrimidin-4-one (Z)-ethyl 3-((5-bromopyridin-2-yl)amino)-2-((tert-butyldimethylsilyl)oxy)acrylate (200 mg×50, 29 mmol) was dissolved in acetic acid (5 mL×50) and stirred at 140° C. under microwave for 3 hours. The mixture was concentrated. The residue was dissolved in ethyl acetate (100 mL), rinsed with sodium carbonate solution (100 mL) and saturated brine (100 mL), dried over sodium sulfate, and concentrated. The resulting residue was purified by column chromatography on silica gel to give the title compound (3.2 g, 46.4%).

1H NMR (400 MHz, CDCl$_3$) ppm δ 8.98 (s, 1H), 8.14 (s, 1H), 8.00-7.98 (d, 1H), 7.79-7.77 (d, 1H).

e) 2,4-difluoro-N-(5-(3-hydroxy-4-oxo-4H-pyrido[1,2-a]pyrimidin-7-yl)-2-methoxypyridin-3-yl) benzsulfamide 7-bromo-3-hydroxy-4H-pyrido[1,2-a]pyrimidin-4-one (0.22 mmol) was dissolved in dioxane(2 mL) and water (0.4 mL), 2,4-dichloro-N-(2-methoxy-5-(4,4,5,5-tetramethyl-1,3,2-dioxaborolan-2-yl)pyridin-3-yl)benzsulfamide (0.22 mmol), potassium carbonate (0.44 mmol) and 1,1'-bis(diphenylphosphino)ferrocene palladium chloride (22 mg) were added under nitrogen. The mixture was reacted at 90° C. under microwave for 1 hour. The liquid mass spectrometry showed that the reaction was complete. The reaction solution was filtered and the organic phase was concentrated to give the crude product. The crude product was purified by preparative HPLC to give white title product.

1H NMR (400 MHz, DMSO-d$_6$) ppm δ 8.93 (s, 1H), 8.41 (s, 1H), 8.08 (s, 1H), 7.96 (s, 2H), 7.79-7.78 (m, 1H), 7.68-7.66 (m, 1H), 7.56 (m, 1H), 7.24-7.20 (m, 1H), 3.68 (s, 3H).

The following one compound was also synthesized by reference to the preparation of compound 101.

| compound | structure | MS(ES) [M + H]+ |
|---|---|---|
| 102 | 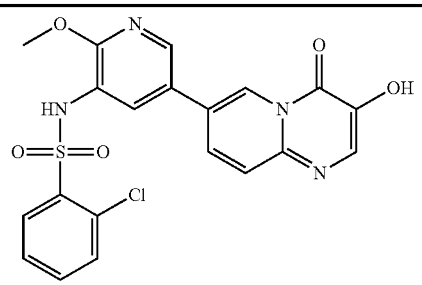 | 459 |

Scheme 10:

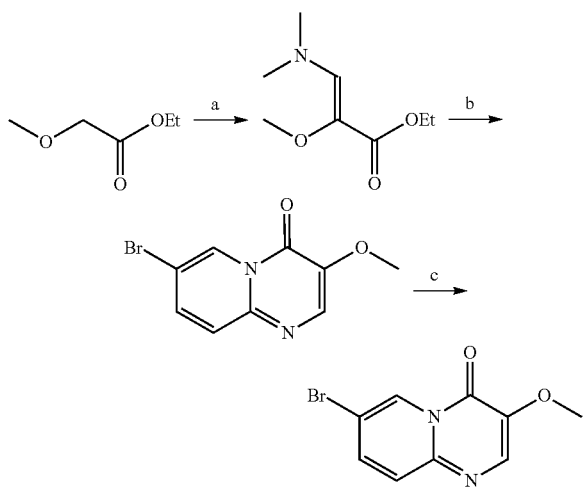

Reaction conditions: a) 1-t-butoxy-N,N,N',N'-tetramethyldiaminomethane, heating; b) 2-amino-5-bromopyridine, acetic acid, heating; c) R boric acid, (borate), palladium reagent (tetrakistriphenylphosphine palladium, [1,1'-bis(diphenylphosphino)ferrocene]palladium chloride, etc.), potassium carbonate, dioxane, water, heating.

Example 103

2,4-difluoro-N-(2-methoxy-5-(3-methoxy-4-oxo-4H-pyrido[1,2-a]pyrimidin-7-yl) pyridin-3-yl) benzsulfamide compound 103 a) (Z)-ethyl 3-(dimethylamino)-2-methoxyacrylate

Ethyl 2-methoxyacetate (2 g, 16.9 mmol) and 1-t-butoxy-N,N,N',N'-tetramethyl diaminomethane (3.5 g, 20.1 mmol) were placed in a round-bottom flask and stirred at reflux overnight. The mixture was concentrated, and the residue was purified by silica gel column chromatography to give the title compound as a yellow oil (2 g, 67.8%).

1H NMR (400 MHz, CDCl$_3$) ppm δ 6.78 (s, 1H), 4.18-4.16 (t, 2H), 3.55 (s, 3H), 3.02 (s, 6H), 1.29-1.26 (q, 3H).

b) 7-bromo-3-methoxy-4H-pyrido[1,2-a]pyrimidin-4-one (Z)-ethyl 3-(dimethylamino)-2-methoxyacrylate (2.5 g, 14.4 mmol) and 2-amino-5-bromopyridine (2.5 g, 14.4 mmol) were dissolved in acetic acid (25 mL) and stirred at 80° C. for 2 hours. The mixture was concentrated. The residue was dissolved in ethyl acetate (30 mL), rinsed with sodium carbonate solution (50 mL) and saturated brine (30 mL), dried over sodium sulfate and concentrated, and the resulting residue was purified by silica gel column chromatography to give the title compound (1.3 g, 35.1%).

1H NMR (400 MHz, CDCl$_3$) ppm δ 9.10 (s, 1H), 8.05 (s, 1H), 7.52 (d, 1H), 7.46 (d, 1H), 4.00 (s, 3H).

c) 2,4-difluoro-N-(2-methoxy-5-(3-methoxy-4-oxo-4H-pyrido[1,2-a]pyrimidin-7-yl)pyridin-3-yl)benzsulfamide 7-bromo-3-methoxy-4H-pyrido[1,2-a]pyrimidin-4-one (0.27 mmol) was dissolved in dioxane(3.5 mL) and water (0.7 mL), and 2,4-dichloro-N-(2-methoxy-5-(4,4,5,5-tetramethyl-1,3,2-dioxaborolan-2-yl)pyridin-3-yl)benzsulfamide (0.33 mmol), potassium carbonate (0.41 mmol) and 1,1'-bis(diphenylphosphino)ferrocene palladium chloride (20 mg) were added under nitrogen. The mixture was reacted at 100° C. under microwave for 2 hours. The liquid mass spectrometry showed that the reaction was complete. The reaction solution was filtered, and the organic phase was concentrated to give the crude product. The crude product was purified by preparative HPLC to give the title product.

1H NMR (400 MHz, CDCl$_3$) ppm δ 8.99 (s, 1H), 8.12 (s, 1H), 8.09 (s, 1H), 7.97-7.93 (m, 2H), 7.66 (s, 2H), 7.08-7.04 (q, 1H), 6.97-6.93 (q, 1H), 4.02-3.98 (d, 6H).

The following 8 compounds were also synthesized by reference to the preparation of compound 103.

| compound | structure | MS (ES) [M + H]+ |
|---|---|---|
| 104 | 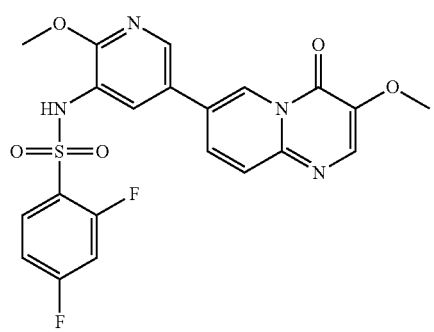 | 491 |

| compound | structure | MS (ES) [M + H]+ |
|---|---|---|
| 105 | 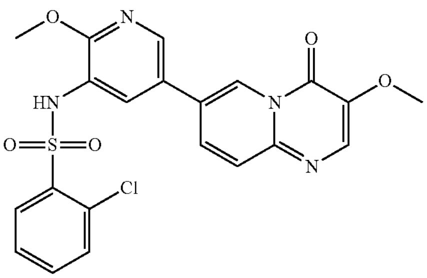 [SMILES: COc1ncc(-c2ccc3ncc(OC)c(=O)n3c2)cc1NS(=O)(=O)c1ccccc1Cl] | 473 |
| 106 | 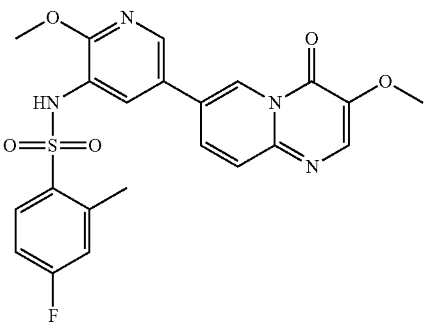 [SMILES: COc1ncc(-c2ccc3ncc(OC)c(=O)n3c2)cc1NS(=O)(=O)c1ccc(F)cc1C] | 471 |
| 107 | 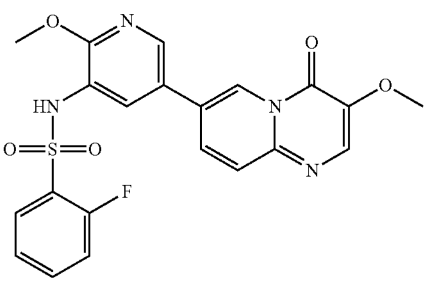 [SMILES: COc1ncc(-c2ccc3ncc(OC)c(=O)n3c2)cc1NS(=O)(=O)c1ccccc1F] | 457 |
| 108 | 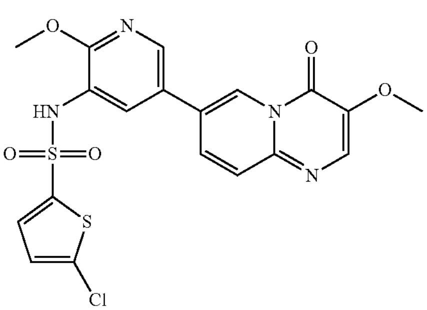 [SMILES: COc1ncc(-c2ccc3ncc(OC)c(=O)n3c2)cc1NS(=O)(=O)c1ccc(Cl)s1] | 479 |
| 109 | 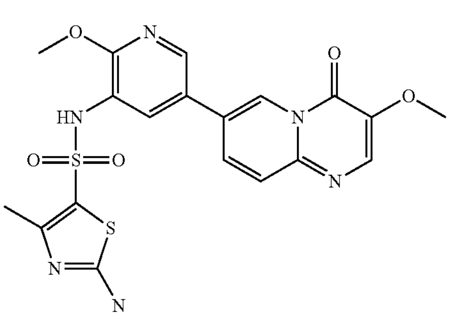 | 475 |

| compound | structure | MS (ES) [M + H]+ |
|---|---|---|
| 110 | 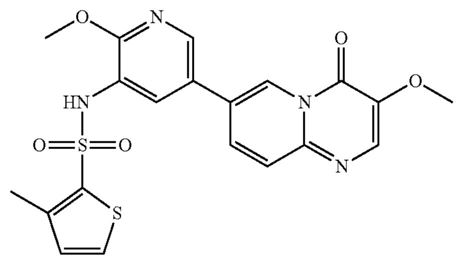 | 459 |
| 111 | 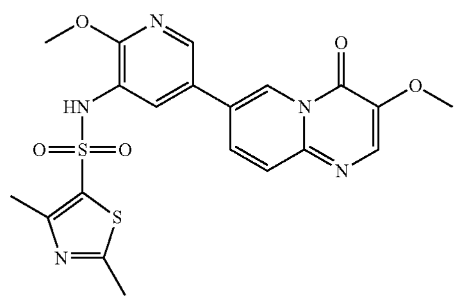 | 474 |

Scheme 11:

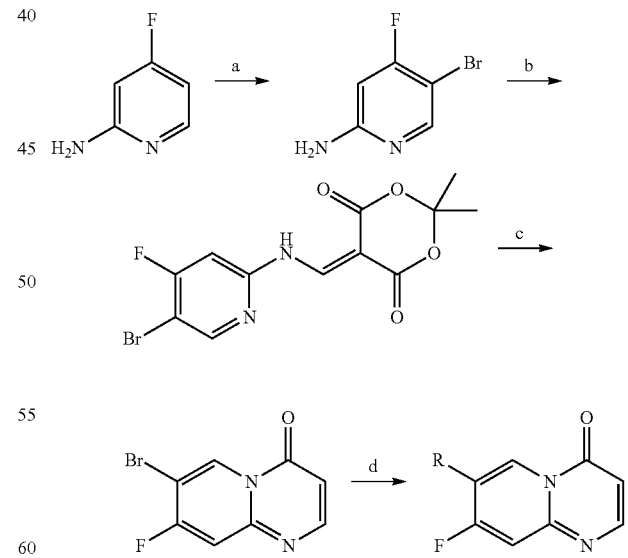

Reaction conditions: a) NBS, MeCN; 2) triethyl orthoformate, 2,2-dimethyl-1,3-dioxane-4,6-dione, heating; EtOH, heating; c) diphenyl ether, reflux; d) R boric acid (borate), palladium reagent (tetrakistriphenylphosphine palladium, [1,1'-bis(diphenylphosphino)ferrocene] palladium chloride, etc.), potassium carbonate, dioxane, water, heating.

Example 112

2,4-difluoro-N-(5-(8-fluoro-4-oxo-4H-pyrido[1,2-a])pyrimidin-7-yl)-2-methoxypyridin-3-yl)benzsulfamide

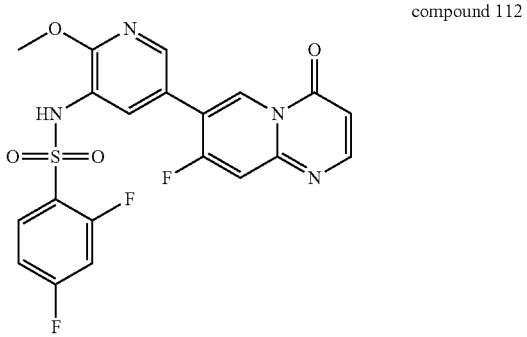 [SMILES: COc1ncc(-c2cn3c(=O)ccnc3cc2F)cc1NS(=O)(=O)c1ccc(F)cc1F]

compound 112 a) 5-bromo-4-fluoropyridin-2-amine

NBS (28.6 g, 0.16 mol) was added in batches to the solution of 4-fluoropyridin-2-amine 2,2,2-trifluoroacetate (18 g, 0.16 mol) in acetonitrile (200 mL). The reaction solution was stirred at 25° C. in dark for 4 hours. The solvent was removed under reduced pressure, and the crude product was purified by flash column chromatography on silica gel to give the title compound as a white solid (15 g, 49%).

1H NMR (400 MHz, CDCl$_3$) ppm δ 8.155-8.131 (d, 1H), 6.301-6.276 (d, 1H), 4.638 (s, 2H)

b) (E)-5-(((5-bromo-4-fluoropyridin-2-yl)imino)methyl)-2,2-dimethyl-1,3-dioxane-4,6-dione Triethyl orthoformate (7.3 g, 0.05 mol) and 2,2-dimethyl-1,3-dioxane-4,6-dione (7.5 g, 0.05 mol) were added to a three-necked round bottom flask equipped with a stirrer. The suspension was stirred at 70° C. for 1 hour. A solution of 5-bromopyridin-2-amine (8 g, 0.042 mol) in ethanol (100 mL) was added dropwise to this mixture. The reaction solution was stirred at 70° C. for 0.5 hours and cooled to 25° C. and filtered. The filter cake was rinsed with ethanol (100 mL×3) to give the title compound as a white solid (11.6 g, 80%).

1H NMR (400 MHz, DMSO-d$_6$) ppm δ 11.477-11.442 (d, 1H), 9.190-9.156 (d, 1H), 8.728-8.705 (d, 1H), 7.854-7.830 (d, 1H), 1.694 (s, 6H).

c) 7-bromo-8-fluoro-4H-pyrido[1,2-a]pyrimidin-4-one (E)-5-(((5-bromo-4-fluoropyridin-2-yl)imino)methyl)-2,2-dimethyl-1,3-dioxane-4,6-dione (11.6 g, 0.034 mol) and diphenyl ether(50 mL) were placed in a 100 mL round-bottomed flask equipped with a stirrer and reacted at 220° C. for 1 hour. TLC showed the reaction was complete. The reaction solution was cooled to 100° C. and then poured into petroleum ether (100 mL). A mixture of hydrochloric acid and ethyl acetate (50 mL) was added and the mixture was filtered to give a solid. The solid was dissolved in methanol (50 mL) and saturated NaHCO$_3$ solution was added to adjust pH=7. The mixture was concentrated under reduced pressure, then water (50 mL) was added. The mixture was extracted with dichloromethane (100 mL×2). The organic phase was dried over Na$_2$SO$_4$, concentrated under reduced pressure and purified by silica gel column chromatography to give the title compound (4 g, 50%).

1H NMR (400 MHz, CDCl$_3$) ppm δ 9.335-9.317 (d, 1H), 8.272-8.256 (d, 1H), 7.371-7.350 (d, 1H), 6.461-6.445 (d, 1H).

d) 2,4-difluoro-N-(5-(8-fluoro-4oxo-4H-pyrido[1,2-a]pyrimidin-7-yl)-2-methoxypyridin-7-yl)-2-methoxypyridin-3-yl)benzsulfamide 7-bromo-8-fluoro-4H-pyrido[1,2-a]pyrimidin-4-one (0.28 mmol) was dissolved in dioxane (2 mL) and water (0.4 mL), and 2,4-difluoro-N-(2-methoxy-5-(4,4,5,5-tetramethyl-1,3,2-dioxaborolan-2-yl)pyridin-3-yl)benzsulfamide (0.28 mmol), potassium carbonate (0.56 mmol) and 1,1'-bis(diphenylphosphino)ferrocene palladium chloride (20 mg) were added under nitrogen. The reaction mixture was placed under microwave conditions at 100° C. for 2 hours. The liquid mass spectrometry showed the reaction was complete. The reaction solution was filtered and concentrated to give crude product which was purified by preparative HPLC to give the title product.

1H NMR (400 MHz, DMSO-d$_6$) ppm δ 10.44 (s., 1H), 9.03-8.96 (m, 1H), 8.30 (br. s., 2H), 7.93-7.85 (m, 1H), 7.83-7.71 (m, 2H), 7.65-7.55 (m, 1H), 7.30-7.21 (m, 1H), 6.46-6.40 (m, 1H), 3.71 (s, 3H).

The following 7 compounds were also synthesized by reference to the preparation of compound 112.

| compound | structure | MS(ES) [M + H]$^+$ |
|---|---|---|
| 113 | 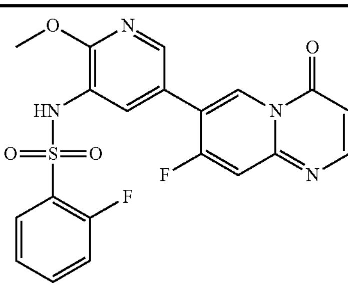 | 445 |
| 114 | 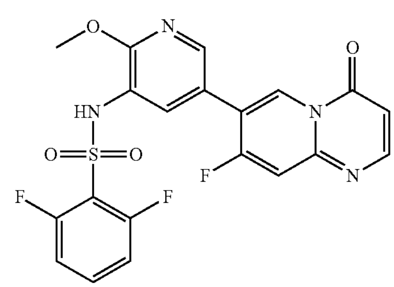 [SMILES: COc1ncc(-c2cn3c(=O)ccnc3cc2F)cc1NS(=O)(=O)c1c(F)cccc1F] | 463 |
| 115 | 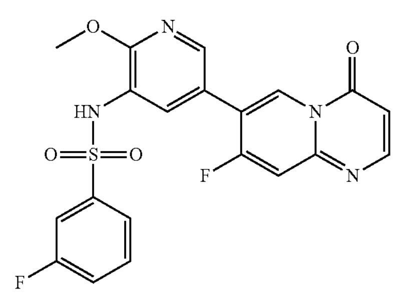 [SMILES: COc1ncc(-c2cn3c(=O)ccnc3cc2F)cc1NS(=O)(=O)c1cccc(F)c1] | 445 |

-continued

| compound | structure | MS(ES) [M + H]+ |
|---|---|---|
| 116 | 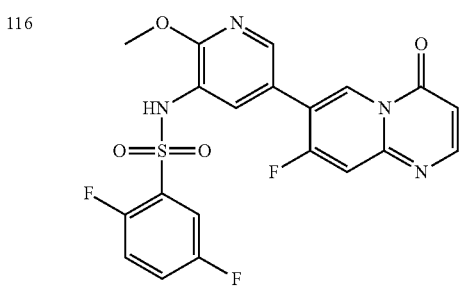 | 463 |
| 117 | 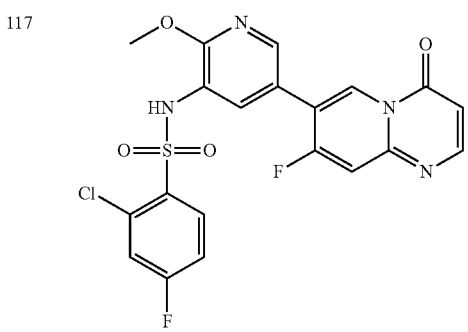 | 479 |
| 118 | 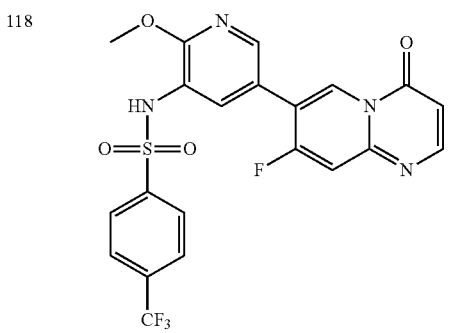 | 495 |
| 119 | 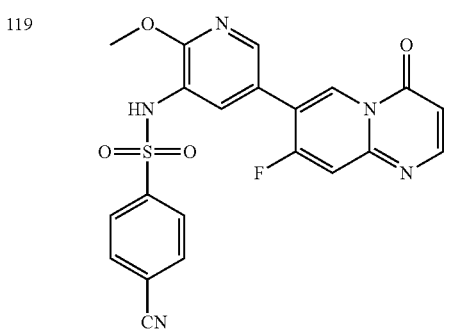 | 452 |

-continued

| compound | structure | MS(ES) [M + H]+ |
|---|---|---|
| 120 | 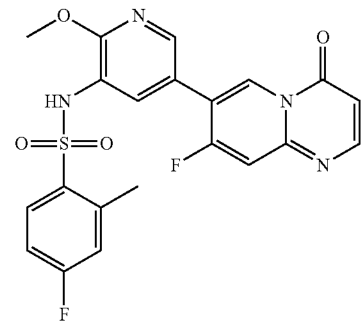 [SMILES: COc1ncc(-c2cn3c(=O)ccnc3cc2F)cc1NS(=O)(=O)c1ccc(F)cc1C] | 459 |

Scheme 12:

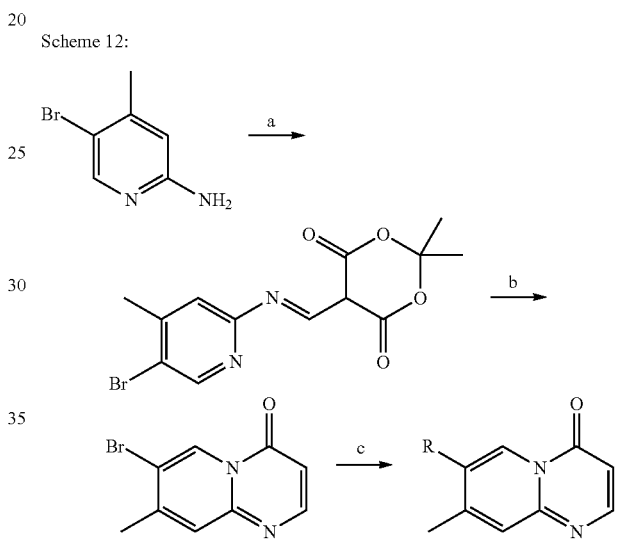

Reaction conditions: a) triethyl orthoformate, 2,2-dimethyl-1,3-dioxan-4,6-dione, heating; EtOH, heating; b) diphenyl ether, reflux; c) R boric acid (borate), palladium reagent (tetrakistriphenylphosphine palladium, [1,1'-bis(diphenylphosphino)ferrocene] palladium chloride, etc.), potassium carbonate, dioxane, water, heating.

Example 121

2,4-difluoro-N-(2-methoxy-5-(8-methyl-4-oxo-4H-pyrido[1,2-a]pyrimidin-7-yl)pyridin-3-yl)benzsulfamide compound 121

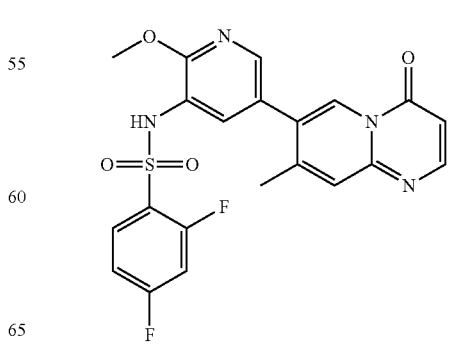

a) (E)-5-(((5-bromo-4-methylpyridin-2-yl)imino)
methyl)-2, 2-dimethyl-1, 3-dioxane-4,6-dione Triethyl orthoformate (1.75 g. 0.01 mol) and 2,2-dimethyl-1,3-dioxane-4,6-dione (1.61 g, 0.014 mol) were placed in a three-necked round-bottom flask equipped with a stirrer, and the reaction was carried out with stirring for 2 hours at 60° C. A solution of 5-bromopyridin-2-amine (2 g, 0.017 mol) in ethanol (20 mL) was added dropwise to the above mixture. The reaction solution was stirred for at 60° C. for 2 hours. The reaction solution was cooled to 25° C. and filtered, and the filter cake was rinsed with ethanol (20 mL×3) to give the title compound as a white solid (2.1 g, 61.76%).

1H NMR (400 MHz, CDCl$_3$) ppm δ 9.342-9.308 (d, 1H), 8.420 (s, 1H), 6.946 (s, 1H).

b)
7-bromo-8-methyl-4H-pyrido[1,2-a]pyrimidin-4-one (E)-5-(((5-bromo-4-fluoropyridin-2-yl)imino)methyl)-2,2-dimethyl-1,3-dioxane-4,6-dione (1.2 g, 0.0035 mol) and diphenyl ether(18 mL) were placed in a 100 mL round-bottomed flask and stirred at 220° C. for 1 hour. TLC showed the reaction was complete. The reaction solution was cooled to 100° C. and poured into petroleum ether (20 mL). A mixed solution of hydrochloric acid and ethyl acetate (20 mL) was added and the mixture was filtered to give a solid. The solid was dissolved in methanol (20 mL) and saturated NaHCO$_3$ solution was added to adjust pH=7. The mixture was concentrated and water (20 mL) was added. The mixture was extracted with dichloromethane (20 mL×2). The organic phase was dried over Na$_2$SO$_4$, concentrated under reduced pressure, and the crude product was purified by silica gel column chromatography to give the title compound (700 mg, 83.3%).

1H NMR (400 MHz, CDCl$_3$) ppm δ 9.236 (s, 1H), 8.277-8.262 (d, 1H), 7.527 (s, 1H), 6.421-6.406 (s, 1H), 2.550 (s, 3H).

c) 2,4-difluoro-N-(2-methoxy-5-(8-methyl-4-oxo-4H-pyrido[1,2-a]pyrimidin-7-yl)pyridin-3-yl)benzsulfamide 7-bromo-8-methyl-4H-pyrido[1,2-a]pyrimidin-4-one (0.28 mmol) was dissolved in dioxane(2 mL) and water (0.44 mL), and 2,4-difluoro-N-(2-methoxy-5-(4,4,5,5-tetramethyl-1,3,2-dioxaborolan-2-yl)pyridin-3-yl)benzsulfamide (0.28 mmol), potassium carbonate (0.56 mmol) and 1,1'-bis(diphenylphosphino)ferrocene palladium chloride (20 mg) were added under nitrogen. The reaction mixture was placed under microwave conditions at 100° C. for 2 hours. The liquid mass spectrometry showed that the reaction was complete. The reaction solution was filtered and the filtrate was concentrated under reduced pressure to give the crude product. The crude product was purified by preparative HPLC to give the title compound.

The following 10 compounds were also synthesized by reference to the preparation of compound 121.

| Example | structure | MS(ES) [M + H]$^+$ |
|---|---|---|
| 122 | 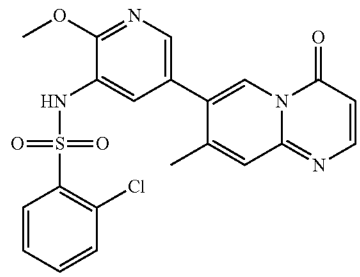 [SMILES: COc1ncc(-c2cn3c(=O)ccnc3cc2C)cc1NS(=O)(=O)c1ccccc1Cl] | 457 |
| 123 | 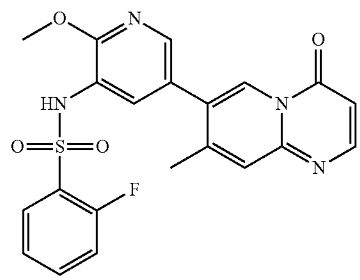 [SMILES: COc1ncc(-c2cn3c(=O)ccnc3cc2C)cc1NS(=O)(=O)c1ccccc1F] | 441 |
| 124 | 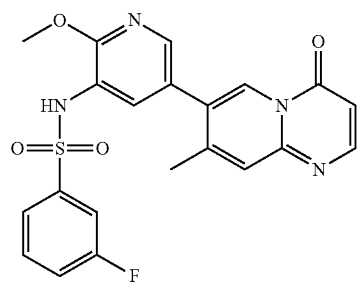 [SMILES: COc1ncc(-c2cn3c(=O)ccnc3cc2C)cc1NS(=O)(=O)c1cccc(F)c1] | 441 |
| 125 | 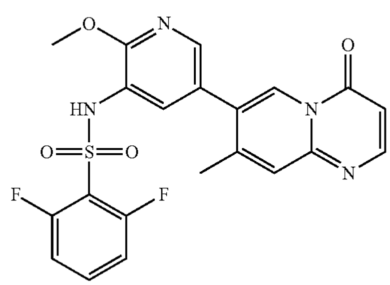 [SMILES: COc1ncc(-c2cn3c(=O)ccnc3cc2C)cc1NS(=O)(=O)c1c(F)cccc1F] | 459 |
| 126 | 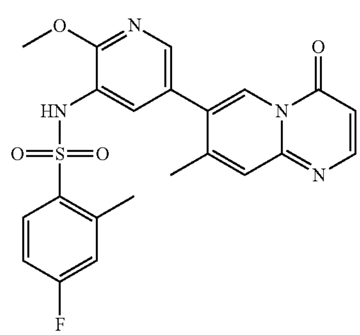 [SMILES: COc1ncc(-c2cn3c(=O)ccnc3cc2C)cc1NS(=O)(=O)c1ccc(F)cc1C] | 455 |

| Example | structure | MS(ES) [M + H]+ |
|---|---|---|
| 127 | 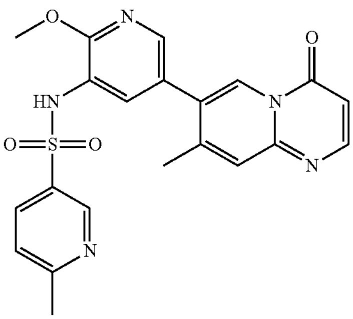 [SMILES: COc1ncc(-c2cn3c(=O)ccnc3cc2C)cc1NS(=O)(=O)c1ccc(C)nc1] | 437 |
| 128 | 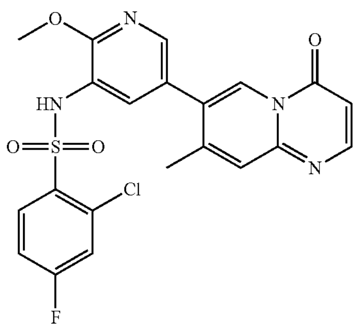 [SMILES: COc1ncc(-c2cn3c(=O)ccnc3cc2C)cc1NS(=O)(=O)c1ccc(F)cc1Cl] | 475 |
| 129 | 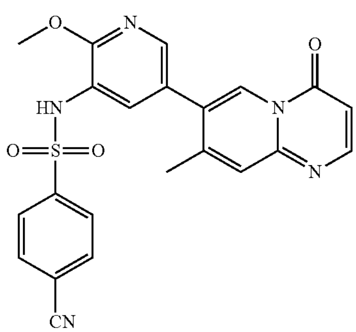 [SMILES: COc1ncc(-c2cn3c(=O)ccnc3cc2C)cc1NS(=O)(=O)c1ccc(C#N)cc1] | 448 |
| 130 | 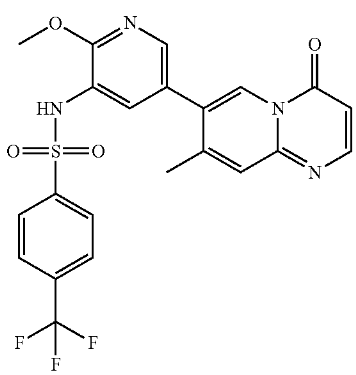 [SMILES: COc1ncc(-c2cn3c(=O)ccnc3cc2C)cc1NS(=O)(=O)c1ccc(C(F)(F)F)cc1] | 491 |
| 131 | 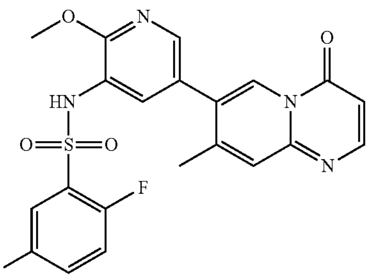 | 459 |

Scheme 13:

Reaction conditions: a) 1-chloro-pyrrolidine-2,5-dione, N,N-dimethylformamide; b) R boric acid (borate), potassium carbonate, palladium catalyst (palladium tetrakistriphenylphosphine, etc.), dioxane, water, heating.

Example 132

N-(5-(3-chloro-4-oxo-4H-pyrido[1,2-a]pyrimidin-7-yl)-2-methoxypyridin-3-yl)-2,4-difluorobenzsulfamide compound 132 a) 7-bromo-3-chloro-4H-pyrido[1,2-a]pyrimidin-4-one 1-chloro-pyrrolidine-2,5-dione (500 mg, 3.75 mmol) was added to the solution of 7-bromo-4H-pyrido[1,2-a]pyrimidin-4-one (800 mg, 3.57 mmol) in N,N-dimethylformamide (10 mL). The reaction mixture was stirred at 25° C. for 14 hours. The reaction solution was then poured into water (10 mL), and extracted with dichloromethane (15 mL) three times. The resulting dichloromethane organic phase was concentrated to give the crude product which was separated by a silica gel column to give an off-white solid (600 mg, 65%).

1H NMR (400 MHz, CDCl$_3$) ppm δ 9.228-9.224 (d, 1H), 8.496 (s, 1H), 7.831-7.801 (m, 1H), 7.616-7.581 (m, 1H).

b) N-(5-(3-chloro-4-oxo-4H-pyrido[1,2-a]pyrimidin-7-yl)-2-methoxypyridin-3-yl)-2,4-difluorobenzsulfamide 2,4-difluoro-N-(2-methoxy-5-(4,4,5,5-tetramethyl-1,3,2-dioxaborolan-2-yl)pyridin-3-yl)benzsulfamide (0.28 mmol), potassium carbonate (0.56 mmol) and [1,1'-bis(diphenylphosphino) ferrocene]palladium chloride (20 mg) were added to the solution of 7-bromo-8-methyl-4H-pyrido[1,2-a]pyrimidin-4-one (0.28 mmol) in dioxane (2 mL) and water (0.4 mL) under nitrogen. The reaction solution was at 100° C. under microwave for two hours and tracked with liquid MS detection. After the reaction was complete, the reaction solution was filtered and the filtrate was concentrated to give the crude product which was isolated by preparative LC column to give the title compound.

1H NMR (400 MHz, DMSO-d$_6$) ppm δ 10.415 (s, 1H), 9.087-9.084 (d, 2H), 8.618 (s, 1H), 8.487-8.481 (d, 1H), 8.361-8.357 (d, 1H), 8.338 (s, 1H), 8.028-8.022 (s, 1H), 7.883-7.860 (d, 1H), 7.792-7.775 (d, 1H), 7.597-7.575 (d, 1H), 7.242-7.226 (d, 1H), 3.687 (s, 3H).

The following 37 compounds were also synthesized by reference to the preparation of compound 132.

| compound | structure | MS(ES) [M + H]$^+$ |
|---|---|---|
| 133 | 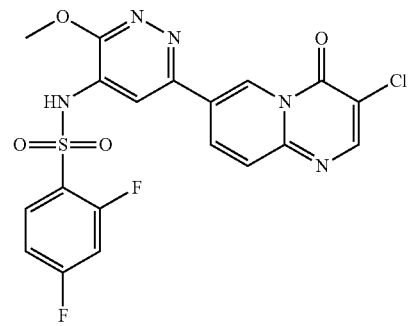 [SMILES: COc1nnc(-c2ccc3ncc(Cl)c(=O)n3c2)cc1NS(=O)(=O)c1ccc(F)cc1F] | 480 |
| 134 | 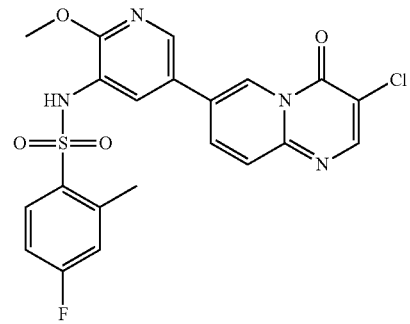 [SMILES: COc1ncc(-c2ccc3ncc(Cl)c(=O)n3c2)cc1NS(=O)(=O)c1ccc(F)cc1C] | 475 |
| 135 | 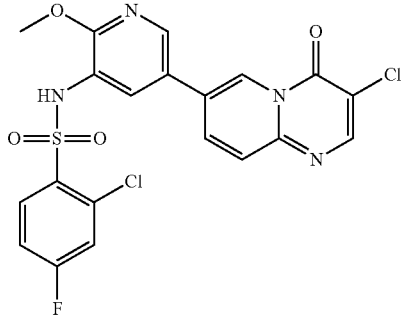 [SMILES: COc1ncc(-c2ccc3ncc(Cl)c(=O)n3c2)cc1NS(=O)(=O)c1ccc(F)cc1Cl] | 495 |
| 136 | 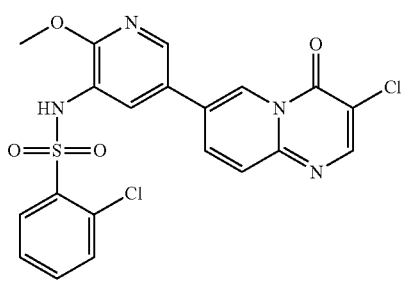 [SMILES: COc1ncc(-c2ccc3ncc(Cl)c(=O)n3c2)cc1NS(=O)(=O)c1ccccc1Cl] | 477 |
| 137 | 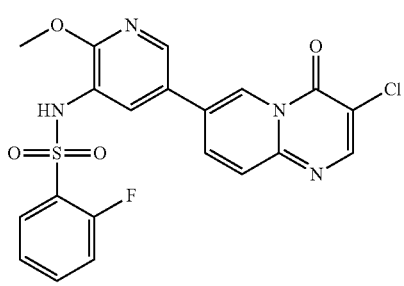 [SMILES: COc1ncc(-c2ccc3ncc(Cl)c(=O)n3c2)cc1NS(=O)(=O)c1ccccc1F] | 461 |
| 138 | 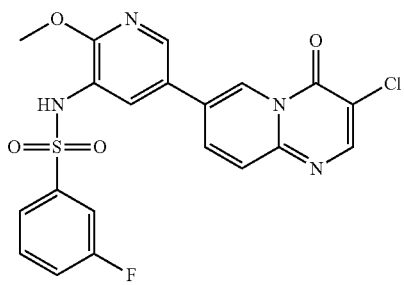 [SMILES: COc1ncc(-c2ccc3ncc(Cl)c(=O)n3c2)cc1NS(=O)(=O)c1cccc(F)c1] | 461 |
| 139 | 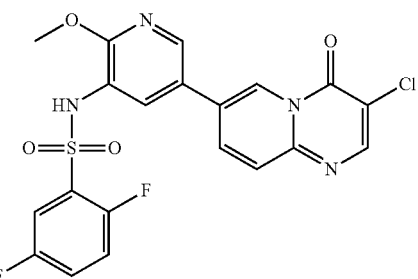 | 479 |

| compound | structure | MS(ES) [M + H]+ |
|---|---|---|
| 140 | 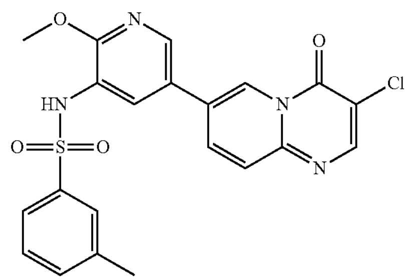 [SMILES: COc1ncc(-c2ccc3ncc(Cl)c(=O)n3c2)cc1NS(=O)(=O)c1cccc(C)c1] | 457 |
| 141 | 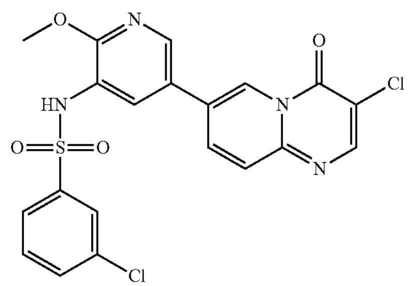 [SMILES: COc1ncc(-c2ccc3ncc(Cl)c(=O)n3c2)cc1NS(=O)(=O)c1cccc(Cl)c1] | 477 |
| 142 | 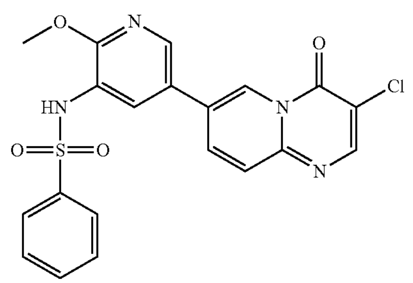 [SMILES: COc1ncc(-c2ccc3ncc(Cl)c(=O)n3c2)cc1NS(=O)(=O)c1ccccc1] | 443 |
| 143 | 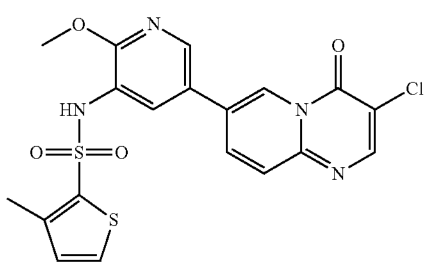 [SMILES: COc1ncc(-c2ccc3ncc(Cl)c(=O)n3c2)cc1NS(=O)(=O)c1sccc1C] | 463 |
| 144 | 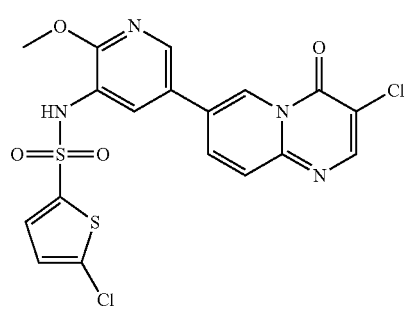 | 483 |

| compound | structure | MS(ES) [M + H]+ |
|---|---|---|
| 145 | 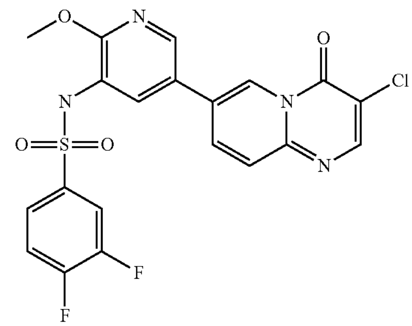 [SMILES: COc1ncc(-c2ccc3ncc(Cl)c(=O)n3c2)cc1NS(=O)(=O)c1ccc(F)c(F)c1] | 479 |
| 146 | 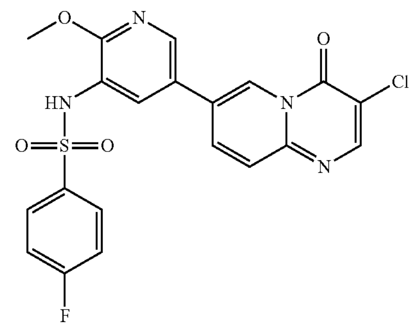 [SMILES: COc1ncc(-c2ccc3ncc(Cl)c(=O)n3c2)cc1NS(=O)(=O)c1ccc(F)cc1] | 461 |
| 147 | 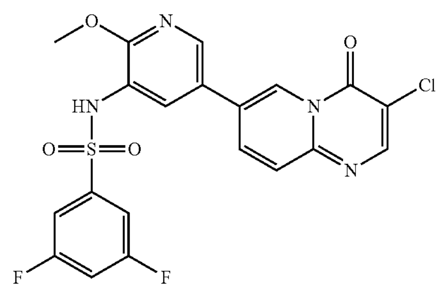 [SMILES: COc1ncc(-c2ccc3ncc(Cl)c(=O)n3c2)cc1NS(=O)(=O)c1cc(F)cc(F)c1] | 479 |
| 148 | 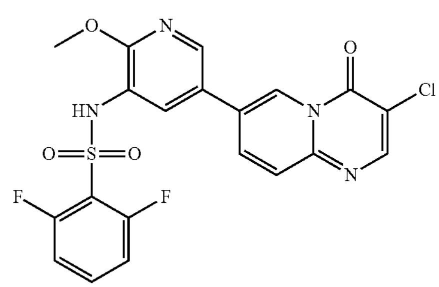 [SMILES: COc1ncc(-c2ccc3ncc(Cl)c(=O)n3c2)cc1NS(=O)(=O)c1c(F)cccc1F] | 479 |
| 149 | 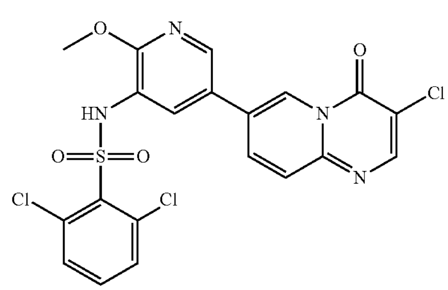 [SMILES: COc1ncc(-c2ccc3ncc(Cl)c(=O)n3c2)cc1NS(=O)(=O)c1c(Cl)cccc1Cl] | 511 |

| compound | structure | MS(ES) [M + H]+ |
|---|---|---|
| 150 | 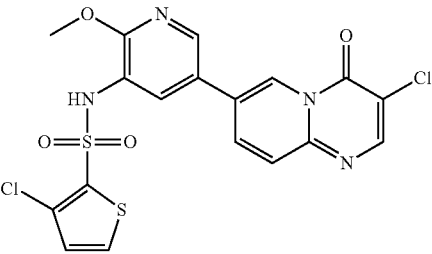 [SMILES: COc1ncc(-c2ccc3ncc(Cl)c(=O)n3c2)cc1NS(=O)(=O)c1sccc1Cl] | 483 |
| 151 | 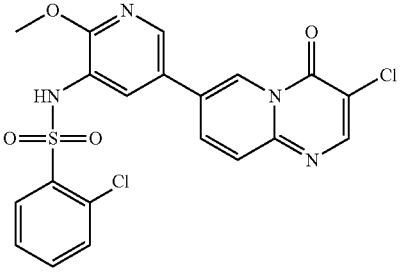 [SMILES: COc1ncc(-c2ccc3ncc(Cl)c(=O)n3c2)cc1NS(=O)(=O)c1ccccc1Cl] | 468 |
| 152 | 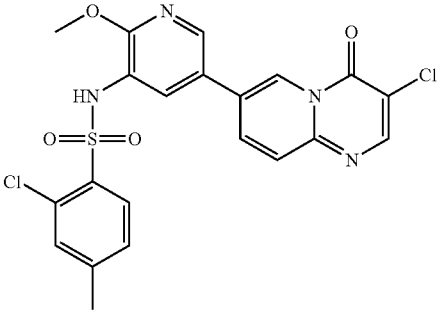 [SMILES: COc1ncc(-c2ccc3ncc(Cl)c(=O)n3c2)cc1NS(=O)(=O)c1ccc(C)cc1Cl] | 491 |
| 153 | 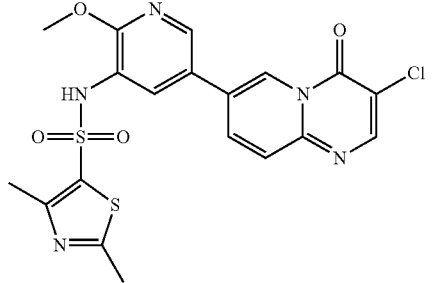 [SMILES: COc1ncc(-c2ccc3ncc(Cl)c(=O)n3c2)cc1NS(=O)(=O)c1sc(C)nc1C] | 478 |
| 154 | 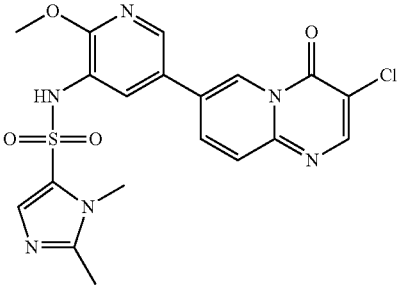 [SMILES: COc1ncc(-c2ccc3ncc(Cl)c(=O)n3c2)cc1NS(=O)(=O)c1cnc(C)n1C] | 461 |
| compound | structure | MS(ES) [M + H]+ |
|---|---|---|
| 155 | 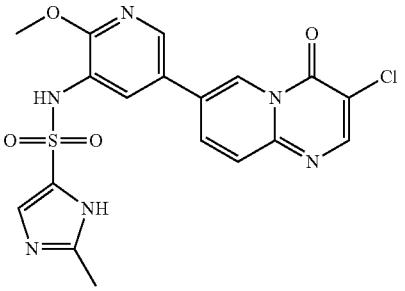 [SMILES: COc1ncc(-c2ccc3ncc(Cl)c(=O)n3c2)cc1NS(=O)(=O)c1cnc(C)[nH]1] | 447 |
| 156 | 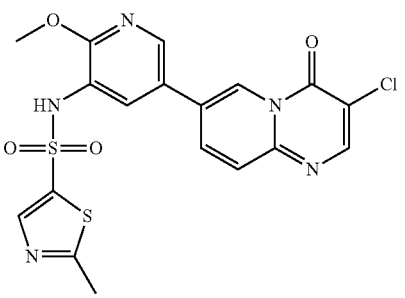 [SMILES: COc1ncc(-c2ccc3ncc(Cl)c(=O)n3c2)cc1NS(=O)(=O)c1cnc(C)s1] | 464 |
| 157 | 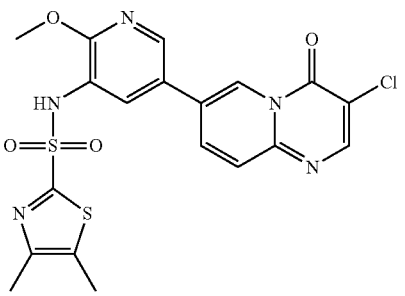 [SMILES: COc1ncc(-c2ccc3ncc(Cl)c(=O)n3c2)cc1NS(=O)(=O)c1nc(C)c(C)s1] | 478 |
| 158 | 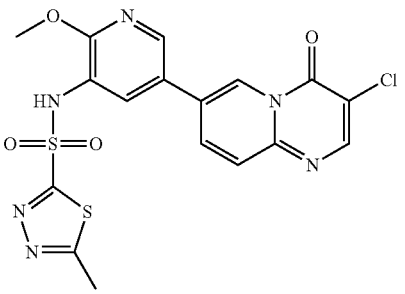 [SMILES: COc1ncc(-c2ccc3ncc(Cl)c(=O)n3c2)cc1NS(=O)(=O)c1nnc(C)s1] | 465 |
| 159 | 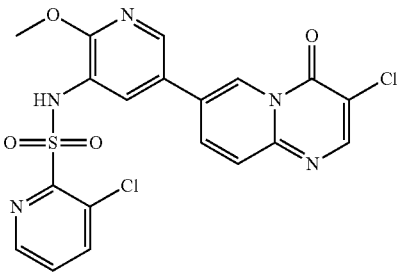 [SMILES: COc1ncc(-c2ccc3ncc(Cl)c(=O)n3c2)cc1NS(=O)(=O)c1ncccc1Cl] | 478 |

-continued

| compound | structure | MS(ES) [M + H]+ |
|---|---|---|
| 160 | 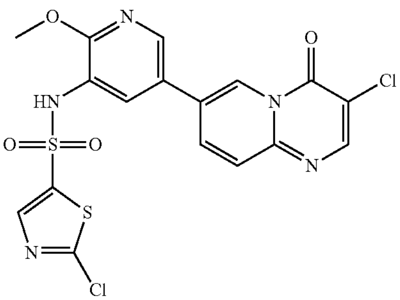 [SMILES: COc1ncc(-c2ccc3ncc(Cl)c(=O)n3c2)cc1NS(=O)(=O)c1cnc(Cl)s1] | 484 |
| 161 | 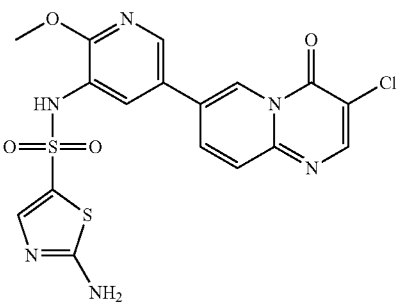 [SMILES: COc1ncc(-c2ccc3ncc(Cl)c(=O)n3c2)cc1NS(=O)(=O)c1cnc(N)s1] | 465 |
| 162 | 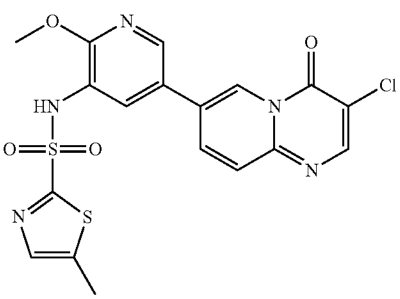 [SMILES: COc1ncc(-c2ccc3ncc(Cl)c(=O)n3c2)cc1NS(=O)(=O)c1ncc(C)s1] | 464 |
| 163 | 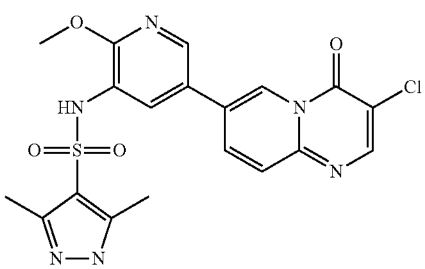 [SMILES: COc1ncc(-c2ccc3ncc(Cl)c(=O)n3c2)cc1NS(=O)(=O)c1c(C)n[nH]c1C] | 461 |
| 164 | 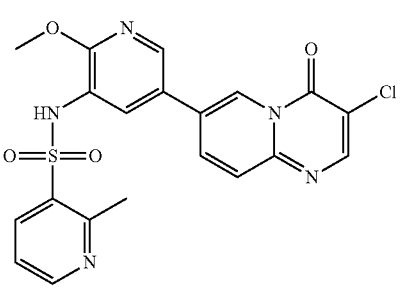 [SMILES: COc1ncc(-c2ccc3ncc(Cl)c(=O)n3c2)cc1NS(=O)(=O)c1cccnc1C] | 458 |

-continued

| compound | structure | MS(ES) [M + H]+ |
|---|---|---|
| 165 | 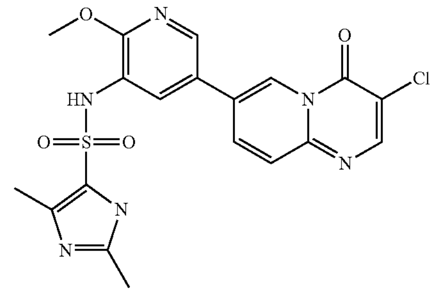 [SMILES: COc1ncc(-c2ccc3ncc(Cl)c(=O)n3c2)cc1NS(=O)(=O)c1[nH]c(C)nc1C] | 461 |
| 166 | 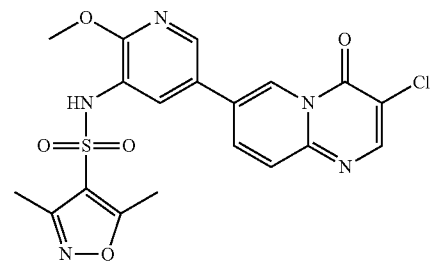 [SMILES: COc1ncc(-c2ccc3ncc(Cl)c(=O)n3c2)cc1NS(=O)(=O)c1c(C)noc1C] | 462 |
| 167 | 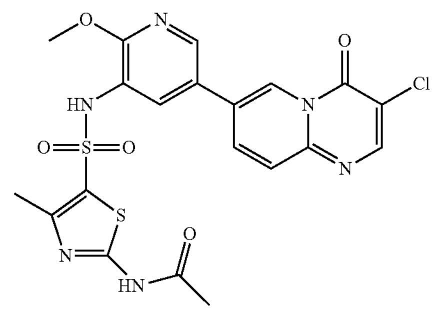 [SMILES: COc1ncc(-c2ccc3ncc(Cl)c(=O)n3c2)cc1NS(=O)(=O)c1sc(NC(C)=O)nc1C] | 521 |
| 168 | 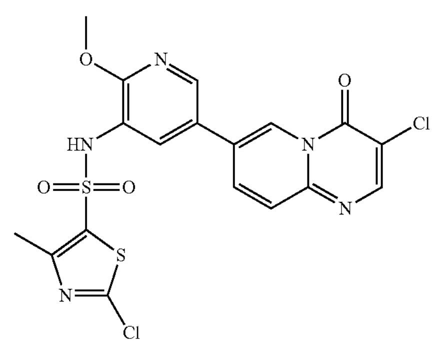 [SMILES: COc1ncc(-c2ccc3ncc(Cl)c(=O)n3c2)cc1NS(=O)(=O)c1sc(Cl)nc1C] | 498 |
| 169 | 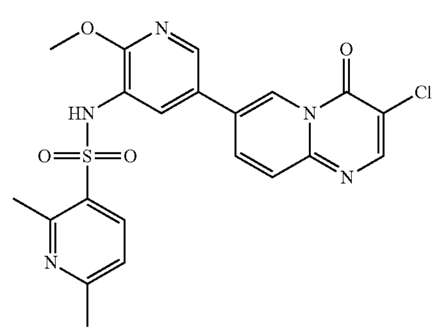 [SMILES: COc1ncc(-c2ccc3ncc(Cl)c(=O)n3c2)cc1NS(=O)(=O)c1ccc(C)nc1C] | 472 |

87
-continued

| compound | structure | MS(ES) [M + H]+ |
|---|---|---|
| 170 | 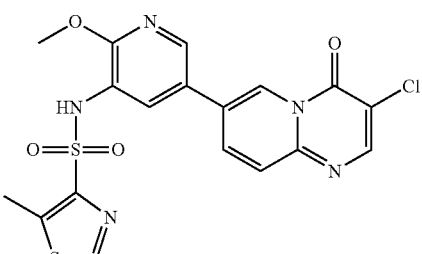 | 479 |

Scheme 14:

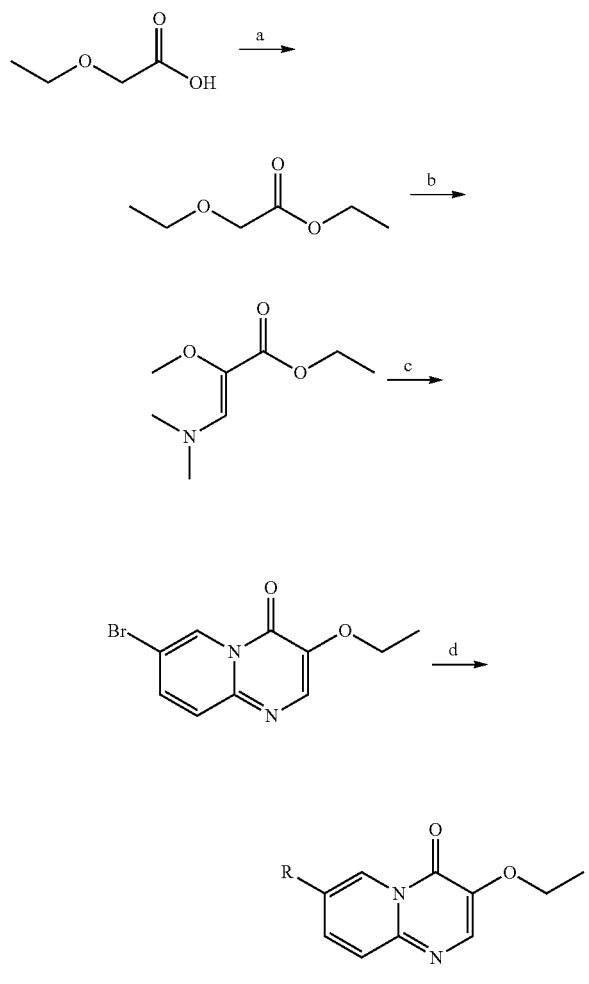

Reaction conditions: a) sulfuric acid, ethanol, heating; b) 1-tert-butoxy-N,N,N',N'-tetraethyldiamine, heating; c) 5-bromopyridin-2-amine, acetic acid, heating; d) R boric acid (borate), palladium reagent (tetrakistriphenylphosphine palladium, [1,1'-bis(diphenylphosphino)ferrocene]palladium chloride, etc.), potassium carbonate, dioxane, water, heating.

88
Example 171

N-(5-(3-ethoxy-4-oxo-4H-pyrido[1,2-a]pyrimidin-7-yl)-2-methoxypyridin-3-yl)-2,4-difluorobenzsulfamide

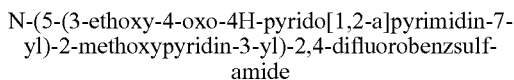
compound 171

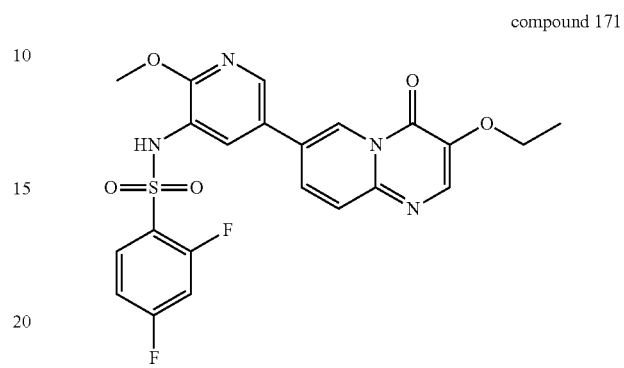

a) ethyl 2-ethoxyacetate

Sulfuric acid (10 mL) was added to the solution of 2-ethoxyacetic acid (20 g, 0.19 mol) in ethanol (200 mL). The resultant reaction solution was reacted at 100° C. for two hours. After the completion of the reaction, the reaction solution was concentrated and diluted with ethyl acetate. The resulting organic phase was rinsed with water twice, dried over anhydrous sodium sulfate and concentrated to a yellow oily liquid (19.5 g, 78%).

b) (Z)-ethyl-3-(dimethylamino)-2-methoxyacrylate 1-tert-butoxy-N,N,N',N'-tetraethyldiamine (2.0 g, 0.011 mol) and ethyl 2-ethoxyacetate (1.5 g, 0.011 mol) were mixed, heated to 80° C., stirred for 12 hours, and concentrated to give a yellow solid (420 mg, 20.4%).
1H NMR (400 MHz, CDCl$_3$) δ 6.80 (s, 1H), 4.19-4.13 (q, 2H), 4.05 (s, 1H), 3.71-3.76 (s, 1H), 3.03 (s, 6H), 1.26-1.29 (t, 6H).

c) 7-bromo-3-ethoxy-4H-pyrido[1,2-a]pyrimidin-4-one

A solution of (Z)-ethyl-3-(dimethylamino)-2-methoxyacrylate (50 mg, 0.267 mmol) and 5-bromopyridin-2-amine (46 mg, 0.267 mmol) in acetic acid was heated to 90° C. and stirred overnight. After the reaction was complete, the reaction solution was concentrated and water (2 mL) was added to dilute the concentrated solution. The pH was adjusted to 7 by saturated sodium carbonate solution and the mixture was extracted with dichloromethane. The organic phase was concentrated to give crude product. The crude product was isolated by flash chromatography column to give the title compound as a yellow solid.
1H NMR (400 MHz, CDCl$_3$) δ 9.11-9.12 (d, 1H), 8.08 (s, 1H), 7.54-7.56 (d, 1H), 7.46-7.48 (d, 1H), 4.2-4.25 (q, 2H), 2.11 (s, 3H).

d) N-(5-(3-ethoxy-4-oxo-4H-pyrido[1,2-a]pyrimidin-7-yl)-2-methoxypyridin-3-yl)-2,4-difluorobenzsulfamide 2,4-difluoro-N-(2-methoxy-5-(4,4,5,5-tetramethyl-1,3,2-dioxaborolan-2-yl)pyridin-3-yl)benzsulfamide (0.28 mmol), potassium carbonate(0.56 mmol) and [1,1'-bis(diphenylphosphino) ferrocene]palladium chloride (20 mg) were added to the mixed solution of 7-bromo-8-methyl-4H-pyrido[1,2-a]pyrimidin-4-one (0.28 mmol) in dioxane (2 mL) and water (0.4 mL) under nitrogen. The reaction solution was placed at 100° C. under microwave for two hours. The reaction was tracked and monitored by LCMS. After completion of the reaction, the reaction mixture was filtered, and the filtrate was concentrated to give crude product which was separated by preparative liquid chromatography to give the title compound.

1H NMR (400 MHz, DMSO-$d_6$) ppm δ 10.4 (s, 1H), 8.95 (s, 1H), 8.44 (s, 1H), 8.22 (s, 1H), 8.04-8.07 (d, 1H), 7.98 (s, 1H), 7.77-7.8 (t, 1H), 7.98 (s, 1H), 7.55-7.60 (t, 1H), 7.21-7.25 (t, 1H), 4.16-4.21 (q, 2H), 3.69 (q, 3H), 1.35-1.39 (t, 3H).

The following 3 compounds were also synthesized by reference to the preparation of compound 171.

Example 175

Scheme 15:

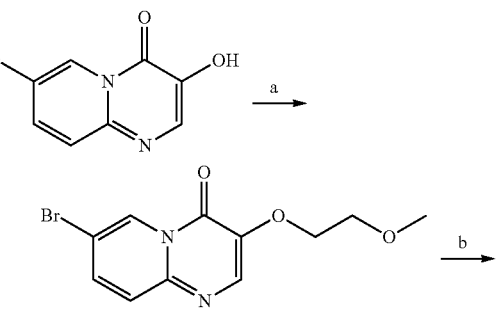

| compound | structure | MS(ES) [M + H]+ |
|---|---|---|
| 172 | 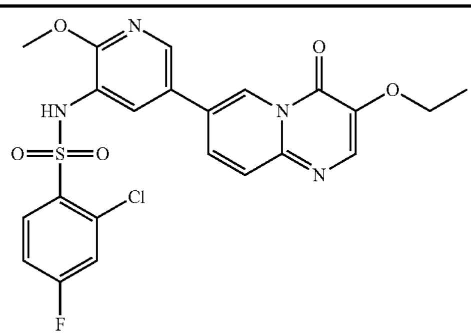 | 505 |
| 173 | 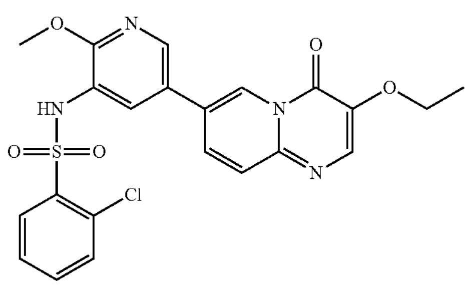 [SMILES: CCOc1cnc2ccc(-c3cnc(OC)c(NS(=O)(=O)c4ccccc4Cl)c3)cn2c1=O] | 487 |
| 174 | 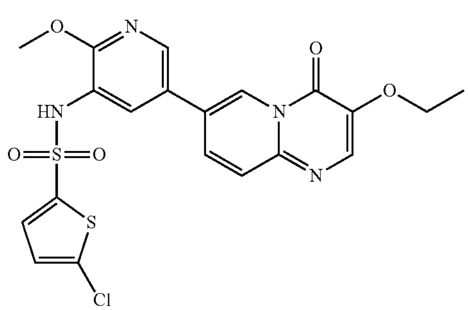 [SMILES: CCOc1cnc2ccc(-c3cnc(OC)c(NS(=O)(=O)c4ccc(Cl)s4)c3)cn2c1=O] | 493 |

91

-continued

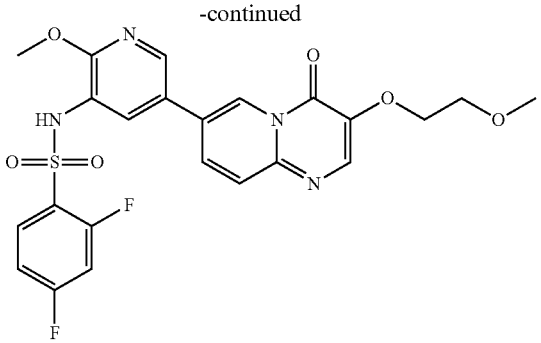

Conditions: a) 2-bromoethylmethyl ether, potassium carbonate, N,N-dimethylformamide, heating; b) R boric acid, (borate), palladium reagent (tetrakistriphenylphosphine palladium, [1,1'-bis(diphenylphosphino)ferrocene] palladium chloride, etc.), potassium carbonate, dioxane, water, heating.

2,4-difluoro-N-(2-methoxy-5-(3-(2-methoxyethoxy)-4-oxo-4H-pyrido[1,2-a]pyrimidin-7-yl)pyridin-3-yl)benzsulfamide compound 175

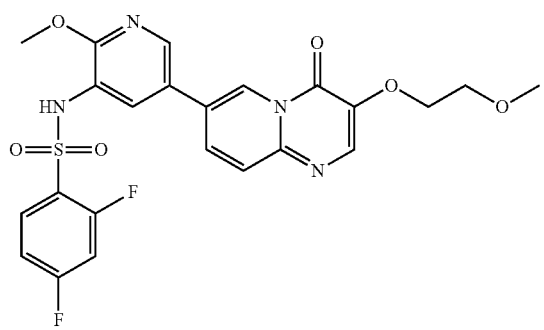

92 a) 7-bromo-3-(2-methoxyethoxy)-4H-pyrido[1,2-a]pyrimidin-4-one 7-bromo-3-hydroxy-4H-pyrido[1,2-a]pyrimidin-4-one (500 mg, 2.08 mmol), 2-bromoethyl methyl ether (350 mg, 2.45 mmol) and potassium carbonate(830 mg, 6.24 mmol) were dissolved in N,N-dimethylformamide (10 mL) and placed in a three-necked round-bottomed flask and stirred at 110° C. for 3 hours. The mixture was rinsed with water (10 mL), extracted with dichloromethane (20 mL×6), dried over anhydrous sodium sulfate, filtered, and concentrated to give the title compound as a yellow solid (250 mg, 40.4%).

b) 2,4-difluoro-N-(2-methoxy-5-(3-(2-methoxyethoxy)-4-oxo-4H-pyrido[1,2-a]pyrimidin-7-yl)pyridin-3-yl)benzsulfamide 7-bromo-3-(2-methoxyethoxy)-4H-pyrido[1,2-a]pyrimidin-4-one (200 mg, 0.67 mmol), 2,4-difluoro-N-(2-methoxy-5-(4,4,5,5-tetramethyl-1,3,2-dioxaborolan-2-yl)pyridin-3-yl)benzsulfamide (257 mg, 0.60 mmol) and potassium carbonate(185 mg, 1.34 mmol) were dissolved in dioxane (2.5 mL) and water (0.5 mL) and placed in a three-necked round-bottomed flask, and [1,1'-bis(diphenylphosphino)ferrocene]palladium chloride (49 mg, 0.067 mmol) was added under nitrogen at room temperature. The mixture was placed under microwave and stirred at 100° C. for 2 hours. Water (5 mL) was added to the mixture which was then extracted with dichloromethane (5 mL×3), dried over anhydrous sodium sulfate, filtered, and concentrated under low pressure. The crude product was purified by preparative HPLC to give the title product as a green solid (25 mg, 24.8%).

1H NMR (400 MHz, DMSO-$d_6$) ppm δ 8.944 (s, 1H), 8.413 (s, 1H), 8.231 (s, 1H), 8.069-8.046 (d, 1H), 7.962 (s, 1H), 7.791-7.755 (t, 1H), 7.723-7.700 (d, 2H), 7.562-7.539 (d, 1H), 7.235-7.197 (t, 1H), 4.248 (s, 2H), 3.680 (s, 5H).

The following 41 compounds were also synthesized by reference to the preparation of compound 175.

| compound | structure | MS(ES) [M + H]+ |
|---|---|---|
| 176 | 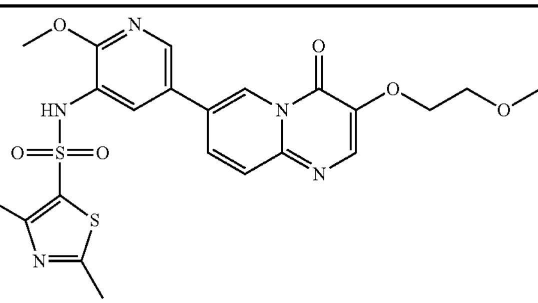 | 518 |
| 177 | 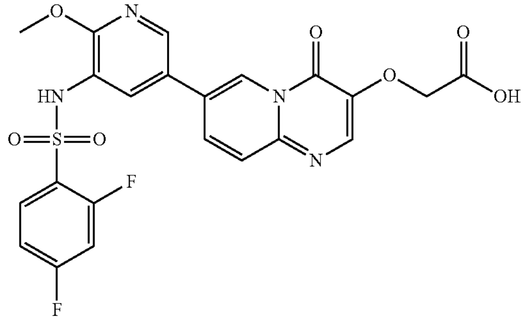 [SMILES: COc1ncc(-c2ccc3ncc(OCC(=O)O)c(=O)n3c2)cc1NS(=O)(=O)c1ccc(F)cc1F] | 519 |

-continued

| compound | structure | MS(ES) [M + H]+ |
|---|---|---|
| 178 | 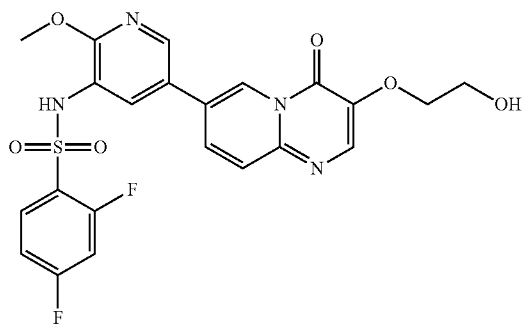 [SMILES: COc1ncc(-c2ccc3ncc(OCCO)c(=O)n3c2)cc1NS(=O)(=O)c1ccc(F)cc1F] | 505 |
| 179 | 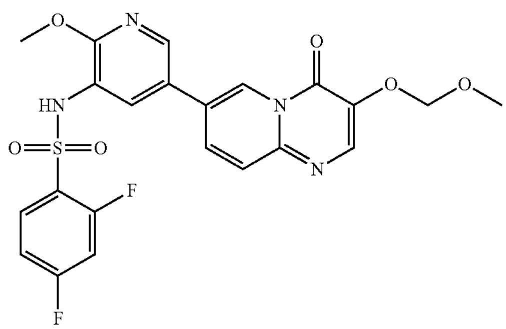 [SMILES: COCOc1cnc2ccc(-c3cnc(OC)c(NS(=O)(=O)c4ccc(F)cc4F)c3)cn2c1=O] | 505 |
| 180 | 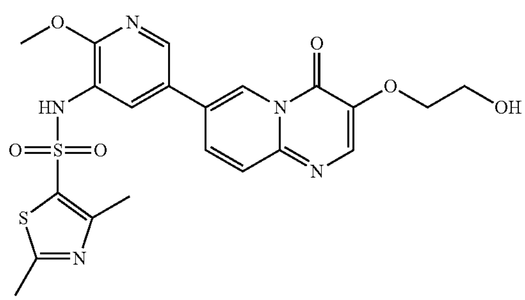 [SMILES: COc1ncc(-c2ccc3ncc(OCCO)c(=O)n3c2)cc1NS(=O)(=O)c1sc(C)nc1C] | 504 |
| 181 | 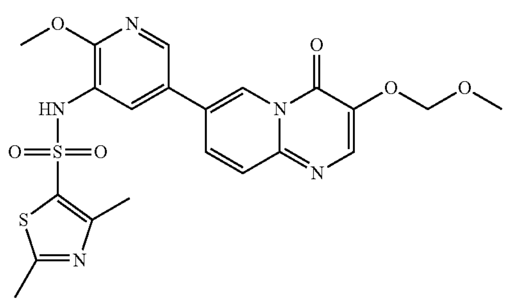 [SMILES: COCOc1cnc2ccc(-c3cnc(OC)c(NS(=O)(=O)c4sc(C)nc4C)c3)cn2c1=O] | 504 |
| 182 | 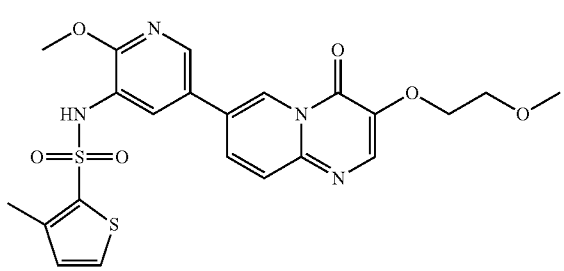 | 503 |

-continued

| compound | structure | MS(ES) [M + H]+ |
|---|---|---|
| 183 | 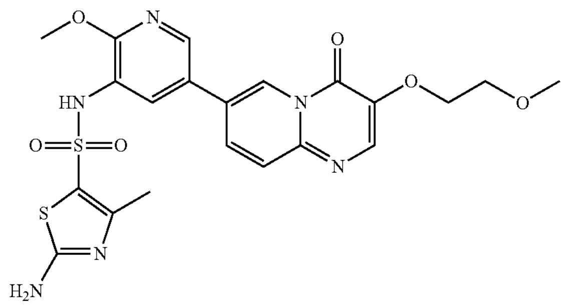 [SMILES: COCCOc1cnc2ccc(-c3cnc(OC)c(NS(=O)(=O)c4sc(N)nc4C)c3)cn2c1=O] | 519 |
| 184 | 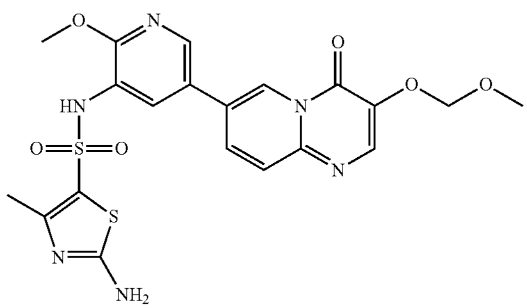 | 505 |
| 185 | 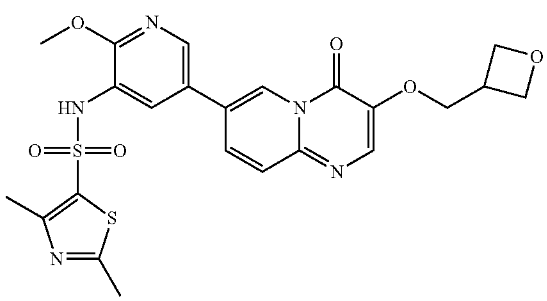 [SMILES: COc1ncc(-c2ccc3ncc(OCC4COC4)c(=O)n3c2)cc1NS(=O)(=O)c1sc(C)nc1C] | 530 |
| 186 | 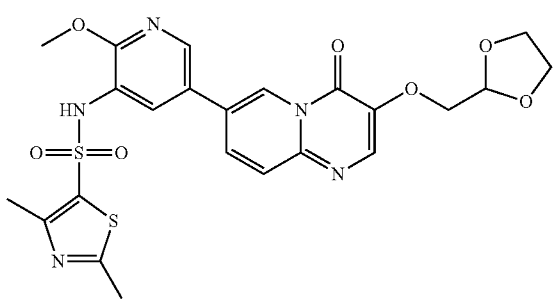 [SMILES: COc1ncc(-c2ccc3ncc(OCC4OCCO4)c(=O)n3c2)cc1NS(=O)(=O)c1sc(C)nc1C] | 546 |
| 187 | 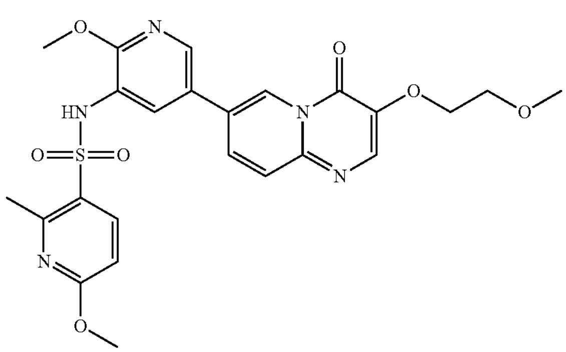 | 528 |

-continued

| compound | structure | MS(ES) [M + H]+ |
|---|---|---|
| 188 | 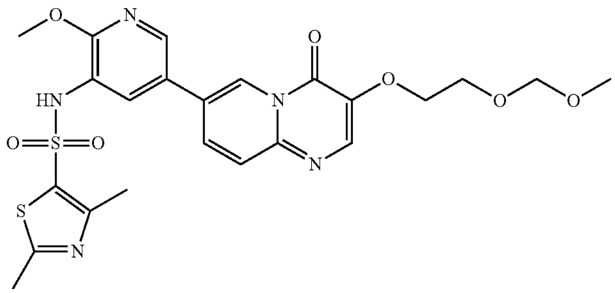 [SMILES: COCOCCOc1cnc2ccc(-c3cnc(OC)c(NS(=O)(=O)c4sc(C)nc4C)c3)cn2c1=O] | 548 |
| 189 | 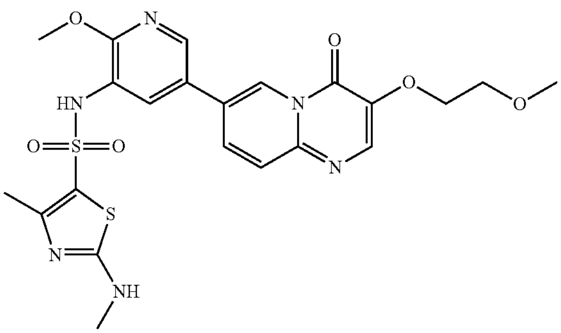 | 533 |
| 190 | 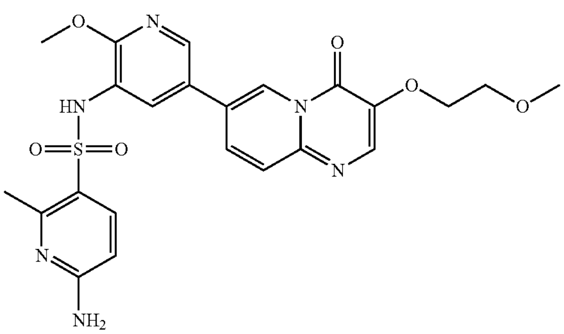 | 513 |
| 191 | 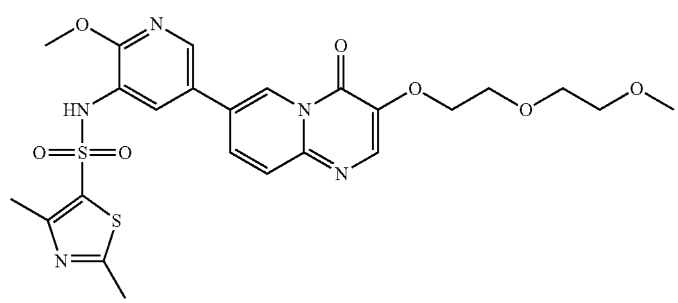 | 562 |
| 192 | 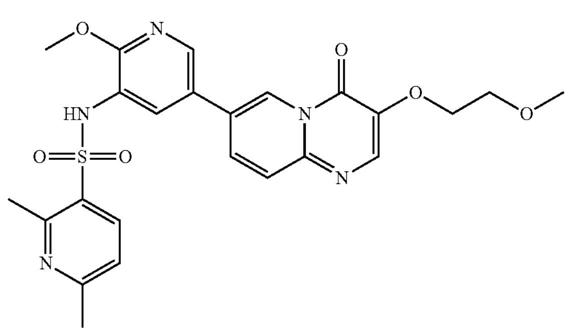 | 512 |

-continued

| compound | structure | MS(ES) [M + H]+ |
|---|---|---|
| 193 | 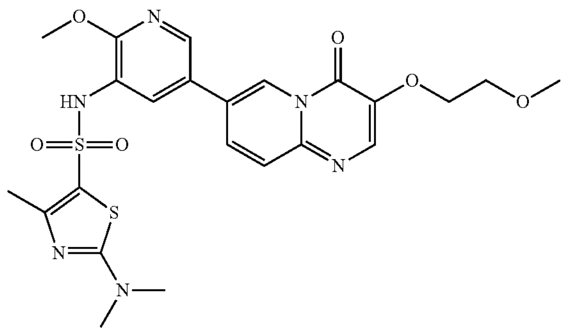 | 547 |
| 194 | 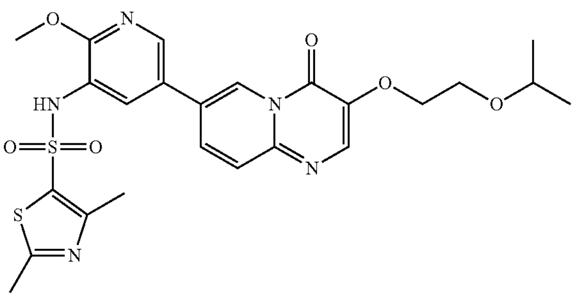 [SMILES: COc1ncc(-c2ccc3ncc(OCCOC(C)C)c(=O)n3c2)cc1NS(=O)(=O)c1sc(C)nc1C] | 546 |
| 195 | 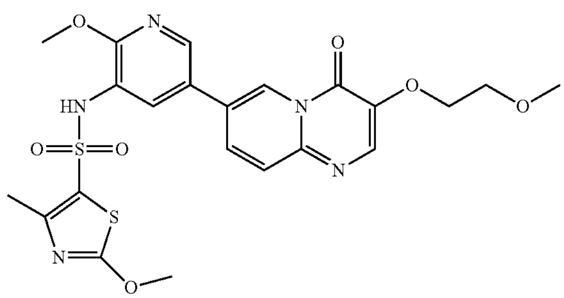 | 534 |
| 196 | 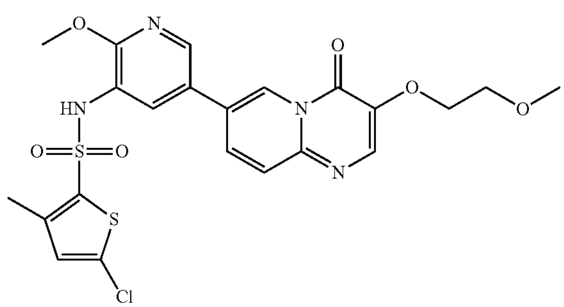 | 537 |
| 197 | 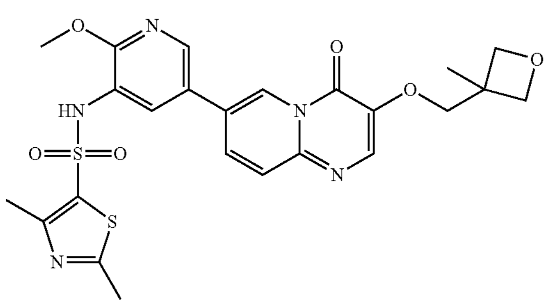 [SMILES: COc1ncc(-c2ccc3ncc(OCC4(C)COC4)c(=O)n3c2)cc1NS(=O)(=O)c1sc(C)nc1C] | 544 |

-continued

| compound | structure | MS(ES) [M + H]+ |
|---|---|---|
| 198 | 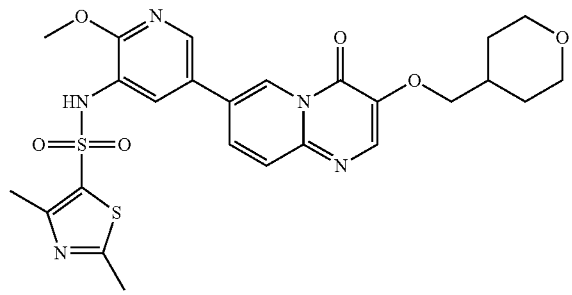 [SMILES: COc1ncc(-c2ccc3ncc(OCC4CCOCC4)c(=O)n3c2)cc1NS(=O)(=O)c1sc(C)nc1C] | 558 |
| 199 | 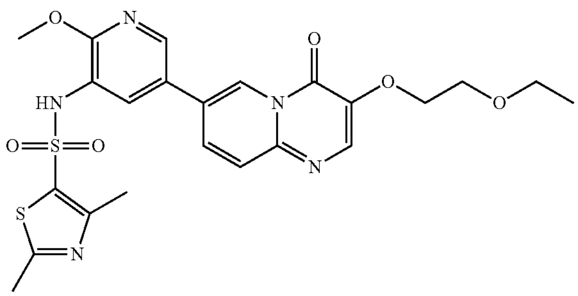 [SMILES: CCOCCOc1cnc2ccc(-c3cnc(OC)c(NS(=O)(=O)c4sc(C)nc4C)c3)cn2c1=O] | 532 |
| 200 | 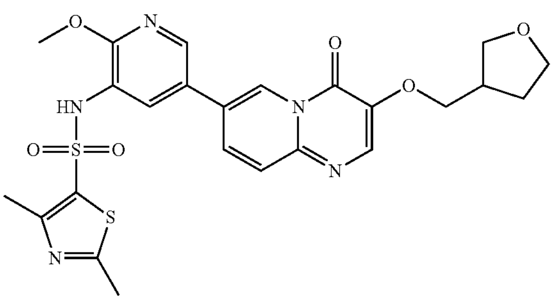 [SMILES: COc1ncc(-c2ccc3ncc(OCC4CCOC4)c(=O)n3c2)cc1NS(=O)(=O)c1sc(C)nc1C] | 544 |
| 201 | 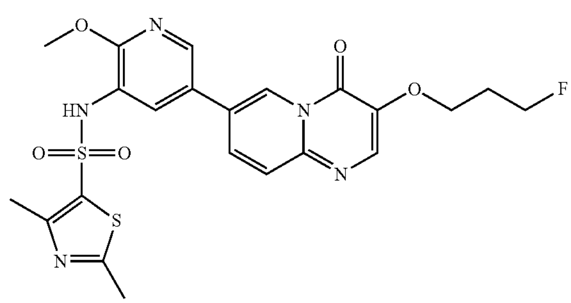 [SMILES: COc1ncc(-c2ccc3ncc(OCCCF)c(=O)n3c2)cc1NS(=O)(=O)c1sc(C)nc1C] | 520 |
| 202 | 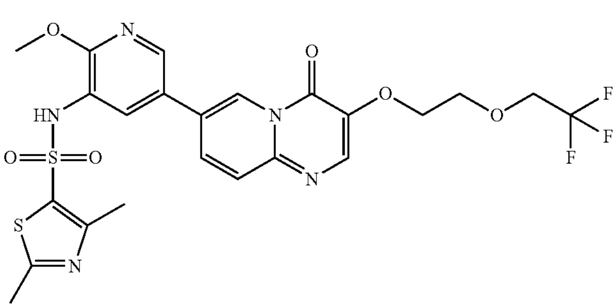 [SMILES: COc1ncc(-c2ccc3ncc(OCCOCC(F)(F)F)c(=O)n3c2)cc1NS(=O)(=O)c1sc(C)nc1C] | 586 |

-continued

| compound | structure | MS(ES) [M + H]+ |
|---|---|---|
| 203 | 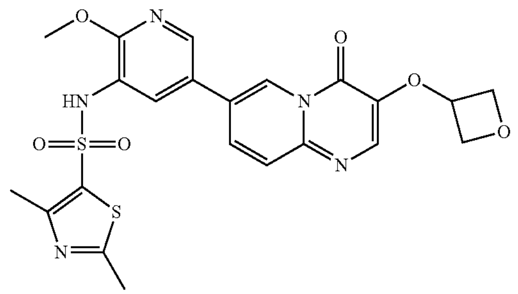 [SMILES: COc1ncc(-c2ccc3ncc(OC4COC4)c(=O)n3c2)cc1NS(=O)(=O)c1sc(C)nc1C] | 516 |
| 204 | 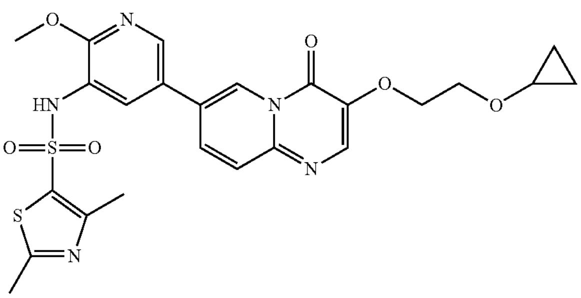 [SMILES: COc1ncc(-c2ccc3ncc(OCCOC4CC4)c(=O)n3c2)cc1NS(=O)(=O)c1sc(C)nc1C] | 544 |
| 205 | 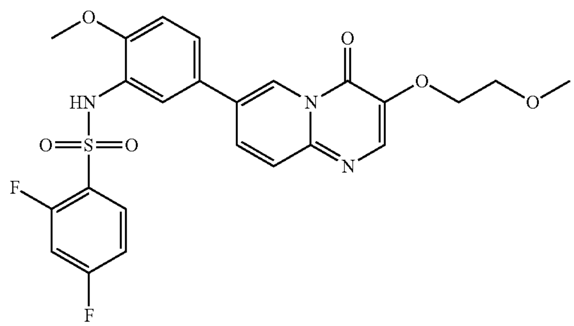 [SMILES: COCCOc1cnc2ccc(-c3ccc(OC)c(NS(=O)(=O)c4ccc(F)cc4F)c3)cn2c1=O] | 518 |
| 206 | 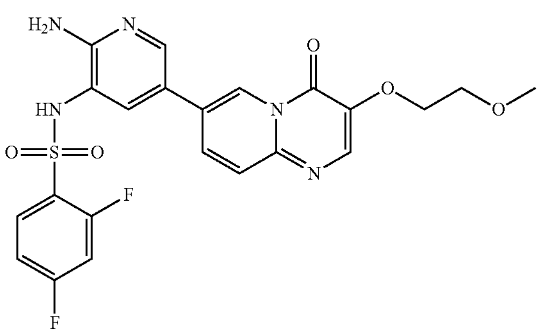 [SMILES: COCCOc1cnc2ccc(-c3cnc(N)c(NS(=O)(=O)c4ccc(F)cc4F)c3)cn2c1=O] | 504 |
| 207 (the former) | 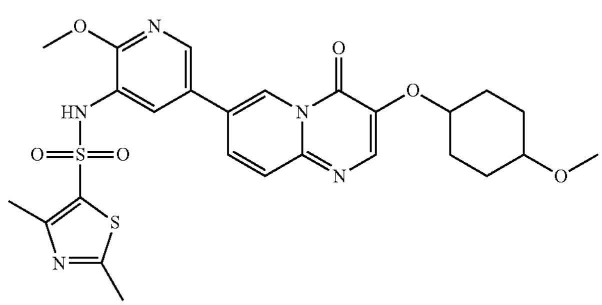 | 572 |

| compound | structure | MS(ES) [M + H]+ |
|---|---|---|
| 208 (the latter) | 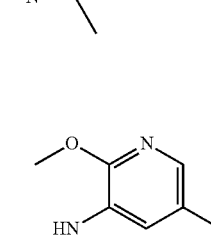 | 572 |
| 209 | 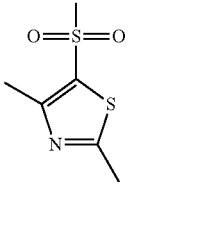 | 546 |
| 210 | 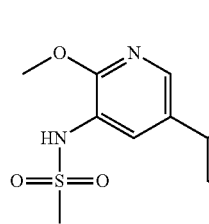 | 421 |
| 211 | 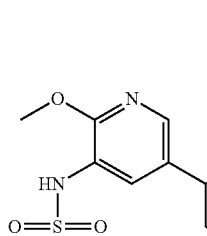 | 447 |
| 212 | 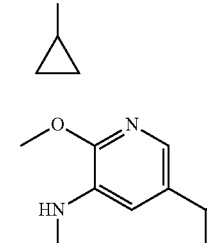 | 489 |

-continued
| compound | structure | MS(ES) [M + H]+ |
|---|---|---|
| 213 | 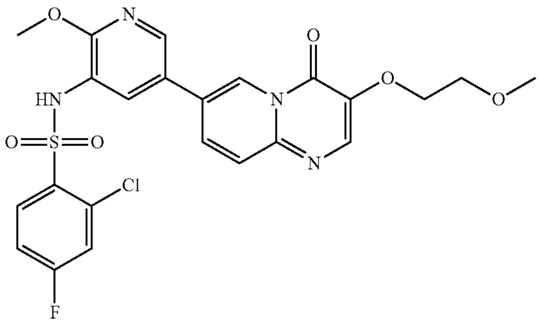 | 535 |
| 214 | 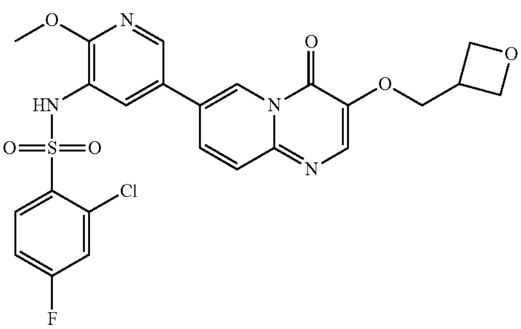 [SMILES: COc1ncc(-c2ccc3ncc(OCC4COC4)c(=O)n3c2)cc1NS(=O)(=O)c1ccc(F)cc1Cl] | 547 |
| 215 | 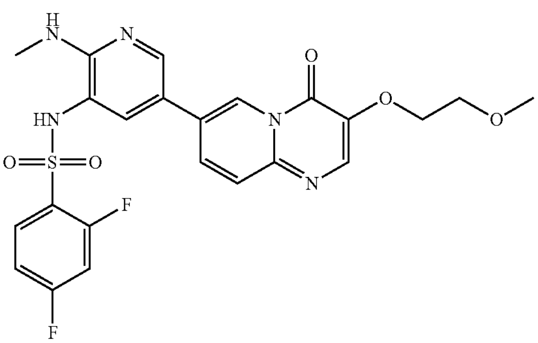 [SMILES: CNc1ncc(-c2ccc3ncc(OCCOC)c(=O)n3c2)cc1NS(=O)(=O)c1ccc(F)cc1F] | 518 |
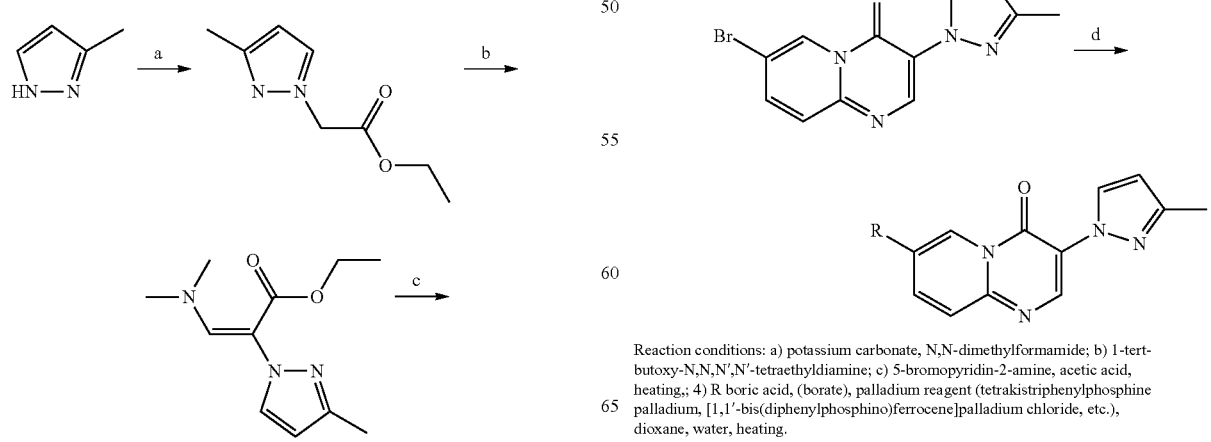
Reaction conditions: a) potassium carbonate, N,N-dimethylformamide; b) 1-tert-butoxy-N,N,N',N'-tetraethyldiamine; c) 5-bromopyridin-2-amine, acetic acid, heating,; 4) R boric acid, (borate), palladium reagent (tetrakistriphenylphosphine palladium, [1,1'-bis(diphenylphosphino)ferrocene]palladium chloride, etc.), dioxane, water, heating.

Example 216

2,4-difluoro-N-(2-methoxy-5-(3-(3-methyl-1H-pyrazol-1-yl)-4-oxo-4H-pyrido[1,2-a]pyrimidin-7-yl)pyridin-3-yl)benzsulfamide

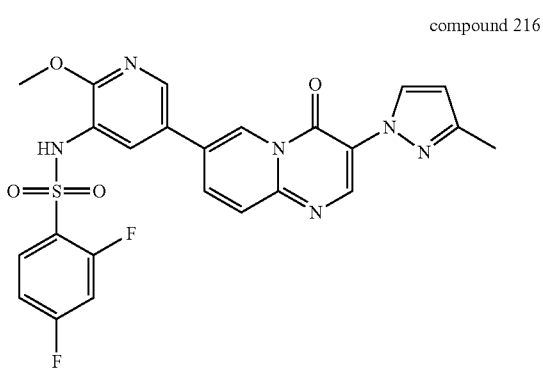 [SMILES: COc1ncc(-c2ccc3ncc(-n4ccc(C)n4)c(=O)n3c2)cc1NS(=O)(=O)c1ccc(F)cc1F]

compound 216 a) ethyl 2-(3-methyl-1H-pyrazol-1-yl)acetate

The solution of 3-methyl-1-H-pyrazole (30 g, 365.9 mmol), ethyl bromoacetate (66.8 g, 402.4 mmol) and potassium carbonate (101 g, 731.8 mmol) in N,N-dimethylformamide (300 mL) in a round bottom flask was refluxed overnight. The reaction solution was cooled and then diluted with 100 mL of water and extracted with dichloromethane (100 mL×3). The resulting dichloromethane organic phase was dried over sodium sulfate and concentrated to give crude product. The crude product was isolated by silica gel chromatography column to give a yellow oily liquid (11 g, 18.03%).

1H NMR (400 MHz, CDCl$_3$) ppm δ 7.43-7.35 (q, 1H), 6.10-6.07 (q, 1H), 4.84-4.82 (d, 2H), 4.25-4.20 (s, 2H), 2.36-2.26 (q, 3H), 1.29-1.26 (q, 3H).

b) (E)-ethyl-3-(dimethylamino)-2-(3-methyl-1H-pyrazol-1-yl)acrylate

Ethyl 2-(3-methyl-1H-pyrazol-1-yl)acetate (4 g, 23.8 mmol) and 1-tert-butoxy-N,N,N',N'-tetraethyldiamine (4.1 g, 23.8 mmol) were mixed and stirred at 100° C. overnight. The reaction mixture was concentrated to give a brown oily crude product (5 g, 94.34%).

1H NMR (400 MHz, CDCl$_3$) ppm δ 7.442 (s, 1H), 6.080 (s, 2H), 4.872-4.853 (d, 4H), 3.778-3.729 (t, 6H), 2.294-2.269 (d, 2H).

c) 7-bromo-3-(3-methyl-1H-pyrazol-1-yl)-4H-pyrido[1,2-a]pyrimidin-4-one

The solution of (E)-ethyl-3-(dimethylamino)-2-(3-methyl-1H-pyrazol-1-yl)acrylate (3.5 g, 150.2 mmol) and 5-bromopyridin-2-amine (2.6 g, 150.2 mmol) in acetic acid (30 mL) in a round bottom flask was placed at 100° C. under microwave for two hours. The reaction mixture was concentrated and then diluted with 50 mL of water and extracted with dichloromethane (50 mL). The resulting dichloromethane organic phase was dried over sodium sulfate and concentrated to give crude product. The crude product was isolated by silica gel column chromatography to give a yellow solid (1.3 g, 28.4%).

1H NMR (400 MHz, CDCl$_3$) ppm δ 9.160 (s, 1H), 8.622-8.616 (d, 1H), 8.327-8.322 (d, 1H), 7.772-7.743 (m, 1H), 7.640-7.628 (m, 1H), 6.297-6.291 (s, 1H), 2.405 (s, 3H).

d) 2,4-difluoro-N-(2-methoxy-5-(3-(3-methyl-1H-pyrazol-1-yl)-4-oxo-4H-pyrido[1,2-a]pyrimidin-7-yl)pyridin-3-yl)benzsulfamide 2,4-difluoro-N-(2-methoxy-5(4,4,5,5-tetramethyl-1,3,2-dioxaborolan-2-yl)pyridin-3-yl)benzsulfamide (0.28 mmol), potassium carbonate (0.56 mmol) and [1,1'-bis(diphenylphosphino) ferrocene]palladium chloride (20 mg) were added to the mixed solution of 7-bromo-3-(3-methyl-1H-pyrazol-1-yl)-4H-pyrido[1,2-a]pyrimidin-4-one (0.28 mmol) in water (0.4 mL) and dioxane (2 mL) under nitrogen. The reaction solution was placed at 100° C. under microwave for two hours. The reaction was monitored by LCMS. After the completion of the reaction, the reaction solution was filtered and concentrated to give crude product which was separated by preparative liquid chromatography to give the title compound.

1H NMR (400 MHz, DMSO-d$_6$) ppm δ 9.159 (s, 1H), 8.945 (s, 1H), 8.582-8.577 (d, 1H), 8.334-8.277 (t, 2H), 7.939-7.889 (t, 2H), 7.837-7.820 (d, 1H), 7.519-7.473 (t, 1H), 7.236-7.195 (t, 1H), 6.376-6.371 (d, 1H), 3.736 (s, 3H), 2.314 (s, 1H).

The following 4 compounds were also synthesized by reference to the preparation of compound 216.

| compound | structure | MS(ES) [M + H]$^+$ |
|---|---|---|
| 217 | 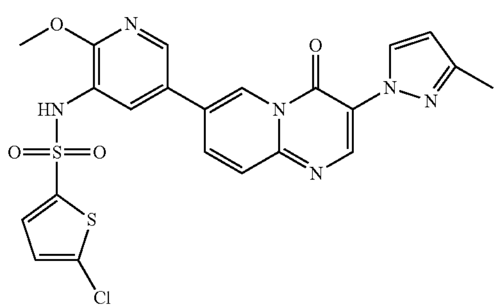 [SMILES: COc1ncc(-c2ccc3ncc(-n4ccc(C)n4)c(=O)n3c2)cc1NS(=O)(=O)c1ccc(Cl)s1] | 529 |

| compound | structure | MS(ES) [M + H]+ |
|---|---|---|
| 218 | 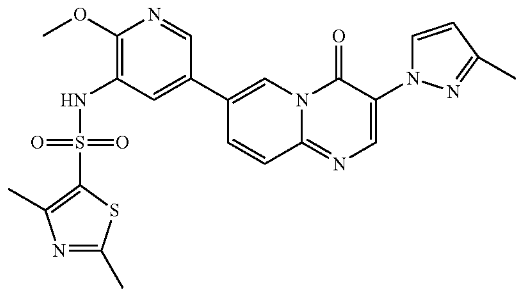 | 524 |
| 219 | 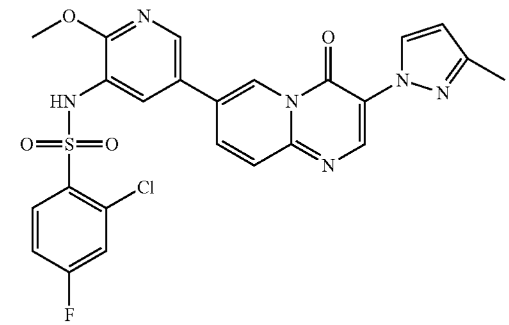 [SMILES: COc1ncc(-c2ccc3ncc(-n4ccc(C)n4)c(=O)n3c2)cc1NS(=O)(=O)c1ccc(F)cc1Cl] | 541 |
| 220 | 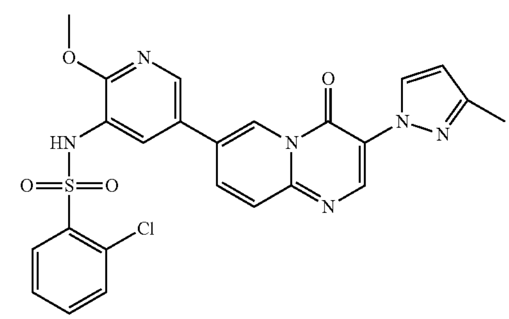 [SMILES: COc1ncc(-c2ccc3ncc(-n4ccc(C)n4)c(=O)n3c2)cc1NS(=O)(=O)c1ccccc1Cl] | 523 |

Scheme 17:

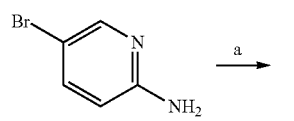
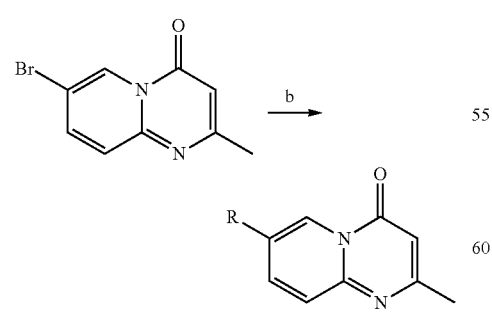

Reaction conditions: a) ethyl acetoacetate, polyphosphoric acid; b) R boric acid, (borate), palladium reagent (tetrakistriphenylphosphine palladium, [1,1′-bis(diphenylphosphino)ferrocene]palladium chloride, etc.), potassium carbonate, dioxane, water, heating.

Example 221

2,4-difluoro-N-(2-methoxy-5-(2-methyl-4-oxo-4H-pyrido[1,2-a]pyrimidin-7-yl)pyridin-3-yl)benzsulfamide compound 221

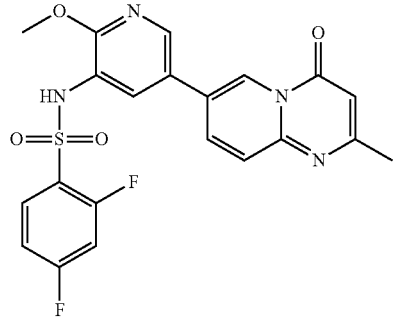

a)
7-bromo-2-methyl-4H-pyrido[1,2-a]pyrimidin-4-one

The mixture containing 5-bromo-pyridin-2-amine hydrochloride (2 g, 11.63 mmol) and ethyl acetoacetate (2.3 g, 17.44 mmol) was dissolved in polyphosphoric acid (10 mL) and stirred at 150° C. for 30 minutes. The mixture was rinsed with ethyl acetate and then sodium hydroxide solution was added to adjust PH value of the mixed system to greater than 9. The ethyl acetate solution was separated, and the aqueous phase was extracted with ethyl acetate (20 mL×3). The combined organic phases were dried over anhydrous sodium sulfate, dried by rotary evaporation, and isolated by column to give the title compound as a yellow solid (3.2 g, 70%).
1H NMR (400 MHz, CDCl$_3$) ppm δ 9.15 (s, 1H), 7.76-7.78 (d, 1H), 7.50-7.52 (d, 2H), 6.36 (s, 1H), 2.47 (s, 3H).

b) 2,4-difluoro-N-(2-methoxy-5-(2-methyl-4-oxo-4H-pyrido[1,2-a]pyrimidin-7-yl)pyridin-3-yl)benzsulfamide 7-bromo-2-methyl-4H-pyrido[1,2-a]pyrimidin-4-one (0.28 mmol) was dissolved in dioxane (2 mL) and water (0.4 mL) and then 2,4-difluoro-N-(2-methoxy-5-(4,4,5,5-tetramethyl-1,3,2-dioxaborolan-2-yl)pyridin-3-yl)bensulfamide (0.28 mmol), potassium carbonate (0.56 mmol) and 1,1'-bis (diphenylphosphino) ferrocene palladium chloride (20 mg) were added to the mixed solution under nitrogen. The reaction mixture was placed under microwave and stirred at 100° C. for two hours. LCMS showed that the reaction was complete. The mixture was filtered, and then dried by rotary evaporation to give crude product which was separated by preparative HPLC to give the title compound.
1H NMR (400 MHz, CD$_3$OD) ppm δ 9.13 (s, 1H), 8.31 (s, 1H), 8.21-8.23 (d, 1H), 8.01 (s, 1H), 7.91-7.93 (m, 1H), 7.73-7.75 (d, 1H), 7.22-7.27 (m, 1H), 7.10-7.14 (m, 1H), 6.43 (s, 1H), 3.87 (s, 3H), 2.50 (s, 3H).

The following 9 compounds were also synthesized by reference to the preparation of compound 221.

| compound | structure | MS(ES) [M + H]+ |
|---|---|---|
| 222 | | 475 |
| 223 | | 491 |
| 224 | 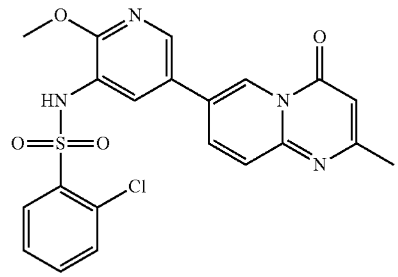 [SMILES: COc1ncc(-c2ccc3nc(C)cc(=O)n3c2)cc1NS(=O)(=O)c1ccccc1Cl] | 457 |
| 225 | 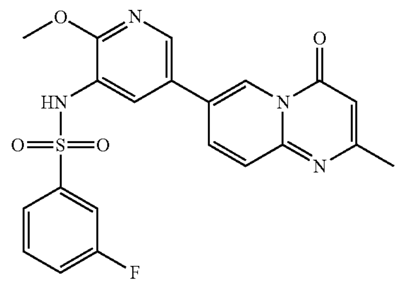 [SMILES: COc1ncc(-c2ccc3nc(C)cc(=O)n3c2)cc1NS(=O)(=O)c1cccc(F)c1] | 441 |
| 226 | 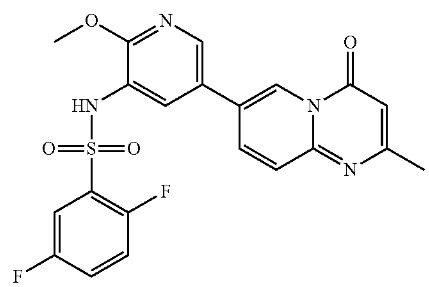 [SMILES: COc1ncc(-c2ccc3nc(C)cc(=O)n3c2)cc1NS(=O)(=O)c1cc(F)ccc1F] | 459 |
| 227 | 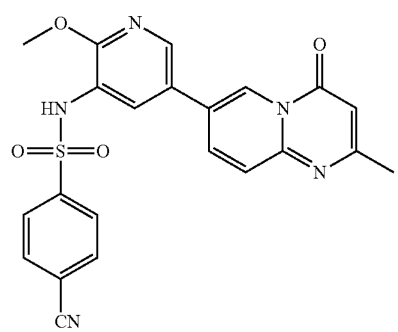 [SMILES: COc1ncc(-c2ccc3nc(C)cc(=O)n3c2)cc1NS(=O)(=O)c1ccc(C#N)cc1] | 448 |
| 228 | 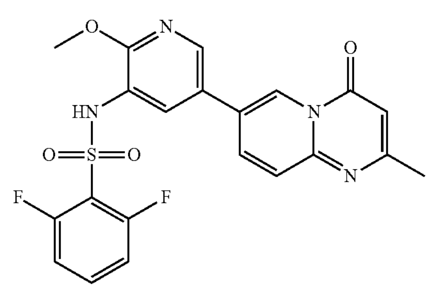 [SMILES: COc1ncc(-c2ccc3nc(C)cc(=O)n3c2)cc1NS(=O)(=O)c1c(F)cccc1F] | 459 |

115
-continued

| compound | structure | MS(ES) [M + H]+ |
|---|---|---|
| 229 | 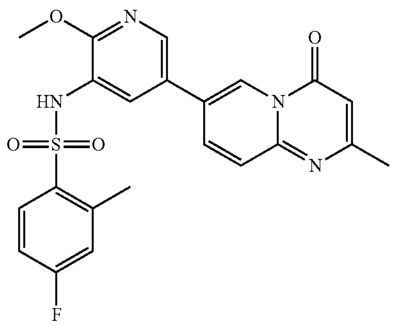 [SMILES: COc1ncc(-c2ccc3nc(C)cc(=O)n3c2)cc1NS(=O)(=O)c1ccc(F)cc1C] | 455 |
| 230 | 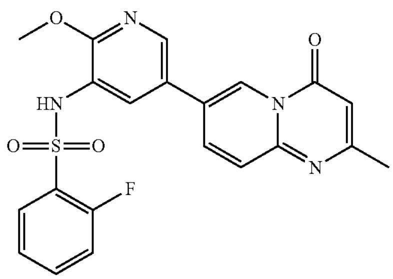 [SMILES: COc1ncc(-c2ccc3nc(C)cc(=O)n3c2)cc1NS(=O)(=O)c1ccccc1F] | 441 |

Scheme 18:

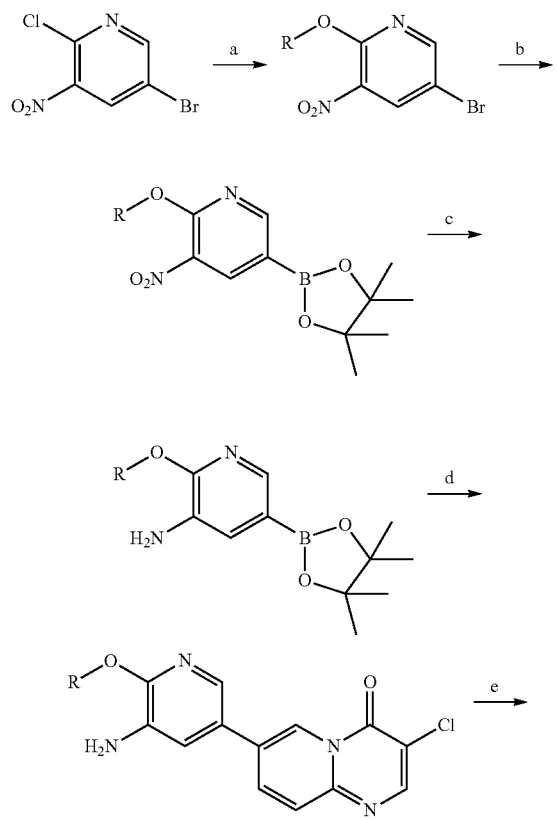

116
-continued

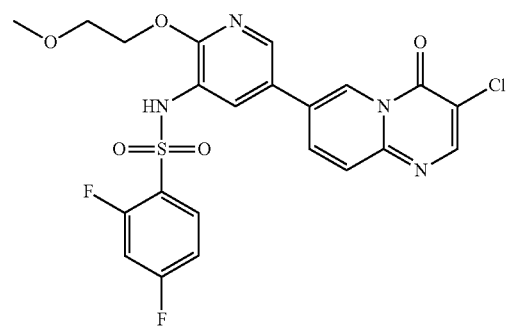

Conditions: a) 5-bromo-2-chloro-3-nitropyridine, R alcohol, potassium hydroxide, potassium carbonate, 2-(2-methoxyethoxy)-N,N-bis[2-(2-methoxyethoxy)ethyl]ethanamine, toluene; b) 4,4,5,5-tetramethyl-2-(4,4,5,5-tetramethyl-1,3,2-dioxoboran-2-yl)-1,3,2-dioxoborane, 1,1'-bis(diphenylphosphino)ferrocene palladium chloride, potassium acetate, dioxane, heating; c) Pd/C, methanol; d) 7-bromo-3-chloro-pyrido[1,2-a]pyrimidin-4-one, 1,1'-bis(diphenylphosphino)ferrocene palladium chloride, potassium caronate, dioxane, water, heating; e) 2,4-difluorobenzene sulfochloride, pyridine.

Example 231

N-[5-(3-chloro-4-oxo-4H-pyrido[1,2-a]pyrimidin-7-yl)-2-(2-methoxy-ethoxy)-pyridin-3-yl]-2,4-difluo-robenzsulfamide compound 231 a) 5-bromo-2-(2-methoxyethoxy)-3-nitropyridine 5-bromo-2-chloro-3-nitropyridine (3.00 g, 12.63 mmol, 1.00 Eq), 2-methoxyethanol (1.15 g, 15.16 mmol, 1.20 Eq) and 2-(2-methoxyethoxy)-N,N-di[2-(2-methoxyethoxy)ethyl]ethanamine (816.96 mg, 2.53 mmol, 0.20 Eq) were added to the mixed solution of potassium hydroxide (1.20 g, 21.47 mmol, 1.70 Eq) and potassium carbonate (2.97 g, 21.47 mmol, 1.70 Eq) in toluene (30 mL). The mixture was stirred at 15° C. under nitrogen for 18 hours. After the reaction was complete, the reaction solution was filtered, and the filtrate was concentrated and purified by silica gel chromatography column (PE: EA=20: 1-4:1) to give the title compound as a yellow solid (1.60 g, 5.77 mmol, 45.72%).
1H NMR (400 MHz, CDCl$_3$) ppm δ 8.41 (d, J=2.4 Hz, 1H), 8.38 (d, J=2.2 Hz, 1H), 4.70-4.53 (m, 2H), 3.85-3.72 (m, 2H), 3.43 (s, 3H)

b) 2-(2-methoxyethoxy)-3-nitro-5-(4,4,5,5-tetram-ethyl-1,3,2-dioxoboran-2-yl)pyridine 1,1'-bis(diphenylphosphino)ferrocene palladium chloride (42.22 mg, 57.70 umol, 0.01 Eq) was added to the mixed solution of 5-bromo-2-(2-methoxyethoxy)-3-nitro-pyridine (1.60 g, 5.77 mmol, 1.00 Eq), 4,4,5,5-tetramethyl-2-(4,4,5,5-tetramethyl-1,3,2-dioxoboran-2-yl)-1,3,2-dioxoborane (1.76 g, 6.92 mmol, 1.20 Eq) and potassium acetate (1.70 g, 17.31 mmol, 3.00 Eq) in dioxane (20 mL). This mixture was stirred at 90° C. under nitrogen for 18 hours. After the reaction was complete, the reaction solution was filtered and the filtrate was concentrated to give a brown oily crude product (2.50 g, 5.55 mmol, yield: 96.24%, purity: 72%).

1H NMR (400 MHz, CDCl$_3$) ppm δ 8.65 (d, J=1.5 Hz, 1H), 8.57 (d, J=1.5 Hz, 1H), 4.71-4.63 (m, 2H), 3.86-3.75 (m, 2H), 3.44 (s, 3H), 1.34 (s, 12H)

c) 2-(2-methoxyethoxy)-5-(4,4,5,5-tetramethyl-1,3,2-dioxoboran-2-yl)pyridin-3-amine Pd/C (150.00 mg) was added to the solution of 2-(2-methoxyethoxy)-3-nitro-5-(4,4,5,5-tetramethyl-1,3,2-dioxoboran-2-yl)pyridine (1.50 g, 3.33 mmol, 1.00 Eq) in methanol (30 mL). This mixture was stirred at 18° C. under hydrogen for 2 hours. After the reaction was complete, the reaction solution was filtered and the filtrate was concentrated to give a yellow oily crude product (1.40 g, 2.38 mmol, yield: 71.46%, purity: 50%).

1H NMR (400 MHz, CDCl$_3$) ppm δ 7.94 (d, J=1.5 Hz, 1H), 7.23 (d, J=1.5 Hz, 1H), 4.57-4.53 (m, 2H), 3.78-3.75 (m, 2H), 3.42 (s, 3H), 1.32 (s, 12H)

d) 7-(5-amino-6-(2-methoxyethoxy)pyridin-3-yl)-3-chloro-4H-pyrido[1,2-a]pyrimidin-4-one 1,1'-bis(diphenylphosphino)ferrocene palladium chloride (5.64 mg, 7.71 umol, 0.01 Eq) and water (1 mL) were added to the mixed solution of 7-bromo-3-chloro-pyrido[1,2-a]pyrimidin-4-one (200.00 mg, 770.74 umol, 1.00 Eq), 2-(2-methoxyethoxy)-5-(4,4,5,5-tetramethyl-1,3,2-dioxoboran-2-yl)pyridin-3-amine (453.43 mg, 770.74 umol, 1.00 Eq) and potassium carbonate (319.57 mg, 2.31 mmol, 3.00 Eq) in dioxane (5 mL). This mixture was stirred under nitrogen at 90° C. for 18 hours. After the reaction was complete, the reaction solution was dried over anhydrous sodium sulfate and filtered, and the filtrate was concentrated under reduced pressure. The residue was purified by silica gel column chromatography (DCM: MeOH=1%-5%) to give the title compound as a yellow solid (270.00 mg, 622.89 umol, yield: 80.82%, purity: 80%).

1H NMR (400 MHz, CDCl$_3$) δ 9.17 (d, J=1.7 Hz, 1H), 8.47 (s, 1H), 7.97 (dd, J=2.1, 9.2 Hz, 1H), 7.79 (d, J=2.0 Hz, 1H), 7.75 (d, J=9.3 Hz, 1H), 7.13 (d, J=2.2 Hz, 1H), 4.62-4.53 (m, 2H), 4.06 (br. s., 2H), 3.82-3.76 (m, 2H), 3.44 (s, 3H)

e) N-[5-(3-chloro-4-oxo-4H-pyrido[1,2-a]pyrimidin-7-yl)-2-(2-methoxy-ethoxy)-pyridin-3-yl]-2,4-difluorobenzsulfamide 2,4-difluorobenzene sulfochloride (91.96 mg, 432.57 umol, 1.50 Eq) was added to the mixed solution of 7-[5-amino-6-(2-methoxyethoxy)pyridin-3-yl]-3-chloro-pyrido[1,2-a]pyrimidin-4-one (125.00 mg, 288.38 umol, 1.00 Eq) in pyridine (3 mL). The mixture was reacted at 15° C. for 4 hours. After the reaction was complete, the reaction solution was concentrated. The residue was dissolved in dichloromethane and rinsed with water and brine. The organic phase was dried over anhydrous sodium sulfate and concentrated. The resultant residue was purified by preparative thin-layer chromatography to give the title compound as a yellow solid (51.32 mg, 98.14 umol, 34.030).

1H NMR (400 MHz, CDCl$_3$) δ 9.12 (d, J=1.7 Hz, 1H), 8.49 (s, 1H), 8.11 (d, J=2.2 Hz, 1H), 7.98 (d, J=2.2 Hz, 1H), 7.96-7.85 (m, 2H), 7.78 (d, J=9.3 Hz, 1H), 7.47 (s, 1H), 7.01 (t, J=8.2 Hz, 1H), 6.97-6.89 (m, 1H), 4.56-4.47 (m, 2H), 3.76-3.67 (m, 2H), 3.42 (s, 3H)

The following 2 compounds were also synthesized by reference to the preparation of compound 232.

| compound | structure | MS(ES) [M + H]+ |
|---|---|---|
| 232 | 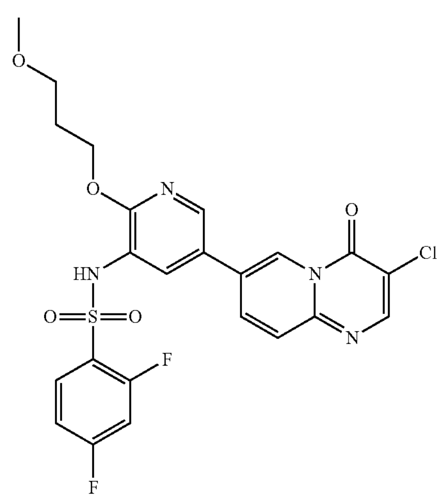 [SMILES: COCCCOc1ncc(-c2ccc3ncc(Cl)c(=O)n3c2)cc1NS(=O)(=O)c1ccc(F)cc1F] | 537 |

-continued

| compound | structure | MS(ES) [M + H]+ |
|---|---|---|
| 233 | 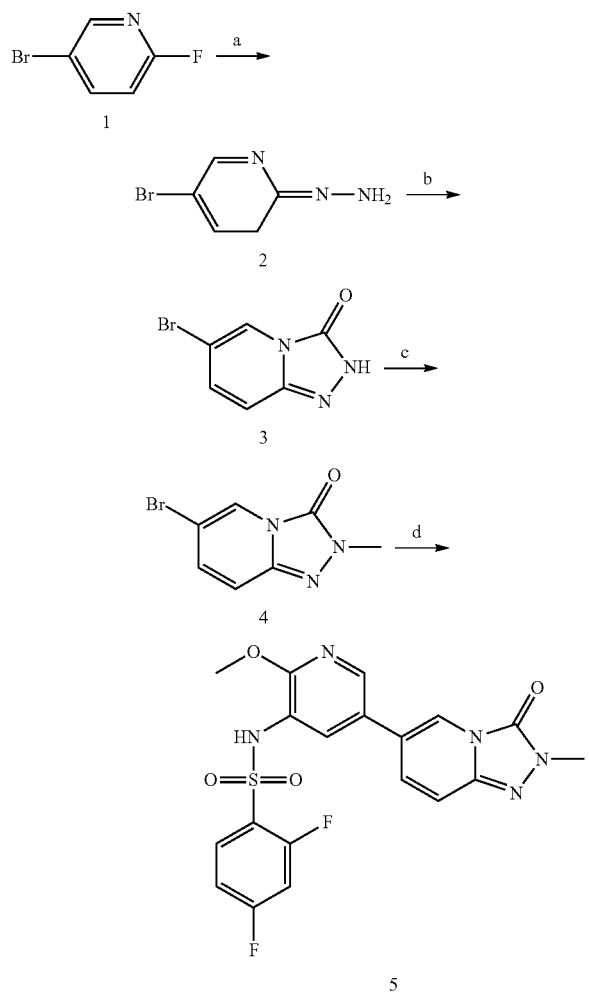 | 535 |

Scheme 19:

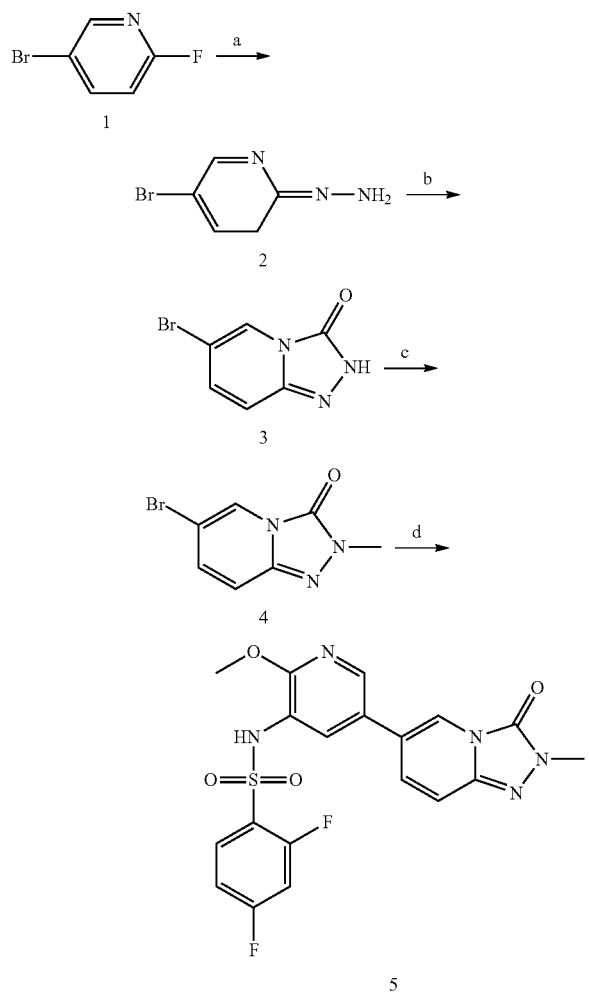

Conditions: a) hydrazine hydrate, ethanol, heating; b) 1,1-carbonyldiimidazole, acetonitrile, heating; c) cesium carbonate, methyl iodide, N,N-dimethylformamide; d) R borate (boric acid), palladium reagent (tetrakistriphenylphosphine palladium, [1,1′-bis(diphenylphosphino)ferrocene]palladium chloride, etc.), potassium carbonate, dioxane, water, heating.

Example 234

2,4-difluoro-N-(2-methoxy-5-(2-methyl-3-oxo-2,3-2H-[1,2,4-]triazolo[4,3-a]pyridin-6-yl)pyridin)-3-yl)benzsulfamide

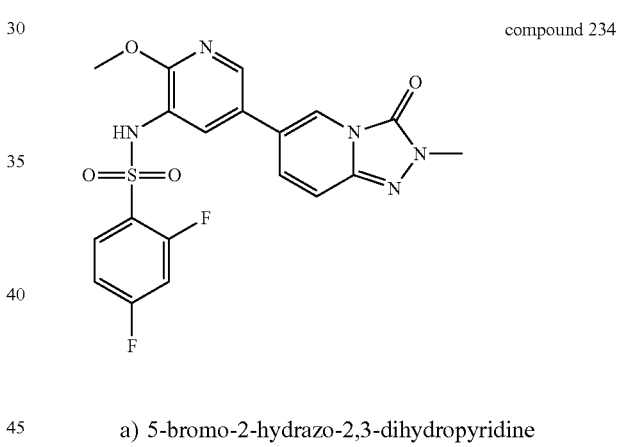

compound 234 a) 5-bromo-2-hydrazo-2,3-dihydropyridine

Hydrazine hydrate (8 g) was added to the solution of 5-bromo-2-fluoro pyridine (2 g, 11.36 mmol) in ethanol (25 mL). The reaction solution was heated to 80° C. and stirred for 16 hours. The reaction solution was cooled to room temperature, concentrated under reduced pressure to remove the solvent by half, filtered, and the filter cake was collected. The crude desired product was obtained by vacuum drying.

b) 6-bromo-[1,2,4]triazolo[4, 3-a]pyridin-3(2H)-one

The solution of 6-bromo-[1,2,4]triazolo[4,3-a]pyridin-3(2H)-one (1 g, 5.32 mmol) and 1,1-carbonyl diimidazole (948 mg, 8.85 mmol) in acetonitrile (10 mL) was warmed to 85° C., and the mixture was stirred at reflux for 2 hours. The reaction solution was cooled to room temperature and stirred for another 16 hours. The reaction mixture was allowed to settle, and filtered, and the filter cake was collected and dried to give crude title product.

c) 6-bromo-2-methyl-[1,2,4]triazolo[4,3-a]pyridin-3(2H)-one

Cesium carbonate (685 mg, 2.1 mmol) and methyl iodide (0.26 mL, 4.2 mmol) were added to the solution of 6-bromo-[1,2,4]triazolo[4,3-a]pyridin-3(2H)-one (150 mg, 0.7 mmol) in anhydrous DMF (3 mL). The reaction solution was stirred at 20° C. for 16 hours. The reaction solution was diluted with ethyl acetate, filtered to remove solids. The filtrate was rinsed with saturated brine, dried over anhydrous sodium sulfate, and concentrated under reduced pressure to give the desired product as a yellow solid (140 mg, 87.5%).

$^1$H NMR (400 MHz, CDCl$_3$) ppm δ 3.67 (s, 3H) 6.97-7.03 (m, 1H) 7.07-7.13 (m, 1H) 7.92 (s, 1H)

d) 2,4-difluoro-N-(2-methoxy-5-(2-methyl-3-oxo-2,3-2H-[1,2,4-]triazolo[4,3-a]pyridin-6-yl) pyridin)-3-yl)benzsulfamide Under nitrogen atmosphere, [1,1'-bis(diphenylphosphino)ferrocene]palladium chloride (10 mg) was added to the mixed solution of 6-bromo-2-methyl-[1,2,4]triazolo[4,3-a]pyridin-3(2H)-one (112 mg, 0.49 mmol), 2,4-difluoro-N-(2-methoxy-5-(4,4,5,5-tetramethyl-1,3,2-dioxaborolan-2-yl) pyridin-3-yl)benzsulfamide (200 mg, 0.47 mmol) and sodium carbonate (124 mg, 1.17 mmol) in 1,4-dioxane (3 mL) and water (1.2 mL). The reaction solution was warmed to 80° C. and stirred for 16 hours. The reaction mixture was filtered. The filtrate was diluted with water, and the aqueous phase was extracted with ethyl acetate (15 mL×3). The combined organic phases were rinsed with saturated brine, dried over anhydrous sodium sulfate, and concentrated, and the residue was purified by a preparative chromatography plate (DCM: MeOH=15:1) to obtain the title compound as white powder (50 mg, 23.81%).

1H NMR (400 MHz, CDCl$_3$) ppm 3.71 (s, 3H) 3.96 (s, 3H) 6.91-7.01 (m, 2H) 7.17-7.23 (m, 2H) 7.79-7.87 (m, 2H) 7.88-7.93 (m, 1H) 8.01 (d, J=2.20 Hz, 1H)

The following one compound was also synthesized by reference to the preparation of compound 234.

| compound | structure | MS(ES) [M + H]$^+$ |
|---|---|---|
| 235 | 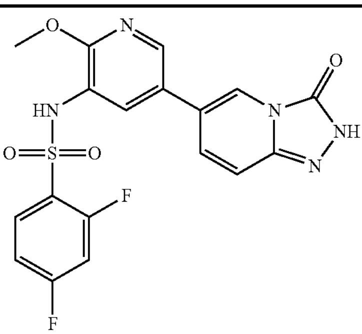 | 434 |

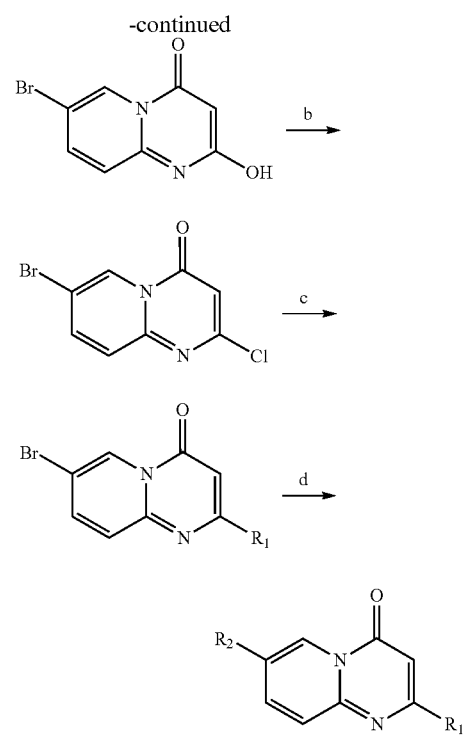

Conditions: a) malonyl dichloride, dichloromethane, room temperature; b) phosphorus oxychloride, reflux; c) R$_1$ amine, heating; d) R$_2$ boron, palladium reagent (tetrakistriphenylphosphine palladium, [1,1'-bis(diphenylphosphino)ferrocene]palladium chloride, etc.), K$_2$CO$_3$, dioxane, water, heating.

Example 236

N-(5-(2-amino-4-oxo-4H-pyrido[1,2-a]pyrimidin-7-yl)-2-methoxypyridin-3-yl)-2,4-dimethylthiazolyl-5-sulfamide

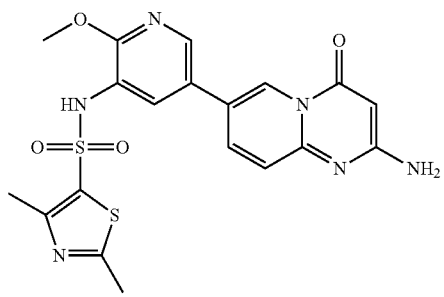

compound 236 a) 7-bromo-2-hydroxy-4H-pyrido[1,2-a]pyrimidin-4-one 2-amino-5-bromopyridine (10.0 g, 57.8 mmol) was dissolved in dichloromethane (100 mL) and placed in a 250 mL round-bottomed flask. Malonyl chloride (9.78 g, 69.36 mmol) was added dropwise at 0° C. and then the reaction Scheme 20:

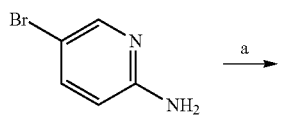

solution was warmed to 15° C. and stirred for 48 hours. The liquid mass spectrometry showed that the reaction was complete. The reaction mixture was filtered, and the filter cake was rinsed with dichloromethane (200 mL) to give the title compound as a yellow solid (13 g, 84%).

b)
7-bromo-2-chloro-4H-pyrido[1,2-a]pyrimidin-4-one 7-bromo-2-hydroxy-4H-pyrido[1,2-a]pyrimidin-4-one (7 g, 29 mmol) was dissolved in phosphorus oxychloride (50 mL) and placed in a 100 mL round-bottomed flask. The mixture was stirred at 120° C. for 18 hour. The liquid mass spectrometry showed that the reaction was complete. The reaction solution was cooled to room temperature and poured slowly into room temperature water (1 L) for quenching. The mixture was extracted with ethyl acetate (300 mL×6). The organic phase was dried over anhydrous sodium sulfate and filtered, and the filtrate was concentrated to give crude product. The crude product was purified by column chromatography on silica gel to give the title compound as a yellow solid (2.9 g, 37%).

1H NMR (400 MHz, DMSO-$d_6$) ppm δ 9.01 (d, 1H), 8.23 (dd, 1H), 7.67 (d, 1H), 6.58 (s, 1H).

c)
2-amino-7-bromo-4H-pyrido[1,2-a]pyrimidin-4-one 7-bromo-2-chloro-4H-pyrido[1,2-a]pyrimidin-4-one (1 g, 3.85 mmol) dissolved in liquid ammonia-ethanol (30 mL-15 mL) was placed in a 100 mL sealed tank and reacted at 80° C. for 48 hours. The liquid mass spectrometry showed that the reaction was complete. The reaction solution was concentrated to give crude product. The crude product was purified by column chromatography on silica gel to give the title compound as a purple solid (90 mg, 9.7%).

1H NMR (400 MHz, DMSO-$d_6$) ppm δ 8.78 (d, 1H), 7.85 (dd, 1H), 7.17 (d, 1H), 6.86 (br. s., 2H), 5.26 (s, 1H).

d) N-(5-(2-amino-4-oxo-4H-pyrido[1,2-a]pyrimidin-7-yl)-2-methoxypyridin-3-yl)-2,4-dimethylthiazolyl-5-sulfamide 2-amino-7-bromo-4H-pyrido[1,2-a]pyrimidin-4-one (72 mg, 210 umol) was dissolved in dioxane (5 mL) and water (1 mL) and N-(2-methoxy-5-(4,4,5,5-tetramethyl-1,3,2-dioxaborolan-2-yl)pyridin-3-yl)-2,4-dimethylthiazolyl-5-sulfamide (89 mg, 210 umol), potassium carbonate (87 mg, 630 umol) and [1,1'-bis(diphenylphosphino)ferrocene]palladium chloride (10 mg) were added. The reaction solution was stirred at 100° C. for 18 hours. The liquid mass spectrometry showed that the reaction was complete. The reaction solution was filtered and concentrated to give crude product. The crude product was purified by preparative HPLC to give the title product as a white solid (30 mg, 30%).

1H NMR (400 MHz, CDCl$_3$) ppm δ 9.11 (d, 1H), 8.16 (d, 1H), 7.99 (d, 1H), 7.81 (dd, 1H), 7.42 (d, 1H), 7.17 (br. s., 1H), 5.59 (s, 1H), 4.87 (br. s., 2H), 3.97 (s, 3H), 2.65 (s, 3H), 2.57 (s, 3H).

The following 2 compounds were also synthesized by reference to the preparation of compound 236.

| compound | structure | MS(ES) [M + H]+ |
|---|---|---|
| 237 | 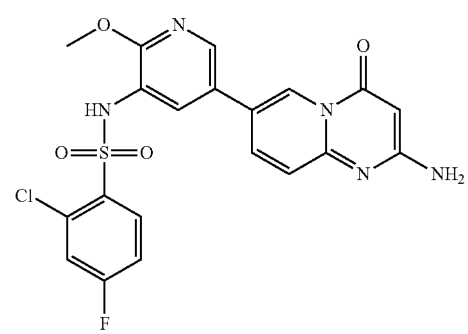 [SMILES: COc1ncc(-c2ccc3nc(N)cc(=O)n3c2)cc1NS(=O)(=O)c1ccc(F)cc1Cl] | 476 |
| 238 | 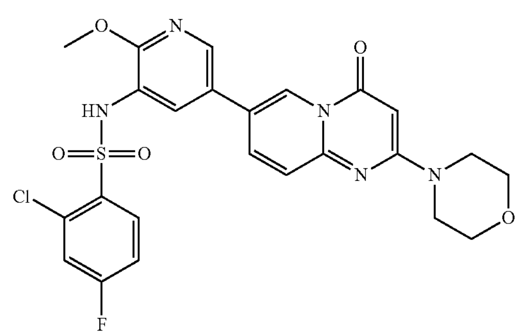 [SMILES: COc1ncc(-c2ccc3nc(N4CCOCC4)cc(=O)n3c2)cc1NS(=O)(=O)c1ccc(F)cc1Cl] | 546 |

Scheme 21:

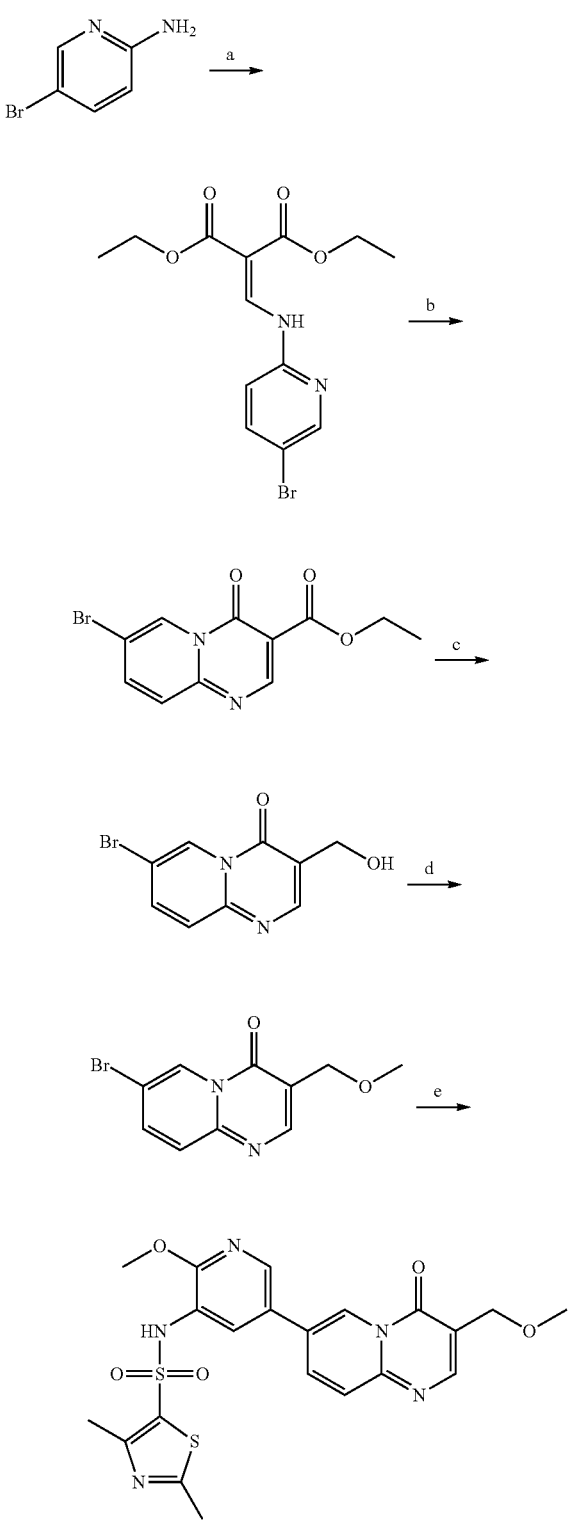

Conditions: a) dimethyl 2-(methoxymethylene)malonate, ethanol, heating; b) phosphorus oxybromide, heating; c) DIBAL-H, tetrahydrofuran, 0° C.; d) methyl iodide, sodium hydride, tetrahydrofuran, 0-15° C.; e) R borate (boric acid), palladium reagent (tetrakistriphenyl phosphine palladium, [1,1'-bis(diphenylphosphino)ferrocene]palladium chloride, etc.), K$_2$CO$_3$, dioxane, water, heating.

Example 239

N-(2-methoxy-5-(3-(methoxymethyl)-4-oxo-4H-pyrido[1,2-a]pyrimidin-7-yl)pyridin-3-yl)-2,4-dimethylthiazolyl-5-sulfamide

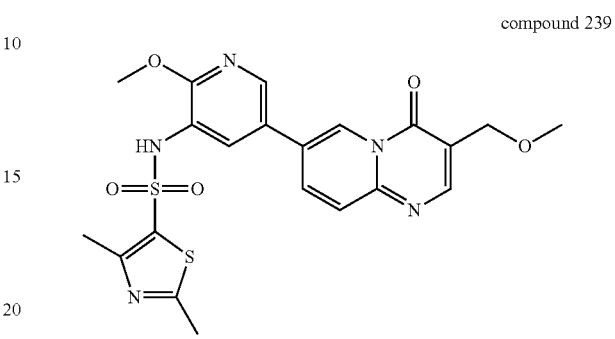

compound 239 a) diethyl 2-(((5-bromopyridin-2-yl)amino)methenyl)malonate 5-bromopyridin-2-amine (5 g, 28.9 mmol) and dimethyl 2-(methoxymethenyl)malonate (5.84 g, 28.9 mmol) were dissolved in ethanol (50 mL) and stirred at 80° C. for 4 hours. The reaction mixture was cooled to room temperature and filtered. The filter cake was rinsed with petroleum ether and drained to give the title compound as a white solid (8.0 g, 81%).

1H NMR (400 MHz, CDCl$_3$) ppm δ 11.12 (d, 1H), 9.08 (d, 1H), 8.40 (d, 1H), 7.76 (dd, 1H), 6.78 (d, 1H), 4.41-4.19 (m, 4H), 1.37 (td, 6H).

b) methyl 7-bromo-4-oxo-4H-pyrido[1,2-a]pyrimidin-3-carboxylate

Diethyl 2-(((5-bromopyridin-2-yl)amino)methenyl)malonate (3.0 g, 8.74 mmol) and phosphorus oxybromide (9.27 g, 32.35 mmol) were placed in a round-bottom flask and the mixture was stirred at 80° C. for 4 hours. The reaction mixture was cooled to room temperature, slowly poured into iced water, adjusted to pH=8 with saturated sodium carbonate solution, and extracted with dichloromethane. The resultant organic phase was rinsed with saturated brine (100 mL), dried over sodium sulfate, and concentrated to give the title compound as a yellow solid (2.0 g, 76.9%).

1H NMR (400 MHz, CDCl$_3$) ppm δ 9.36 (d, 1H), 9.05-8.98 (m, 1H), 7.96 (dd, 1H), 7.65 (d, 1H), 4.42 (q, 2H), 1.47-1.37 (m, 3H).

c) 7-bromo-3-(hydroxymethyl)-4H-pyrido[1,2-a]pyrimidin-4-one

Methyl 7-bromo-4-oxo-4H-pyrido[1,2-a]pyrimidin-3-carboxylate (800 mg, 2.69 mmol) was dissolved in tetrahydrofuran (20 mL) and DIBAL-H (4 mL) was added at 0° C. The mixture was allowed to react at 0° C. for 3 hours. The saturated ammonium chloride solution (20 mL) was added to the reaction solution to quench the reaction. The resultant mixture was extracted with ethyl acetate (20 mL×3). The organic phase was dried over anhydrous sodium sulfate and filtered, and the filtrate was concentrated to give the crude product. The crude product was purified by column chromatography on silica gel to give the title compound (110 mg, 16%).

d) 7-bromo-3-(methoxymethyl)-4H-pyrido[1,2-a]pyrimidin-4-one 7-bromo-3-(hydroxymethyl)-4H-pyrido[1,2-a]pyrimidin-4-one (110 mg, 431 umol) was dissolved in tetrahydrofuran (3 mL) and sodium hydride (26 mg, 647 umol, purity 60%) was added at 0° C. The reaction solution was stirred at 20° C. for one hour and then methyl iodide (183 mg, 1.29 mmol) was added. The reaction solution was stirred at 20° C. for 6 hours. The liquid mass spectrometry showed that the reaction was complete. The reaction mixture was poured into iced water (30 mL) for quenching, and then extracted with ethyl acetate (20 mL×3). The organic phase was dried over anhydrous sodium sulfate and filtered, and the filtrate was concentrated to give a crude product which was purified by preparative thin layer chromatography to give the title compound (23 mg, 19.8%).

e) N-(2-methoxy-5-(3-(methoxymethyl)-4-oxo-4H-pyrido[1,2-a]pyrimidin-7-yl)pyridin-3-yl)-2,4-dimethylthiazolyl-5-sulfamide 7-bromo-3-(methoxymethyl)-4H-pyrido[1,2-a]pyrimidin-4-one (23 mg, 85 umol) was dissolved in dioxane (2.5 mL) and water (0.5 mL), and N-(2-methoxy-5-(4,4,5,5-tetramethyl-1,3,2-dioxaborolan-2-yl)pyridin-3-yl)-2,4-dimethylthiazolyl-5-sulfamide (36 mg, 85 umol), potassium carbonate (24 mg, 170 umol) and [1,1'-bis(diphenylphosphino) ferrocene]palladium chloride (10 mg) were added. The mixture was reacted at 100° C. under microwave for 1 hour. The liquid mass spectrometry showed that the reaction was complete. The reaction solution was concentrated to give crude product. The crude product was purified by preparative HPLC to give the title product as a pale yellow solid (18 mg, 43.2%).

1H NMR (400 MHz, CDCl₃) ppm δ 9.20 (s, 1H), 8.42 (s, 1H), 8.18 (d, 1H), 8.03 (s, 1H), 7.98-7.85 (m, 2H), 7.20 (s, 1H), 4.57 (s, 2H), 3.99 (s, 3H), 3.50 (s, 3H), 2.64 (s, 3H), 2.57 (s, 3H), 1.23 (s, 2H).

Scheme 22:

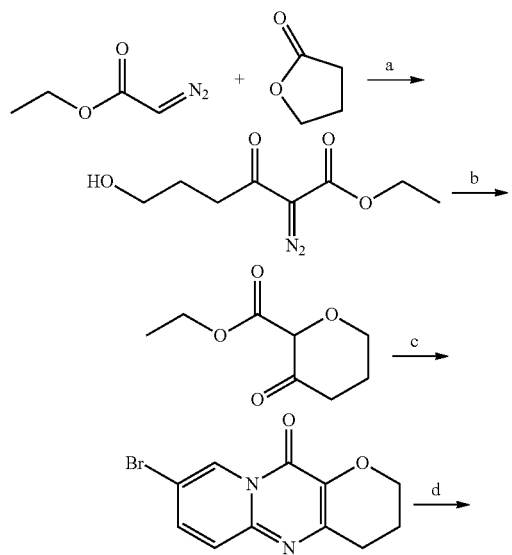

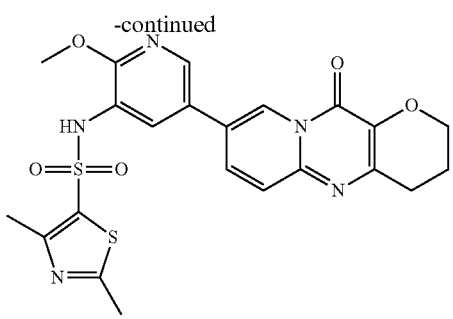

Conditions: a) LDA, tetrahydrofuran, -78° C.; b) Rh reagent, toluene, heating; c) 5-bromopyridin-2-amine, acetic acid, 110° C.; d) R borate, palladium reagent (tetrakistriphenylphosphinepalladium, [1,1'-bis(diphenylphosphino)ferrocene]palladium chloride, etc.), K₃PO₄, tetrahydrofuran, water, heating.

Example 240

2-methoxy-5-(11-oxo-2,3,4,11-tetrahydro-pyrano[3,2-d]pyrido[1,2-a]pyrimidin-8-yl)pyridin-3-yl)-2,4-dimethylthiazolyl-5-sulfamide compound 240

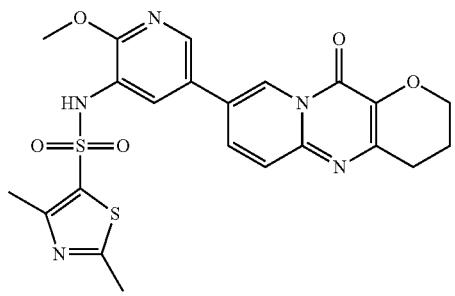

a) ethyl 2-diazo-6-hydroxy-3-oxohexanoate

Ethyl diazoacetate (6.00 g, 52.59 mmol) and tetrahydrofuran (60 mL) were placed in a three-necked round-bottomed flask and lithium diisopropylamide (5.63 g, 52.59 mmol) was slowly added dropwise at −78° C. under nitrogen. The mixture was stirred at −78° C. for 0.5 hours. Tetrahydrofuran-2-one (4.07 g, 47.33 mmol) was slowly added dropwise at −78° C. under nitrogen and stirred at −78° C. for 2 hours. TLC showed the reaction was complete. The saturated ammonium chloride solution (300 mL) was added to the mixture and extracted with ethyl acetate (200 mL×3). The combined organic phases were rinsed with saturated brine (200 mL×2), dried over anhydrous sodium sulfate, filtered, concentrated and isolated by silica gel chromatography to give the title compound (4.00 g, 38%).

¹H NMR (400 MHz, CDCl₃) ppm δ 1.34 (t, 3H), 1.90-1.97 (m, 2H), 3.00 (t, 2H), 3.70 (t, 2H), 4.32 (q, 2H).

b) ethyl 3-oxotetrahydro-2H-pyran-2-carboxylate

Ethyl 2-diazo-6-hydroxy-3-oxohexanoate (316.00 mg, 1.58 mmol) and toluene(40 mL) were placed in a 250 mL round-bottomed flask and the solution of rhodium acetate dimer (6.29 mg, 14.22 umol) in toluene (40 mL) was slowly added dropwise at 80° C. under nitrogen and stirred at 80°

C. for 1 hour. TLC showed the reaction was complete. The reaction solution was cooled to room temperature and purified by column chromatography on silica gel to give the title compound (180 mg, yield: 67%).

$^1$H NMR (400 MHz, CDCl$_3$) ppm δ 1.34 (t, 3H), 1.94-1.98 (m, 2H), 2.38 (t, 2H), 3.95 (t, 2H), 4.33 (q, 2H), 10.36 (s, 1H).

c) 8-bromo-3,4-dihydro-pyrano[3,2-D]pyrido[1,2-a]pyrimidin11(2H)-one

Ethyl 3-oxotetrahydro-2H-pyran-2-carboxylate (90 mg, 0.53 mmol) and 2-amino-5-bromopyridine (90.44 mg, 0.53 mmol) were dissolved in acetic acid (2 mL). The mixture was reacted at 110° C. for 5 hours. The liquid mass spectrometry showed that the reaction was complete. The reaction solution was concentrated to give crude product which was purified by preparative thin layer chromatography to give the title product (25 mg, yield: 17%).

d) 2-methoxy-5-(11-oxo-2,3,4,11-tetrahydro-pyrano[3,2-d]pyrido[1,2-a]pyrimidin-8-yl)pyridin-3-yl)-2,4-dimethylthiazolyl-5-sulfamide

[5-[(2,4-dimethylthiazol-5-yl)sulfonyl]-6-methoxy-3-pyridyl]boric acid (18.31 mg, 0.054 mmol), K$_3$PO$_4$ (33.98 mg, 0.16 mmol) and [1,1'-bis(diphenylphosphino)ferrocene]palladium chloride (3.48 mg, 0.0054 mmol) were added to the solution of 8-bromo-3,4-dihydro-pyrano[3,2-D]pyrido[1,2-a]pyrimidin11(2H)-one (15.00 mg, 0.054 mmol) in tetrahydrofuran (4 mL) and water (1 mL) and the mixture was reacted at 80° C. for 5 hours. The liquid mass spectrometry showed that the reaction was complete. The reaction solution was filtered and concentrated to give crude product. The crude product was purified by preparative HPLC to give the title product (12.00 mg, yield: 27%).

$^1$H NMR (400 MHz, CDCl$_3$) ppm δ 2.14-2.20 (m, 2H), 2.45 (s, 3H), 2.61 (s, 3H), 2.91 (t, 2H), 3.85 (s, 3H), 4.30 (t, 2H), 7.58 (dd, 1H), 7.91 (dd, 1H), 8.06 (d, 1H), 8.30 (d, 1H), 8.96 (d, 1H).

Scheme 23:

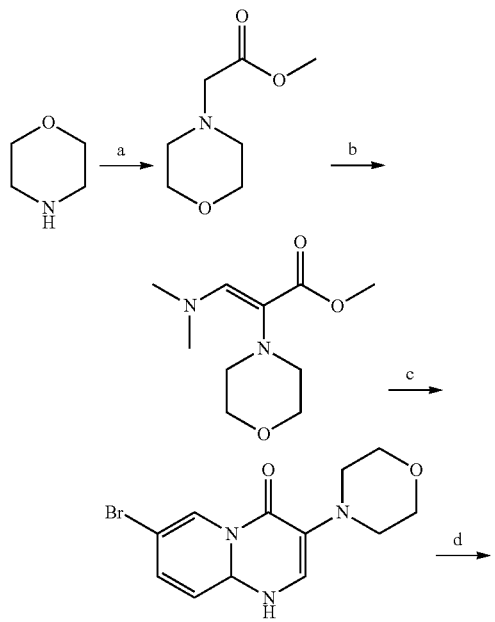

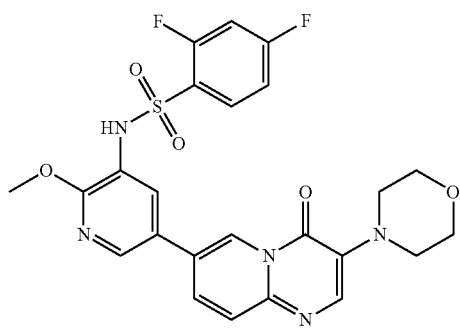

Conditions: a) methyl bromoacetate, potassium hydroxide, potassium carbonate, dichloromethane, 40° C.; b) 1-t-butoxy-N,N,N',N'-tetramethyl-methanediamine, toluene, heating; c) 5-bromopyridin-2-amine, acetic acid, 110° C.; d) R borate, palladium reagent (tetrakistriphenyl phosphine palladium, [1,1'-bis(diphenylphosphino)ferrocene]palladium chloride, etc.), K$_2$PO$_4$, tetrahydrofuran, water, heating.

Example 241

2,4-difluoro-N-(2-methoxy-5-(3-morpholinyl-4-oxo-4H-pyrido[1,2-a]pyrimidin-7-yl)pyridin-3-yl) benzsulfamide compound 241 a) methyl 2-morpholinoacetate

Morpholine (2.00 g, 22.9 mmol), methyl bromoacetate (4.80 g, 31.4 mmol), potassium hydroxide (1.33 g, 23.6 mmol), potassium carbonate (3.30 g, 23.9 mmol) and dichloromethane (50 mL) were placed in a 100 mL round-bottomed flask and stirred at room temperature for 12 hours and then stirred at 40° C. for 6 hours. TLC showed the reaction was complete. The reaction solution was cooled to room temperature and rinsed with saturated brine (10 mL×3), dried over anhydrous sodium sulfate, filtered and concentrated. The residue was purified by silica gel column chromatography (petroleum ether/ethyl acetate, 1/3) to give the title compound (2.80 g, 77%).

1H NMR (400 MHz, CDCl$_3$) ppm δ 2.56-2.59 (m, 4H), 3.22 (s, 2H), 3.73 (s, 3H), 3.74-3.76 (m, 4H).

b) Methyl 7-methyl (E)-3-(dimethylamino)-2-morpholino-prop-2-enoate

Methyl 2-morpholinoacetate (1.80 g, 11.3 mmol), 1-t-butoxy-N,N,N',N'-tetramethyl-methanediamine (2.36 g, 13.6 mmol) and toluene (50 mL) were placed in a 100 mL round-bottomed flask and stirred at 120° C. for 10 hours. TLC showed the reaction was complete. The reaction solution was concentrated to give the title compound (2.08 g, 86%) which was used in the next step without further purification.

c) 7-bromo-3-morpholino-2,3-dihydropyrido[1,2-a]pyrimidin-4-one

Methyl 7-methyl (E)-3-(dimethylamino)-2-morpholino-prop-2-enoate (300 mg, 1.40 mmol), 5-bromo-2-aminopyridine (484 mg, 2.80 mmol) and acetic acid (5 mL) were placed in a 10 mL round-bottomed flask and heated at reflux for 4 hours. LCMS showed the reaction was complete. The reaction solution was concentrated and the residue was purified by silica gel column chromatography (petroleum ether/ethyl acetate, 5/1 to 1/1) to give the title compound (80 mg, 18%).

1H NMR (400 MHz, CD$_3$OD) ppm δ 3.23-3.25 (m, 4H), 3.88-3.90 (m, 4H), 7.52 (d, 1H), 7.77-7.80 (m, 1H), 8.02 (s, 1H), 9.09 (s, 1H).

d) 2,4-fluoro-N-(2-methoxy-5-(3-morpholinyl-4-oxo-4H-pyrido[1,2-a]pyrimidin-7-yl)pyridin-3-yl)benzsulfamide 7-bromo-3-morpholino-2,3-dihydropyrido[1,2-a]pyrimidin-4-one (50 mg, 0.160 mmol), 2,4-difluoro-N-[2-methoxy-5-(4,4,5,5-tetramethyl-1,3,2-dioxaborolan-2-yl)-3-pyridinyl]benzsulfamide (68 mg, 0.160 mmol), potassium phosphate (68 mg, 0.320 mmol), tetrahydrofuran (1 mL) and water (0.1 mL) were placed in a 10 mL round-bottomed flask and 1,1'-bis(ditert-butylphosphino)ferrocene]palladium dichloride (10 mg) was added under nitrogen. The mixture was stirred at 70° C. for 2 hours. LCMS showed the reaction was complete. The reaction solution was concentrated and the residue was purified by preparative HPLC to give the title product (20 mg, 24%).

1H NMR (400 MHz, DMSO-d$_6$) ppm δ 3.16-3.25 (m, 4H), 3.69 (s, 3H), 3.75-3.83 (m, 4H), 7.17-7.27 (m, 1H), 7.55-7.13 (m, 1H), 7.70 (d, 1H), 7.78-7.80 (m, 1H), 7.98 (s, 1H), 8.03 (s, 1H), 8.44 (s, 1H), 8.98 (s, 1H).

The following 43 compounds were also synthesized by reference to the preparation of compound 175.

| compound | structure | MS(ES) [M + H]$^+$ |
|---|---|---|
| 242 | 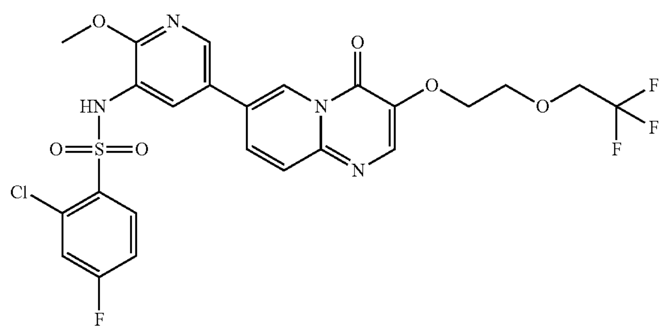 [SMILES: COc1ncc(-c2ccc3ncc(OCCOCC(F)(F)F)c(=O)n3c2)cc1NS(=O)(=O)c1ccc(F)cc1Cl] | 603 |
| 243 | 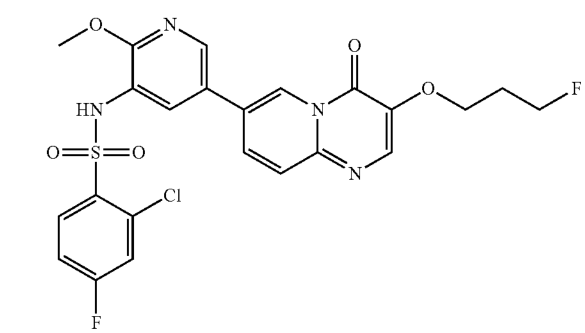 [SMILES: COc1ncc(-c2ccc3ncc(OCCCF)c(=O)n3c2)cc1NS(=O)(=O)c1ccc(F)cc1Cl] | 537 |
| 244 | 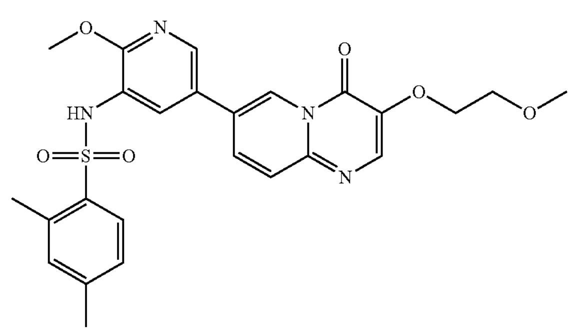 | 511 |

-continued
| compound | structure | MS(ES) [M + H]+ |
|---|---|---|
| 245 | 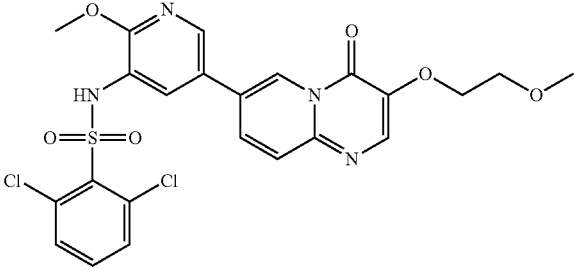 [SMILES: COCCOc1cnc2ccc(-c3cnc(OC)c(NS(=O)(=O)c4c(Cl)cccc4Cl)c3)cn2c1=O] | 551 |
| 246 | 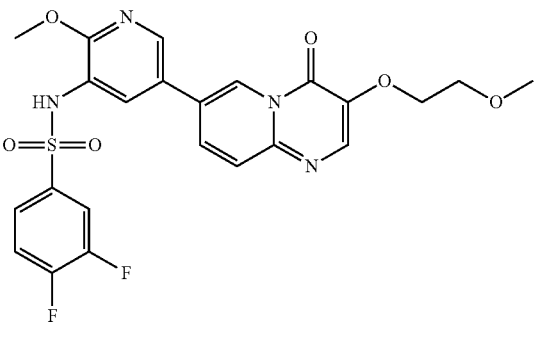 [SMILES: COCCOc1cnc2ccc(-c3cnc(OC)c(NS(=O)(=O)c4ccc(F)c(F)c4)c3)cn2c1=O] | 519 |
| 247 | 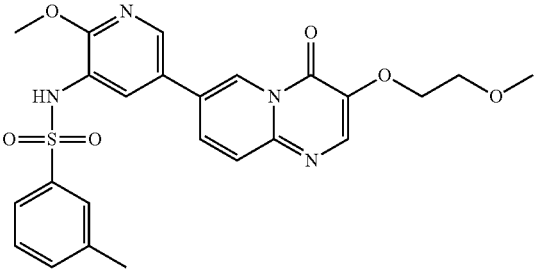 [SMILES: COCCOc1cnc2ccc(-c3cnc(OC)c(NS(=O)(=O)c4cccc(C)c4)c3)cn2c1=O] | 497 |
| 248 | 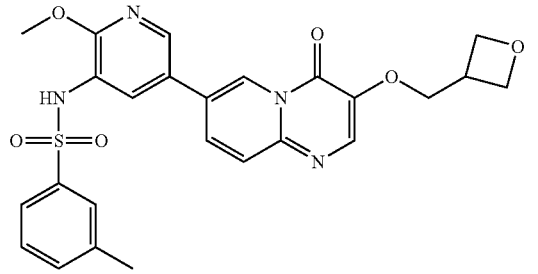 [SMILES: COc1ncc(-c2ccc3ncc(OCC4COC4)c(=O)n3c2)cc1NS(=O)(=O)c1cccc(C)c1] | 509 |
| 249 | 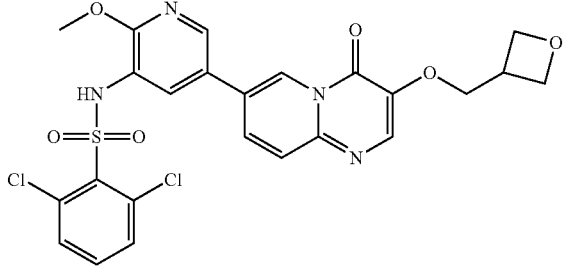 [SMILES: COc1ncc(-c2ccc3ncc(OCC4COC4)c(=O)n3c2)cc1NS(=O)(=O)c1c(Cl)cccc1Cl] | 563 |

-continued

| compound | structure | MS(ES) [M + H]+ |
|---|---|---|
| 250 | 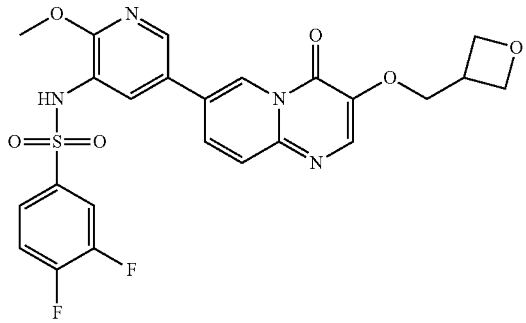 [SMILES: COc1ncc(-c2ccc3ncc(OCC4COC4)c(=O)n3c2)cc1NS(=O)(=O)c1ccc(F)c(F)c1] | 531 |
| 251 | 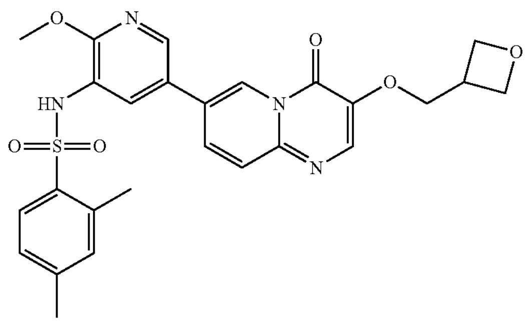 [SMILES: COc1ncc(-c2ccc3ncc(OCC4COC4)c(=O)n3c2)cc1NS(=O)(=O)c1ccc(C)cc1C] | 523 |
| 252 | 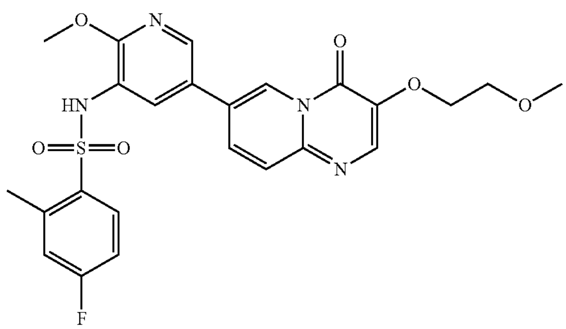 | 515 |
| 253 | 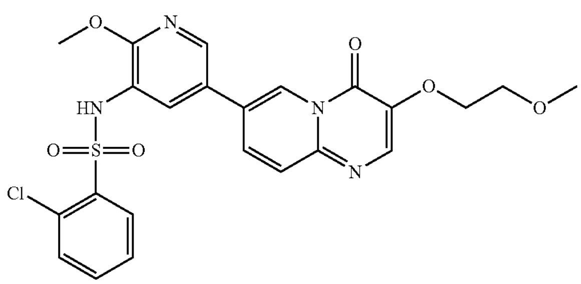 [SMILES: COCCOc1cnc2ccc(-c3cnc(OC)c(NS(=O)(=O)c4ccccc4Cl)c3)cn2c1=O] | 517 |
| 254 | 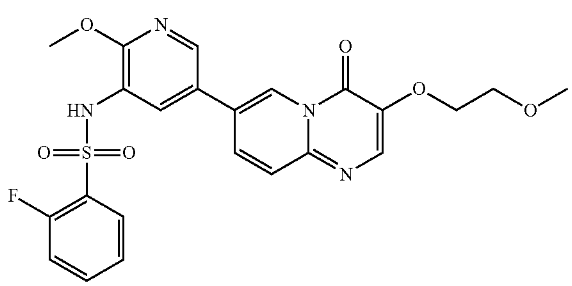 [SMILES: COCCOc1cnc2ccc(-c3cnc(OC)c(NS(=O)(=O)c4ccccc4F)c3)cn2c1=O] | 501 |

-continued

| compound | structure | MS(ES) [M + H]+ |
|---|---|---|
| 255 | 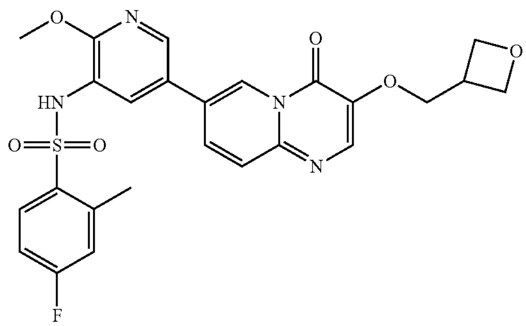 [SMILES: COc1ncc(-c2ccc3ncc(OCC4COC4)c(=O)n3c2)cc1NS(=O)(=O)c1ccc(F)cc1C] | 527 |
| 256 | 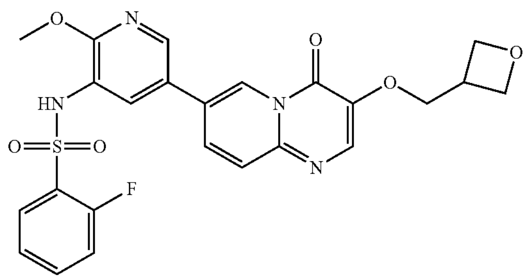 | 513 |
| 257 | 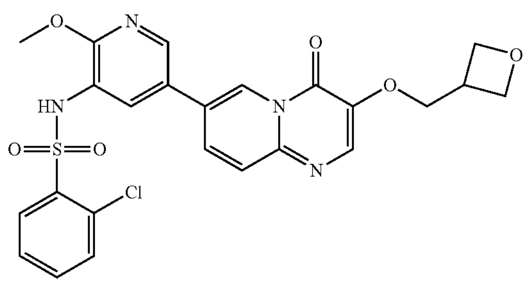 [SMILES: COc1ncc(-c2ccc3ncc(OCC4COC4)c(=O)n3c2)cc1NS(=O)(=O)c1ccccc1F] | 529 |
| 258 | 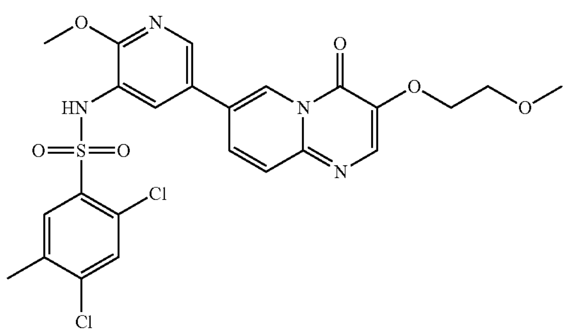 | 565 |
| 259 | 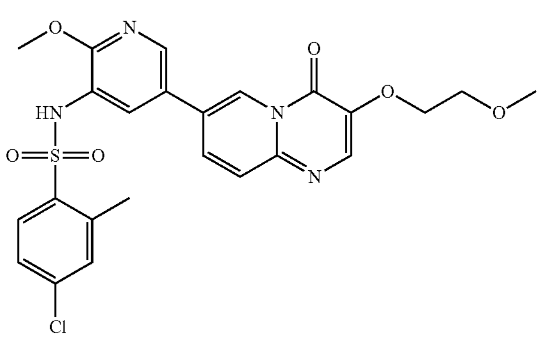 [SMILES: COCCOc1cnc2ccc(-c3cnc(OC)c(NS(=O)(=O)c4ccc(Cl)cc4C)c3)cn2c1=O] | 531 |

-continued

| compound | structure | MS(ES) [M + H]+ |
|---|---|---|
| 260 | 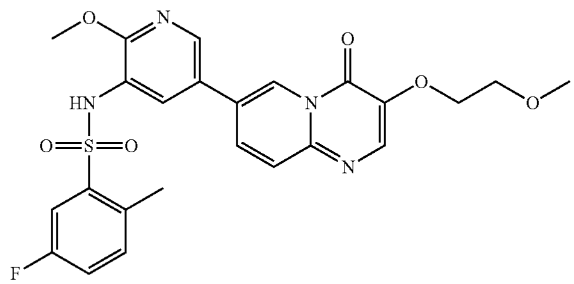 [SMILES: COCCOc1cnc2ccc(-c3cnc(OC)c(NS(=O)(=O)c4cc(F)ccc4C)c3)cn2c1=O] | 515 |
| 261 | 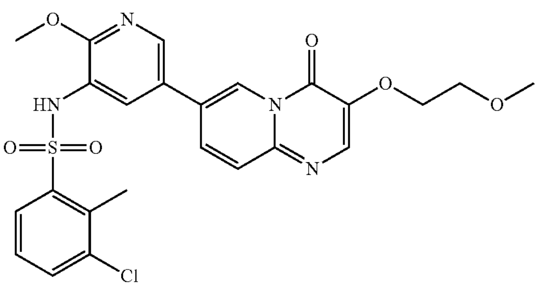 [SMILES: COCCOc1cnc2ccc(-c3cnc(OC)c(NS(=O)(=O)c4cccc(Cl)c4C)c3)cn2c1=O] | 531 |
| 262 | 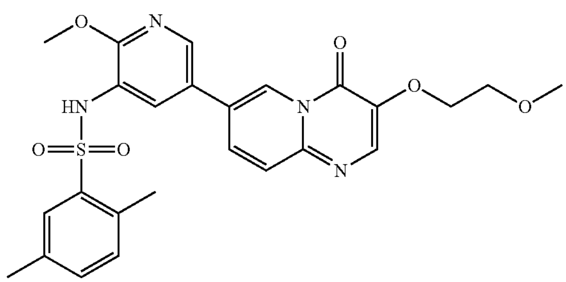 | 511 |
| 263 | 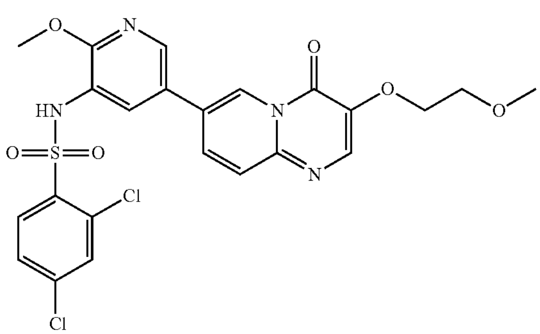 | 551 |
| 264 | 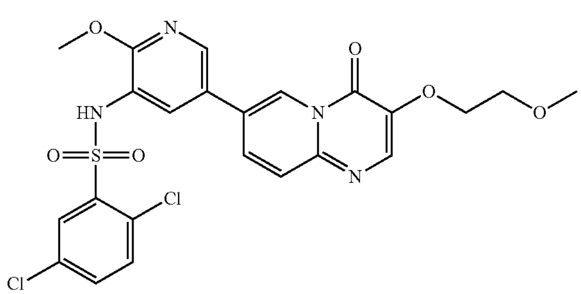 | 551 |

-continued

| compound | structure | MS(ES) [M + H]+ |
|---|---|---|
| 265 | 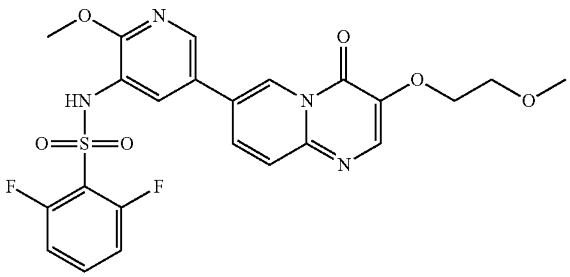 [SMILES: COCCOc1cnc2ccc(-c3cnc(OC)c(NS(=O)(=O)c4c(F)cccc4F)c3)cn2c1=O] | 519 |
| 266 | 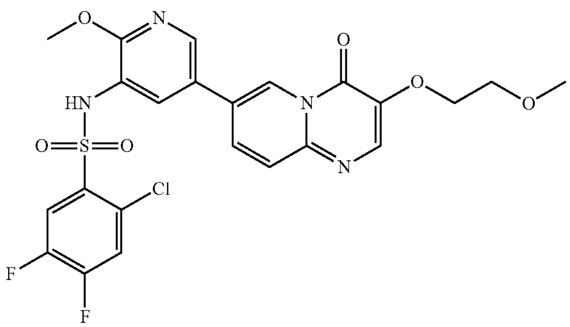 [SMILES: COCCOc1cnc2ccc(-c3cnc(OC)c(NS(=O)(=O)c4cc(F)c(F)cc4Cl)c3)cn2c1=O] | 553 |
| 267 | 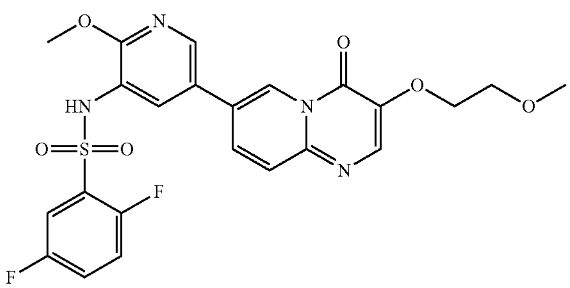 [SMILES: COCCOc1cnc2ccc(-c3cnc(OC)c(NS(=O)(=O)c4cc(F)ccc4F)c3)cn2c1=O] | 519 |
| 268 | 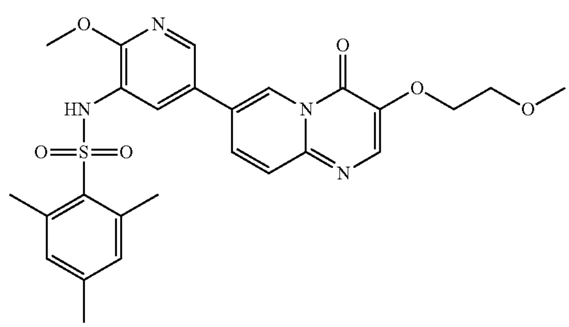 | 525 |
| 269 | 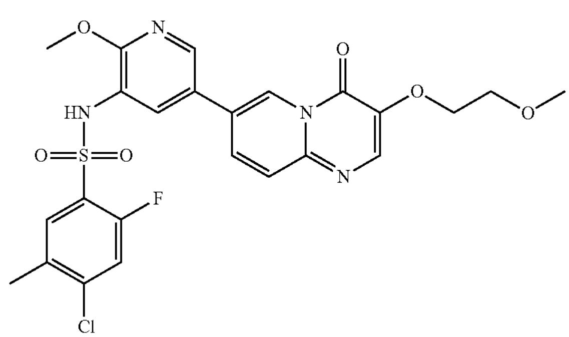 | 549 |

-continued
| compound | structure | MS(ES) [M + H]+ |
|---|---|---|
| 270 | 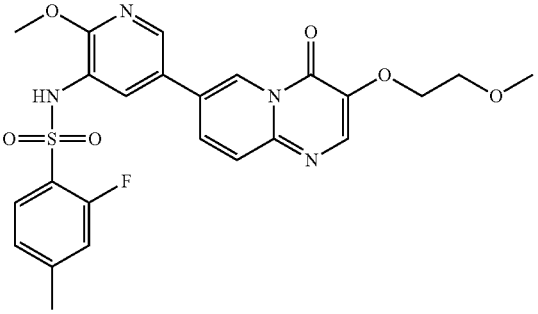 [SMILES: COCCOc1cnc2ccc(-c3cnc(OC)c(NS(=O)(=O)c4ccc(C)cc4F)c3)cn2c1=O] | 515 |
| 271 | 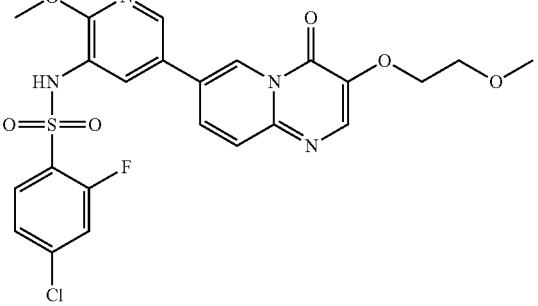 | 535 |
| 272 | 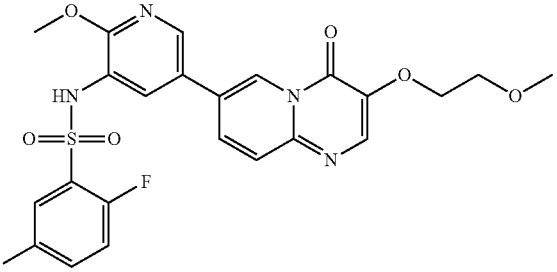 | 535 |
| 273 | 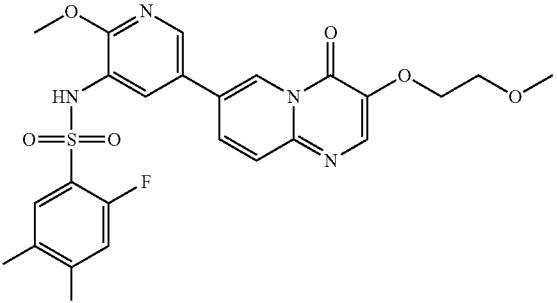 | 553 |
| 274 | 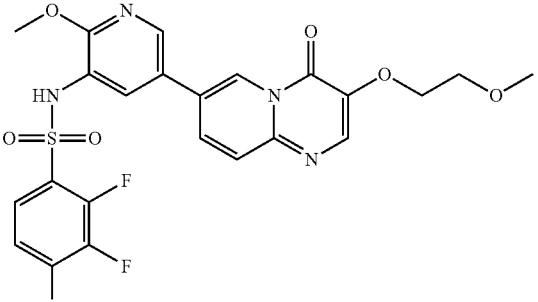 | 537 |

| compound | structure | MS(ES) [M + H]+ |
|---|---|---|
| 275 | 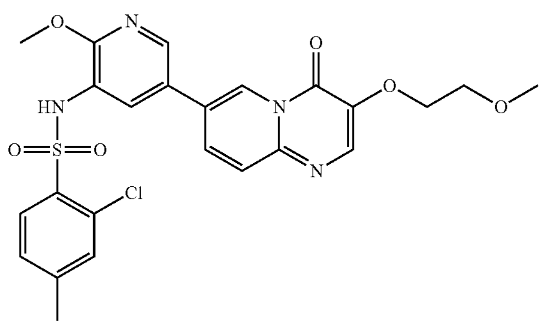 [SMILES: COCCOc1cnc2ccc(-c3cnc(OC)c(NS(=O)(=O)c4ccc(C)cc4Cl)c3)cn2c1=O] | 531 |
| 276 | 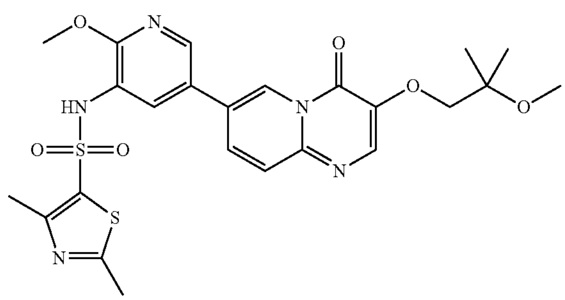 | 546 |
| 277 | 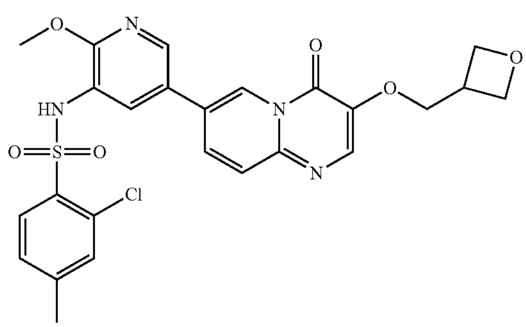 [SMILES: COc1ncc(-c2ccc3ncc(OCC4COC4)c(=O)n3c2)cc1NS(=O)(=O)c1ccc(C)cc1Cl] | 543 |
| 278 | 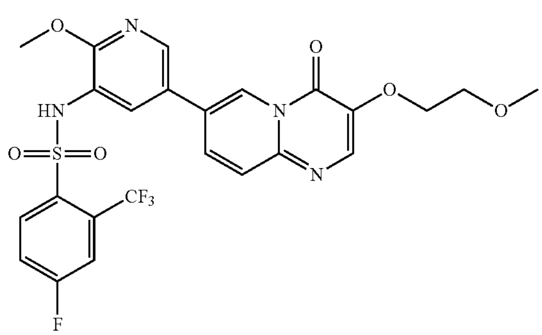 [SMILES: COCCOc1cnc2ccc(-c3cnc(OC)c(NS(=O)(=O)c4ccc(F)cc4C(F)(F)F)c3)cn2c1=O] | 569 |

| compound | structure | MS(ES) [M + H]+ |
|---|---|---|
| 279 | 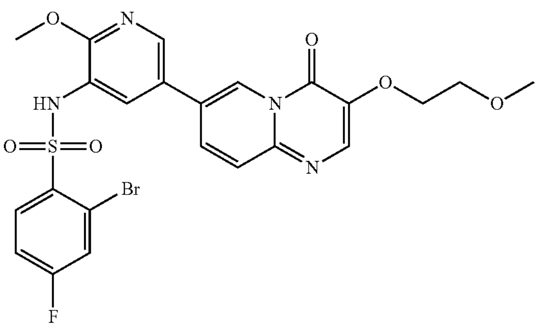 [SMILES: COCCOc1cnc2ccc(-c3cnc(OC)c(NS(=O)(=O)c4ccc(F)cc4Br)c3)cn2c1=O] | 579 |
| 280 | 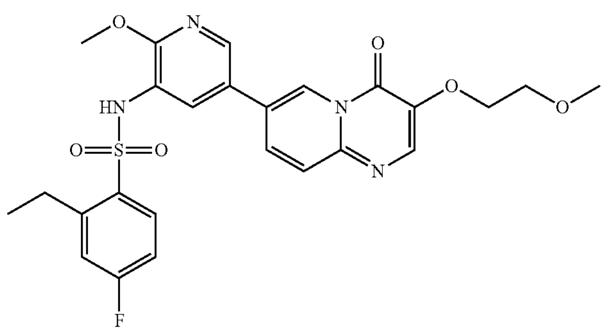 [SMILES: CCc1cc(F)ccc1S(=O)(=O)Nc1cc(-c2ccc3ncc(OCCOC)c(=O)n3c2)cnc1OC] | 529 |
| 281 | 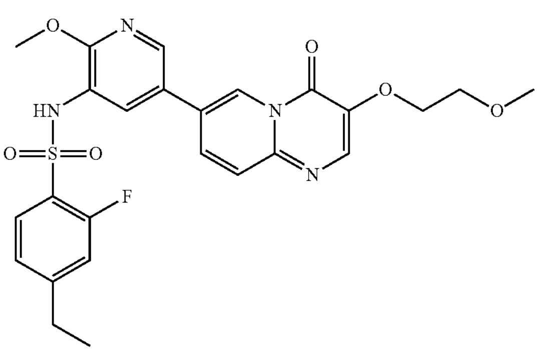 [SMILES: CCc1ccc(S(=O)(=O)Nc2cc(-c3ccc4ncc(OCCOC)c(=O)n4c3)cnc2OC)c(F)c1] | 529 |
| 282 | 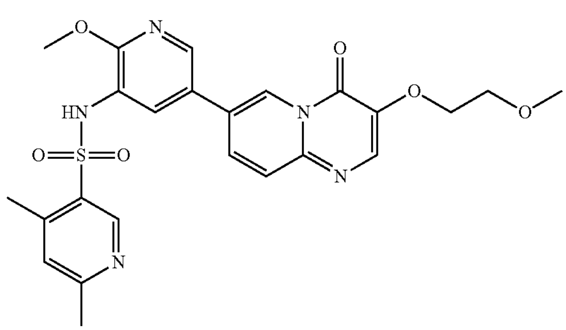 | 512 |

| compound | structure | MS(ES) [M + H]+ |
|---|---|---|
| 283 | 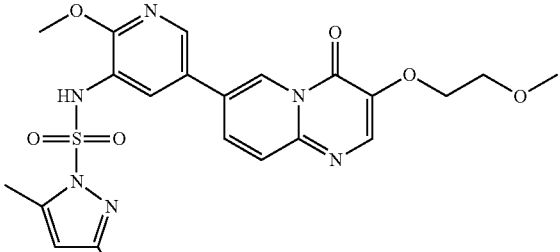 | 501 |
| 284 | 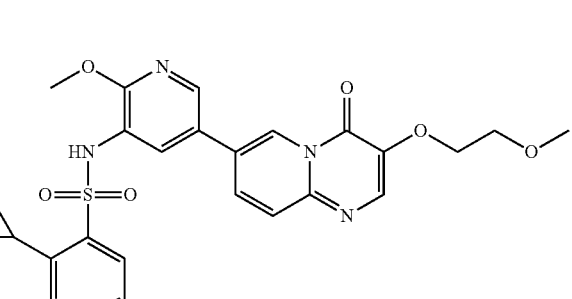 | 541 |

Example In Vitro Tests of Cell Activities

Experimental Steps and Methods:

1) MCF-7 cells were inoculated at the density of 2.5× $10^4$ cells/well into 96-well plates (the culture medium used should be a complete culture medium containing 10% FBS).

2) On the next day, the medium in each well was drawn out. A certain concentration (preliminary screening) or a series of concentration ($IC_{50}$ test) of compounds were dissolved in a culture medium without serum and added to the 96-well plates to culture cells for 2 hours.

3) Insulin was dissolved in a culture medium without serum, added to the cultured cells and incubated for 30 minutes, wherein the final concentration of insulin was 10 mg/ml.

4) A lysis solution was prepared according to the following method during the waiting period for the reaction:

a) Enhancer solution was removed from the refrigerator to melt in advance.

b) Enhancer solution was diluted 10 times with the 5× Lysis Buffer to give a concentrated lysis solution.

c) The concentrated lysis solution was diluted 5 times with double distilled water to give the lysis solution.

5) The medium in each well was completely removed and each well was quickly rinsed with PBS once.

6) 150 µl of the freshly prepared lysis solution was added to each well and shaked at room temperature for 10 minutes.

7) After confirming that all cells were detached, the lysis solution together with the cell fragments was transferred into a 1.5 ml tube.

8) The tube was shaked on vortes mixer to make the lysis solution and cells mix completely and then the mixture was centrifugated at 4° C. under 12000 g for 10 minutes.

9) The number of strips of ELISA-one micro-well plate that is required was calculated. The needless strips were removed from the frame, put back into the storage bag and sealed. Before the strips of micro-well plate were used, 200 µl of double distilled water was used to rinse each well to remove preservative.

10) 50 µl of antibody mixture was added to each well. (The antibody mixture solution was prepared by mixing the medium antibody reagent and the enzyme labeled antibody reagent with an equal proportion. The preparation of antibody mixture didn't need vortex.)

11) 25 µl of cell lysates was added to each well of ELISA-One micro-well plate. The micro-well plate was covered with adhesive sealing film and incubated on a micro-well plate oscillation instrument at room temperature for 1 hour.

12) Each well was rinsed with 150 µl of 1× rinsing buffer 3 times. After the last rinsing, the rinsing buffer in the well was completely removed. If necessary, the 1× rinsing buffer could be allowed to stay in the micro-well plate for up to 30 minutes so that the substrate mixed solution could be prepared during such time period.

13) The substrate mixed solution should be prepared just before each use, 10 µl of the substrate mixed solution was added to each well and the micro-well plate was sealed with tin-foil and incubated on the micro-well plate oscillation instrument at room temperature for 10 minutes.

14) 10 μl of stop solution was added to each well and mixed slightly (5-10 seconds) on the micro-well plate oscillation instrument.

15) The corresponding ELISA-One filter group was assembled and used to read the fluorescence signal intensity. The test results were shown in table 1.

TABLE 1

The test results of in vitro cell activity

| compound | % inhibition | | | IC50 | |
| | AKT | p70s6k | conc. | p-AKT(nM) | p-p70S6K(nM) |
|---|---|---|---|---|---|
| 1 | 97.5 | 42.4 | 1 μM | A | B |
| 2 | 94.2 | 50.8 | 1 μM | C | D |
| 3 | 95.9 | 52.4 | 1 μM | B | B |
| 4 | 95.6 | 50.8 | 1 μM | A | C |
| 5 | 26.0 | 12.3 | 1 μM | NT | NT |
| 6 | 53.0 | 25.3 | 1 μM | B | D |
| 7 | 81.3 | 50.1 | 1 μM | NT | NT |
| 8 | 84.6 | 60.5 | 1 μM | NT | NT |
| 9 | 76.0 | 38.4 | 1 μM | NT | NT |
| 10 | 81.9 | 27.8 | 1 μM | NT | NT |
| 11 | 94.7 | 52.3 | 1 μM | B | C |
| 12 | 95.4 | 91.5 | 1 μM | B | C |
| 13 | 78.3 | 53.0 | 1 μM | NT | NT |
| 14 | 81.4 | 47.3 | 1 μM | NT | NT |
| 15 | 93.3 | 91.7 | 1 μM | NT | NT |
| 16 | 91.6 | 75.1 | 1 μM | A | D |
| 17 | 81.1 | 34.1 | 1 μM | NT | NT |
| 18 | 85.7 | 46.2 | 1 μM | NT | NT |
| 19 | 91.2 | 74.1 | 1 μM | A | D |
| 20 | 93.8 | 89.9 | 1 μM | A | C |
| 21 | 94.1 | 91.2 | 1 μM | B | C |
| 22 | 94.5 | 94.0 | 1 μM | A | C |
| 23 | 95.7 | 93.9 | 1 μM | A | C |
| 24 | 94.6 | 93.2 | 1 μM | B | C |
| 25 | 95.1 | 94.1 | 1 μM | A | B |
| 26 | 95.6 | 93.7 | 1 μM | A | B |
| 27 | 94.8 | 93.5 | 1 μM | NT | NT |
| 28 | 96.2 | 93.9 | 1 μM | A | B |
| 29 | 59.6 | 26.5 | 1 μM | NT | NT |
| 30 | 95.0 | 93.4 | 1 μM | A | B |
| 31 | 67.8 | 45.5 | 1 μM | NT | NT |
| 32 | 75.1 | 84.2 | 0.5 μM | C | C |
| 33 | −40.9 | 0.8 | 0.5 μM | NT | NT |
| 34 | 97.0 | 95.6 | 0.5 μM | A | B |
| 35 | 93.3 | 86.0 | 0.5 μM | A | A |
| 36 | 96.4 | 94.7 | 0.5 μM | A | A |
| 37 | 95.8 | 90.3 | 0.5 μM | A | C |
| 38 | 91.5 | 79.4 | 0.5 μM | A | D |
| 39 | −28.6 | 7.1 | 0.5 μM | NT | NT |
| 40 | 18.1 | 13.7 | 0.5 μM | NT | NT |
| 41 | −10.1 | 0.1 | 0.5 μM | NT | NT |
| 42 | 9.1 | 5.1 | 0.5 μM | NT | NT |
| 43 | 17.8 | 16.2 | 0.5 μM | NT | NT |
| 44 | 6.3 | 4.7 | 0.5 μM | NT | NT |
| 45 | 15.2 | −1.0 | 0.5 μM | NT | NT |
| 46 | 60.3 | 13.3 | 0.5 μM | NT | NT |
| 51 | 64.1 | 13.6 | 0.5 μM | NT | NT |
| 52 | 69.3 | 50.3 | 0.5 μM | NT | NT |
| 53 | 68.0 | 40.9 | 0.5 μM | NT | NT |
| 54 | 83.1 | 50.8 | 0.5 μM | NT | NT |
| 55 | 65.7 | 42.3 | 0.5 μM | NT | NT |
| 56 | 80.2 | 53.3 | 0.5 μM | NT | NT |
| 57 | 58.6 | 47.2 | 0.5 μM | NT | NT |
| 58 | 60.3 | 32.8 | 0.5 μM | NT | NT |
| 59 | 59.7 | 26.5 | 0.5 μM | NT | NT |
| 60 | 67.9 | 43.9 | 0.5 μM | NT | NT |
| 61 | 78.9 | 89.7 | 0.5 μM | A | A |
| 62 | 90.2 | 90.8 | 0.5 μM | A | B |
| 63 | 89.5 | 92.9 | 0.5 μM | A | A |
| 64 | 87.8 | 91.7 | 0.5 μM | A | A |
| 65 | 84.8 | 89.7 | 0.5 μM | A | B |
| 66 | 89.0 | 91.3 | 0.5 μM | A | A |
| 67 | 85.8 | 89.7 | 0.5 μM | A | A |
| 68 | 88.0 | 90.3 | 0.5 μM | A | B |
| 69 | 85.4 | 87.6 | 0.5 μM | A | B |
| 70 | 75.4 | 99.0 | 0.5 μM | B | B |
| 71 | 63.2 | 20.7 | 0.5 μM | NT | NT |
| 72 | 51.1 | 10.2 | 0.5 μM | NT | NT |
| 73 | 40.5 | −2.1 | 0.5 μM | NT | NT |
| 74 | 74.1 | 26.0 | 0.5 μM | NT | NT |
| 76 | 54.3 | 12.2 | 0.5 μM | NT | NT |
| 77 | 50.0 | 4.8 | 0.5 μM | NT | NT |
| 78 | 72.6 | 32.6 | 0.5 μM | NT | NT |
| 79 | 63.3 | 15.9 | 0.5 μM | NT | NT |
| 80 | 54.6 | 14.4 | 0.5 μM | NT | NT |
| 81 | 90.1 | 85.5 | 0.5 μM | A | C |
| 82 | 92.1 | 88.1 | 0.5 μM | A | C |
| 83 | 95.0 | 87.9 | 0.5 μM | A | B |
| 84 | 93.8 | 88.7 | 0.5 μM | A | B |
| 85 | 95.8 | 88.3 | 0.5 μM | A | B |
| 86 | 92.8 | 88.1 | 0.5 μM | A | C |
| 87 | 92.1 | 88.1 | 0.5 μM | A | C |
| 88 | 94.8 | 91.0 | 0.5 μM | A | C |
| 89 | 93.0 | 88.1 | 0.5 μM | A | C |
| 90 | 92.7 | 87.9 | 0.5 μM | A | C |
| 91 | 94.6 | 89.2 | 0.5 μM | A | B |
| 92 | | | | A | NT |
| 93 | | | | A | NT |
| 94 | | | | A | NT |
| 95 | | | | C | NT |
| 96 | | | | D | NT |
| 97 | | | | D | NT |
| 98 | | | | D | NT |
| 99 | | | | A | NT |
| 101 | 25.0 | 8.6 | 0.25 μM | NT | NT |
| 102 | 37.3 | 18.2 | 0.25 μM | NT | NT |
| 103 | 94.5 | 89.4 | 0.5 μM | A | B |
| 104 | 95.2 | 91.7 | 0.5 μM | A | A |
| 105 | 95.4 | 90.3 | 0.5 μM | A | A |
| 106 | 96.2 | 91.8 | 0.5 μM | A | B |
| 107 | 94.5 | 91.0 | 0.5 μM | A | B |
| 108 | 92.4 | 82.5 | 0.25 μM | A | A |
| 109 | | | | A | NT |
| 110 | | | | B | NT |
| 111 | | | | A | NT |
| 112 | 40.8 | 3.6 | 0.5 μM | NT | NT |
| 113 | −7.6 | 4.6 | 0.5 μM | NT | NT |
| 114 | 53.0 | −1.2 | 0.5 μM | NT | NT |
| 115 | 43.6 | 6.5 | 0.5 μM | NT | NT |
| 116 | 52.3 | 6.7 | 0.5 μM | NT | NT |
| 117 | 63.7 | 16.6 | 0.5 μM | NT | NT |
| 118 | 27.8 | 11.5 | 0.5 μM | NT | NT |
| 121 | −27.1 | −2.2 | 0.5 μM | NT | NT |
| 122 | −26.6 | 1.2 | 0.5 μM | NT | NT |
| 123 | −82.1 | 6.7 | 0.5 μM | NT | NT |
| 124 | −48.0 | 2.8 | 0.5 μM | NT | NT |
| 125 | 23.5 | 5.0 | 0.5 μM | NT | NT |
| 126 | −12.7 | 2.4 | 0.5 μM | NT | NT |
| 127 | 22.0 | −5.3 | 0.5 μM | NT | NT |
| 128 | −1.1 | 0.4 | 0.5 μM | NT | NT |
| 129 | −24.2 | 1.2 | 0.5 μM | NT | NT |
| 130 | 2.3 | 2.6 | 0.5 μM | NT | NT |
| 131 | −27.0 | 4.5 | 0.5 μM | NT | NT |
| 132 | 93.0 | 88.8 | 0.5 μM | A | C |
| 133 | | | | D | NT |
| 134 | 94.9 | 87.7 | 0.5 μM | A | B |
| 135 | 95.2 | 87.6 | 0.5 μM | A | B |
| 136 | 95.5 | 87.2 | 0.5 μM | A | B |
| 137 | 93.3 | 87.1 | 0.5 μM | A | C |
| 138 | 68.9 | 73.8 | 0.5 μM | NT | NT |
| 139 | 93.7 | 88.5 | 0.5 μM | A | B |
| 140 | 94.8 | 90.5 | 0.5 μM | A | B |
| 141 | 96.1 | 88.1 | 0.5 μM | A | A |
| 142 | 94.8 | 90.8 | 0.5 μM | A | B |
| 143 | 95.7 | 87.7 | 0.5 μM | A | A |
| 144 | 95.8 | 89.4 | 0.5 μM | A | A |
| 145 | 94.9 | 90.5 | 0.5 μM | A | C |
| 146 | 77.6 | 83.7 | 0.25 μM | NT | NT |
| 147 | 80.3 | 81.3 | 0.25 μM | B | B |

TABLE 1-continued

The test results of in vitro cell activity

| compound | % inhibition AKT | % inhibition p70s6k | conc. | IC50 p-AKT(nM) | IC50 p-p70S6K(nM) |
|---|---|---|---|---|---|
| 148 | 88.9 | 86.3 | 0.25 μM | B | B |
| 149 | 92.0 | 80.7 | 0.25 μM | A | A |
| 150 | 93.5 | 82.3 | 0.25 μM | A | A |
| 151 | 93.2 | 83.6 | 0.25 μM | A | A |
| 152 | 94.0 | 83.9 | 0.25 μM | A | A |
| 153 | 91.6 | 83.5 | 0.25 μM | A | A |
| 154 | 85.4 | 92.6 | 0.25 μM | C | B |
| 155 | 29.8 | 42.2 | 0.25 μM | NT | NT |
| 156 | 77.9 | 74.114 | 0.25 μM | B | C |
| 157 | 79.2 | 90.8 | 0.25 μM | A | B |
| 158 | −21.8 | 5.1 | 0.25 μM | NT | NT |
| 159 | 68.6 | 84.8 | 0.25 μM | C | C |
| 160 | 61.9 | 71.6 | 0.25 μM | NT | NT |
| 161 | 79.5 | 41.0 | 0.25 μM | B | D |
| 162 | 77.8 | 64.9 | 0.25 μM | B | C |
| 163 | 78.1 | 88.8 | 0.25 μM | C | B |
| 164 | 79.4 | 89.6 | 0.25 μM | A | B |
| 165 | 49.5 | 63.7 | 0.25 μM | NT | NT |
| 166 | 66.5 | 89.2 | 0.25 μM | C | C |
| 167 | | | | C | NT |
| 168 | | | | A | NT |
| 169 | | | | A | NT |
| 170 | | | | A | NT |
| 171 | 76.3 | 73.4 | 0.25 μM | B | C |
| 172 | 83.5 | 74.4 | 0.25 μM | A | C |
| 173 | 88.9 | 82.6 | 0.25 μM | NT | NT |
| 174 | 92.5 | 78.4 | 0.25 μM | A | A |
| 175 | 75.2 | 65.4 | 0.25 μM | B | C |
| 176 | | | | A | A |
| 177 | | | | D | NT |
| 178 | | | | B | NT |
| 179 | | | | A | A |
| 180 | | | | A | NT |
| 181 | | | | A | NT |
| 182 | | | | D | NT |
| 183 | | | | A | NT |
| 184 | | | | B | NT |
| 185 | | | | A | NT |
| 186 | | | | A | NT |
| 187 | | | | A | NT |
| 188 | | | | A | NT |
| 189 | | | | A | NT |
| 190 | | | | A | NT |
| 191 | | | | A | NT |
| 192 | | | | A | NT |
| 193 | | | | A | NT |
| 194 | | | | A | NT |
| 195 | | | | A | NT |
| 196 | | | | A | NT |
| 197 | | | | A | NT |
| 198 | | | | A | NT |
| 199 | | | | A | NT |
| 200 | | | | A | NT |
| 201 | | | | A | NT |
| 202 | | | | A | NT |
| 203 | | | | A | NT |
| 204 | | | | A | NT |
| 205 | | | | B | NT |
| 207 | | | | B | |
| 208 | | | | A | |
| 209 | | | | A | |
| 212 | | | | D | |
| 213 | | | | B | |
| 214 | | | | A | |
| 215 | | | | D | NT |
| 216 | 34.1 | 31.0 | 0.25 μM | NT | NT |
| 217 | 54.0 | 67.7 | 0.25 μM | NT | NT |
| 218 | 85.2 | 85.0 | 0.25 μM | C | C |
| 219 | 41.7 | 13.4 | 0.25 μM | NT | NT |
| 220 | 51.2 | 11.0 | 0.25 μM | NT | NT |
| 221 | −42.0 | 6.8 | 0.25 μM | NT | NT |
| 222 | −26.7 | 2.0 | 0.25 μM | NT | NT |
| 223 | 17.9 | −1.5 | 0.25 μM | NT | NT |
| 226 | 14.8 | 4.6 | 0.5 μM | NT | NT |
| 229 | 31.7 | 1.4 | 0.5 μM | NT | NT |
| 230 | 43.5 | 8.8 | 0.5 μM | NT | NT |
| 231 | | | | D | NT |
| 232 | | | | D | NT |
| 234 | | | | D | NT |
| 235 | | | | C | NT |
| 236 | | | | B | NT |
| 239 | | | | A | NT |
| 242 | | | | C | NT |
| 243 | | | | A | NT |
| 244 | | | | B | NT |
| 245 | | | | A | NT |
| 246 | | | | C | NT |
| 247 | | | | C | NT |
| 248 | | | | B | NT |
| 249 | | | | A | NT |
| 250 | | | | B | NT |
| 251 | | | | C | NT |
| 252 | | | | D | NT |
| 253 | | | | A | NT |
| 254 | | | | B | NT |
| 255 | | | | C | NT |
| 256 | | | | A | NT |
| 257 | | | | A | NT |
| 260 | | | | C | NT |
| 261 | | | | B | NT |
| 262 | | | | B | NT |
| 263 | | | | B | NT |
| 265 | | | | C | NT |
| 266 | | | | C | NT |
| 268 | | | | C | NT |
| 271 | | | | B | NT |
| 272 | | | | A | NT |
| 273 | | | | C | NT |
| 274 | | | | B | NT |
| 275 | | | | A | NT |
| 276 | | | | A | NT |
| 277 | | | | A | NT |
| 278 | | | | A | NT |
| 279 | | | | A | NT |
| 280 | | | | A | NT |
| 281 | | | | A | NT |

Note:
A ≤ 50 nM; 50 nM < B ≤ 100 nM; 100 nM < C ≤ 250 nM; 250 nM < D; NT indicates no detection.

Conclusion: The compounds of the present invention have significant inhibitory effect on mTOR/PI3K.

Example In Vitro Enzyme Activity Assay

1. The experimental procedures and methods of PI3K (p110α) kinase assay:

1) Experimental Objective

The objective was to evaluate the inhibitory effect of the subject samples on PI3K (p110α) kinase activity at molecular level.

2) Experimental Method

PI3K HTRF Assay a) Primary instrument

PerkinElmer Envision 2104 Multilabel Reader.

b) Primary reagents

PI 3-Kinase HTRF Assay (384 wells) was purchased from Upstate (Millipore) company: PI3K (p110α) kinase was made in our lab.

c) Experimental procedures

Each solution was prepared according to the instructions provided in the Kinase PI 3-Kinase HTRF Assay. The kinase reaction was carried out in white 384-well plates (Proxiplate-384 plus), 0.5 μl of DMSO (the concentration was consistent with the highest concentration of DMSO for the test compounds) was added to each of the two control wells with and without enzyme, and then 0.5 µl of a series of different concentrations of the test compounds was added to each well to be tested. The kinase reaction liquid (10 µM substrate PIP2, 0.5 ng PI3K (p110α)) was added to the control well containing enzyme and the test wells, while only working reaction liquid (10 µM substrate PIP2) was added to the control well without enzyme, and finally, 5 µM ATP working reaction liquid was added to activate the reaction. After the reaction was carried out at room temperature for 30 min, the stop solution was added to each well to terminate the kinase reaction. After the mixture was fully mixed, the detection liquid was added to each well and fully mixed. The plate was sealed with Parafilm and placed in the dark. After incubated overnight, the mixture was detected. The setting conditions of the detector were shown in the following table.

TABLE 2

The setting conditions of the Multilabel Reader

| Excitation | 330-380 nm |
| --- | --- |
| Emission | 665-667.5 nm and 620-635 nm |
| Counting Delay | 50 usec |
| Counting window | (integration time) 400 usec |

HTRF (Homogeneous Time-Resolved Fluorescence) data were calculated according to the following formula:
HTRF Radio = Emission at 665 nm/Emission at 620 nm × 10000
Relative inhibitory rate (%) = (HTRF value of the test well − HTRF value of the control well with enzyme)/(HTRF value of the control well without enzyme − HTRF value of the control well with enzyme) × 100

The $IC_{50}$ value was calculated through the GraphPad software after plotting the relative inhibitory rate versus concentration.

2. Experimental Procedures and Methods of the mTOR Kinase Assay

1) Experiment Objective

The objective was to evaluate the inhibitory effect of the subject samples on the mTOR kinase activity at molecular level.

2) Experiment Method mTOR Kinase Assay a) Primary instrument

PerkinElmer Envision 2104 Multilabel Reader.

b) Primary reagents

The mTOR Kinase Assay (384 wells) was purchased from PerkinElmer company; the mTOR kinase was made in our lab.

c) Experiment procedures

Each solution was prepared according to the instructions provided in the mTOR Kinase Assay. The kinase reaction was carried out in white 384-well plates (Proxiplate-384 plus). 2.5 µl of DMSO (the concentration was consistent with the highest concentration of DMSO for the test compounds) was added to each of the two control wells with and without enzyme, and then 2.5 µl of a series of different concentrations of the test compounds was added to each test well. ULight-4E-BP1 (Thr37/46) PeptideATP mix (the final concentration of ATP was 100 µM) and 5 µl of mTOR kinase were added to the control well containing enzyme as well as the test wells, and fully mixed. The plate was sealed with Parafilm and incubated for 2 h. Then 5 µl of stop solution was added and incubated for 5 minutes. Afterwards, 5 µl of Detection Mix (Eu-anti-phospho-4E-BP1 (Thr37/46) Antibody, the final concentration was 2 nM) was added and incubated for 1 h, and then the mixture was detected. The setting conditions of the detector were shown in the following table.

TABLE 3

The setting conditions of Multilabel Reader

| Excitation | 320-340 nm |
| --- | --- |
| Emission | 665 nm and 615 nm |
| Counting Delay | 50 usec |
| Counting window | (integration time) 400 usec |

HTRF (Homogeneous Time-Resolved Fluorescence) data were calculated according to the following formula:
HTRF Radio = Emission at 665 nm/Emission at 615 nm × 10000
Relative inhibitory rate (%) = {1 − (HTRF value of the test well − HTRF value of the control well with enzyme)/(HTRF value of the control well with enzyme − HTRF value of the control well without enzyme)} × 100%

The $IC_{50}$ value was calculated through the GraphPad software after plotting the relative inhibitory rate versus concentration.

The test results were shown in table 4.

TABLE 4

The results of the In vitro enzyme activity assay

| Example | mTOR enzyme activity_IC50 | PI3K (p110α) enzyme activity_IC50 |
| --- | --- | --- |
| 1 | C | B |
| 25 | C | B |
| 26 | C | B |
| 28 | C | B |
| 30 | C | A |
| 36 | B | B |
| 61 | A | C |
| 81 | B | B |
| 83 | B | A |
| 104 | C | B |
| 132 | B | B |
| 135 | B | A |
| 144 | A | A |
| 149 | B | B |
| 150 | B | A |
| 153 | B | A |
| 174 | D | A |
| 242 | | A |
| 243 | | A |
| 244 | | A |
| 245 | | A |
| 246 | | A |
| 247 | | A |
| 249 | | A |
| 250 | | A |
| 251 | | A |
| 252 | | B |
| 253 | | A |
| 255 | | A |
| 257 | | A |
| 258 | | B |
| 260 | | A |
| 261 | | A |
| 262 | | A |
| 263 | | A |
| 265 | | A |
| 268 | | B |
| 269 | | B |
| 271 | | A |
| 275 | | A |
| 277 | | A |
| 282 | | A |
| 283 | | B |
| 284 | | B |

Note:
A ≤ 1 nM; 1 nM < B ≤ 10 nM; 10 nM < C ≤ 50 nM; 50 nM < D ≤ 100 nM.

In Vivo Pharmacodynamics Experiment:

The studies were conducted to examine if the drugs to be tested have in vivo efficacy in the ovarian cancer SK-OV-3 animal model and the prostate cancer PC-3M animal model. The descriptions relating to the animal feeding, feed ingredients, experiment observation, experiment criteria, experiment termination as well as data analysis were as follows.

animal feeding: The animals arrived in the experimental environment and were fed for 3-7 days before starting the experiment. Animals were housed in IVF (independent air supply system) cages (5 animals per cage) in SPF-grade animal rooms. All cages, padding and drinking water were required to be sterilized before use, and the sterilization records were shown in the annex. When operating, all laboratory personnel in the animal room should wear protective clothing and latex gloves. Each cage information card should indicate the number of animals in the cage, gender, strain, date of receipt, dosage regimen, experiment number, group, and date of commencement of the experiment. Cages, feed and water were replaced twice a week. Feeding environment and light conditions were as follows.

temperature: 20-26° C.

humidity: 40-70% photoperiod: 12 h with light, 12 h without light

Feed ingredients: Feed conformed to the food identification standards of experimental animals. The maximum pollutant content was in a controllable range and inspected by the manufacturer. Drinking water sterilized through high pressure was used for drink.

Animal groups: animals were weighed before dosing and tumor volume was measured. The animals were randomly grouped according to tumor volume (randomized block design).

Observation: The implement of formulation of the protocol and any modifications need to be evaluated and approved by WuXi APP Tec (Shanghai) Laboratory Animal Ethics Committee (IACUC). The use and welfare of laboratory animals will be governed by the rules of the International Laboratory Animal Assessment and Accreditation Council (AAALAC). The health condition and death status of the animals were monitored daily. The routine inspections included observation of tumor growth and the effect of drug treatment on the daily behavior of animals such as, activities, intake of food and water, weight changes (measured twice a week), appearance or other abnormal status. The number of animal deaths and side effects in each group were recorded based on the number of animals in each group. The relevant records were attached.

Experiment criteria: The experiment criteria was to investigate whether the tumor growth was inhibited, delayed or cured. Tumor diameter was measured twice a week using vernier calipers. Tumor volume was calculated according to the following formula: $V=0.5a \times b^2$, a and b indicated the long diameter and short diameter of the tumor, respectively. Tumor growth inhibition (TGI) of the compound was evaluated in T-C(days) and TiC (%). T-C(days) indicates tumor growth delay. T represents the average number of days for the tumor in the administration group to reach a pre-set volume (e.g., 1.000 mm³), and C represents the average number of days for the tumor in the control group to reach the same volume. The percentage of TIC (%) reflects the ratio of tumor growth inhibition, and T and C represents the tumor weight (tumor volume) of the administration group and control group on a given day, respectively.

The ratio of tumor growth inhibition was calculated by the following formula:

$TGI(\%)=[1-(Ti-T0)/(Vi-V0)] \times 100$, wherein, Ti is the average volume of the tumors of a given administration group on a given day, T0 is the average volume of the tumors of that administration group at the beginning of the administration. Vi is the average volume of the tumors of the vehicle control group on a given day (the same day as Ti), V0 is the average volume of the tumors of the vehicle control group at the beginning of the administration. At the end of the experiment, the tumor weight was measured and the percentage of T/C was calculated. T and C represent the tumor weight of the administration group and the vehicle control group, respectively.

experiment termination: If the animal's health condition continued to deteriorate, or the tumor volume exceeded 2,000 mm³, or the animal had serious illness or pain, the animal needed to be euthanized. Veterinarians were notified and the animal was euthanized in the following circumstances:

The animals became thin significantly, and the weight loss was greater than 20%.

The animals were unable to freely feed and drink.

The average tumor volume in the control group reached 2,000 mm³ and the experiment was terminated.

Animals exhibited the following clinical manifestations and continued to deteriorate:

Piloerection

Arched back

Pale ear, nose, eye or foot

Breathing hastily

Seizures

Continuous diarrhea

Dehydration

Slow movement

Sound

Data analysis: Three or more groups were compared with one-way ANOVA. If F value had significant difference, multiple comparisons should be performed after ANOVA analysis. All data analysis was performed using SPSS 17.0, p<0.05 was considered significant difference.

In Vivo Pharmacodynamics Experiment of Test Drugs in Subcutaneous Xenograft Tumor Models of Human Ovarian Cancer SK-OV-3 Cells:

Experiment Design

Cell culture: Human ovarian cancer SK-OV-3 cells (ATCC, Manassas, Va., batch number: HTB-77) were cultured in monolayer in vitro in McCoy's 5A medium supplemented with 10% FBS, 100 U/ml penicillin and 100 µg/ml streptomycin at 37° C. in a 5% $CO_2$ incubator. Trypsin-EDTA was used for routine digestion and passage twice a week. When the cell confluence was 80%-90%, and the number reached the requirements, the cells were collected, counted, and inoculated.

Animals: BALB/c nude mice, female, 4 weeks old, 12-14 g of body weight, were provided by Shanghai Sippr-BK Laboratory Animal Co., Ltd.

Tumor inoculation: 0.2 ml (1×10⁷) SK-OV-3 cells (with matrix gel, 1:1 volume ratio) were inoculated subcutaneously into the right back of each mouse. When the average volume of tumors reached approximately 100 to 200 mm³, the mice were divided into groups and drugs were administrated to each group.

In vivo pharmacodynamics results: see FIG. 1.

In Vivo Pharmacodynamics Experiment Study of the Test Drugs in Subcutaneous Xenograft Tumor Models of Human Prostate Cancer PC-3M Cells:

Experiment objective: to investigate the in vivo pharmacodynamics of the test compounds in subcutaneous xenograft tumor models of human prostate cancer PC-3M cells Experiment Design Cell culture: Human prostate cancer PC-3M cells were cultured in RPMI-1640 medium supplemented with 10% FBS, 100 U/ml penicillin and 100 g/ml streptomycin at 37° C. in a 5% $CO_2$ incubator. Trypsin-EDTA was used for routine digestion and passage twice a week. When the cell confluence reached 80%-90%, and the number reached the requirements, the cells were collected, counted, and inoculated.

Animals: BALB/c nude mice, male, 4 weeks old, 12-14 g of body weight, were provided by Shanghai Sippr-BK Laboratory Animal Co., Ltd.

Tumor inoculation: 0.2 ml (1×10) PC-3M cells were inoculated subcutaneously into the right back of each mouse. When the average volume of tumors reached approximately 150 to 200 mm³, the mice were divided into groups and drugs were administrated to each group. Experiment grouping and dosing regimens were shown in the following table.

In vivo pharmacodynamics results: see FIG. 2-1, FIG. 2-2. FIG. 2-3a and FIG. 2-3b.

The invention claimed is:

1. A compound of formula (I), or a pharmaceutically acceptable salt thereof,

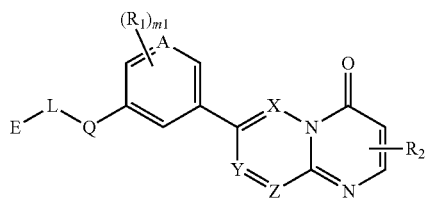
(I)

wherein,

E is selected from the group consisting of $C_{3-6}$ cycloalkyl or $C_{1-6}$ alkyl substituted by $R_3$, and the number of $R_3$ is 0, 1, 2 or 3; or E is selected from the group consisting of

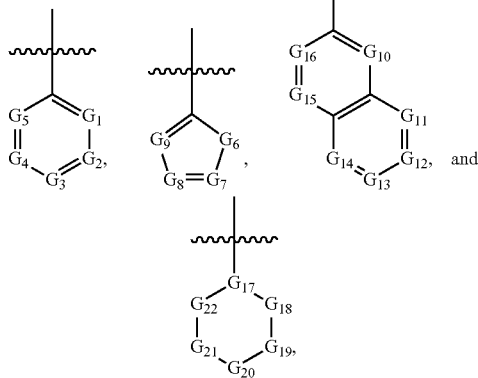

or E is selected from the group consisting of

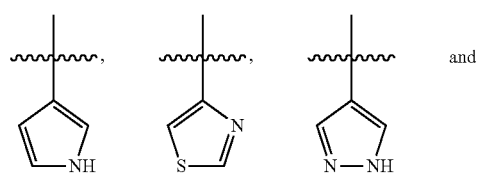

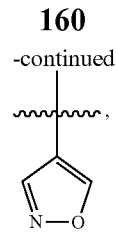

optionally substituted by 1, 2, or 3 $R_3$, wherein, zero, one, two or three of $G_{1-5}$ are selected from N, and the others are selected from $C(R_3)$;

$G_6$ is selected from the group consisting of —$C(R_3)(R_3)$—, —$N(R_3)$—, —O—, and —S—;

zero, one, or two of $G_{7-9}$ are N, and the others are selected from $C(R_3)$;

zero or one of $G_{10-16}$ is N, and the others are selected from $C(R_3)$;

$G_{17}$ is selected from N and $C(R_3)$;

Zero or one of $G_{18-22}$, is —O—, and the others are selected from —$C(R_3)(R_3)$—;

one of L and Q is —$S(=O)_2NH$—, and the other is a single bond;

A is N or CH;

zero or one of X, Y, and Z is N, and the others are CH;

$m_1$ is 1;

$R_1$, $R_2$, and $R_3$ are independently selected from the group consisting of H, F, Cl, Br, I, CN, $OR_a$, $N(R_b)(R_c)$, $C_{1-3}$ alkyl optionally substituted by $R_d$,

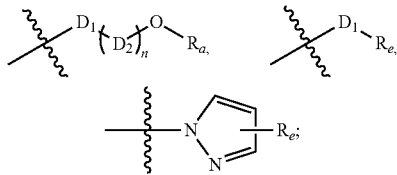

$D_1$ is selected from the group consisting of a single bond, —$C(R_e)(R_e)$—, —$C(=O)N(R_a)$—, —$N(R_a)$—, —$S(=O)_2 N(R_a)$—, and —O—;

$D_2$ is —$C(R_a)(R_a)$—;

n is selected from 1, 2, 3, 4, 5, or 6;

$R_a$, $R_b$, and $R_c$, are independently selected the group consisting of H, $C_{3-6}$ cycloalkyl or $C_{1-6}$ alkyl optionally substituted by $R_d$;

$R_e$ is selected from the group consisting of H, $C_{1-6}$ alkyl or alkoxy optionally substituted by $R_d$, and $C_{3-6}$ cycloalkyl optionally substituted by $R_d$;

$R_d$ is selected from the group consisting of F, Cl, Br, I, CN, OH, CHO, COOH, $CH_3$, $CF_3$, $CH_3O$, and $CH_3CH_2O$, and the number of $R_d$ is selected from 0, 1, 2, or 3;

optionally, $R_a$ and $R_a$ in the same $D_2$, two $D_2$, or $R_a$ and one $D_2$, together with the same carbon atom or oxygen atom to which they both attach, form one 3-, 4-, 5- or 6-membered carbocyclic rings or oxygen-containing heterocyclic rings, wherein the number of oxygen atom is 1 or 2.

2. The compound of formula (I) or a pharmaceutically acceptable salt thereof according to claim 1, wherein E is selected from the group consisting of methyl, ethyl, propyl,

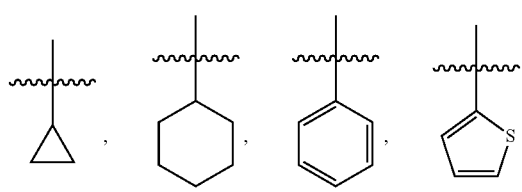

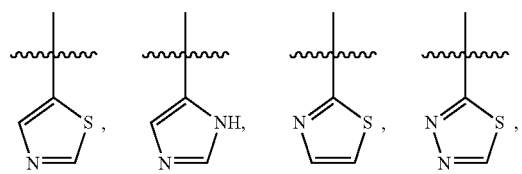

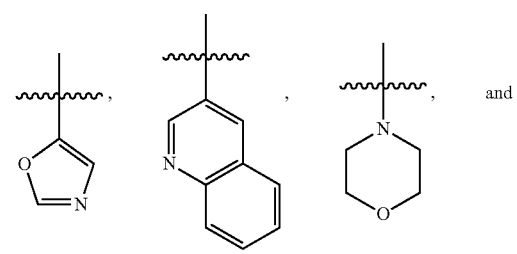

optionally substituted by 1, 2, or 3 $R_3$.

3. The compound of formula (I) or a pharmaceutically acceptable salt thereof according to claim 1, wherein E is selected from the group consisting of

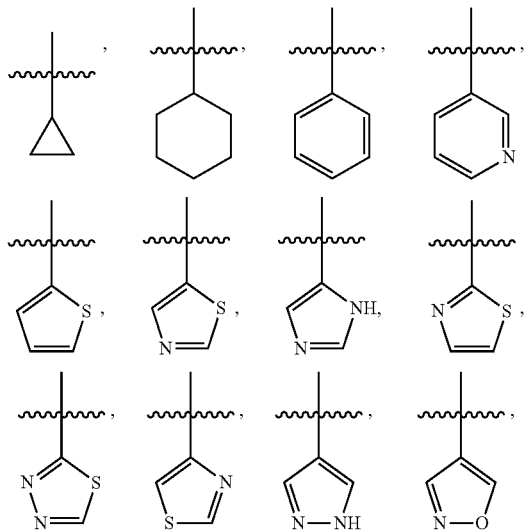

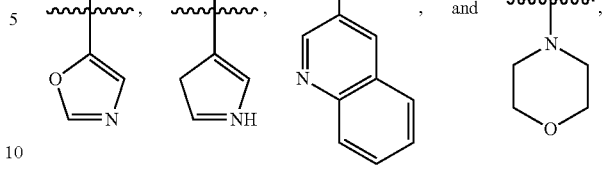

the above group being optionally substituted by 1, 2, or 3 halogen, OH, $OC_{1-3}$ alkyl, CN, $NH_2$, $NH(C_{1-3}$ alkyl), $N(C_{1-3}$ alkyl$)_2$, $C_{1-3}$ alkyl, trifluoromethyl, trifluoroethyl, C(=O)$NH_2$, $C_{1-3}$ alkylC(=O), $C_{1-3}$ alkylC(=O)NH, $C_{1-3}$ alkylS(=O), $C_{1-3}$ alkylS(=O)NH, $C_{1-3}$ alkylS(=O)$_2$ or $C_{1-3}$ alkyl S(=O)$_2$NH.

4. The compound of formula (I) or a pharmaceutically acceptable salt thereof according to claim 1, wherein the ring formed between $R_a$ and $R_a$ in the same $D_2$, two $D_2$, or $R_a$ and one $D_2$ is selected from the group consisting of cyclopropyl, cyclobutyl, cyclopentyl, cyclohexyl, oxetanyl, 1,3-dioxolanyl.

5. The compound of formula (I) or a pharmaceutically acceptable salt thereof according to claim 1, wherein $R_1$, $R_2$, and $R_3$ are independently selected from the group consisting of H, F, Cl, Br, I, CN, OH, $NH_2$, methyl, ethyl, propyl, methoxy, ethoxy, methylamino, dimethylamino, halomethyl, haloethyl, halopropyl, aminomethyl, aminoethyl, aminopropyl, cyclopropyl,

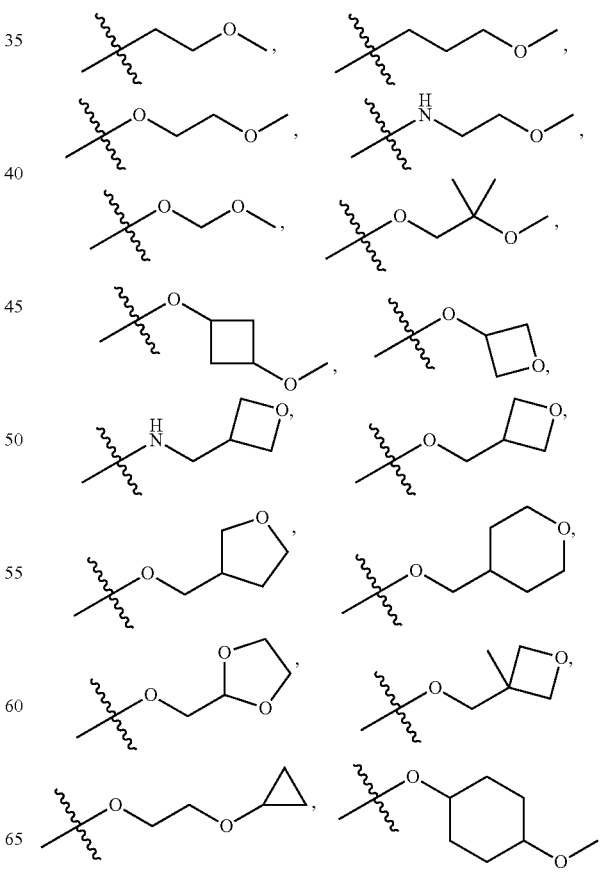

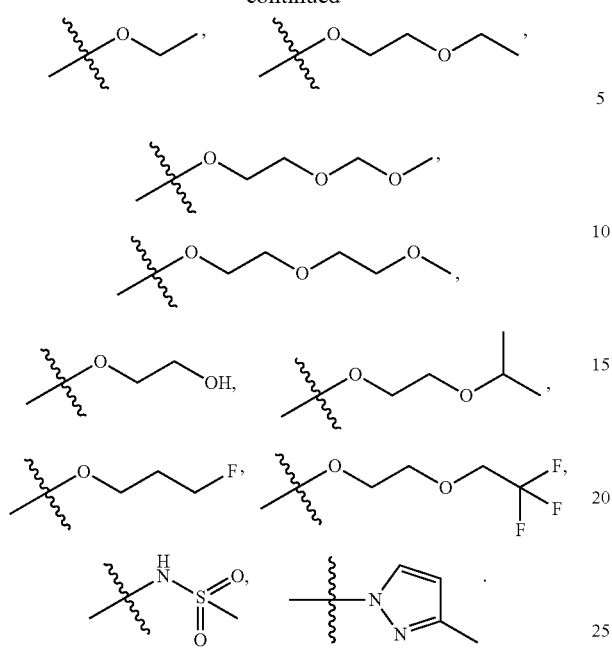
6. The compound of formula (I) or a pharmaceutically acceptable salt thereof according to claim 1, wherein the compound is selected from the group consisting of
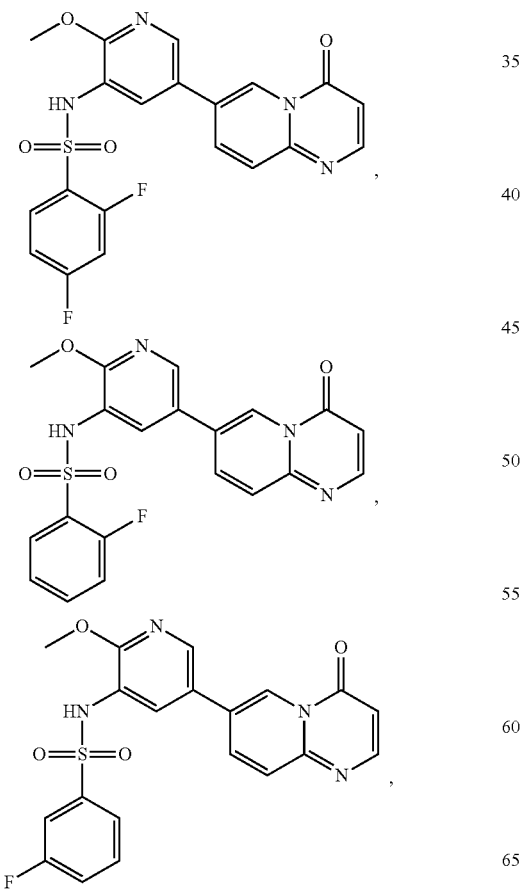
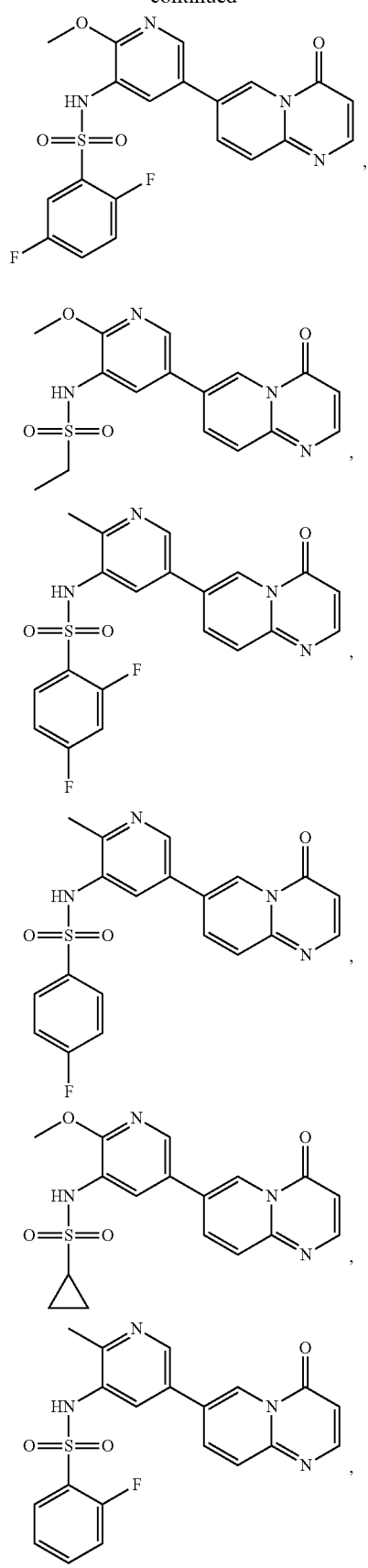

-continued
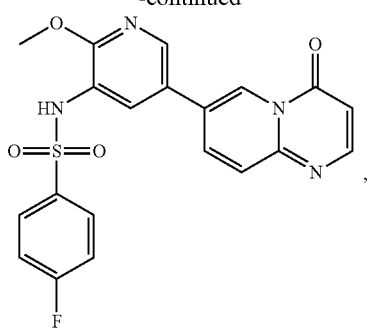
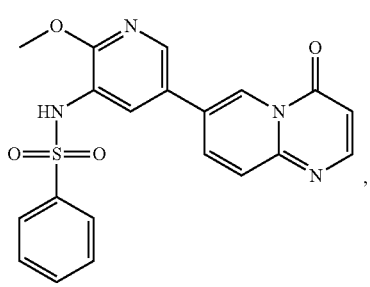
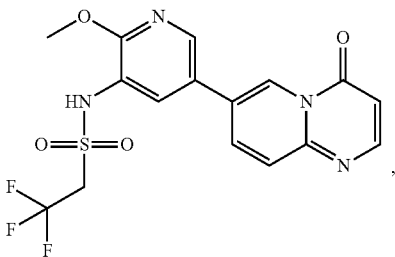
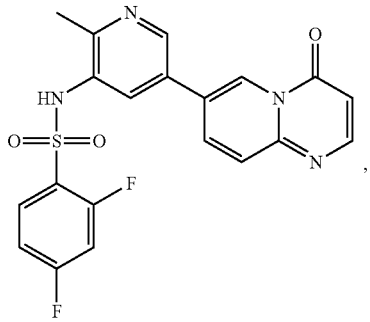
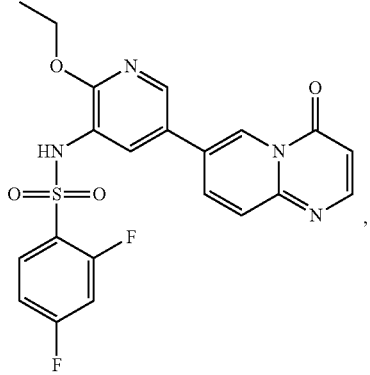
-continued
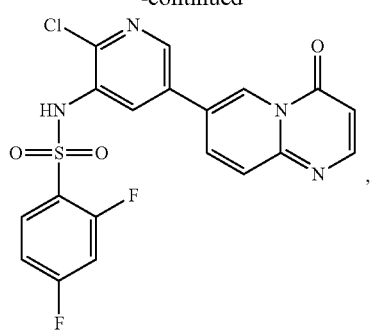
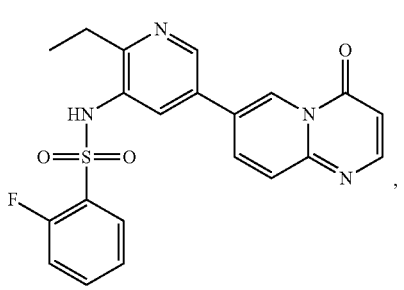
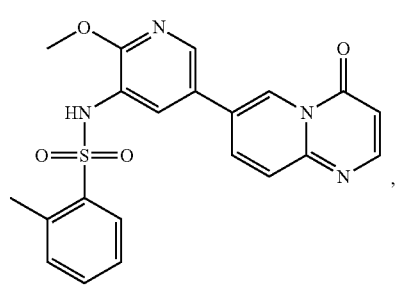

167
-continued
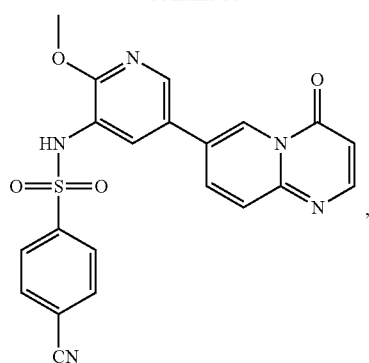
,
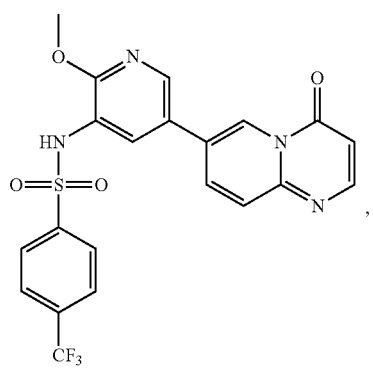
,
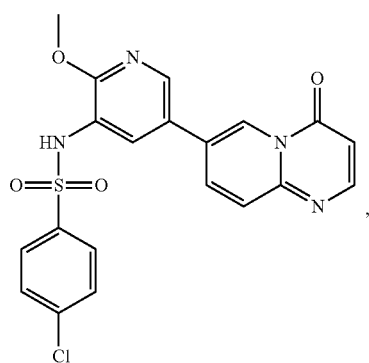
,
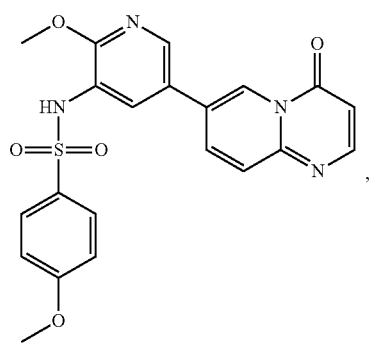
,
168
-continued
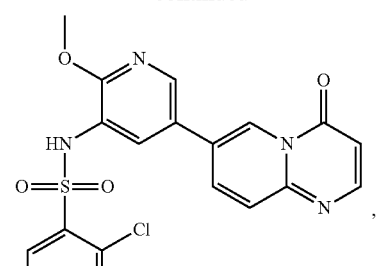
,
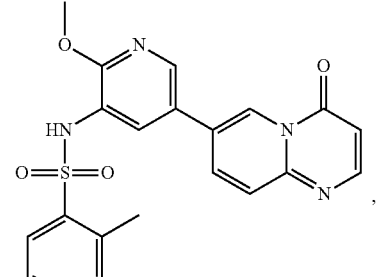
,
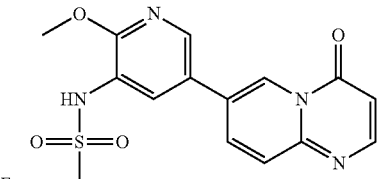
,
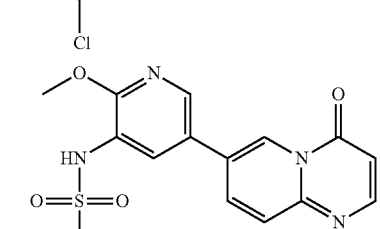
,
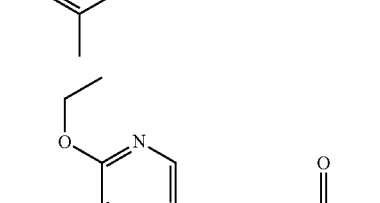
,
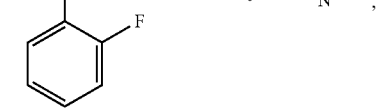

169
-continued
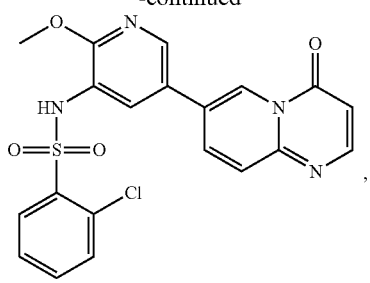
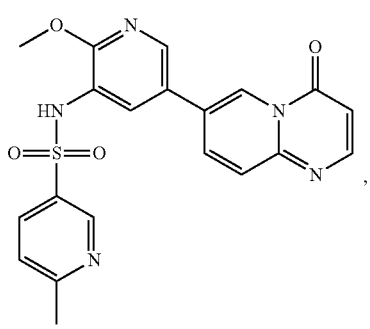
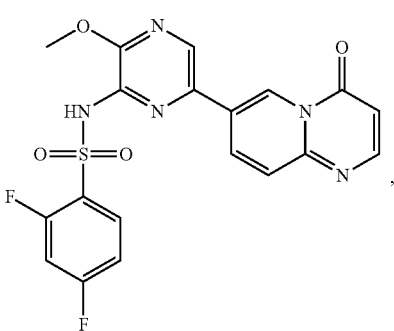
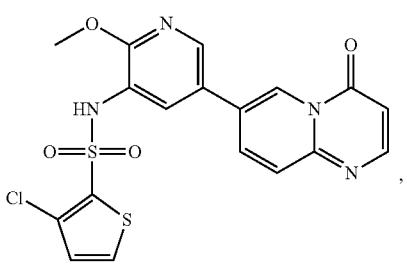
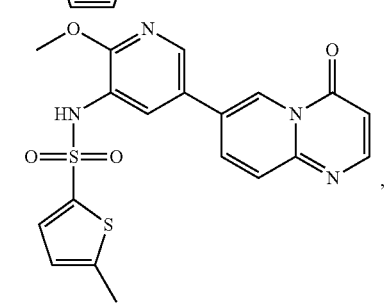
170
-continued
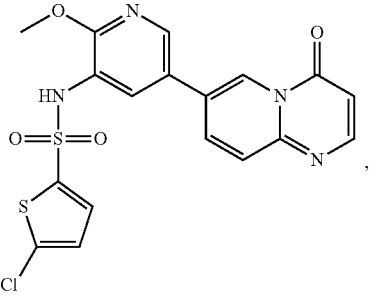
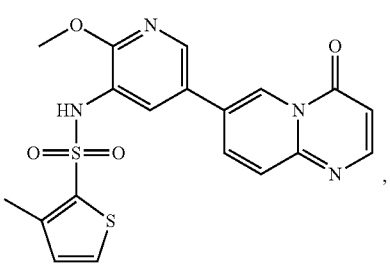
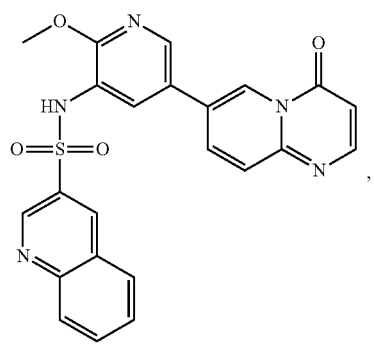
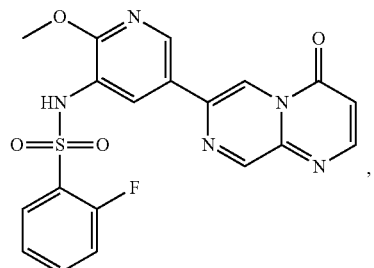
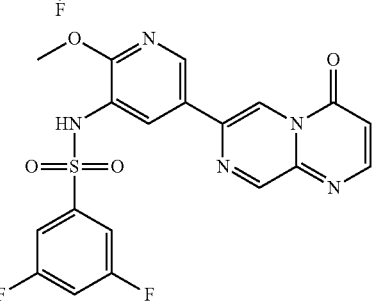

171
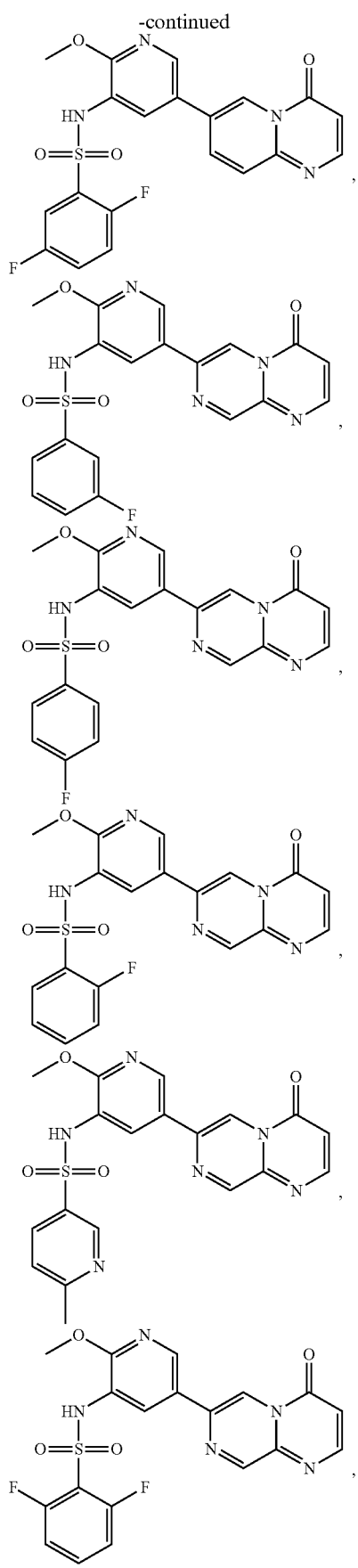
172
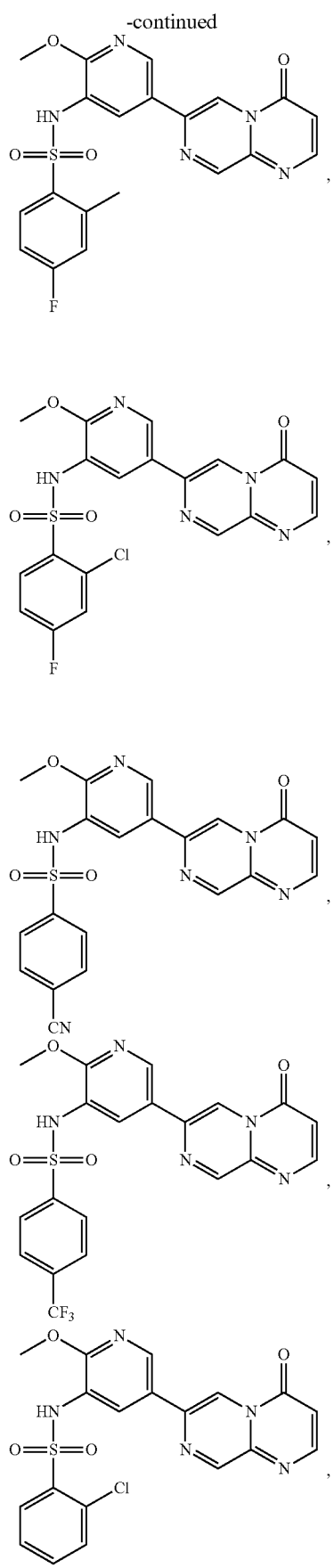

173
-continued
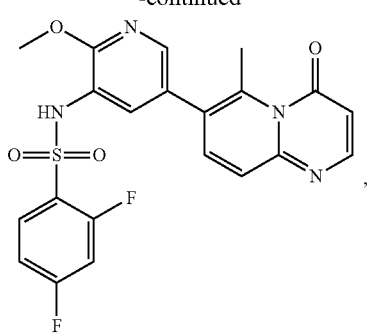,
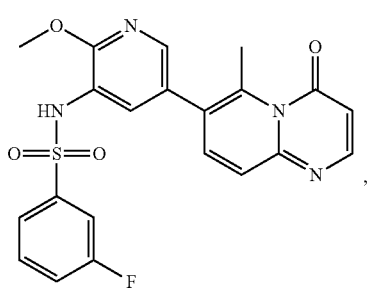,
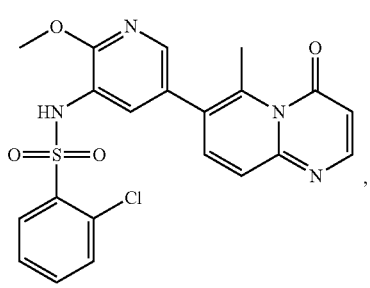,
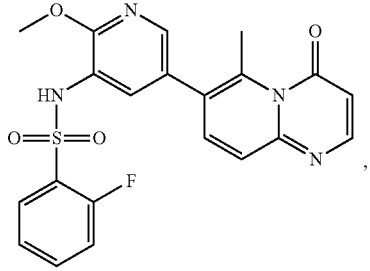,
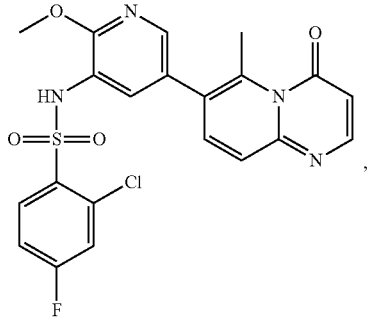,
174
-continued
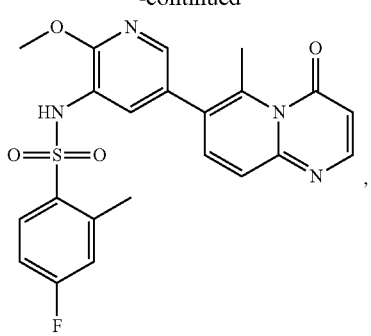,
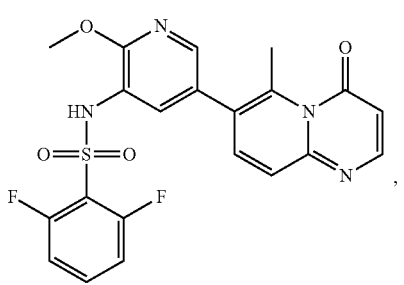,
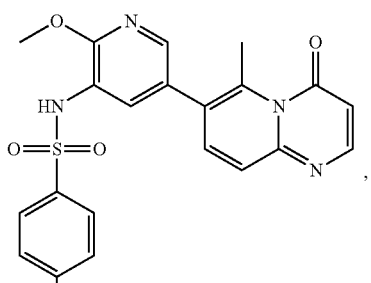,
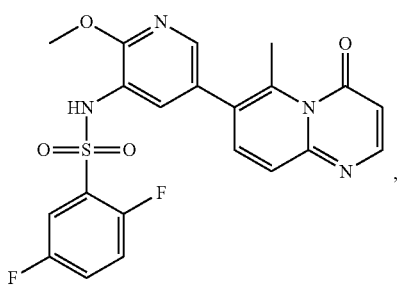,
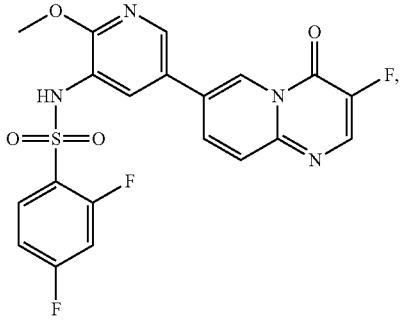, -continued
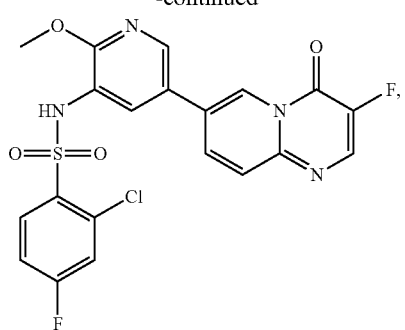
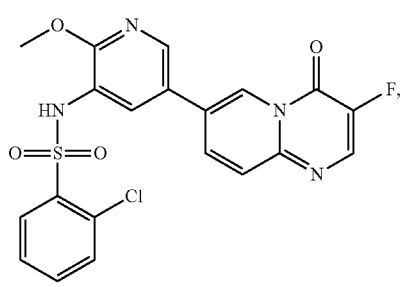
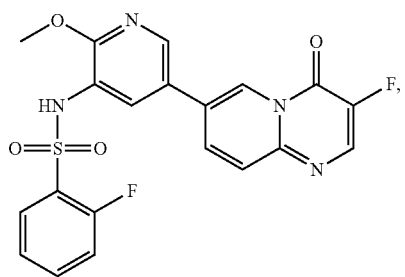
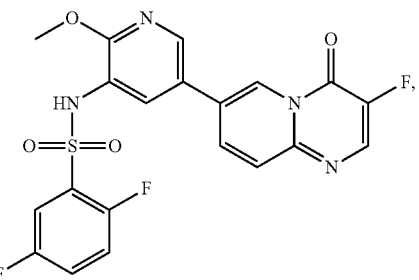
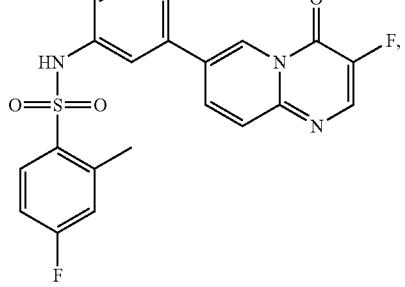
-continued
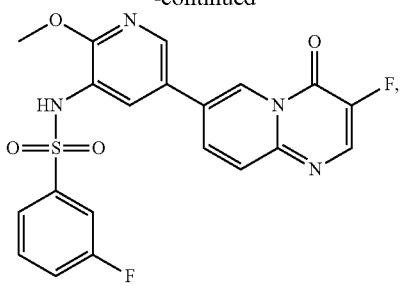
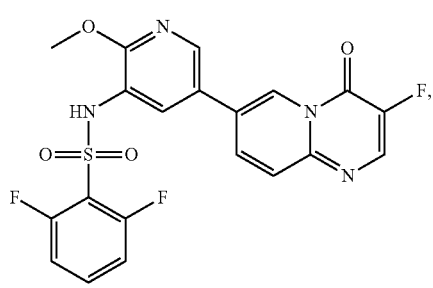
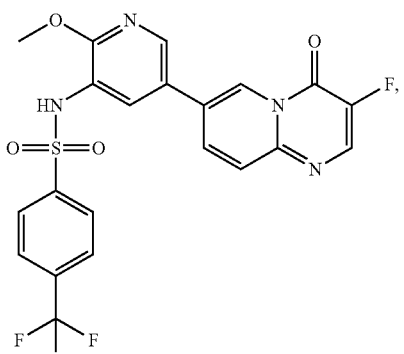
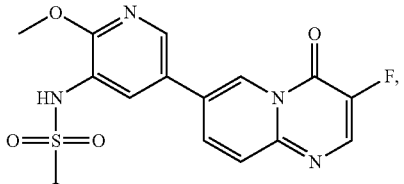
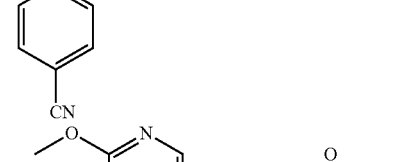
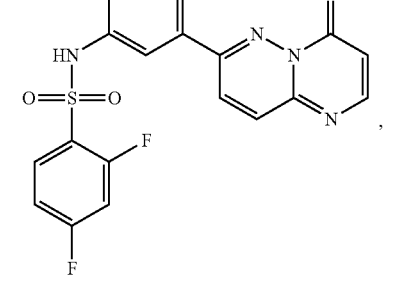

177
-continued
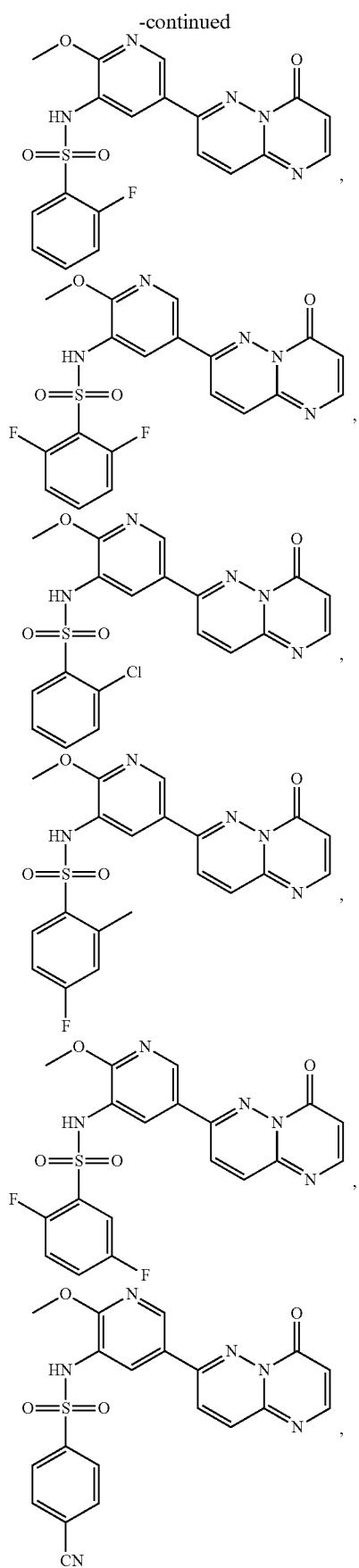
178
-continued
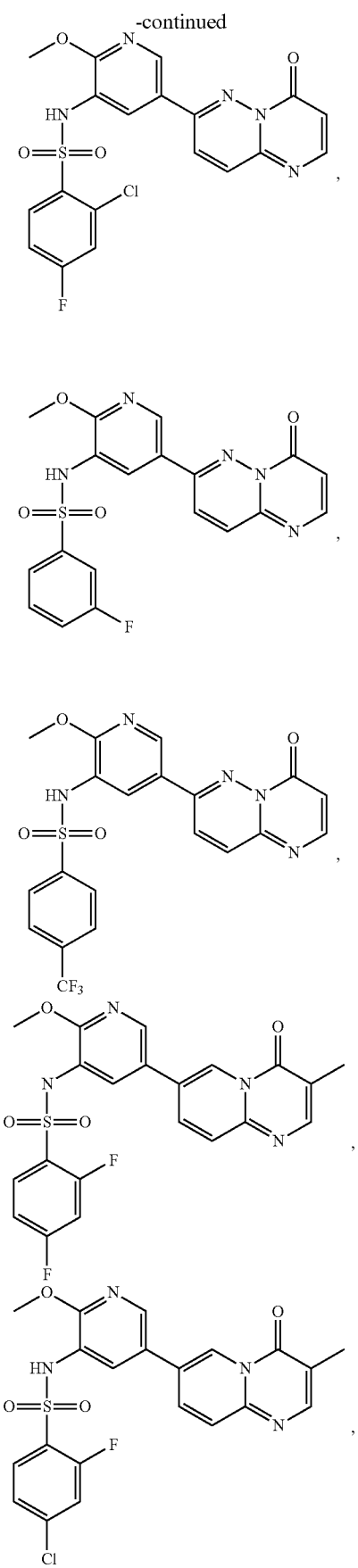

179
-continued
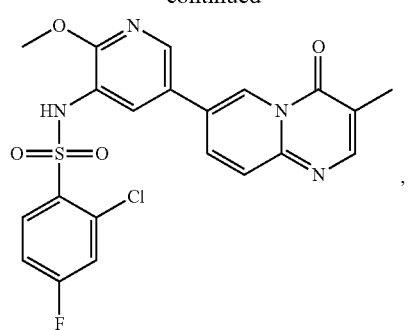
,
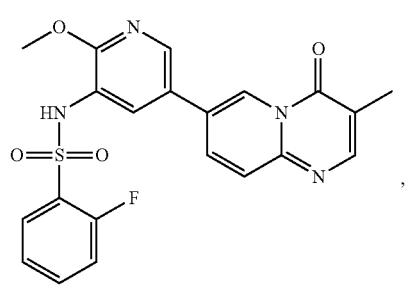
,
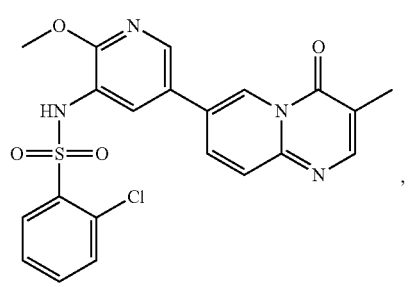
,
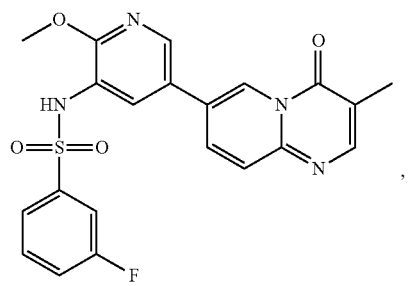
,
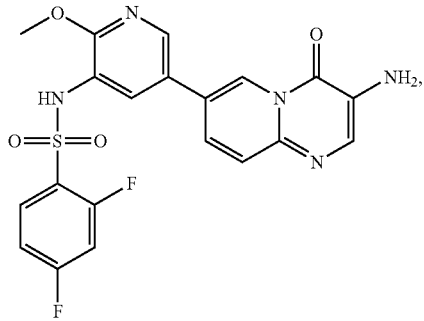
180
-continued
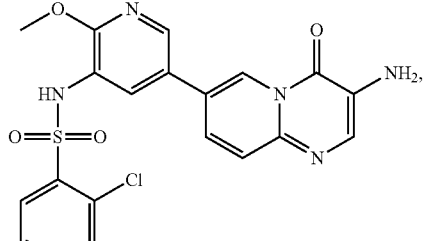
,
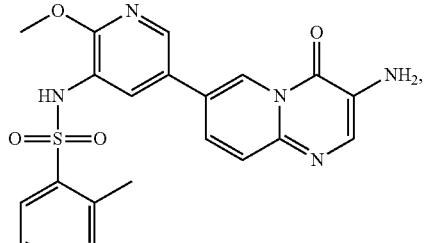
,
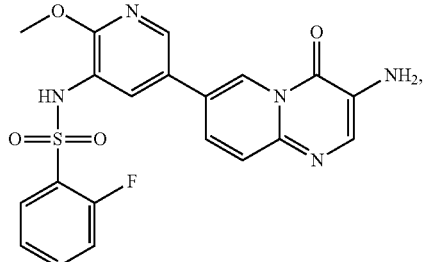
,
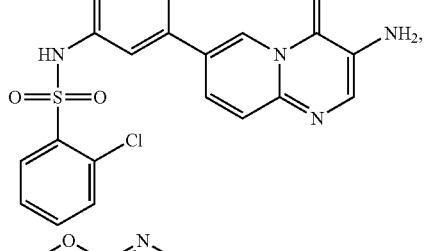
,
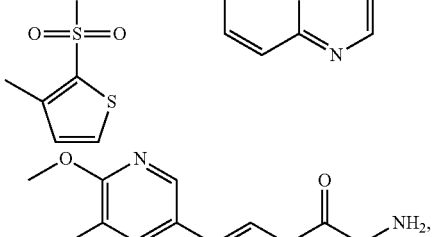
,
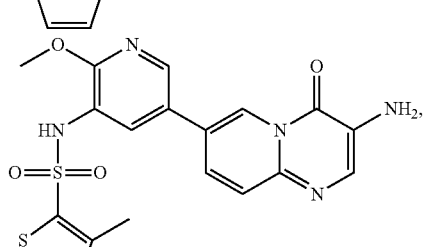
, -continued
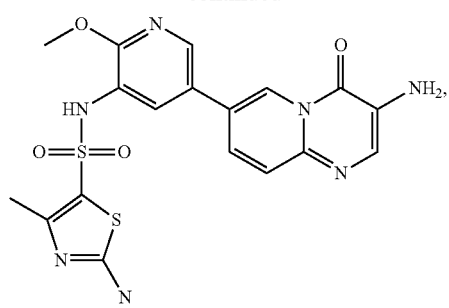
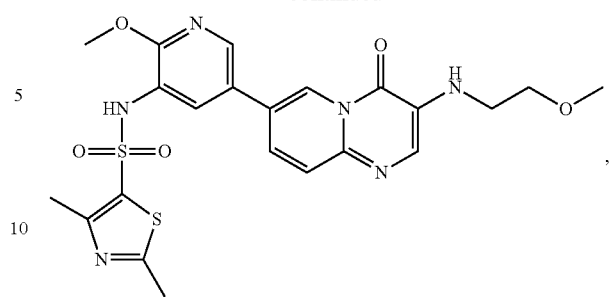
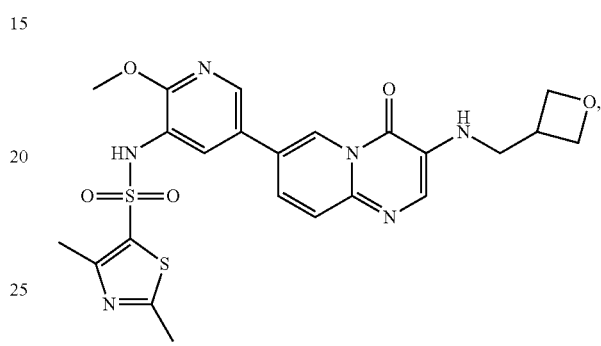
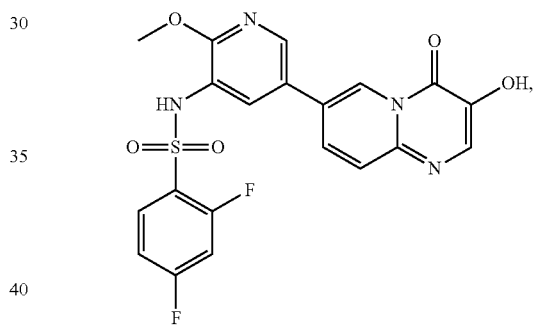
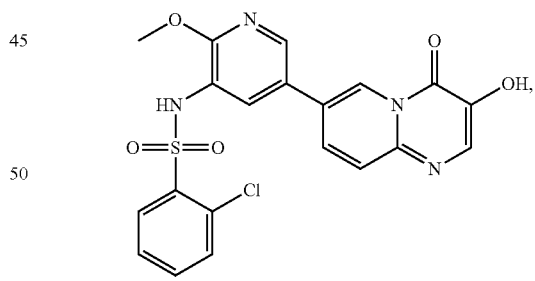
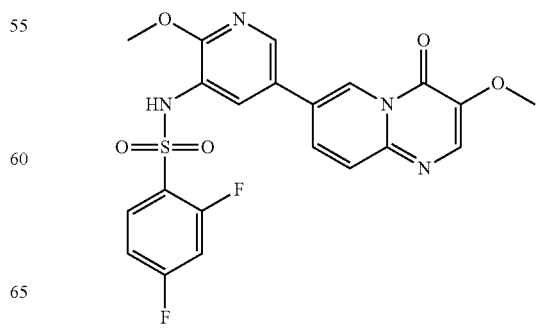

183
-continued
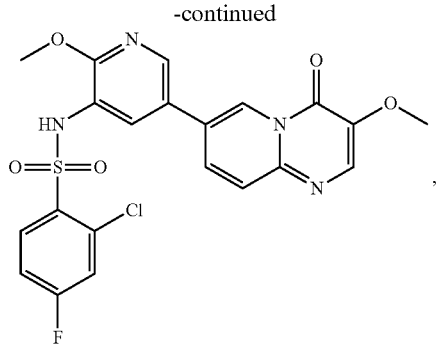
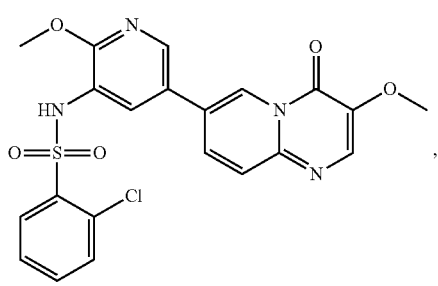
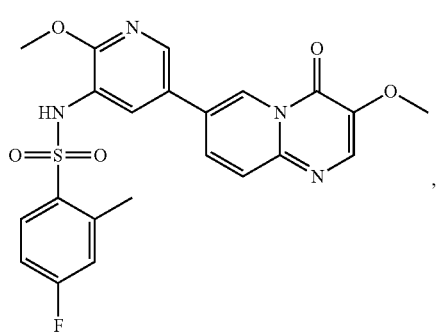
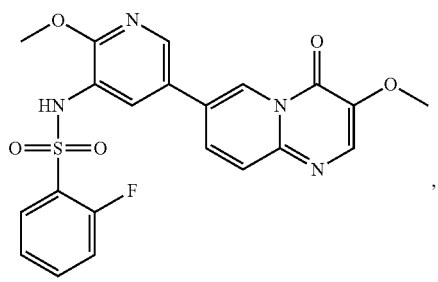
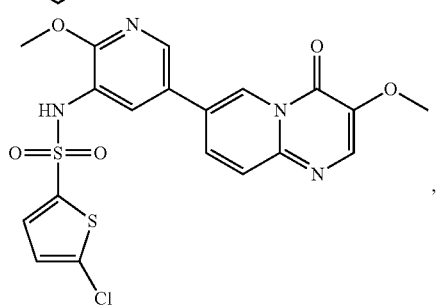
184
-continued
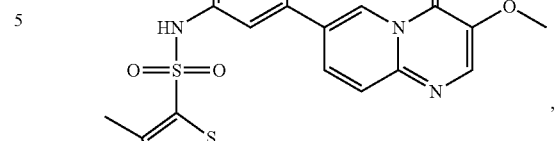
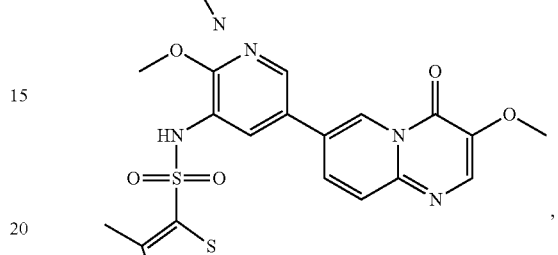
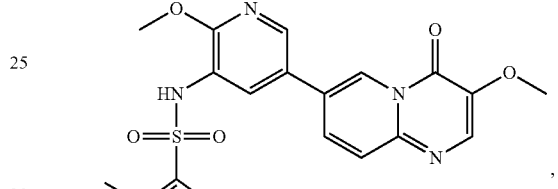
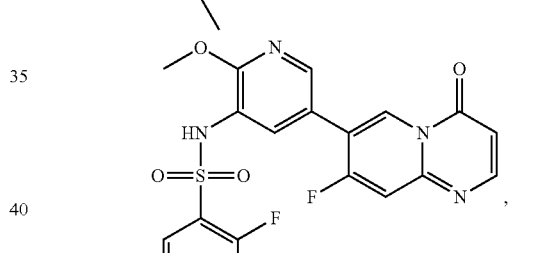
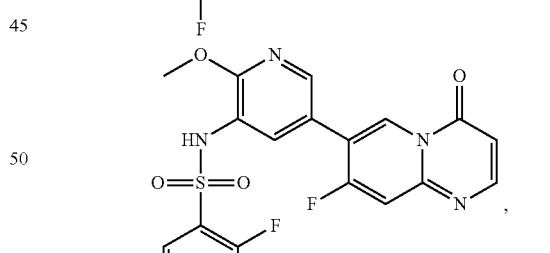
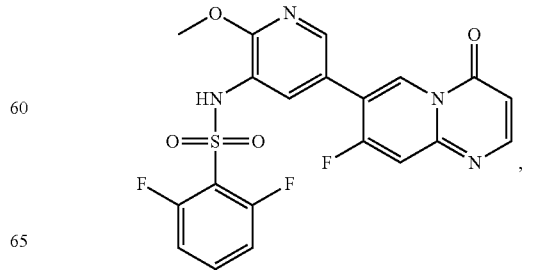

-continued
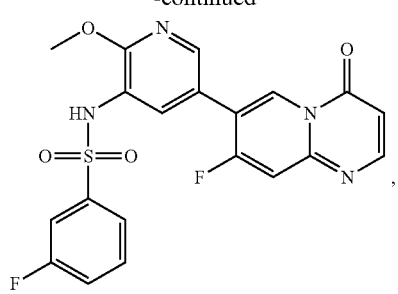
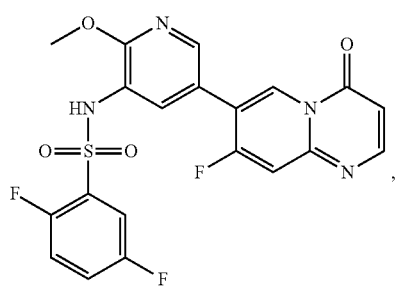
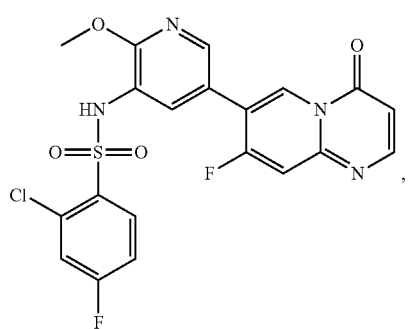
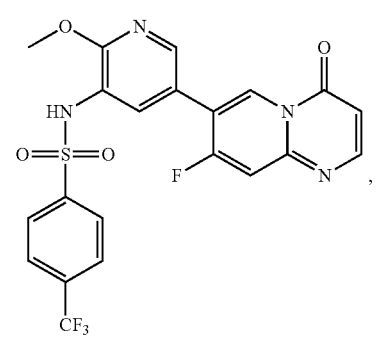
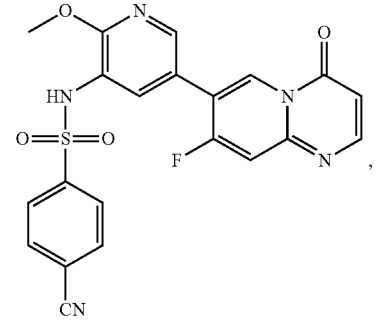
-continued
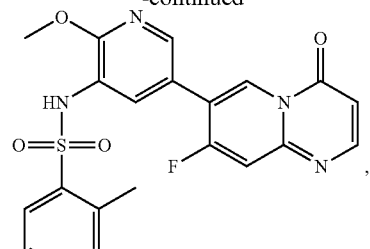
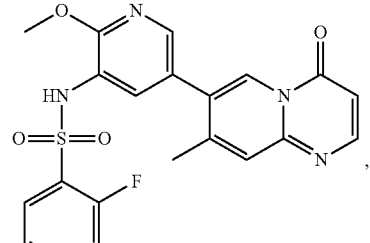
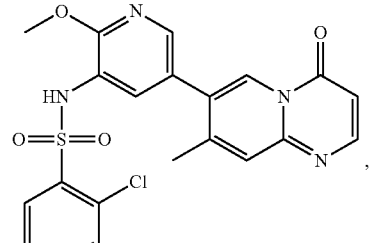
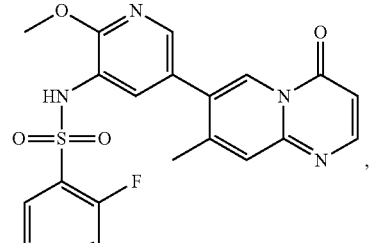
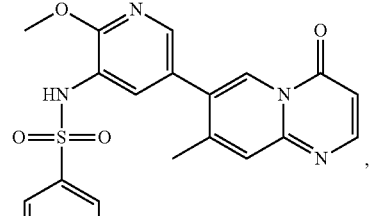
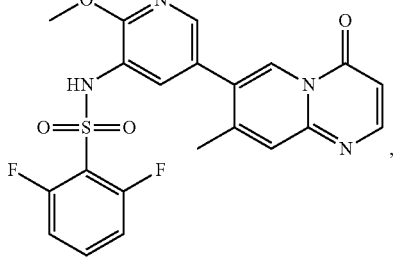

187
-continued
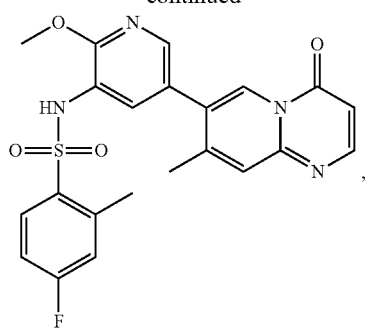
,
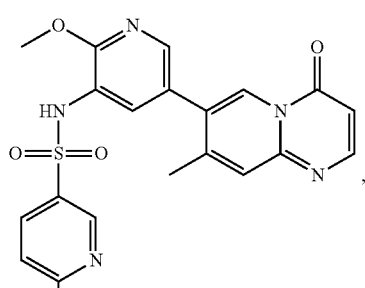
,
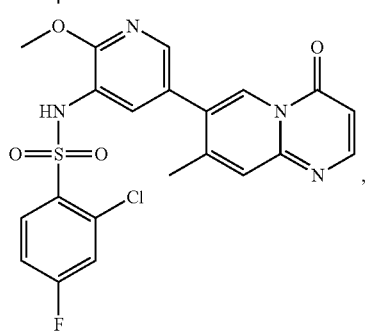
,
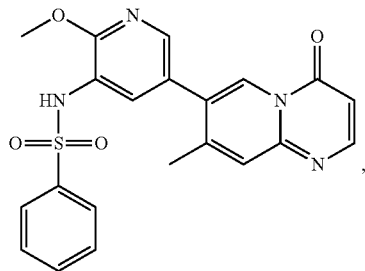
,
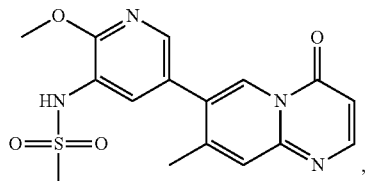
,
188
-continued
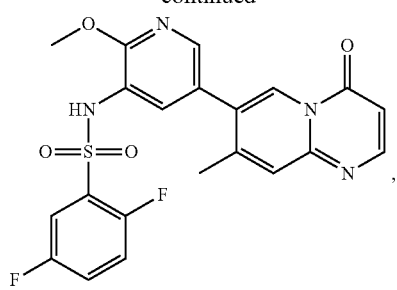
,
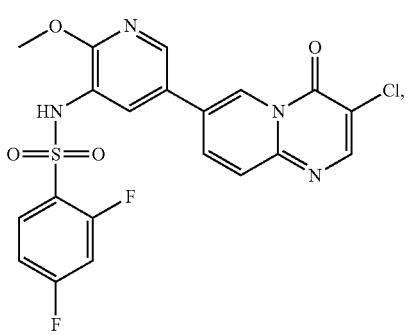
,
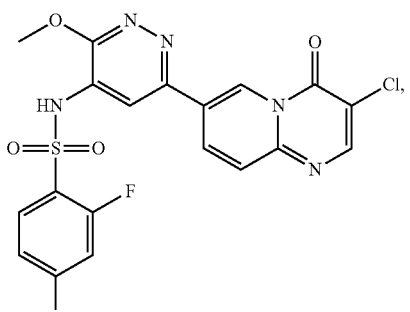
,
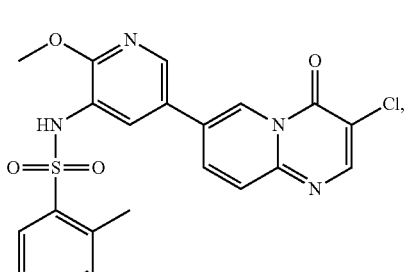
,
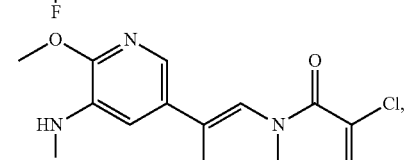
,

189
-continued
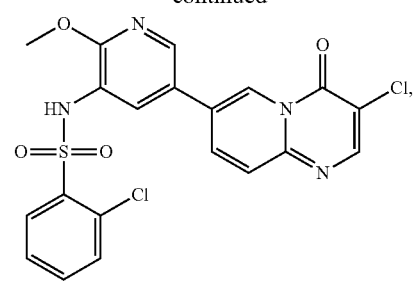
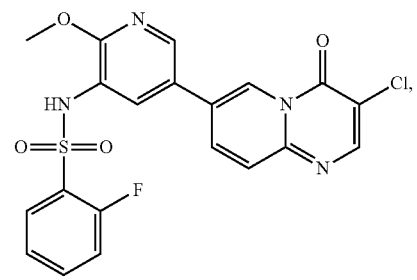
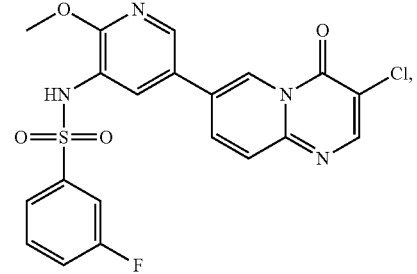
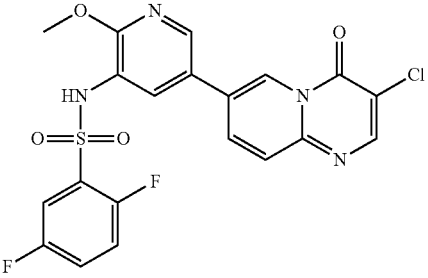
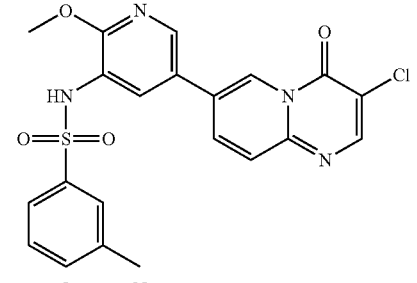
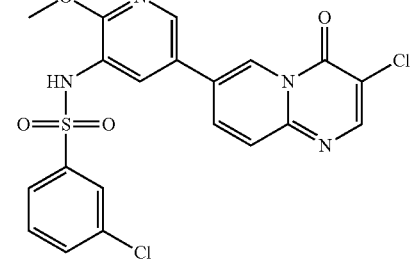
190
-continued
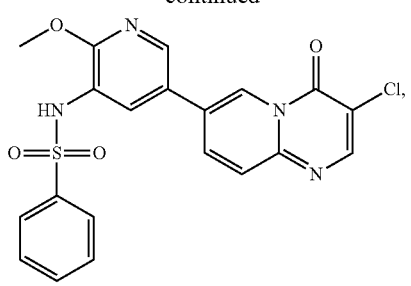
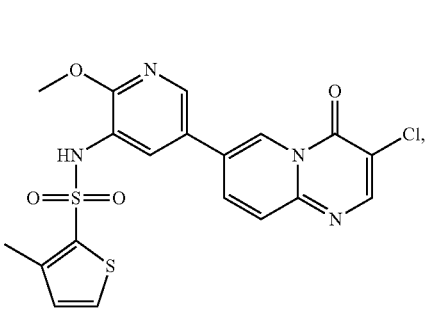
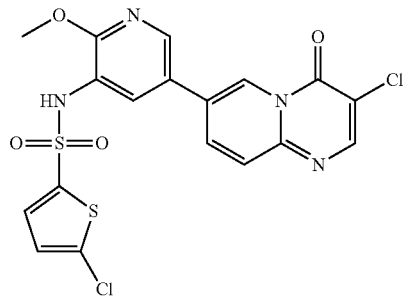
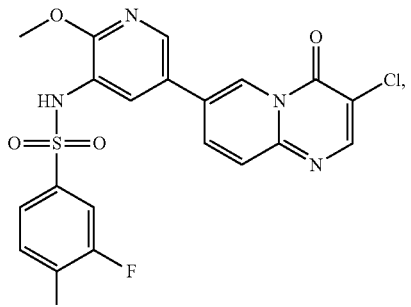
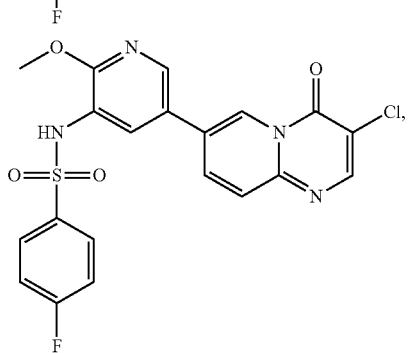

191
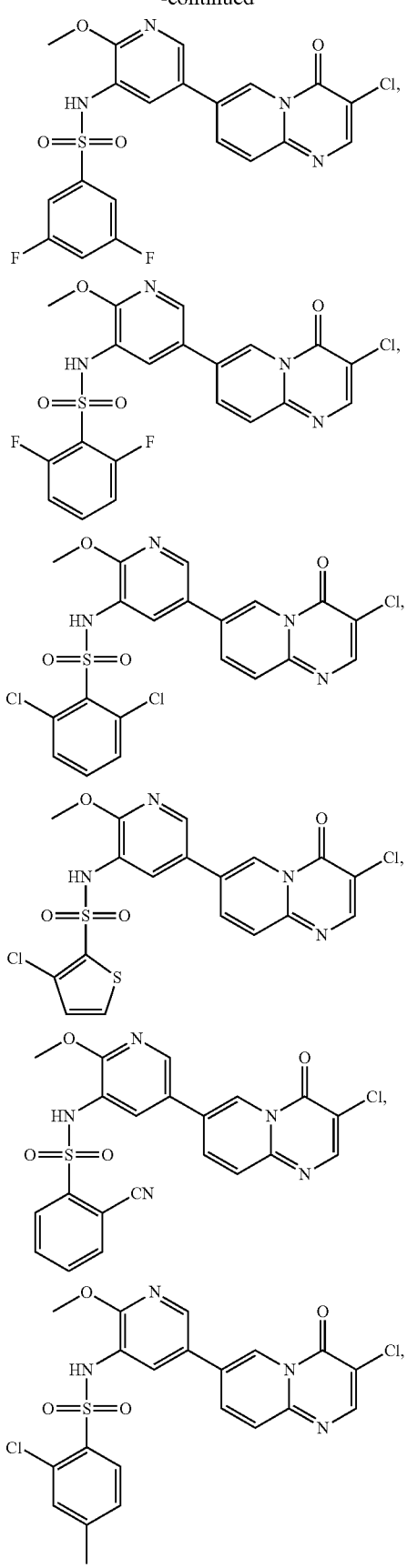
192
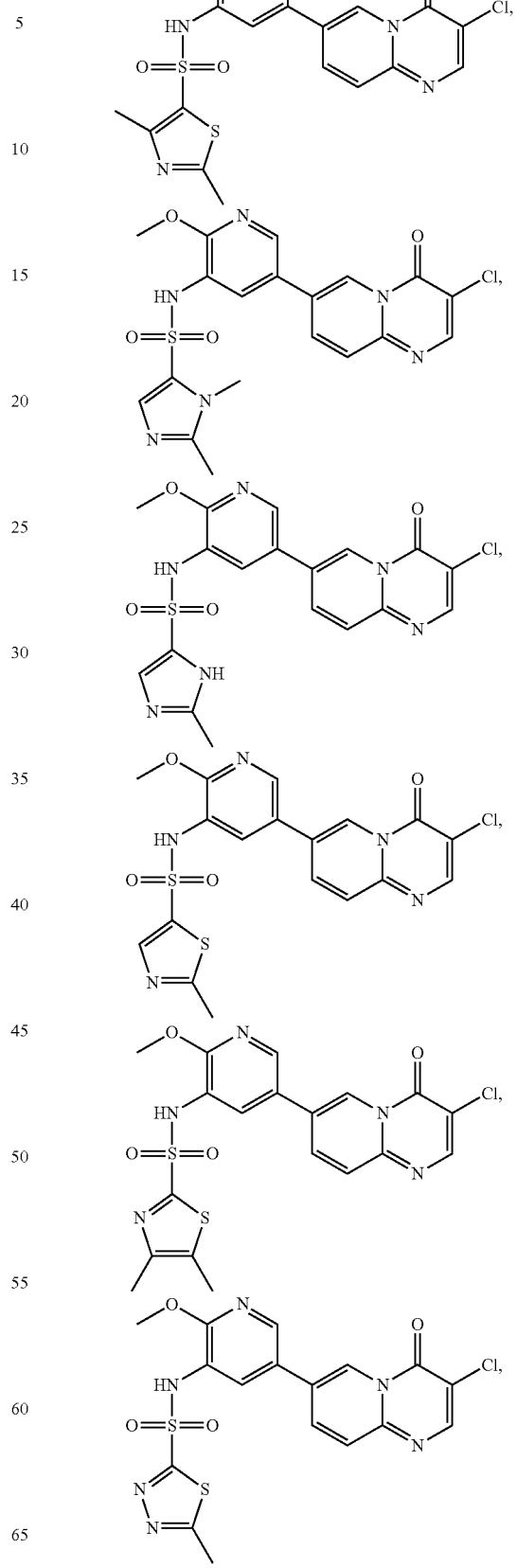

193
-continued
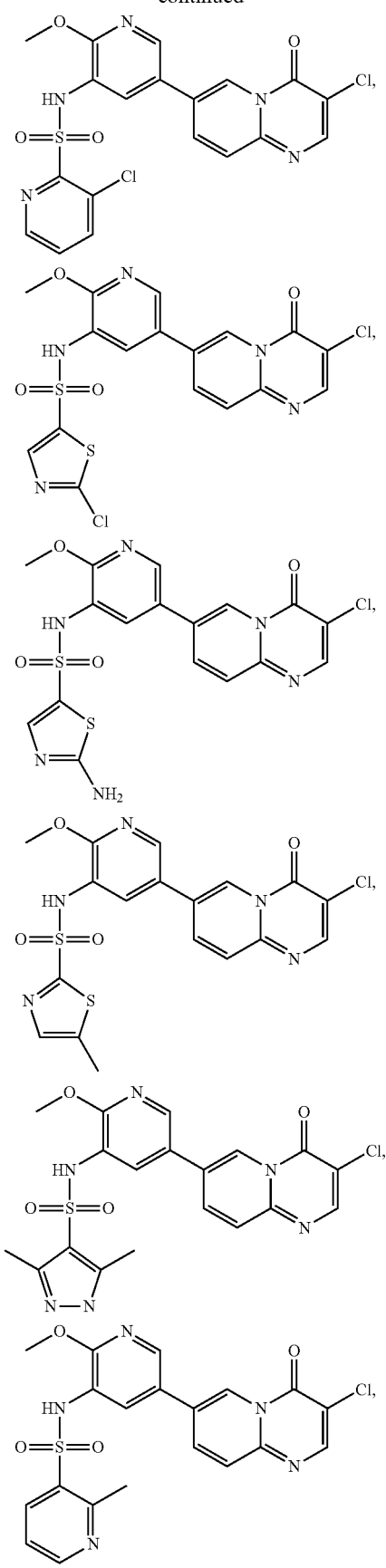
194
-continued
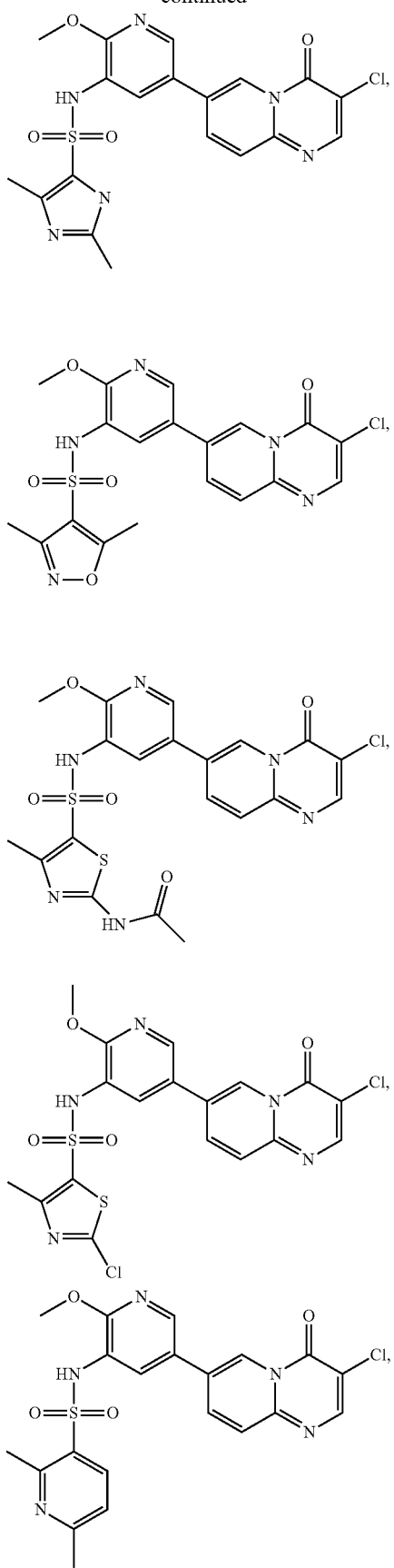

195
-continued
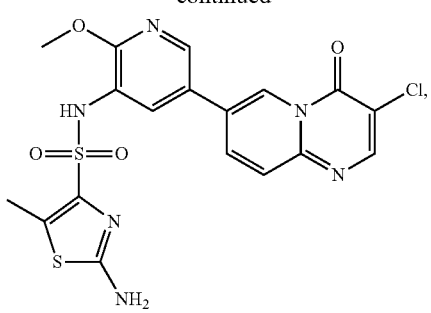
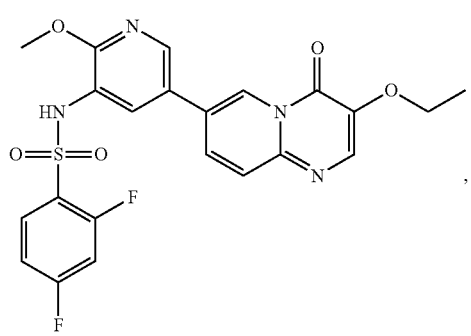
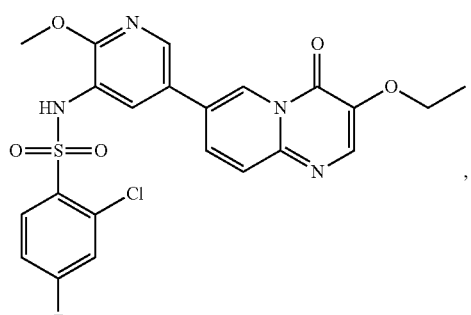
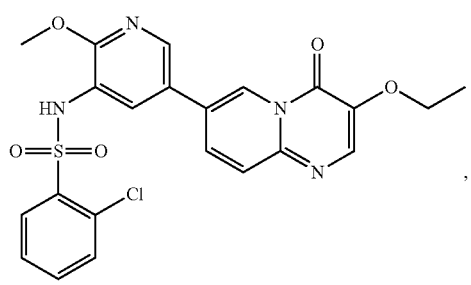
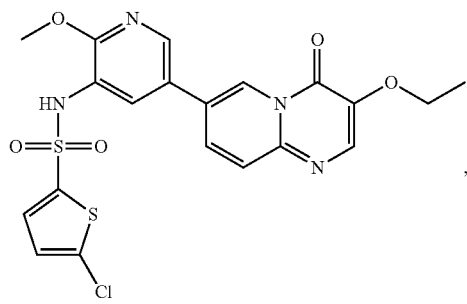
196
-continued
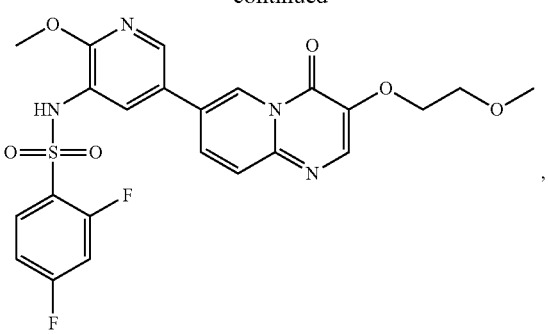
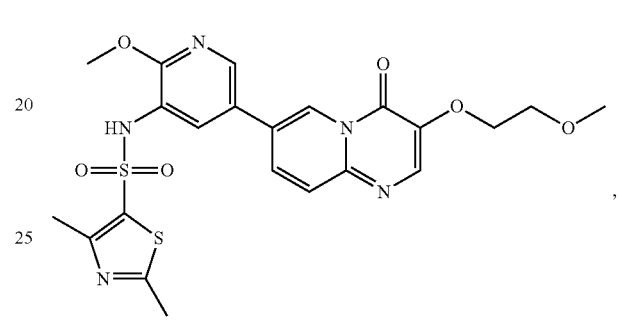
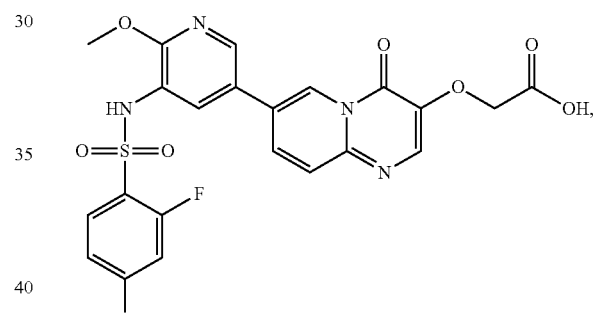
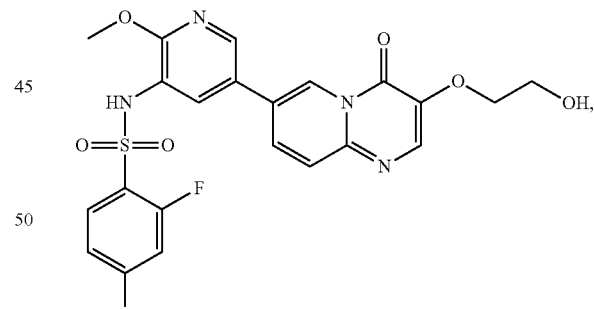
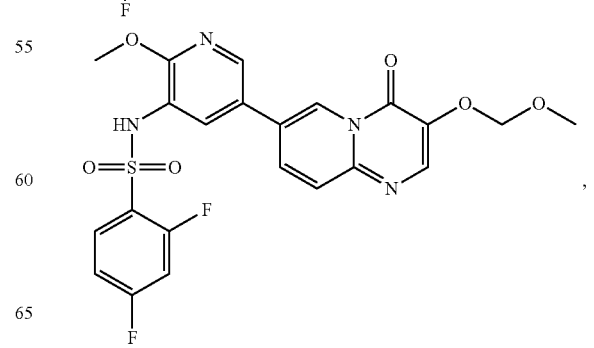

197
-continued
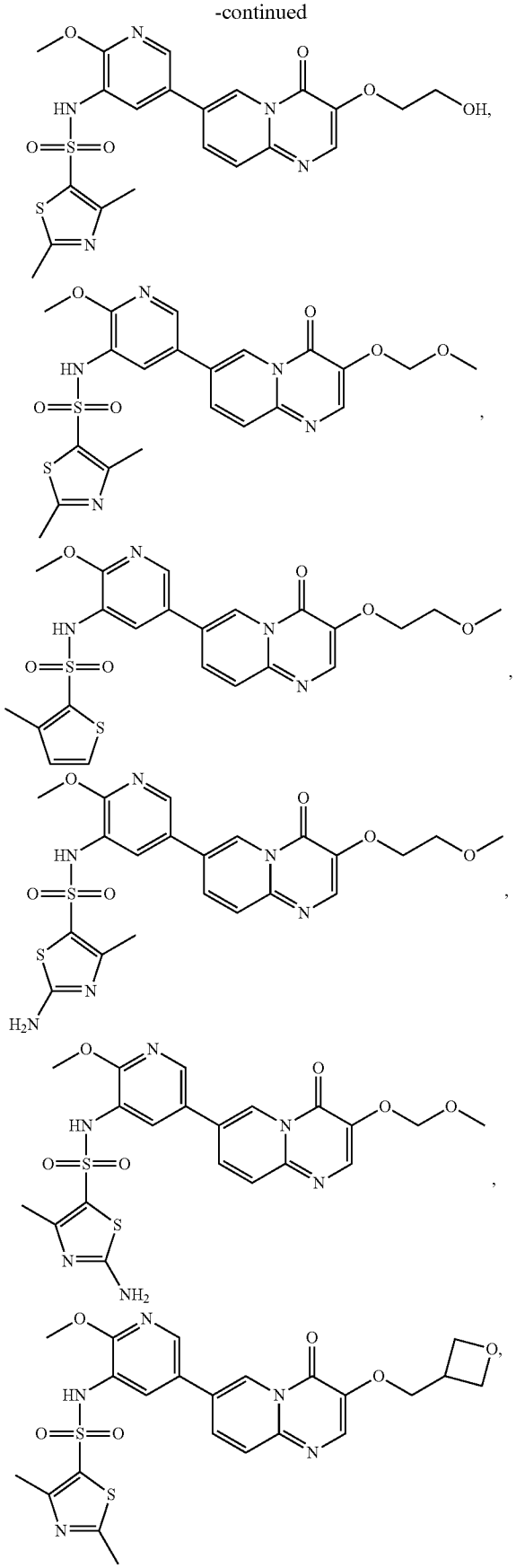
198
-continued
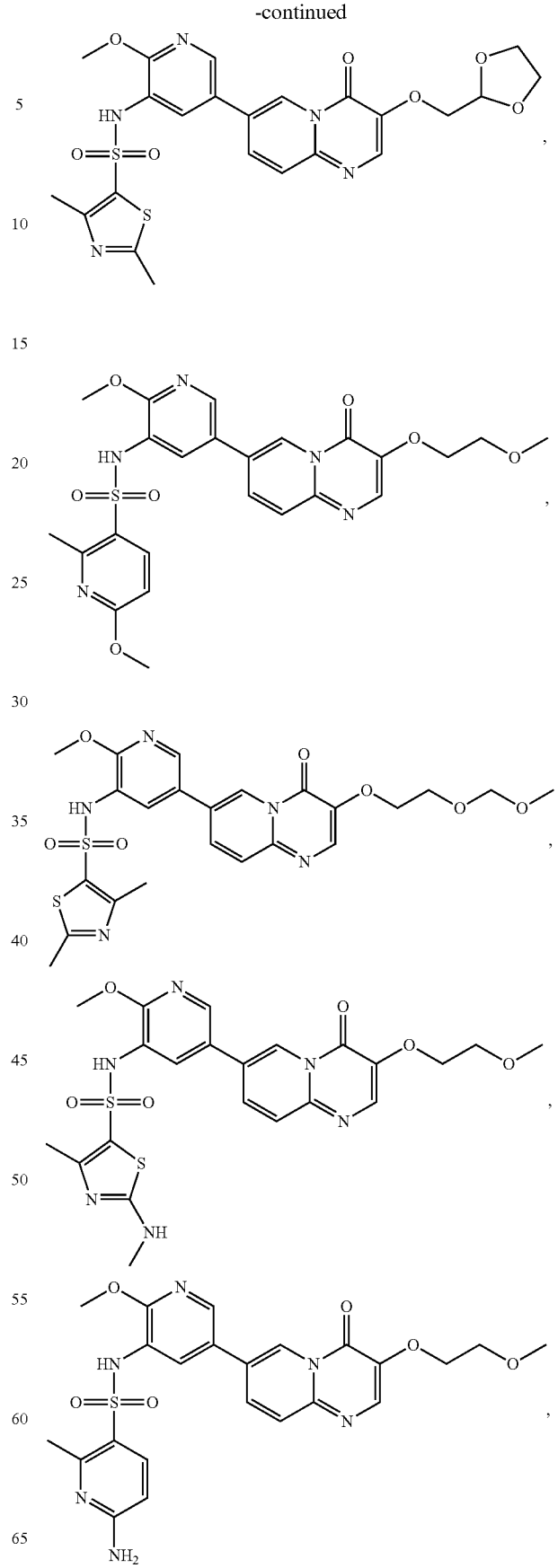

199
-continued
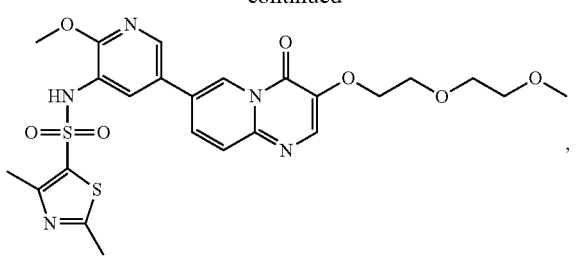
,
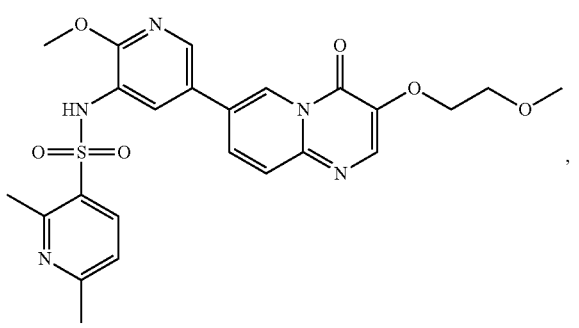
,
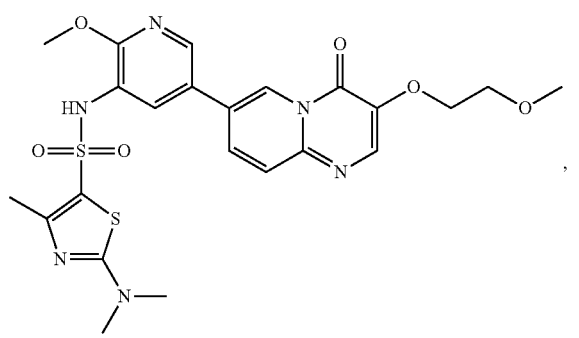
,
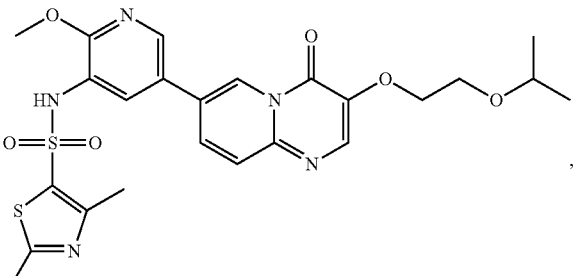
,
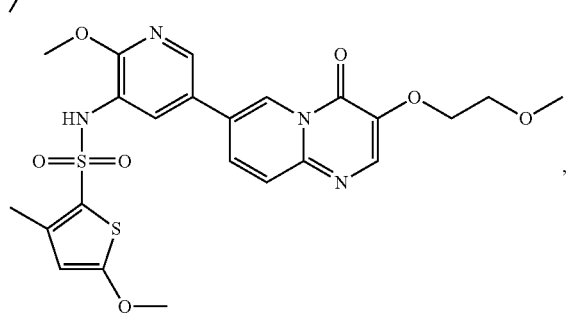
,
200
-continued
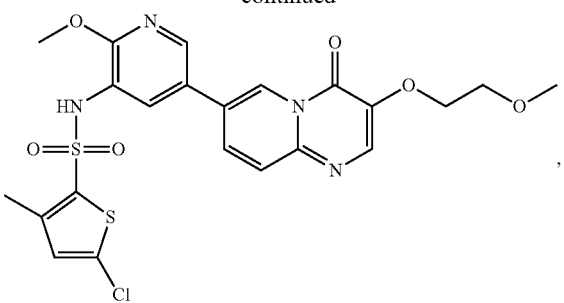
,
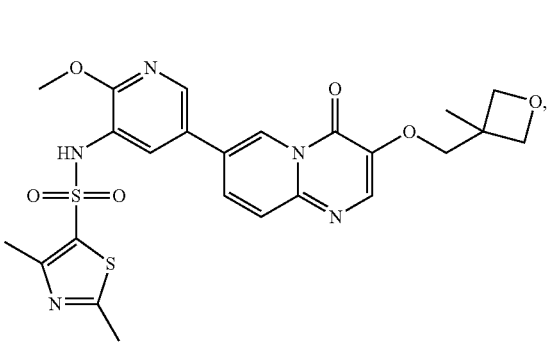
,
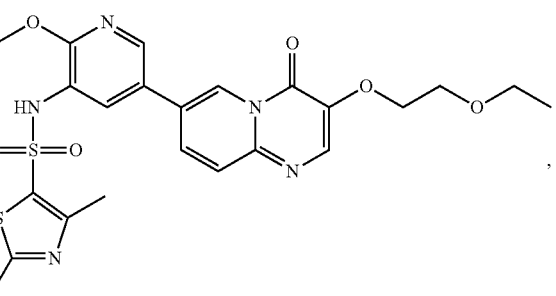
, 201
-continued
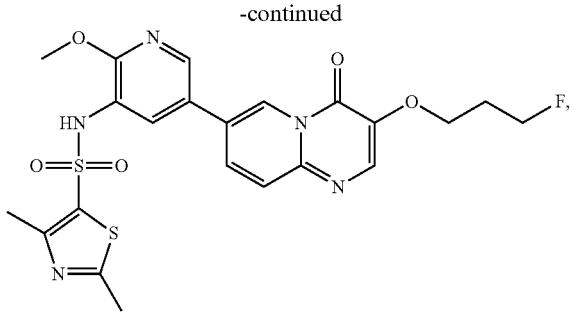
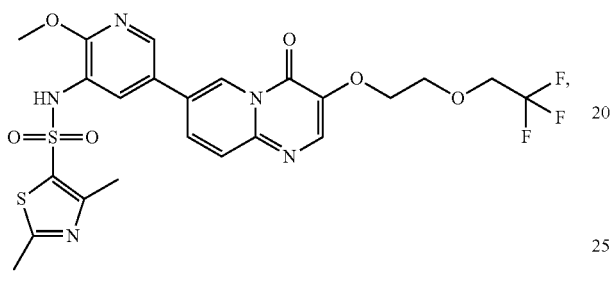
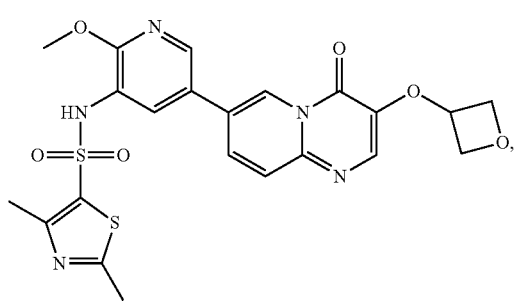
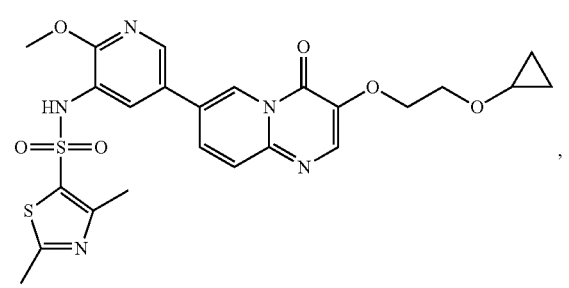
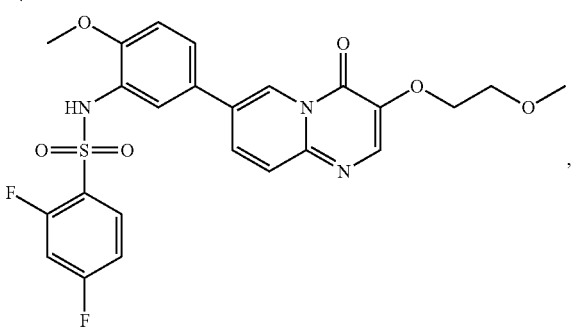
202
-continued
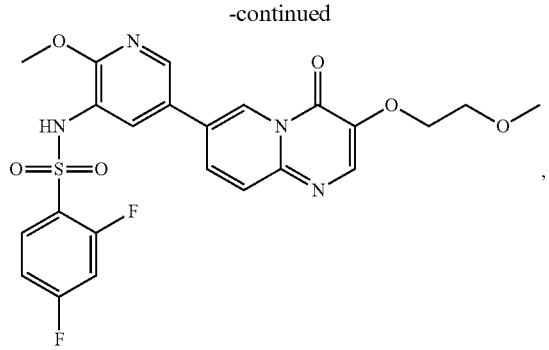
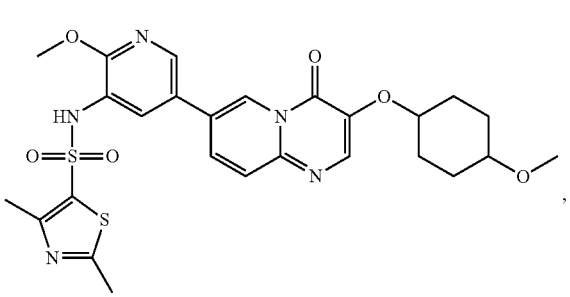
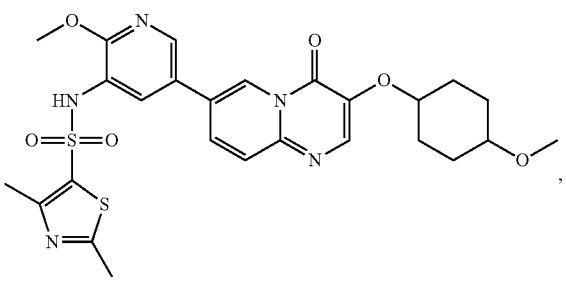
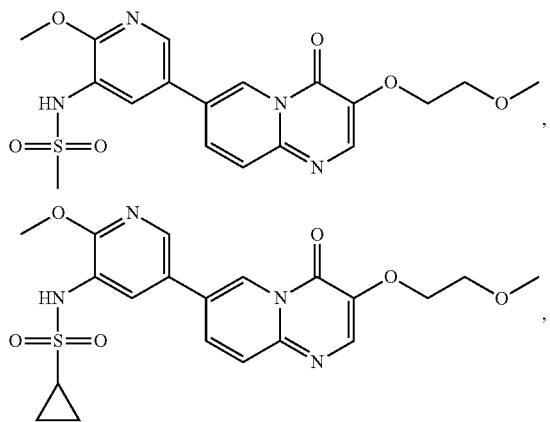

203
-continued
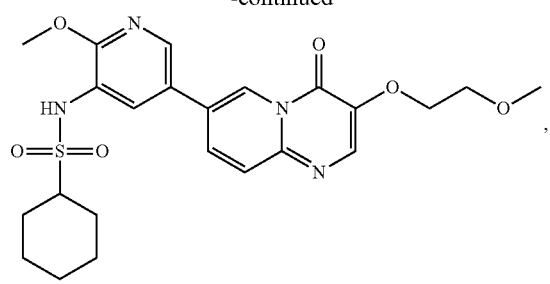
,
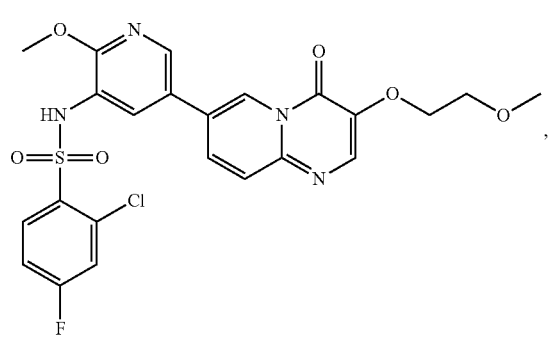
,
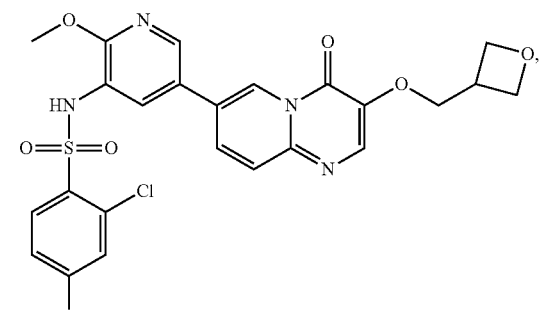
,
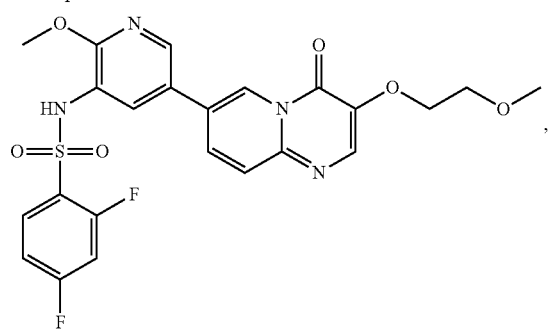
,
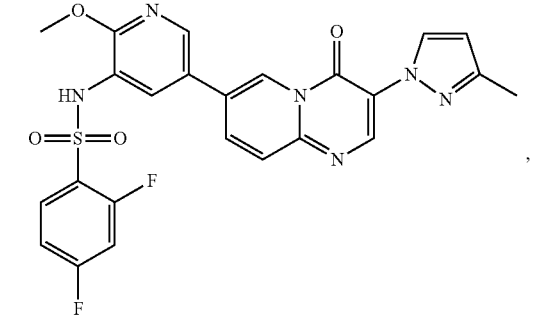
,
204
-continued
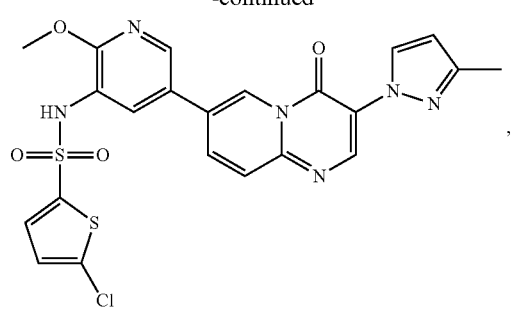
,
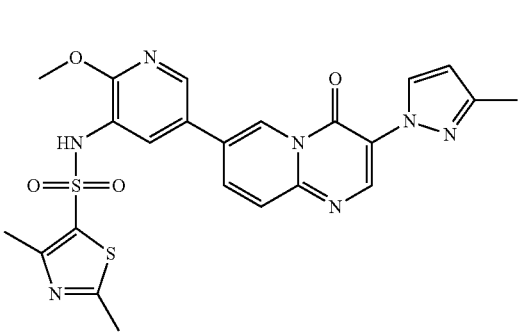
,
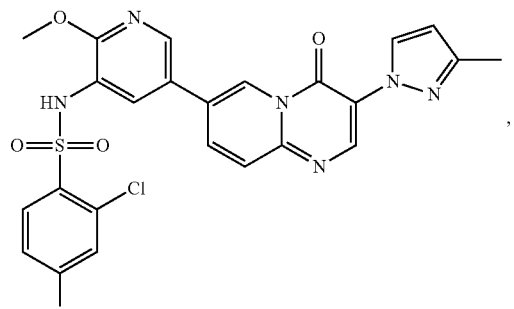
,
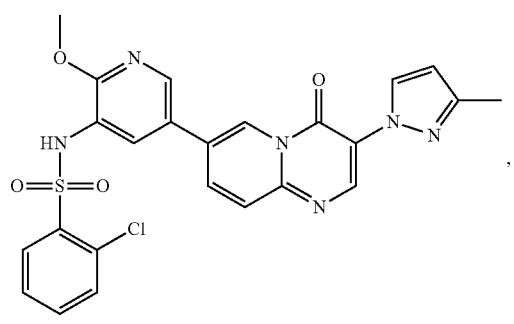
,
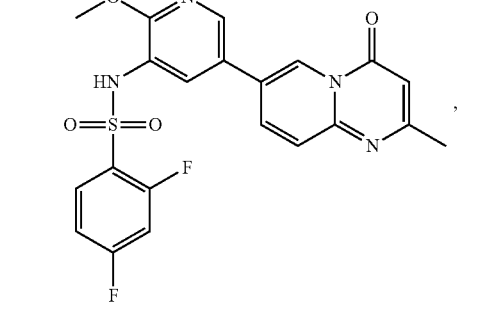
, 205
-continued
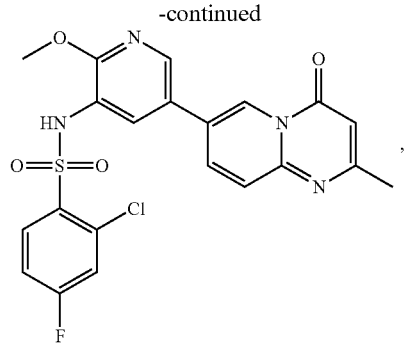
,
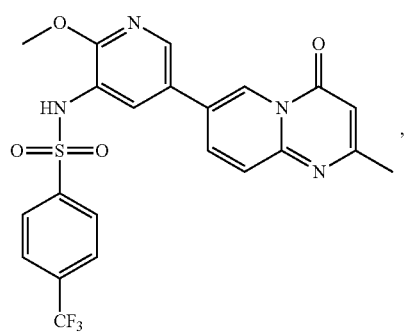
,
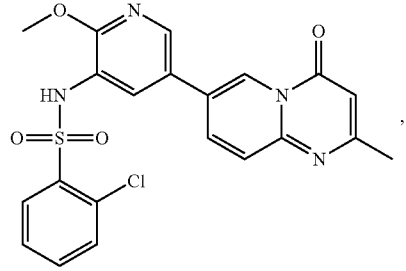
,
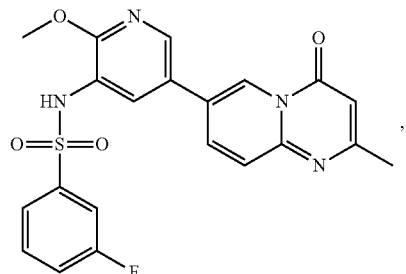
,
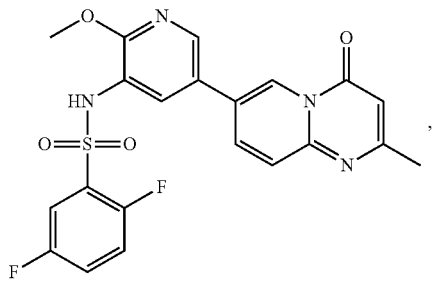
,
206
-continued
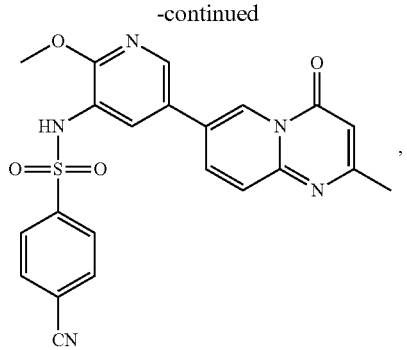
,
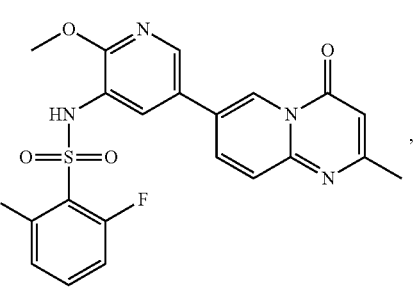
,
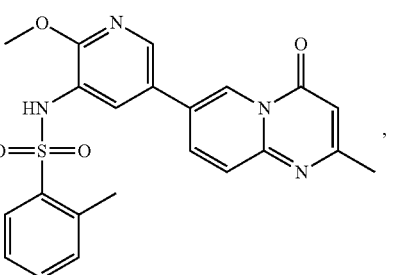
,
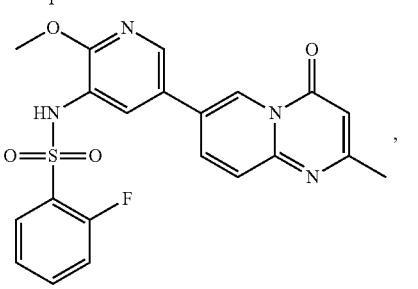
,
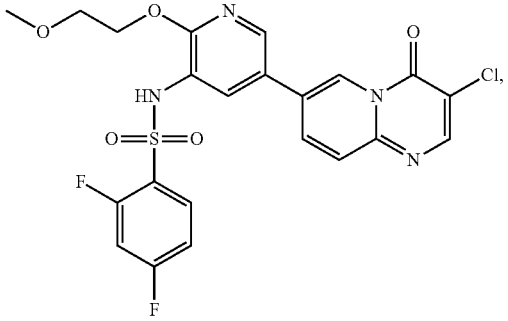

207
-continued
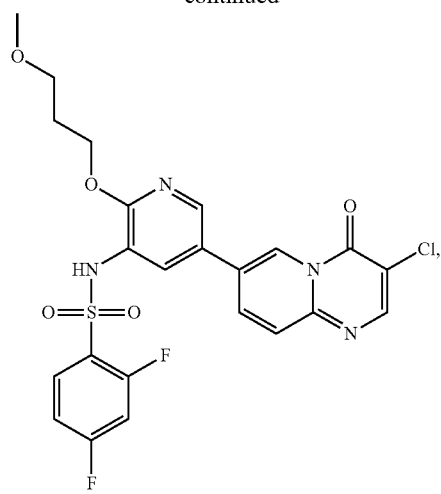
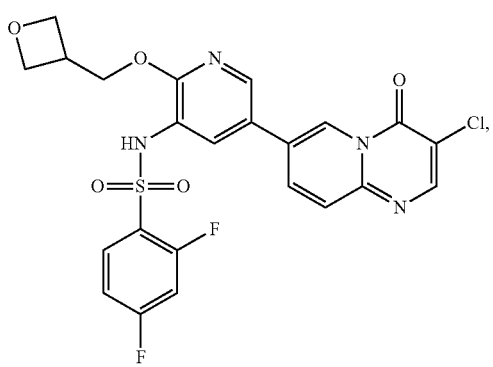
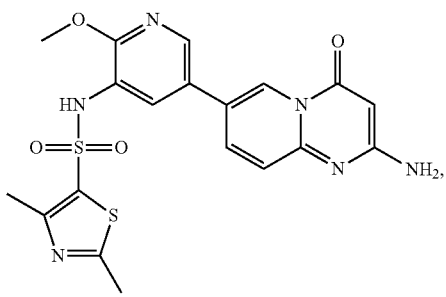
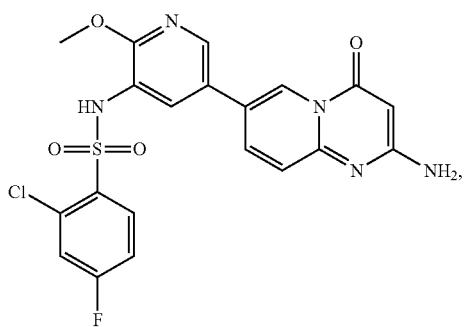
208
-continued
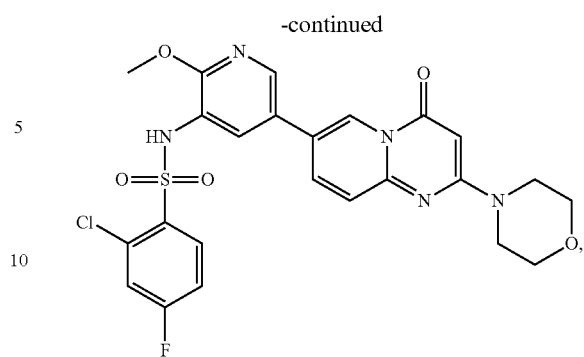
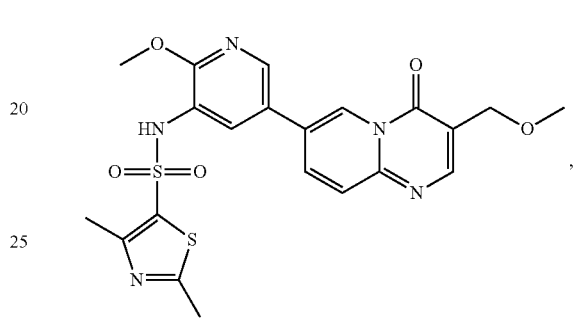
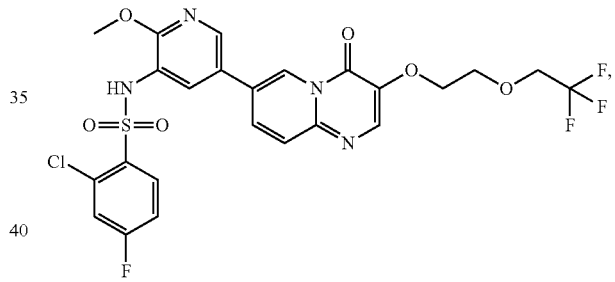
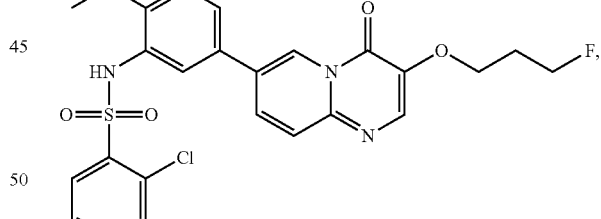
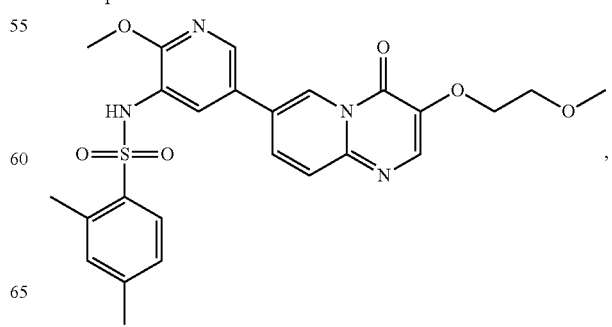

209
-continued
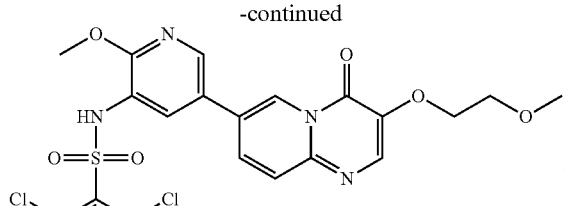
,
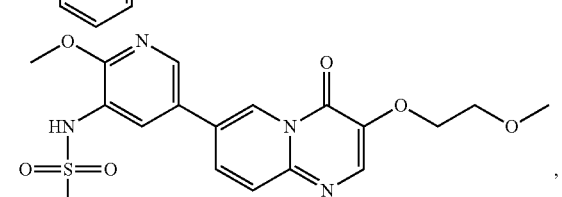
,
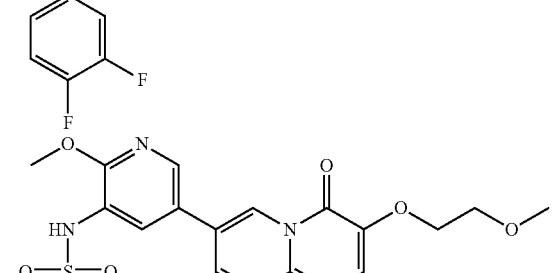
,
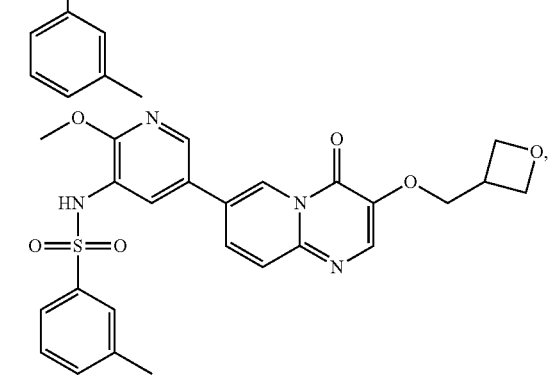
,
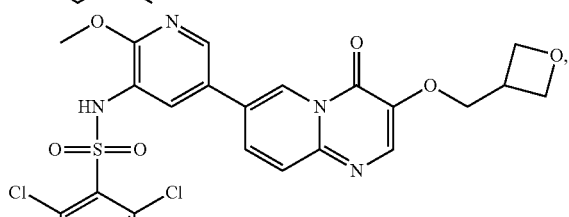
,
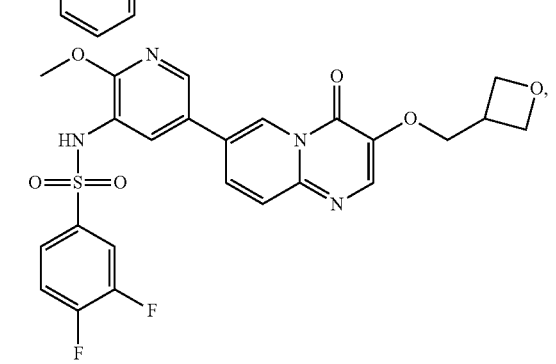
,
210
-continued
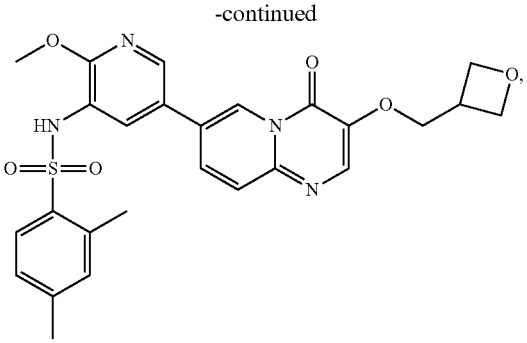
,
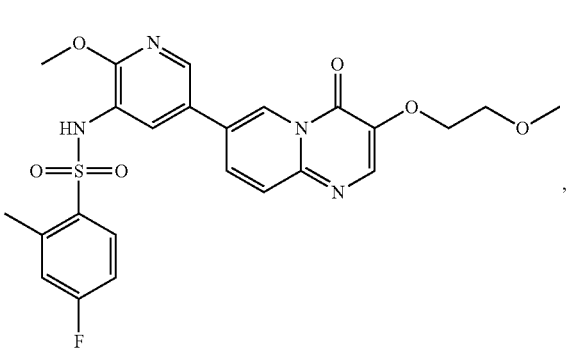
,
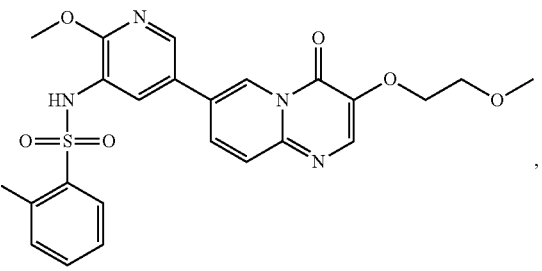
,
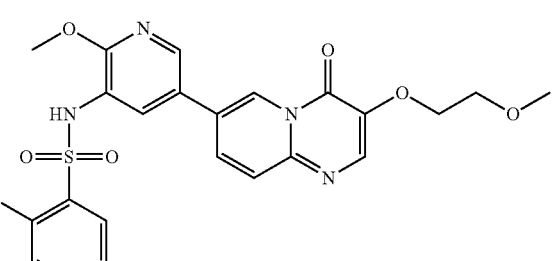
,
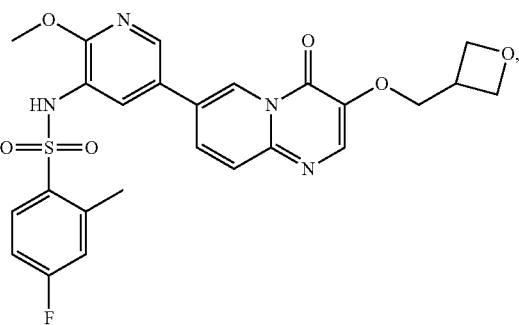
, 211
-continued
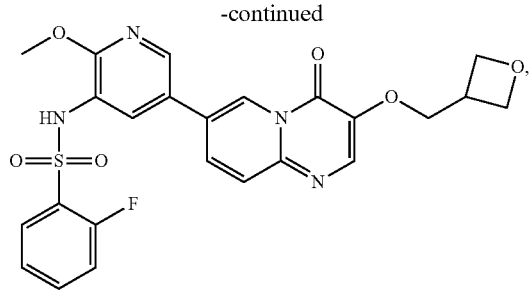
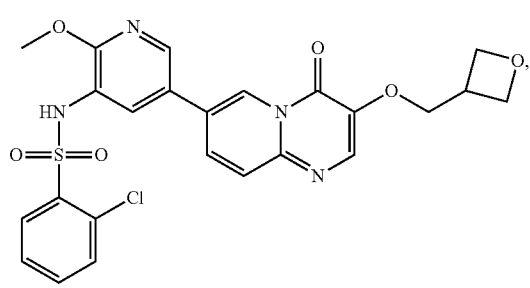
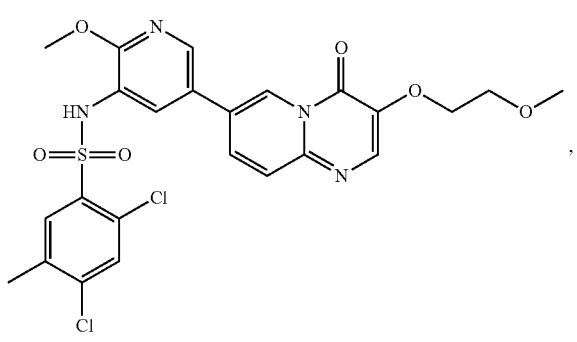
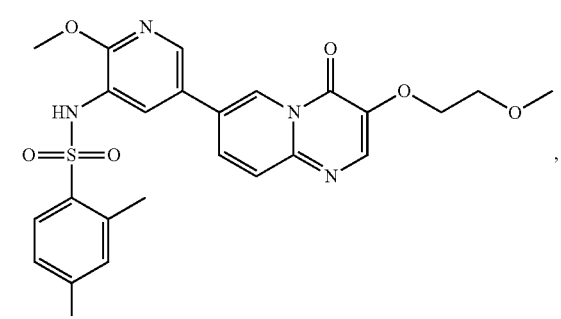
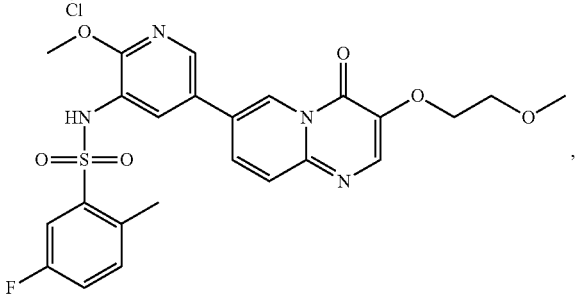
212
-continued
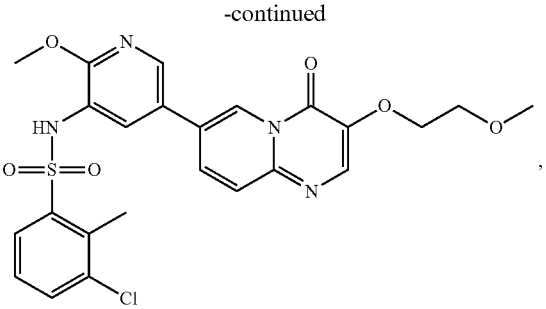
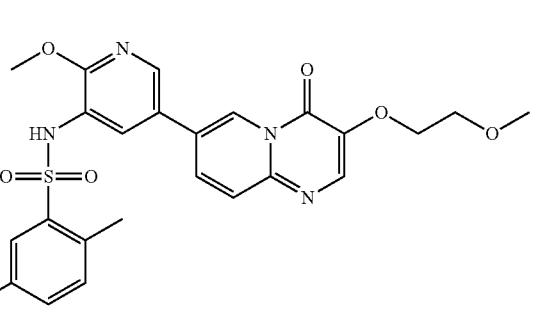
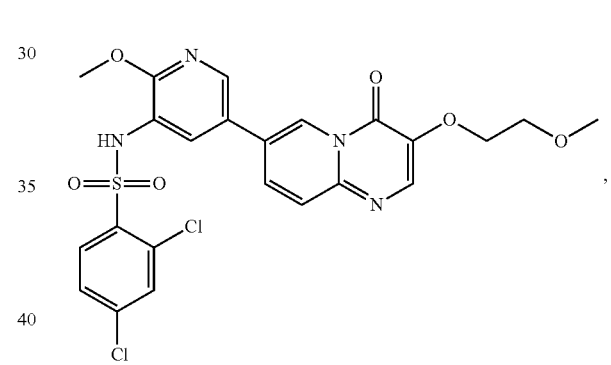
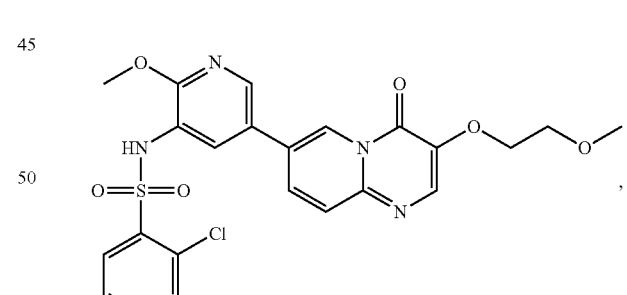
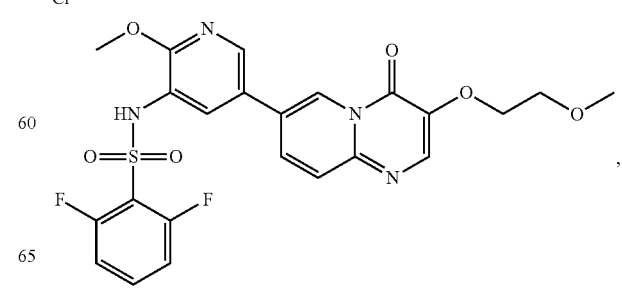

213
-continued
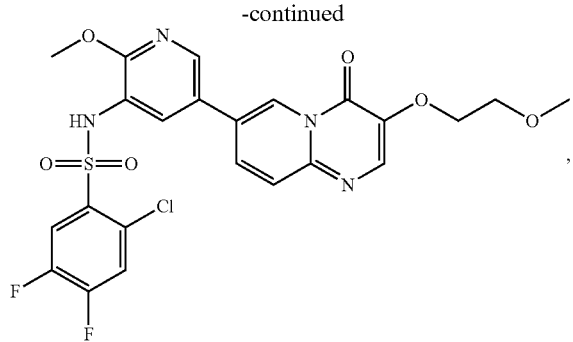
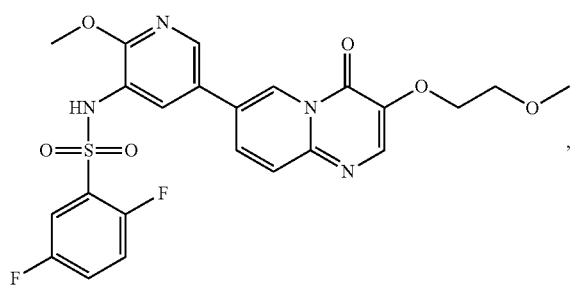
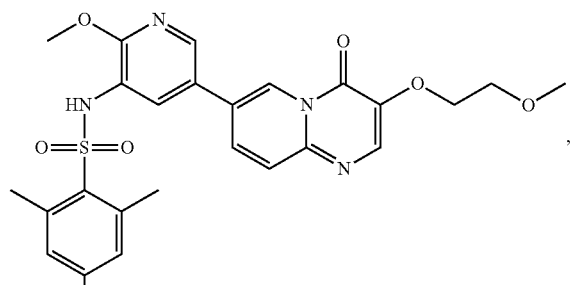
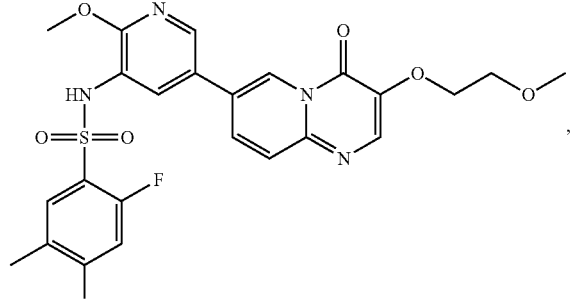
,
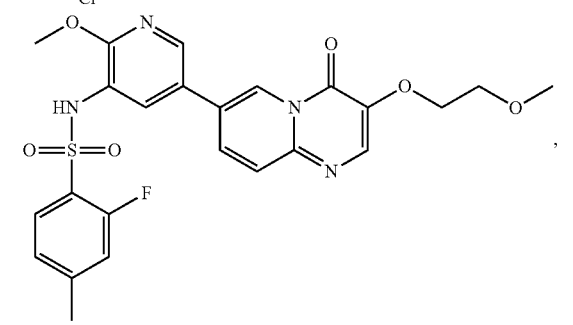
,
214
-continued
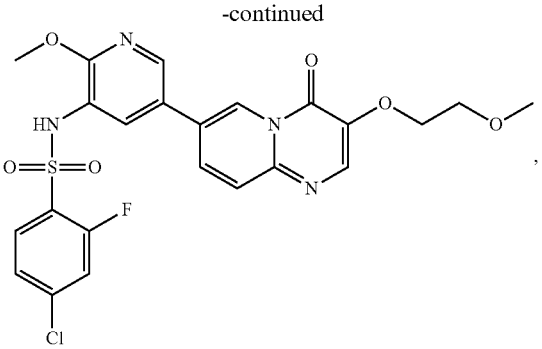
,
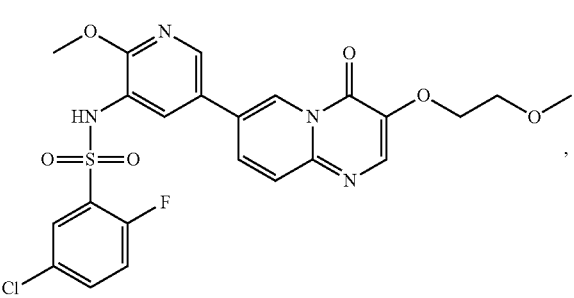
,
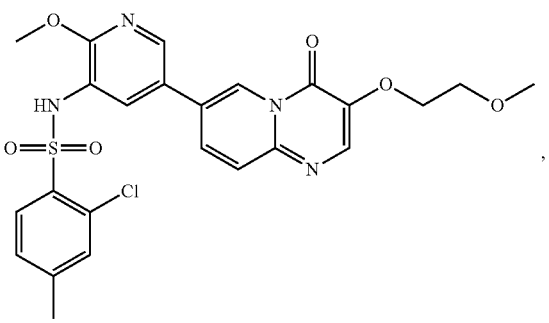
, 215
-continued
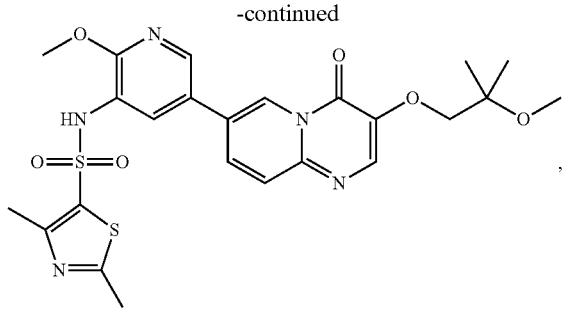
,
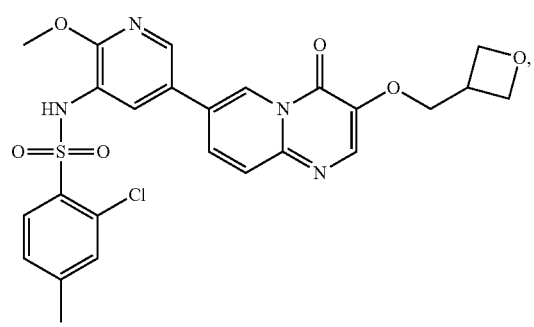
,
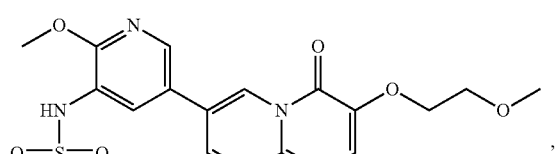
,
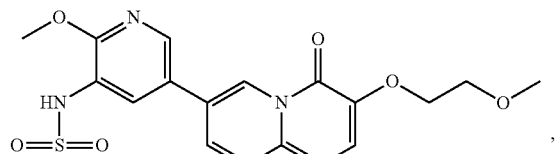
,
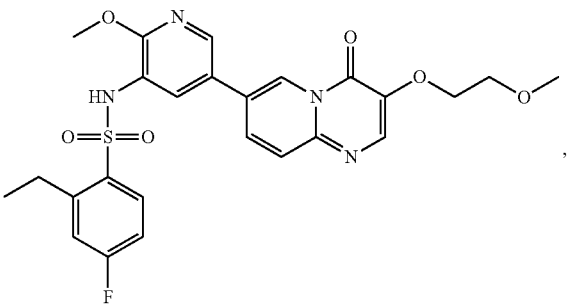
216
-continued
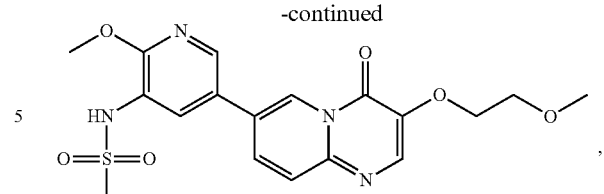
,
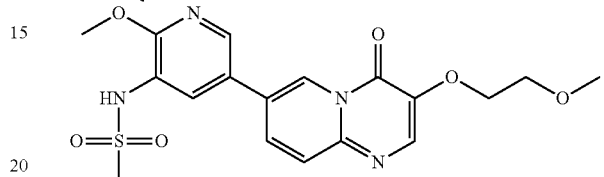
,
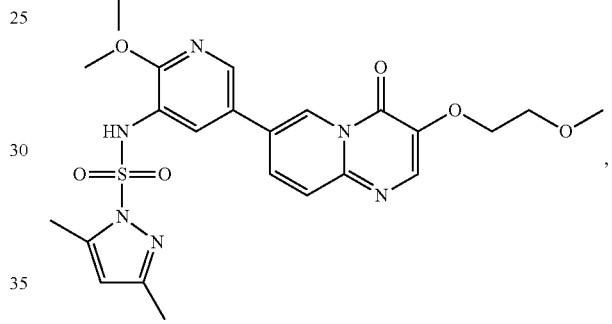
,
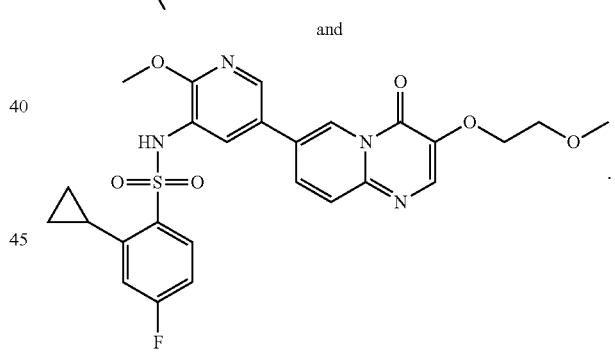
and
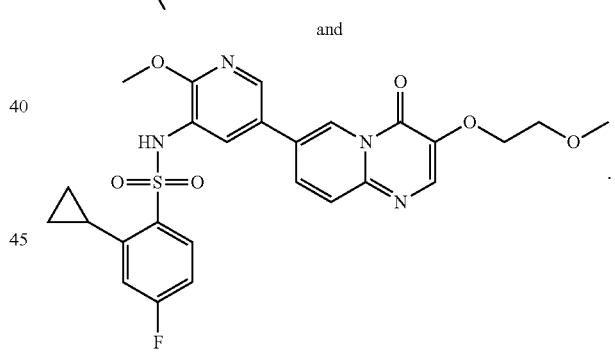
.
7. The compound of forms 1a (I) or a pharmaceutically acceptable salt thereof according to claim 1, wherein E is selected from the group consisting of
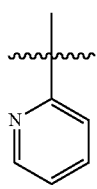 [SMILES: *c1ccccn1]
and $C_{1-3}$ alkyl, the above group being optionally substituted by 1, 2, or 3 halogen, OH, $OC_{1-3}$ alkyl, CN, $NH_2$, $NH(C_{1-3}$ alkyl), $N(C_{1-3}$ alkyl$)_2$, $C_{1-3}$ alkyl, trifluoromethyl, trifluoroethyl, C(=O)NH₂, C₁₋₃ alkylC(=O), C₁₋₃ alkylC(=O)NH, C₁₋₃ alkylS(=O), C₁₋₃ alkylS(=O)NH, C₁₋₃ alkylS(=O)₂ or C₁₋₃ alkyl S(=O)₂NH.
8. The compound of formula (1) or a pharmaceutically acceptable salt thereof according to claim 1, wherein E is selected from the group consisting of
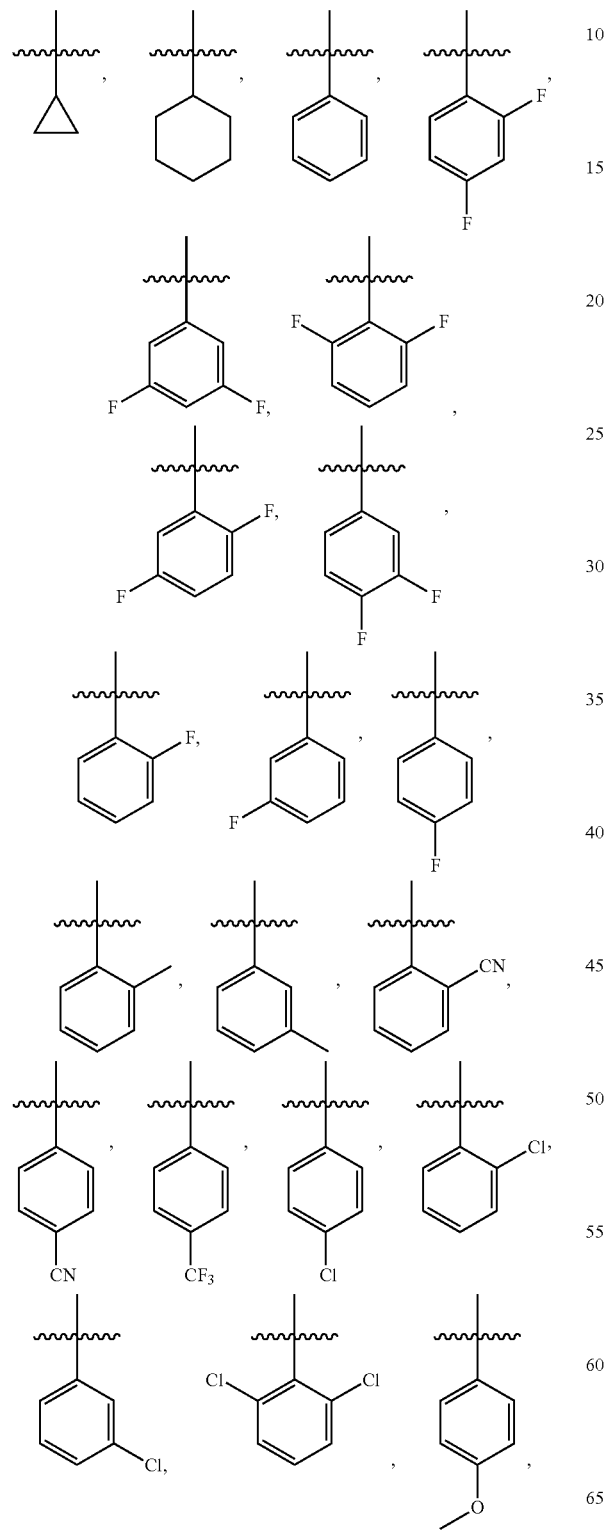
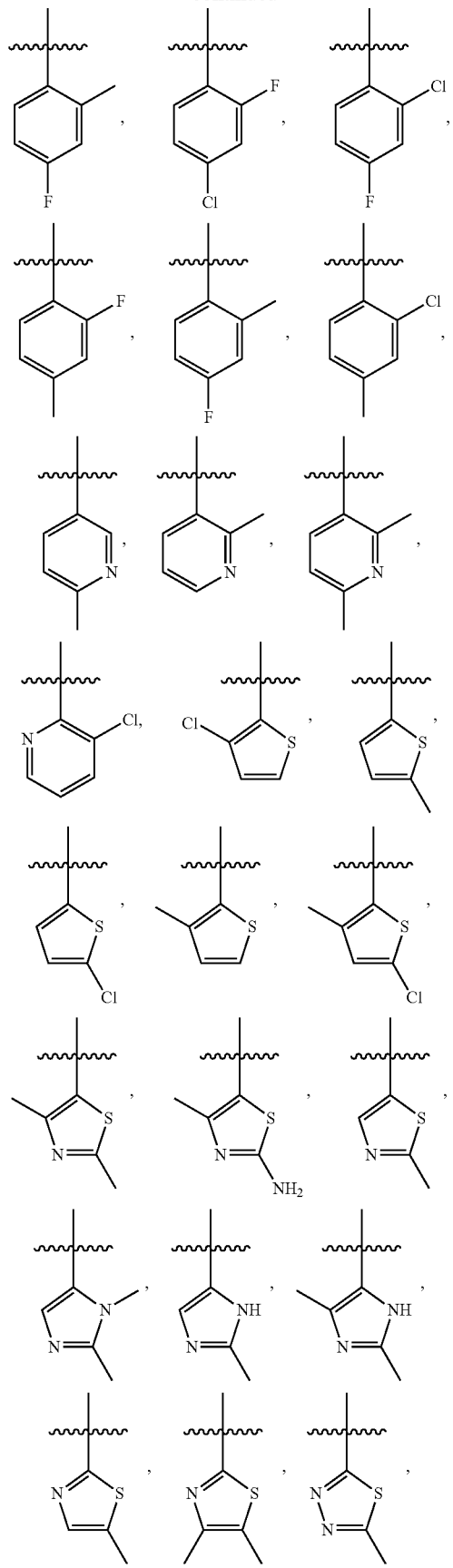

219
-continued
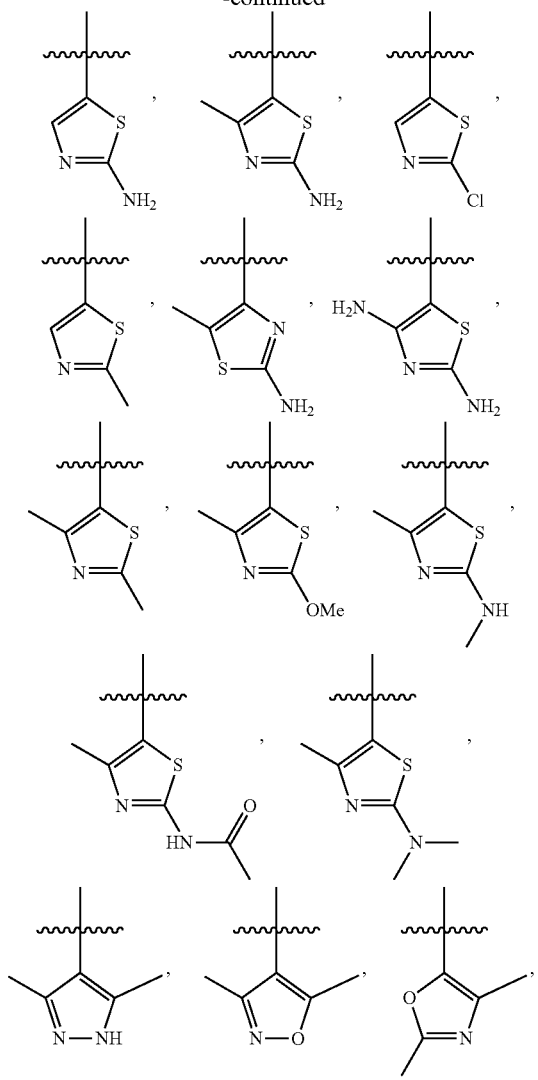
220
-continued
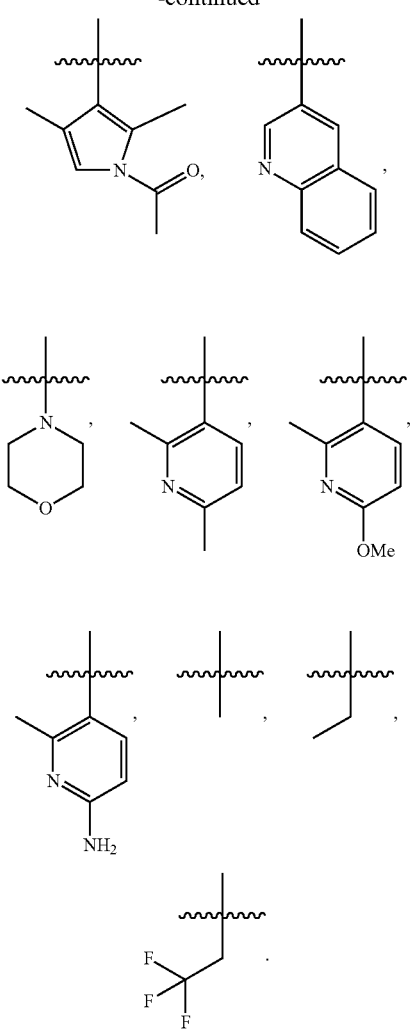
* * * * *